(12) United States Patent
Castelhano et al.

(10) Patent No.: US 7,501,407 B2
(45) Date of Patent: *Mar. 10, 2009

(54) PYRIMIDINE A$_{2B}$ SELECTIVE ANTAGONIST COMPOUNDS, THEIR SYNTHESIS AND USE

(75) Inventors: Arlindo Castelhano, New City, NY (US); Bryan McKibben, Hopewell Junction, NY (US); Arno Steinig, East Northport, NY (US); Eric Collington, Knebworth (GB)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/992,239

(22) Filed: Nov. 18, 2004

(65) Prior Publication Data

US 2005/0119271 A1    Jun. 2, 2005

Related U.S. Application Data

(63) Continuation of application No. 10/326,204, filed on Dec. 20, 2002, now Pat. No. 6,916,804.

(60) Provisional application No. 60/342,595, filed on Dec. 20, 2001.

(51) Int. Cl.
*C07D 403/12* (2006.01)
*C07D 403/14* (2006.01)
*A61K 31/505* (2006.01)

(52) U.S. Cl. .............. 514/217.06; 514/218; 514/235.8; 514/256; 514/252.14; 544/122; 544/329; 540/575; 540/601

(58) Field of Classification Search .......... 540/575, 540/601; 544/122, 329; 514/217.06, 218, 514/235.8, 256, 252.14

See application file for complete search history.

(56) References Cited

U.S. PATENT DOCUMENTS

| | | | |
|---|---|---|---|
| 3,037,980 A | 6/1962 | Hitchings et al. | |
| 3,910,913 A | 10/1975 | Kim et al. | |
| 5,208,240 A | 5/1993 | Peet et al. | |
| 5,296,484 A | 3/1994 | Coghlan et al. | |
| 5,409,930 A | 4/1995 | Spada et al. | |
| 5,516,894 A | 5/1996 | Reppert | |
| 5,580,870 A | 12/1996 | Barker et al. | |
| 5,639,913 A | 6/1997 | Lidor et al. | |
| 5,646,130 A | 7/1997 | Shi | |
| 5,646,156 A | 7/1997 | Jacobson | |
| 5,681,941 A | 10/1997 | Cook et al. | |
| 5,710,158 A | 1/1998 | Myers et al. | |
| 5,714,493 A | 2/1998 | Myers et al. | |
| 5,721,237 A | 2/1998 | Myers et al. | |
| 5,747,498 A | 5/1998 | Schnur et al. | |
| 5,780,450 A | 7/1998 | Shade | |
| 5,780,481 A | 7/1998 | Jacobson et al. | |
| 5,834,609 A | 11/1998 | Horne et al. | |
| 5,877,180 A | 3/1999 | Linden et al. | |
| 5,877,218 A | 3/1999 | Herzig et al. | |

(Continued)

FOREIGN PATENT DOCUMENTS

DE     3145287 A1     5/1993

(Continued)

OTHER PUBLICATIONS

Singh et al., Immune Therapy in inflammatory bowel disease and models of colitis, British Journal of Surgery, 88:1558-1569, 2001.*

(Continued)

*Primary Examiner*—Deepak Rao
(74) *Attorney, Agent, or Firm*—John P. White; Cooper & Dunham LLP

(57) ABSTRACT

The subject invention provides compounds having the structure:

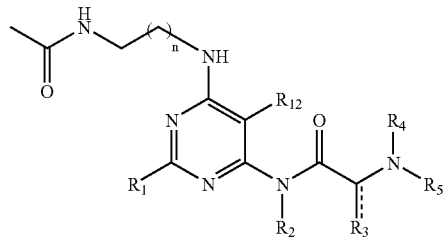

wherein $R_1$ is substituted or unsubstituted phenyl or a 5-6 membered heterocyclic or heteroaromatic ring containing from 1 to 5 heteroatoms; $R_2$ is hydrogen, or a substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety; $R_3$ is hydrogen, or a substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or $R_2$ and $R_3$ are joined to form a heterocyclic ring; wherein the dashed line represents a second bond which may be present or absent, and when present $R_3$ is oxygen; $R_4$ and $R_5$ are each independently substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or $R_4NR_5$ together form a substituted or unsubstituted monocyclic or bicyclic, heterocyclic or heteroaryl moiety containing from 1 to 6 heteroatoms;

$R_{12}$ is hydrogen, alkyl, halogen or cyano; and n is 0, 1, 2, 3 or 4, or an enantiomer, or a specific tautomer, or a pharmaceutically acceptable salt thereof and a method for treating a disease associated with the $A_{2b}$ adenosine receptor by administering a therapeutically effective amount of the compounds of the invention.

7 Claims, No Drawings

U.S. PATENT DOCUMENTS

| | | | |
|---|---|---|---|
| 5,877,221 A | 3/1999 | Cohen et al. | |
| 5,880,159 A | 3/1999 | Herzig et al. | |
| 5,889,026 A | 3/1999 | Alanine et al. | |
| 5,914,349 A | 6/1999 | Cohen et al. | |
| 5,935,964 A | 8/1999 | Baraldi et al. | |
| 5,962,458 A | 10/1999 | Lohmann et al. | |
| 5,994,408 A | 11/1999 | Cohen et al. | |
| 6,103,899 A | 8/2000 | Horne et al. | |
| 6,117,878 A | 9/2000 | Linden | |
| 6,465,456 B2 | 10/2002 | Springer et al. | |
| 6,664,252 B2 | 12/2003 | Castelhano et al. | |
| 6,673,802 B2 | 1/2004 | Castelhano et al. | |
| 6,680,322 B2 | 1/2004 | Castelhano et al. | |
| 6,680,324 B2 | 1/2004 | Castelhano et al. | |
| 6,686,366 B1 | 2/2004 | Castelhano et al. | |
| 6,800,633 B2 | 10/2004 | Castelhano et al. | |
| 6,878,716 B1 | 4/2005 | Castelhano et al. | |
| 6,916,804 B2 * | 7/2005 | Castelhano et al. | 514/217.06 |
| 7,160,890 B2 | 1/2007 | Castelhano et al. | |
| 7,202,252 B2 | 4/2007 | Wilson et al. | |
| 2003/0139427 A1 | 7/2003 | Castelhano et al. | |
| 2003/0229067 A1 | 12/2003 | Castelhano et al. | |
| 2004/0082598 A1 | 4/2004 | Castelhano et al. | |
| 2004/0082599 A1 | 4/2004 | Castelhano et al. | |
| 2005/0043332 A1 | 2/2005 | Castelhano et al. | |
| 2005/0090513 A1 | 4/2005 | Castelhano et al. | |
| 2008/0070936 A1 | 3/2008 | Castelhano et al. | |

FOREIGN PATENT DOCUMENTS

| | | |
|---|---|---|
| EP | 322242 A2 | 6/1989 |
| EP | 0514540 | 11/1992 |
| EP | 0682027 A1 | 11/1995 |
| EP | 0729758 A2 | 9/1996 |
| EP | 0773023 | 5/1997 |
| EP | 1246623 | 8/2006 |
| GB | 915303 | 1/1963 |
| IN | 157280 | 2/1986 |
| JP | 09291089 | 5/1999 |
| WO | 9320078 | 10/1993 |
| WO | 9413676 | 6/1994 |
| WO | 9417090 | 8/1994 |
| WO | 9419349 | 9/1994 |
| WO | 9424136 | 10/1994 |
| WO | 9511681 | 5/1995 |
| WO | 9518617 | 7/1995 |
| WO | 9519774 | 7/1995 |
| WO | 9519970 | 7/1995 |
| WO | 9520597 | 8/1995 |
| WO | 9619478 | 6/1996 |
| WO | 9702266 | 1/1997 |
| WO | 9705138 | 2/1997 |
| WO | 9733879 | 9/1997 |
| WO | 9747601 | 12/1997 |
| WO | 9807726 | 2/1998 |
| WO | 9808382 | 3/1998 |
| WO | 9822465 | 5/1998 |
| WO | 9829397 | 7/1998 |
| WO | 9857651 | 12/1998 |
| WO | 9906053 | 2/1999 |
| WO | 9908460 | 2/1999 |
| WO | 9933815 | 7/1999 |
| WO | 9942093 | 8/1999 |
| WO | 9962518 | 12/1999 |
| WO | 9964407 | 12/1999 |
| WO | 0003741 | 1/2000 |
| WO | 0139777 | 6/2001 |
| WO | 02057267 | 7/2002 |
| WO | 03048120 | 6/2003 |
| WO | 03053361 | 7/2003 |
| WO | 03053366 | 7/2003 |

OTHER PUBLICATIONS

Robinson, Medical Therapy of Inflammatory Bowel Disease for the 21$^{st}$ Century, Eur J Surg. Suppl 582:90-98, 1998.*

Feoktistov et al., Adenosine A2B receptors, Pharmacological Reviews, vol. 49, No. 4, pp. 381-402, 1997.*

Baraldi et al., Pyrazolo-triazolo-pyrimidine derivatives as adenosine receptor antagonists: a possible template for adenosine receptor subtypes?, Current Pharmaceutical Design, vol. 8, No. 26, pp. 2299-2332, 2002.*

Bremer et a., Therapy of Crohn's Disease in childhood, Expert Opin. Pharmacother. 3(7):809-825, 2002.*

Meade et al., PubMed Abstract (Life Sci. 69(11):1255-40) Aug. 2001.*

Simone, Oncology: Introduction, Cecil Textbook of Medicine, 20$^{th}$ Edition, vol. 1, pp. 1004-1010, 1996.*

U.S. Appl. No. 10/010,092, filed Oct. 30, 2001, Castelhano et al.

Baraldi et al. "Pyrazolo-triazolo-pyrimidine derivatives as adenosine receptor antagonists: a possible template for adenosine receptor subtypes", Curr. Pharm. Design 8: 2299-2332, 2002.

Blazynski C., (1990) "Discrete Distributions of Adenosine Receptors in Mammalian Retina", *Journal of Neurochemistry,* 53: 648-655.

Braas K.M., et al., (1987) "Endogenous adenosine and adenosine receptors localized to ganglion cells of the retina", *Proceedings of the National Academy of Science,* 84: 3906-3910.

Christofi, F.L. et al. (2001), "Differential Gene Expression of Adenosine A1, A2a, A2b, and A3 Receptors in the Human Enteric Nervous System", J. Comp. Neurol. 439(1): 46-64.

Corset, V. et al. (2000), "Netrin-1-mediated axon outgrowth and cAMP productions requires interaction with adenosine A2b receptor", Nature, 407 (6805): 747-750.

Dubey, R.K. et al. (2001), "$A_{2B}$ Receptors Mediate the Antimitogenic Effects of Adenosine in Cardiac Fibroblasts", Hypertension 37: 716-721.

Faivre, K. et al., (2001) "Suppression of Cellular Invasion by Activated G-Protein Subunits Gαo, Gαi1, and Gαi3 and Sequestration of Gβγ", Mol. Pharmacol. 60: 363-372.

Feoktistov, I. and Biaggioni, I., (1997) "Adenosine $A_{2B}$ Receptors", Pharmacol. Rev. 49(4): 381-402.

Feoktistov, I. et al., (2002) "Differential Expression of Adenosine Receptors in Human Endothelial Cells", Circulation Research 90: 531-538.

Feoktistove, I. et al., (1998) "Adenosine $A_{2B}$ receptors: a novel therapeutic target in asthma", TiPS 19: 148-153.

Gao, Z. et al., "$A_{2B}$ Adenosine and P2Y$_2$ Receptors Stimulate Mitogen-activated Protein Kinase in Human Embryonic Kidney-293 Cells" *J. Bio. Chem.* (1999) 274(9): 5972-5980.

Grant, M.B. et al., (2001) "Proliferation, Migration, and ERK Activation in Human Retinal Endothelial Cells through $A_{2B}$ Adenosine Receptor Stimulation", Invest. Opthalmol. Vis. Sci. 42(9): 2068-2073.

Haynes, J. Jr. et al., (1999) "5-(N-ethylcarboxamido) adenosine desensitizes the $A_{2b}$-adenosine receptor in lung circulation", Am. J. Physiol. 276(6): H1877-H1883.

Linden, J. et al., (1998) "The Structure and Function of A1 and A2B Adenosine Receptors" Life Sciences 62(17-18): 1519-1524.

Meade et al., PubMed Abstract (Life Sci. 69(11):1225-40) Aug. 2001.

Mirabet, M. et al., (1999) "Expression of A2B adenosine receptors in human lymphocytes: their role in T cell activation" J. Cell. Sci. 112(4): 491-502.

Muller, C. E. and Stein, B. (1996) "Adenosine Receptor Antagonist: Structure and Potential Therapeutic Applications", *Current Pharmaceutical Design,* 2: 501-530.

Muller, C. E. (1997) "$A_1$-Adenosine Receptor Antagonists", *Exp. Opin. Ther. Patents* 7(5): 419-440.

Nyce J. W. and Metzger J. W., (1997) "DNA antisense therapy for asthma in an animal model", *Nature,* 385: 721-725.

Ralevic, V. And Burnstock, G., (1998) "Receptors for Purines and Pyrimidines", Pharmacol. Rev. 50(3): 413-492.

Regnauld, K. et al., (2002) "G-protein αolf subunit promotes cellular invasion, survival, and neuroendocrine differentiation in digestive and urogenital epithelial cells", Oncogene 21(25): 4020-4031.

Strohmeier, G. R. et al., (1995) "The $A_{2b}$ Adenosine Receptor Mediates cAMP Responses to Adenosine Receptor Agonists in Human Intestinal Epithelia", J. Bio. Chem., 270:2387-2394.

Van Niel, M.B. et al., "Fluorianation of 3-(3-(Piperidin-1-yl)propyl)indoles and 3-(3-(Piperazin-1-yl)propyl) indoles Gives Selective Human 5-Htid Receptor Ligands with Improved Pharmokinetic Profiles" J. Med. Chem. (1999) 42(12): 2087-2104.

Williams, E. F. et al., (1994) "Nucleoside transport sites in a cultured human retinal cell line established by SV-40 T antigen gene", Current Eye Research, 13: 109-118.

Woods, C. L. and Blazynski, C. (1991) "Characterization of Adenosine $A_1$-receptor Binding Sites in Bovine Retinal Membranes", Experimental Eye Research, 53: 325-331.

Abbracchio M., et al., (1997) "Modulation of Apoptosis by Nervous System: a Possible Role for the $A_3$ Receptor", Ann. NY. Acad. Sci., 825: 11-22.

Abbracchio M., et al., (1999) "Brain Adenosine Receptors as Targets for Therapeutic Intervention in Neurodegenerative Diseases", Ann. NY. Acad. Sci, 890: 79-92.

Aoyama S. et al. (2000) "Rescue of Locomotor Impairment in Dopamine D2 Receptor-Deficient Mice by an Adenosine A2a Receptor Antagonist" J. Neuroscience 20(15):5848-5852.

Avila, M.Y. (2001) "A1-A2a and A3-Subtype Adenosine receptors Modulate Intraocular Pressure in the Mouse" J. of Pharmacol. 241-245.

Banker, G.S. et al., Modern Pharmaceutics, 3rd ed., Marcel Dekker, New York, 1996, p. 596.

Baraldi, P.G. et al. (1996) "Pyrazolo [4,3-e]-1,2,4 triazolo [1,5-c]pyrimidine Derivatives: Potent and Selective A2a Adenosine Antagonists" J. Med. Chem. 39:1164-1171.

Baraldi P., et al., (2000) "New potent and selective human adenosine $A_3$ receptor antagonists", Tips, 21:456-459.

Baraldi, P.G. et al., (1999) "A1 and A3 adenosine receptor agonists: an overview." Expert Opinion on Therapeutic Patents, 9(5):515-527.

Baraldi, P.G. et al., (2004) "Allosteric modulators for the A1 adenosine receptor." Expert Opinion on Therapeutic Patents, 14(1):71-79.

Baraldi P.G. (2003) "Recent developments in the field of A2A and A3 adenosine receptor antagonists" Eur. J. Med. Chem. 38(4) 36779.

Barrett, R.J. (1996) "Realizing the Potential of Adenosine-Receptor-Based Therapeutics" Proc. West. Pharmacol. Soc. 39: 61-66.

Barrett, R.J. et al., "N-0861 selectively antagonizes adenosine A1 receptors in vivo" European J. Pharmacology (1992) 216: 9-16.

Borman, S. (2001) "A3 Receptors" C&EN, 79(7).

Bradford M.M., (1976) "A Rapid and Sensitive Method for the Quantitation of Microgram Quantities of Protein Utilizing the Principle of Protein-Dye Binding", Anal. Biochem., 72: 248.

Brand A., et al., (2001) "Adenosine A1 and A3 receptors mediate inhibition of synaptic transmission in rat cortical neurons", Neuropharmacology, 40: 85-95.

Bremer et al. (2002) "Therapy of Crohn's Disease in Childhood", Expert Opin. Pharmacother. 3(7): 809-825.

Broach, J. R., et al., (1983) "Vectors for high level, inducible expression of cloned genes in yeast", Inouye (ed)., Experimental Manipulation of Gene Expression. Academic Press, New York, 83-117.

Bundy, G.L. et al. (1995) "Synthesis of Novel 2,4-Diaminopyrrolo-[2,3-d-d]pyrimidines with Antioxidant, Neuroprotective, and Antiasthma Activity" J. Med. Chem. 38:4161-4163.

Campbell, R.M. et al., "Selective $A_1$-Adenosine Receptor Antagonists Identified Using Yeast Saccharaomyces cerevisae Functional Assays" Bioorg. & Med. Chem. Lett. (1999) 9(16): 2413-2418.

Casavola V., et al., (1998) "Adenosine A3 receptor activation increases cystolic calcium concentration via calcium influx in A6 cells", Drug Development Research, 43 (1): 62.

Cheng, Y. and Prusoff, W. H. (1973) "Relationship Between The Inhibition Constant ($K_i$) And The Concentration Of Inhibitor Which Causes 50 Per Cent Inhibition ($I_{50}$) Of An Ezymatic Reaction", Biochem. Pharmacol., 22:3099-3109.

Christianson, T. W. et al., (1992) "Multifunctional yeast high-copy-number shuttle vectors", Gene, 110:119-122.

Coney, A.M. et al. (1998) "Role of Adenosine and its Receptors in the Vasodilation Inducted in the Cerebral Cortex of the Rat by Systemic Hypoxia" J. Physiol. 509:507-518.

Cooper, J.A. (1995) "Adenosine Receptor-induced Cyclic AMP Generation and Inhibtion of 5-hydroxytryptamine release in Human Platelets" Br. J. Clin. Pharmacol. 40:43-50.

Cummings, J. et al., "Antagonism of the Cardiodepressant Effects of Adenosine during Acute Hypoxia" Academic Emergency Medicine (2000), 7(8): 618-624.

DeNinno, M.P. in Annual Reports in Medicinal Chemistry, vol. 33, (Academic Press: San Diego, 1998), pp. 111-120.

Dhainaut, A. et al., "New Purines and Purine Analogs as Modulators of Multidrug Resistance" J. Med. Chem. (1996) 39: 4099-4108.

Dooley, M.J. et al., "Theoretical Structure-Activity Studies of Adenosine A1 Ligands: Requirements for Receptor Affinity" Bioorg. Med. Chem. (1996), 4(6): 923-934.

Duzic, E. et al., (1992) "Factors Determining the Specificity of Signal Transduction by Guanine Nucleotide-binding Protein-coupled Receptors", J. Biol. Chem., 267: 9844-9851.

Ezeamuzie C., et al., (1999), British Journal of Pharmacology, 127: 188-194.

Fishman P (2003) "Pharmacology and therapeutic applications of A3 receptor subtype" Curr. Top. Med. Chem. 3(4) 463-9.

Fozard J., et al., (1996) "Mast cell degranulation following adenosine A3 receptor activation in rats", European Journal of Pharmacology, 298: 293-297.

Franco M., et al., (1999) "Adenosine Regulates Renal Nitric Oxide Production in Hypothyroid Rats", Journal of the American Society of Nephrology, 1681-1688.

Gao, E. et al., "Adenosine A1 Receptor Antagonist Prolongs Survival in the Hypoxic Rat" J. Cardiovascular Pharm. (2001) 38: 384-394.

Ghiardi, G.J. et al. (1999) "The Purine Nucleoside Adenosine in Retinal Ischemia-Reperfusion Injury" Vision Research 39:2519-2535.

GenBank accession # S46950.

GenBank accession Nos. S45235 and S56143.

Guerra L., et al., (1998) "Adenosine A3 receptor activation increases cytosolic calcium influx in A6 cells", Nephrology Dialysis Transplantation, 13 (6): A5.

Guo, Y. et al., (2001) "Targeted deletion of A3 adenosine receptor confers resistance to myocardial ischemic injury and does not prevent early preconditioning." J Mol Cell Cardiol, 33:825-830.

Hart, H. et al., Organic Chemistry, A Short Course, (Houghton Mifflin: 1995), p. 121.

Herndon, J.L. et al., (1992) Herndon, J.L. et al., "Ketanserin Analogs: Structure-Affinity Relationships for 5-HT2 and 5-HT1C Serotonin Receptor Binding", J. Med. Chem. 35(26): 4903-4910.

Hoeschst India Ltd., India Pharmacologically active pyrimido "[4,5-b]indoles and their salts." Database accession No. 106:84629 HCA XP002121648.

Iwamura, H. et al. (1996) "Quantitative Aspects of the Receptor Binding of Cytokinin Agonists and Antagonists" J. Med. Chem., 26: 838-844.

Jacobson K.A., et al., (1997) "Pharmacological Characterization of Novel A3 Adenosine Receptor-selective Antagonists", Neuropharmacology, 36 (9): 1157-1165.

Jacobson K.A., et al., (1998) "Adenosine A3 receptors: novel ligands and paradoxical effects", Tips, 19:184-191.

Jorgensen, A. et al. (1985) "Synthesis of 7H-Pyrrolo[2,3-d]pyrimidin-4-amines" Liebigs, Ann. Chem., pp. 142-148.

Kaiser, S.M. and R.J. Quinn (1999) "Adenosine receptors as potential therapeutic targets" Drug Discovery Today 4(12): 542-551.

Kakemi, K. et al., "Synthesis of . . . acid." Database Chemasold Online! Chemical Abstracts Service, Columbus Ohio, US XP 002121649.

Kanda, T. et al. (1998) "Adenosine A2a Receptors Modify Motor Function in MPTP-treated Common Marmosets" Neuroreport 9:2857-2860.

Kanda, T. et al. (2000) "Combined Use of the Adenosine A2a Antagonist KW-6002 with L-DOPA or with Selective D1 or D2 Dopamine Agonists Incrases Antiparkinsonian Activity but not Dyskensia in MPTP-Treated Monkeys" Experimental Neurology 162:321-327.

Kang, Y. et al., (1990) "Effects of Expression of Mammalian Gα and Hybrid Mammalian-Yeast Gα Proteins on the Yeast Pheromone Response Signal Transduction Pathway", *Mol. Cell. Biol.*, 10: 2582-2590.

Kiichiro, K. et al. "Synthesis of pyrazinecarboxylic acid derivs.—(II) derivs. of 3-aminopyrazinecarboxylic acid" Chem. Abstracts 56:8713.

Kiichiro, K. et al. "Synthesis of pyrazinecarboxylic acid derivs.—(II) derivs. of 3-aminopyrazinecarboxylic acid" (1961) *Yakugaku Zasshi* 81: 1650-1653 (Abstract only).

Kiritsy, J.A. et al., (1978) "Synthesis and Quantitative Structure-Activity Relationships of Some Antibacterial 3-Formylrifamycin SV N-(4-Substituted phenyl) piperazinoacethydrazones" J. Med. Chem. 21(12): 1301-1307.

Klumpp, D.A. et al., (1999) "Synthesis of Aryl-Substituted Piperidines by Superacid Activation of Piperidones" J. Org. Chem. 64(18): 6702-6705.

Knutsen, L.J.S. et al. (2001) *Curr. Opin. Invest. Drugs* 2(5):668-673.

Kopf, S.R. et al. (1999) "Adenosine and Memory Storage: Effect of A1 and A2 Receptor Antagonists" *Psychopharmacology* 146:214-219.

Lee T., et al., (1999) "Protective effects of renal ischemic preconditioning and adenosine pretreatment: role of A1 and A3 receptors", 72$^{nd}$ *Scientific Sessions of the American Heart Association*, Atlanta, GA, p. 197.

Lee T., et al., (2000) "Protective effects of renal ischemic preconditioning and adenosine pretreatment: role of A1 and A3 receptors", *Am. J. Physiol. Renal Physiol.*, 278: F380-F387.

Li, J.M. et al. (1998) "Adenosine A2a Receptors Incrase Arterial Endothelial Cell Nitric Oxide" *J. Surg. Res.* 80:357-364.

Marx, D. et al. (2001) "Therapy of Bronchial Asthma with Adenosine Receptor Agonists or Antagonists" *Drug News Perspect.* 14(2): 89-100.

Mautner, H.G., (1961) "Potential Deoxyribonucleic Acid Crosslonking Agents. 8,8'-Bispurines", *J. Org. Chem.* 26(6):1914-1917.

Mitchell, C.H. et al., "Adenosine A3 Receptor Activation Reduces Cell Volume and Activates C1 Current in Human Ciliary Epithelial Cells", *FASEB J*, A134 (Abstract only).

Michell, C.H. (1999) "A3 adenosine receptors regulate C1-channels of nonpigmented ciliary epithelial cells" Am. J. Physiol. 276 C659-C666.

Montesinos, M.C. et al. (2002) "Adenosine Promotes Wounds Healings and Mediates Angiogenesis in Response to Tissue Injury Via Occupancy of A2a Receptors" *American Journal of Pathology* 160(6):2009-2018.

Muller, C. E. et al. (1990) "7-Deaza-2-phenyladenines: Structure-Activity Relationships of Potent A1 Selective Adenosine Receptor Antagonists" *J. Med. Chem.*, 33: 2822-2828.

Muller, C. E., et al., (1997) "Synthesis and Structure-Activity Relationships of 3,7-Dimethyl-1-propargylxanthine Derivatives, A$_{2A}$-Selective Adenosine Receptor Antagonists", *J. Med. Chem.*, 40: 4396-4405.

Muller, E. C. et al. (1996) "Chiral Pyrrolo[2,3-d]pyrimidine and Pyrimido[4,5,-b]indole Derivatives: Structure-Activity Relationships of Potent, Highly Steroselective A$_1$-Adenosine Receptor Antaogonist" *J. Med. Chem.*, 39:2482-2491.

Müller, C.E. (2001) "A3 Adenosine Receptor Antagonists" Mini Reviews in Med. Chem. 1(4) 339.

Müller, C.E. et al., (2002) J. Med. Chem. 45(16): 3440-3450.

Nagarathnam, D. et al., (1998) "Design and Synthesis of Novel α1 a Adrenoceptor-Selective Dihydropyridine Antagonists for the Treatment of Benign Prostatic Hyperplasia", J. Med. Chem. 41(26): 5320-5333.

Nishiyama, A. et al. (2001) "Interactions of Adenosine A1 and A2 a Receptors on Renal Microvascular Reactivity" *Am. J. Physiol. Renal Physiol.* 280:F406-414.

Nyce J.W. (1997) "DNA Antisense thrapy for asthma in an animal model" 385: 721. Walker (1997) Am. J. Respir. Cell Mol. Biol. 161: 531.

Ohana G., et al., (2001) "Differential Effect of Adenosine on Tumor and Normal Cell Growth: Focus on the A3 Adenosine Receptor", *Journal of Cellular Physiology*, 186: 19-23.

Phillips, J.W. (1995) The Effects of Selective A1 and A2a Adenosine Receptor Antagonists on Cerebral Ischemic Injury in the Gerbil.

Polosa (2002) "Adenosine-receptor subtypes: their relevance to adenosine-mediated responses in asthma and chronic obstructive pulmonary disease", Eur. Respir. Journal 20,488-496.

Priego, E.-M. et al., (2002) J. Med. Chem., 45(16): 3337-3344.

Nishiyama, A. et al., "Adenosine A1 Receptor Antagonist KW-3902 Prevents Hypoxia-Induced Renal Vasoconstriction" *J. Pharm. Exp. Ther.* (1999), 291: 988-993.

Regulation of Downstream Effectors By GPCRs, (1999) *FASEB J.*, Abstracts 147.1-147.6.

Reshkin J., et al., (2000) "Activation of A3 Adenosine Receptor Induces Calcium Entry and Chloride Secretion in A6 Cells", *J. Membrane Biol.*, 178: 103-113.

Robinson, "Medical Therapy of Inflammatory Bowel Disease for the 21st Century", Eur J Surg. Suppl 582:90-98, 1998.

Sawynok J., et al., (1997) "Adenosine A3 receptor activation produces nociceptive behaviour and edema by release of histamine and 5-hydroxytryptamine", *European Journal of Pharmacology*, 333: 1-7.

Seela, F., and Lupke, U., (1977) *U. Chem. Ber.*, 110:1462-1469.

Shan, Daxian et al., *J. Pharmaceutical Sci.*, (1997) 86:765-767.

Shiozaki, S. et al. (1999) "Actions of Adenosine A2a Receptor Antagonist K W-6002 on Drug-induced Catalepsy and hypokinesia Caused by Reserpine of MPTP" *Psychopharmacology* 147:90-95.

Simone, Oncology: Introduction Cecil Textbook of Medicine, 20th Edition, vol. 1, pp. 1004-1010, 1996.

Singh et al., "Immune therapy in inflammatory bowel disease and models of colitis", British Journal of Surgery, 88: 1558-1569, 2001.

Svenningsson, P. et al. (1999) "Distribution, Biochemistry and Function of Striatal Adenosien A2a Receptors" *Prog. Neurobiol.* 59(4):355-396.

Szkotak, A.J. et al., "Regulation of K$^+$ current in human airway epithelial cells by exogenous and autocrine adenosine" *Am. J. Physiol. Cell Physiol.* (2001), 281: C1991-C2002.

Tanaka, H. et al. "Preparation and formulation of fused pyrimidine compounds as CRF receptor antagonists." Database accession No. 129:109098 HCA XP002121647.

Taomoto, M. ety al. (2000) "Localization of Adenosine A2 Receptor in Retinal Development and Oxygen-Induced Retinopathy" *Investigative Ophthamology & Visual Science* 41(1):230-243.

PCT International Preliminary Examination Report issued in PCT International Application No. PCT/US00/32702.

PCT International Preliminary Examination Report issued in PCT International Application No. PCT/US2001/054280, filed Nov. 30, 2001.

PCT International Preliminary Examination Report issued in PCT International Application No. PCT/US200/38055, filed Nov. 27, 2002.

PCT International Preliminary Examination Report issued in PCT International Application No. PCT/US2002/40890, filed Dec. 20, 2002.

PCT International Preliminary Examination Report issued in PCT International Application No. PCT/US2002/41273, filed Dec. 20, 2002.

Partial European Search Report; for EP Application No. 06 01 6543. 8; completed Oct. 4, 2006.

Partial European Search Report; for EP Application No. 01 99 7029; completed Dec. 21, 2004.

Pichler, H. et al. "Synthese von 7-unsubstituierten 7H-Pyrrolo[2,3-d]-pyrimidinen" Liebigs Ann. Chemie. 9:1485-1505.

Supplemental European Search Report; for EP Application No. 02 80 5676; issued Feb. 7, 2005.

Hungarian Patent No. HU P9303515 (corresponds to WO 94/13676).

Hungarian Patent No. HU P9501230 (corresponds to EP 0682027).

Hungarian Patent No. HU P9602016 (corresponds to WO 95/19970).

Hungarian Patent No. HU P9402829 (corresponds to WO 93/20078).

Hungarian Patent No. HU P9602017 (corresponds to WO 95/19774).

Chen, Y.L. et al. (1997) *J. Med. Chem.* 40:17.

Varani, K. et al. (1998) "[3H]-SCH 58261 Labelling of Functional A2a Adenosine Receptors in Human Neutrophil Membranes" Br. J. Pharmacol. 123:1723-1731.

Venugopalan, B. et al. (1998) "Synthesis of 6,7-Dimethoxypyrimido[4,5-b]-indoles as Potential Antihypertensive Agents" J. Heterocyclic Chem., 25: 1663-1669.

Von Lubitz D., et al., (1999) "Stimulation of Adenosine A3 Receptors in Cerebral Ischemia", Ann. NY. Acad. Sci., 890: 93-106.

Von Lubitz, D., et al., (1999) "Chronic administration of adenosine A3 receptor agonist and cerebral ischemia: neuronal and glial effects", European Journal of Pharmacology, 367: 157-163.

Welch, W.J. "Adenosine type 1 receptor antagonists in fluid retaining disorders" Expert Opin. Investig. Drugs (2002), 11(11): 1553-1562.

West, R. A. et al. (1961) "2-Alkyl(aryl)-and 2,7-Dimethyl-4-substituted Aminopyrrolo[2,3-d]pyrimidines" J. Org. Chem.., 26: 3809-3810.

Wolff, Manfred E., Burger's Medicinal Chemistry and Drug Discovery, 5th ed., vol. 1: Principles and Practice, John Wiley & Sons, 1995, pp. 975-977.

Yan, Luo et al. (2003) Expert Opinion on Emerging Drugs, vol. 8, No. 2 pp. 537-576.

Yao Y., et al., (1997) "Adenosine A3 Receptor Agonists Protect HL-60 and U-937 Cells from Apoptosis Induced by A3 Antagonists", Biochemical And Biophysical Research Communications, 232: 317-322.

Zhao Z., et al., (2000) "A role for the A3 Adenosine receptor in determining tissue levels of cAMP and blood pressure: studies in knock-out mice", Biochimica et Biophysica Acta, 1500: 280-290.

Zhao, Z. et al., "Bioactivation of 6,7-Dimethyl-2,4-di-l-pyrrolidinyl-7H-pyrrolo[2,3-d]pyrimidine (U-89843) to Reactive Intermediates that Bind Covalently to Macromolecules and Produce Genotoxicity" Chem. Res. Toxicol., (1996) 9: 1230-1239.

International Search Report issued in PCT International Application No. PCT/US99/12135, filed Jun. 1, 1999.

International Search Report issued in PCT International Application No. PCT/US00/32702, filed Dec. 1, 2000.

International Search Report issued in PCT International Application No. PCT/US2001/045280, published Nov. 30, 2001.

International Search Report issued in PCT International Application No. PCT/US2002/38055, published Nov. 27, 2002.

International Search Report issued in PCT International Application No. PCT/US2002/40890, published Nov. 27, 2002.

International Search Report issued in PCT International Application No. PCT/US2002/41273, filed Dec. 20, 2002.

PCT International Preliminary Examination Report issued in PCT International Application No. PCT/US99/12135.

12228867, Aug. 15, 2008, Castelhano, A. et al.

12231029, Aug. 27, 2008, Castelhano, A. et al.

* cited by examiner

PYRIMIDINE $A_{2B}$ SELECTIVE ANTAGONIST COMPOUNDS, THEIR SYNTHESIS AND USE

This application is a continuation of U.S. Ser. No. 10/326,204 filed Dec. 20, 2002 now U.S. Pat. No. 6,916,804, which claims the benefit of U.S. Provisional Application No. 60/342,595, filed Dec. 20, 2001.

Throughout this application, various publications are referenced by full citations. The disclosures of these publications in their entireties are hereby incorporated by reference into this application in order to more fully describe the state of the art as known to those skilled therein as of the date of the invention described and claimed herein.

BACKGROUND OF THE INVENTION

Adenosine is an ubiquitous modulator of numerous physiological activities, particularly within the cardiovascular and nervous systems. The effects of adenosine appear to be mediated by specific cell surface receptor proteins. Adenosine modulates diverse physiological functions including induction of sedation, vasodilation, suppression of cardiac rate and contractility, inhibition of platelet aggregability, stimulation of gluconeogenesis and inhibition of lipolysis. In addition to its effects on adenylate cyclase, adenosine has been shown to open potassium channels, reduce flux through calcium channels, and inhibit or stimulate phosphoinositide turnover through receptor-mediated mechanisms (See for example, C. E. Muller and B. Stein "Adenosine Receptor Antagonists: Structures and Potential Therapeutic Applications," *Current Pharmaceutical Design*, 2:501 (1996) and C. E. Muller "$A_1$-Adenosine Receptor Antagonists," *Exp. Opin. Ther. Patents* 7(5):419 (1997)).

Adenosine receptors belong to the superfamily of purine receptors which are currently subdivided into $P_1$ (adenosine) and $P_2$ (ATP, ADP, and other nucleotides) receptors. Four receptor subtypes for the nucleoside adenosine have been cloned so far from various species including humans. Two receptor subtypes ($A_1$ and $A_{2a}$) exhibit affinity for adenosine in the nanomolar range while two other known subtypes $A_{2b}$ and $A_3$ are low-affinity receptors, with affinity for adenosine in the low-micromolar range. $A_1$ and $A_3$ adenosine receptor activation can lead to an inhibition of adenylate cyclase activity, while $A_{2a}$ and $A_{2b}$ activation causes a stimulation of adenylate cyclase.

A few $A_1$ antagonists have been developed for the treatment of cognitive disease, renal failure, and cardiac arrhythmias. It has been suggested that $A_{2a}$ antagonists may be beneficial for patients suffering from Morbus Parkinson (Parkinson's disease). Particularly in view of the potential for local delivery, adenosine receptor antagonists may be valuable for treatment of allergic inflammation and asthma. Available information (for example, Nyce & Metzger "DNA antisense Therapy for Asthma in an Animal Model" *Nature* (1997) 385: 721-5) indicates that in this pathophysiologic context, $A_1$ antagonists may block contraction of smooth muscle underlying respiratory epithelia, while $A_{2b}$ or $A_3$ receptor antagonists may block mast cell degranulation, mitigating the release of histamine and other inflammatory mediators. $A_{2b}$ receptors have been discovered throughout the gastrointestinal tract, especially in the colon and the intestinal epithelia. It has been suggested that $A_{2b}$ receptors mediate cAMP response (Strohmeier et al., *J. Bio. Chem.* (1995) 270: 2387-94).

$A_{2b}$ receptors have also been implicated in wide variety of physiological activities, thereby suggesting that treatment of associated disorders can be effected by blocking the $A_{2b}$ receptor. For example, $A_{2b}$ receptor sites play a role in the degranulation of mast cells and hence in the treatment of asthma, myocardial reperfusion injury, allergic reactions including but not limited to rhinitis, poison ivy induced responses, urticaria, scleroderm arthritis, other autoimmune diseases and inflammatory bowel diseases (Gao, Z. et al., *J. Biol. Chem.* (1999), 274(9):5972-5980, Linden, J. et al., *Life Sciences* (1998), 62(17-18):1519-1524 and U.S. Pat. No. 6,117,878, issued Sep. 12, 2000). $A_{2b}$ receptors have also been shown to inhibit the growth of cardiac fibroblasts, thereby suggesting that they may prevent cardiac remodeling associated with hypertension, myocardial infarction and myocardial reperfusion after ischemia (Dubey, R. K. et al., *Hypertension* (2001), 37:716-721), mediate the role of adenosine in lymphocyte activation (Mirabet, M. et al., *J. Cell. Sci.* (1999), 112(4):491-502), regulate vasodilation and growth (Ralevic, V. and Burnstock, G., *Pharmacol. Rev.* (1998), 50(3):413-492, Corset, V. et al., *Nature* (2000), 407 (6805):747-750, and Haynes, J. Jr. et al., *Am. J. Physiol.* (1999), 276(6):H1877-83), participate in neural reflexes in the human gut (Christofi, F. L. et al., *J. Comp. Neurol.* (2001), 439(1):46-64), and regulate retinal angiogenesis—thereby suggesting the use of $A_{2b}$ antagonists in treating diseases associated with abberant neovascularization such as diabetic retinopathy and retinopathy of prematurity (Grant, M. B. et al., *Invest. Opthalmol. Vis. Sci.* (2001), 42(9):2068-2073). They are also involved in the modulation of intestinal tone and secretion and neurotransmission and neurosecretion (Feoktistov, I. and Biaggioni, I., *Pharmacol. Rev.* (1997), 49(4):381-402).

$A_{2b}$ receptors are also coupled to Gs/Gq signaling which has been shown to be involved in cellular transformations such as cellular invasion (Faivre, K. et al., *Molecular Pharmacology* (2001), 60:363-372 and Regnauld, K. et al., *Oncogene* (2002), 21(25):4020-4031), thereby suggesting that treatment of cancer can be effected with $A_{2b}$ antagonists.

Adenosine receptors have also been shown to exist on the retinas of various mammalian species including bovine, porcine, monkey, rat, guinea pig, mouse, rabbit and human (See, Blazynski et al., "Discrete Distributions of Adenosine Receptors in Mammalian Retina," *Journal of Neurochemistry*, volume 54, pages 648-655 (1990); Woods et al., "Characterization of Adenosine $A_1$-Receptor Binding Sites in Bovine Retinal Membranes," *Experimental Eye Research*, volume 53, pages 325-331 (1991); and Braas et al., "Endogenous adenosine and adenosine receptors localized to ganglion cells of the retina," *Proceedings of the National Academy of Science*, volume 84, pages 3906-3910 (1987)). Recently, Williams reported the observation of adenosine transport sites in a cultured human retinal cell line (Williams et al., "Nucleoside Transport Sites in a Cultured Human Retinal Cell Line Established By SV-40 T Antigen Gene," *Current Eye Research*, volume 13, pages 109-118 (1994)).

Compounds which regulate the uptake of adenosine have previously been suggested as potential therapeutic agents for the treatment of retinal and optic nerve head damage. In U.S. Pat. No. 5,780,450 to Shade, Shade discusses the use of adenosine uptake inhibitors for treating eye disorders. Shade does not disclose the use of specific $A_3$ receptor inhibitors. The entire contents of U.S. Pat. No. 5,780,450 are hereby incorporated herein by reference. Compounds specific to the adenosine $A_1$, $A_{2a}$ and $A_3$ receptors and their uses thereof have been previously disclosed in PCT International Publication Nos. WO 99/62518 and WO 01/39777 A1. The entire contents of PCT International Publication Nos. WO 99/62518 and WO 01/39777 A1 are hereby incorporated herein by reference.

PCT International Publication No. WO 99/64407 generically discloses α-(1-piperazinyl)acetamido arenecarboxylic acid derivatives as antidaibetic agents. However, the compounds disclosed differ from the compounds of the present invention in that they have a carboxylic acid group rather than an amino group attached to the central ring. In addition, the cited application does not exemplify any compounds in which the central ring is pyrimidine or any compounds which have a phenyl ring or a heterocyclic ring attached to the central aryl ring.

PCT International Publication No. WO 97/47601 discloses fused heterocyclic compounds having $D_4$ and $D_2$ receptor activity. The disclosed compounds differ from the compounds of the present invention in that the central ring structure is bicyclic in WO 97/47601 rather than monocyclic as in the compounds of the present invention, and the central ring structure in WO 97/47601 does not allow for an additional aminoalkyl substituent.

Additional adenosine receptor antagonists are needed as pharmacological tools and are of considerable interest as drugs for the above-referenced disease states and/or conditions.

SUMMARY OF THE INVENTION

The subject invention provides compounds having the structure:

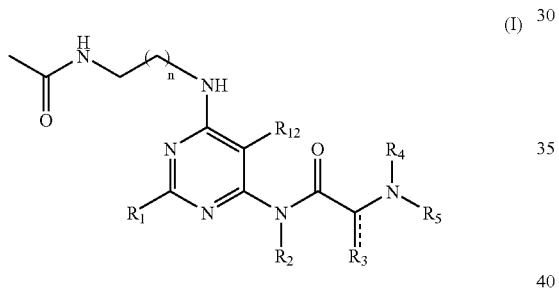

(I)

wherein $R_1$ is substituted or unsubstituted phenyl or a 5-6 membered heterocyclic or heteroaromatic ring containing from 1 to 5 heteroatoms;

$R_2$ is hydrogen, or a substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety;

$R_3$ is hydrogen, or a substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or $R_2$ and $R_3$ are joined to form a heterocyclic ring;

wherein the dashed line represents a second bond which may be present or absent, and when present $R_3$ is oxygen;

$R_4$ and $R_5$ are each independently substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or $R_4NR_5$ together form a substituted or unsubstituted monocyclic or bicyclic, heterocyclic or heteroaryl moiety containing from 1 to 6 heteroatoms;

$R_{12}$ is hydrogen, alkyl, halogen or cyano; and n is 0, 1, 2, 3 or 4, or an enantiomer, or a specific tautomer, or a pharmaceutically acceptable salt thereof.

The subject invention also provides compounds having the structure:

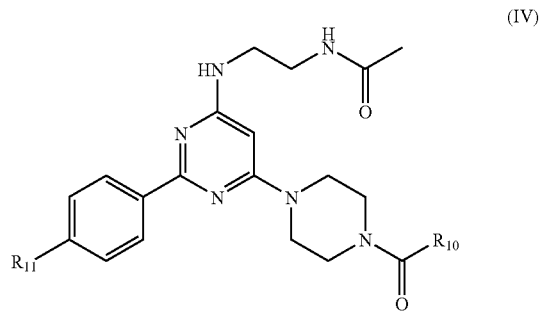

(IV)

wherein $R_{10}$ is substituted or unsubstituted alkyl, —C(O)-alkyl, —C(O)—O-alkyl, alkoxy, cycloalkyl, alkenyl, or a substituted or unsubstituted, monocyclic or bicyclic aryl, heterocyclic or heteroaryl moiety containing from 1 to 6 heteroatoms; and $R_{11}$ is a hydrogen or halogen atom.

The subject invention further provided compounds having the structure:

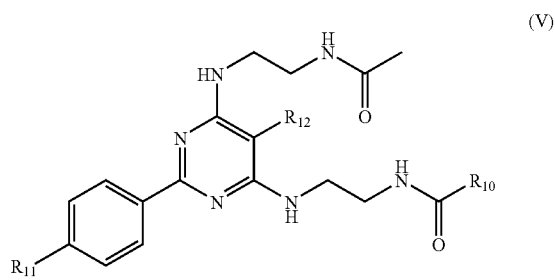

(V)

wherein, $R_{10}$ is substituted or unsubstituted alkyl, —C(O)-alkyl, —C(O)—O-alkyl, alkoxy, cycloalkyl, alkenyl, or a substituted or unsubstituted monocyclic or bicyclic aryl, heterocyclic or heteroaryl moiety containing from 1 to 6 heteroatoms;

$R_{11}$ is a hydrogen or halogen atom; and $R_{12}$ is hydrogen, alkyl, halogen or cyano.

The subject invention further provides compounds having the structure:

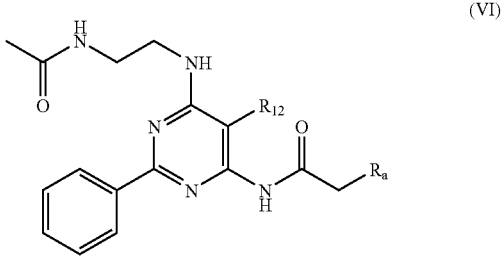

(VI)

wherein $R_a$ is Cl, Br or I; and $R_{12}$ is hydrogen, alkyl, halogen or cyano.

The subject invention further provides compounds having the structure:

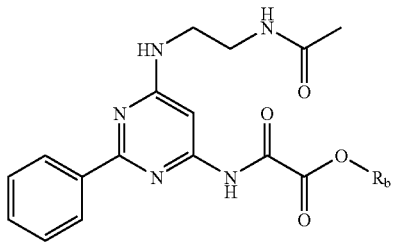

(VII)

wherein $R_b$ is hydrogen or methyl.

The subject invention further provides compounds having the structure:

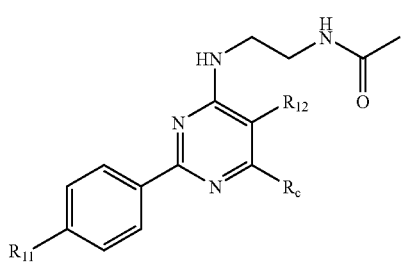

(VIII)

wherein,
$R_c$ is a halogen atom;
$R_{11}$ is a hydrogen or halogen atom; and
$R_{12}$ is hydrogen, alkyl, halogen or cyano.

The subject invention also provides the use of the compound of any one of Structures I-VIII for manufacturing a medicament useful for treating a disease associated with the $A_{2b}$ adenosine receptor in a subject, wherein the disease associated with the $A_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor or is associated with mast cell degranulation, vasodilation, hypertension, hypersensitivity or the release of allergic mediators.

DETAILED DESCRIPTION

The subject invention provides compounds having the structure:

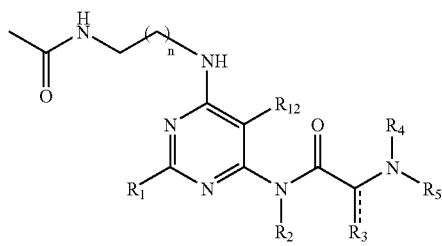

(I)

wherein
$R_1$ is substituted or unsubstituted phenyl or a 5-6 membered heterocyclic or heteroaromatic ring containing from 1 to 5 heteroatoms;
$R_2$ is hydrogen, or a substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety;
$R_3$ is hydrogen, or a substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or $R_2$ and $R_3$ are joined to form a heterocyclic ring;
wherein the dashed line represents a second bond which may be present or absent, and when present $R_3$ is oxygen;
$R_4$ and $R_5$ are each independently substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or
$R_4NR_5$ together form a substituted or unsubstituted monocyclic or bicyclic, heterocyclic or heteroaryl moiety containing from 1 to 6 heteroatoms;
$R_{12}$ is hydrogen, alkyl, halogen or cyano; and
n is 0, 1, 2, 3 or 4, or an enantiomer, or a specific tautomer, or a pharmaceutically acceptable salt thereof.

In one embodiment of Structure I, $R_3$ is hydrogen, or a substituted or unsubstituted alkyl or aryl.

In another embodiment of Structure I, any heterocyclic or heteroaryl ring, if present, is a piperazine, piperidine, (1,4) diazepan, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydroisoquinoline, indole, isoindole, triazaspiro[4.5]decane, morpholine, furan or an isothiazole ring.

In another embodiment, the subject invention provides compounds having the structure:

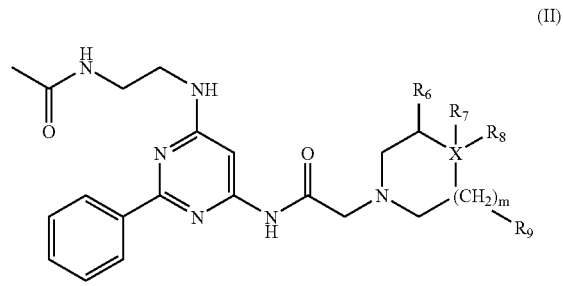

(II)

wherein,
$R_6$ and $R_9$ are each, independently, hydrogen or alkyl;
$R_7$ is hydrogen, OH, an alkoxy, an ester, an acetal, a ketal or CN;
$R_8$ is a substituted or unsubstituted aryl, aryloxy, or alkylaryl;
X is C or N;
wherein when X is N, $R_7$ or $R_8$ is absent;
wherein when X is C, $R_7XR_8$ may form a 3-8 membered carbocyclic or heterocyclic ring; and
m is 1 or 2.

In one embodiment of Structure II, $R_7$ is hydrogen, OH, or CN.

In another embodiment, the compound is selected from the group consisting of:

N-[6-(2-Acetylaminoethylamino)-2-phenylpyrimidin-4-yl]-2-[4-(3-chlorophenoxy)-piperidin-1-yl]-acetamide;
N-[6-(2-Acetylaminoethylamino)-2-phenylpyrimidin-4-yl]-2-[4-(2-chlorophenoxy)-piperidin-1-yl]-acetamide;
N-[6-(2-Acetylaminoethylamino)-2-phenylpyrimidin-4-yl]-2-[4-(4-methoxybenzyl)-piperidin-1-yl]-acetamide;
N-[6-(2-Acetylaminoethylamino)-2-phenylpyrimidin-4-yl]-2-[4-(4-fluorobenzyl)-piperidin-1-yl]-acetamide;
N-[6-(2-Acetylaminoethylamino)-2-phenylpyrimidin4-yl]-2-[4-(2-chlorobenzyl)-piperidin-1-yl]-acetamide;
N-[6-(2-Acetylaminoethylamino)-2-phenylpyrimidin-4-yl]-2-[4-(3-chlorobenzyl)-piperidin-1-yl]-acetamide;
N-[6-(2-Acetylaminoethylamino)-2-phenylpyrimidin-4-yl]-2-[4-(4-chlorobenzyl)-piperidin-1-yl]-acetamide;
N-[6-(2-Acetylaminoethylamino)-2-phenylpyrimidin-4-yl]-2-(4-benzylpiperazin-1-yl)-acetamide;
N-[6-(2-Acetylaminoethylamino)-2-phenylpyrimidin-4-yl]-2-[4-(4-methoxybenzyl)-piperazin-1-yl]-acetamide;
N-[6-(2-Acetylaminoethylamino)-2-phenylpyrimidin-4-yl]-2-[4-(2-methoxybenzyl)-piperazin-1-yl]-acetamide;
N-[6-(2-Acetylaminoethylamino)-2-phenylpyrimidin-4-yl]-2-[4-(3-methoxybenzyl)-piperazin-1-yl]-acetamide;
N-[6-(2-Acetylaminoethylamino)-2-phenylpyrimidin-4-yl]-2-[4-(4-chlorobenzyl)-piperazin-1-yl]-acetamide;
N-[6-(2-Acetylaminoethylamino)-2-phenylpyrimidin-4-yl]-2-[4-(3-chlorobenzyl)-piperazin-1-yl]-acetamide;
N-[6-(2-Acetylaminoethylamino)-2-phenylpyrimidin-4-yl]-2-[4-(2-chlorobenzyl)-piperazin-1-yl]-acetamide;
N-[6-(2-Acetylaminoethylamino)-2-phenylpyrimidin-4-yl]-2-[4-(3-fluorobenzyl)-piperazine-1-yl]-acetamide;
N-[6-(2-Acetylaminoethylamino)-2-phenylpyrimidin-4-yl]-2-[4-(2-fluorobenzyl)-piperazine-1-yl]-acetamide;
N-[6-(2-Acetylaminoethylamino)-2-phenylpyrimidin-4-yl]-2-[4-(3-trifluoromethylbenzyl)-piperazine-1-yl]-acetamide;
N-[6-(2-Acetylaminoethylamino)-2-phenylpyrimidin-4-yl]-2-(4-cyclohexylmethylpiperazin-1-yl)-acetamide;
N-[6-(2-Acetylaminoethylamino)-2-phenylpyrimidin-4-yl]-2-(4-phenethylpiperazin-1-yl)-acetamide;
N-[6-(2-Acetylaminoethylamino)-2-phenylpyrimidin-4-yl]-2-(4-phenethyl-[1,4]diazepan-1-yl)-acetamide;
N-[6-(2-Acetylaminoethylamino)-2-phenylpyrimidin-4-yl]-2-(4-benzyl-[1,4]diazepan-1-yl)-acetamide;
N-[6-(2-Acetylaminoethylamino)-2-phenylpyrimidin-4yl]-2-[4-(2-fluorobenzyl)-[1,4]diazapan-1-yl]-acetamide;
N-[6-(2-Acetylaminoethylamino)-2-phenylpyrimidin-4yl]-2-[4-(3-fluorobenzyl)-[1,4]diazapan-1-yl]-acetamide;
N-[6-(2-Acetylaminoethylamino)-2-phenylpyrimidin-4yl]-2-[4-(4-fluorobenzyl)-[1,4]diazapan-1-yl]-acetamide;
N-[6-(2-Acetylaminoethylamino)-2-phenylpyrimidin-4yl]-2-[4-(2-trifluoromethylbenzyl)-[1,4]diazapan-1-yl]-acetamide;
N-[6-(2-Acetylaminoethylamino)-2-phenylpyrimidin-4-yl]-2-[4-(3-trifluoromethylbenzyl)-[1,4]diazepan-1-yl]-acetamide;
N-[6-(2-Acetylaminoethylamino)-2-phenylpyrimidin-4yl]-2-[4-(4-trifluoromethylbenzyl)-[1,4]diazapan-1-yl]-acetamide;
N-[6-(2-Acetylaminoethylamino)-2-phenylpyrimidin-4yl]-2-(4-pyridin-3-ylmethyl-[1,4]diazapan-1-yl)-acetamide;
N-[5-(2-Acetylaminoethylamino)-biphenyl-3-yl]-2-[4-(3-chlorobenzyl)-[1,4]diazepan-1-yl]-acetamide;
N-[5-(2-Acetylaminoethylamino)-biphenyl-3-yl]-2-(4-pyridin-2-ylmethyl-[1,4]diazepan-1-yl)-acetamide;
N-[5-(2-Acetylaminoethylamino)-biphenyl-3-yl]-2-[4-(6-methylpyridin-2-ylmethyl)-[1,4]diazepan-1-yl]-acetamide;
N-(6-{[2-(acetylamino)ethyl]amino}-2-phenylpyrimidin-4-yl)-2-{4-[2-nitro-4-(trifluoromethyl)phenyl]piperazin-1-yl}acetamide;
N-(6-{[2-(acetylamino)ethyl]amino}-2-phenylpyrimidin-4-yl)-2-[4-(4-tert-butylbenzyl)piperazin-1-yl]acetamide;
N-(6-{[2-(acetylamino)ethyl]amino}-2-phenylpyrimidin-4-yl)-2-{4-[(2E)-3-phenylprop-2-enyl]piperazin-1-yl}acetamide, and
N-(6-{[2-(acetylamino)ethyl]amino }-2-phenylpyrimidin-4-yl)-2-(4-benzylpiperidin-1-yl)acetamide.

In another embodiment, the compound is N-[6-(2-Acetylaminoethylamino)-2-phenylpyrimidin-4-yl]-2-[4-(4-chlorophenyl)-4-hydroxypiperidin-1-yl]-acetamide.

In a further embodiment, the subject invention provides compounds having the structure:

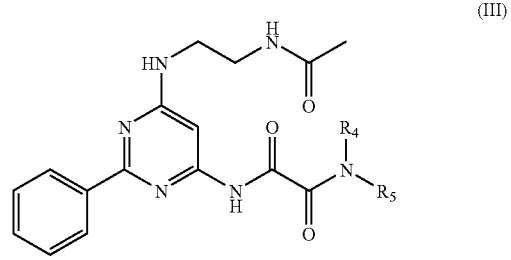

(III)

wherein $R_4$ and $R_5$ are each independently substituted or unsubstituted alkyl, —C(O)-alkyl, —C(O)—O-alkyl, alkoxy, cycloalkyl, alkenyl, monocyclic or bicyclic aryl, heteroaryl or heterocyclic moiety, or $R_4NR_5$ together form a substituted or unsubstituted, monocyclic or bicyclic, heterocyclic or heteroaryl moiety containing from 1 to 6 heteroatoms.

In one embodiment of Structure III, $R_4$ and $R_5$ are each independently substituted or unsubstituted alkyl, —C(O)-alkyl, —C(O)—O-alkyl, cycloalkyl, alkenyl, monocyclic or bicyclic aryl, heteroaryl or heterocyclic moiety, or $R_4NR_5$ together form a substituted or unsubstituted, monocyclic or bicyclic, heterocyclic or heteroaryl moiety containing from 1 to 6 heteroatoms.

In another embodiment of Structure III, $R_4$ and $R_5$ are each independently substituted or unsubstituted alkyl, —C(O)-alkyl, —C(O)—O-alkyl, cycloalkyl, alkenyl, monocyclic or bicyclic aryl, heteroaryl or heterocyclic moiety.

In another embodiment, $R_4$ and $R_5$ are each independently substituted or unsubstituted alkyl, —C(O)-alkyl, —C(O)—O-alkyl, cycloalkyl, alkenyl, monocyclic or bicyclic aryl, heteroaryl or heterocyclic moiety.

In another embodiment, any heterocyclic or heteroaryl ring, if present, is a piperazine, piperidine, (1,4)diazepan, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydroisoquinoline, indole, isoindole, triazaspiro[4.5]decane, morpholine, furan or an isothiazole ring.

The subject invention also provides compounds having the structure:

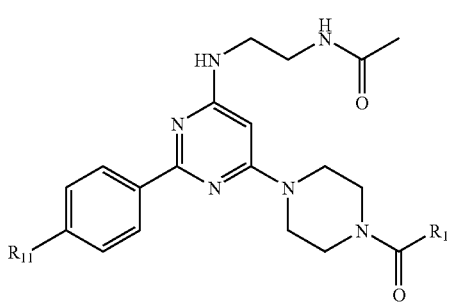

(IV)

wherein $R_{10}$ is substituted or unsubstituted alkyl, —C(O)-alkyl, —C(O)—O-alkyl, alkoxy, cycloalkyl, alkenyl, or a substituted or unsubstituted, monocyclic or bicyclic aryl, heterocyclic or heteroaryl moiety containing from 1 to 6 heteroatoms; and $R_{11}$ is a hydrogen or halogen atom.

In one embodiment of Structure IV, $R_{10}$ is a substituted or unsubstituted alkyl, —C(O)-alkyl, —C(O)—O-alkyl, cycloalkyl, alkenyl, or a substituted or unsubstituted, monocyclic or bicyclic aryl, heterocyclic or heteroaryl moiety containing from 1 to 6 heteroatoms.

In a further embodiment, $R_{11}$ is hydrogen.

In a further embodiment, $R_{11}$ is a halogen atom.

In a further embodiment of Structure IV, any heterocyclic or heteroaryl ring, if present, is a piperazine, piperidine, (1,4)diazepan, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydroisoquinoline, indole, isoindole, triazaspiro[4.5]decane, morpholine, furan or an isothiazole ring.

The subject invention further provided compounds having the structure:

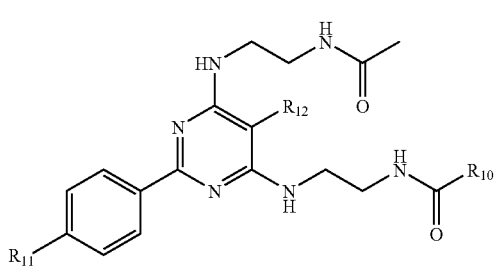

(V)

wherein, $R_{10}$ is substituted or unsubstituted alkyl, —C(O)-alkyl, —C(O)—O-alkyl, alkoxy, cycloalkyl, alkenyl, or a substituted or unsubstituted monocyclic or bicyclic aryl, heterocyclic or heteroaryl moiety containing from 1 to 6 heteroatoms;

$R_{11}$ is a hydrogen or halogen atom; and $R_{12}$ is hydrogen, alkyl, halogen or cyano.

In one embodiment of Structure V, $R_{10}$ is substituted or unsubstituted alkyl, —C(O)-alkyl, —C(O)—O-alkyl, cycloalkyl, alkenyl, or a substituted or unsubstituted monocyclic or bicyclic aryl, heterocyclic or heteroaryl moiety containing from 1 to 6 heteroatoms and $R_{12}$ is hydrogen or methyl.

In a further embodiment, $R_{11}$ is hydrogen.

In a further embodiment, $R_{12}$ is hydrogen.

In a further embodiment, $R_{12}$ is methyl.

In a further embodiment, $R_{11}$ is a halogen atom.

In a further embodiment, $R_{12}$ is hydrogen.

In a further embodiment, $R_{12}$ is methyl.

In a further embodiment, any heterocyclic or heteroaryl ring, if present, is a piperazine, piperidine, (1,4)diazepan, pyrazine, pyridine, pyrrolidine, pyrazole, pyrimidine, thiophene, imidazole, azetidine, pyrrole, benzothiazole, benzodioxolane, dithiolane, oxathiine, imidazolidine, quinoline, isoquinoline, dihydroisoquinoline, indole, isoindole, triazaspiro[4.5]decane, morpholine, furan or an isothiazole ring.

The subject invention further provides compounds having the structure:

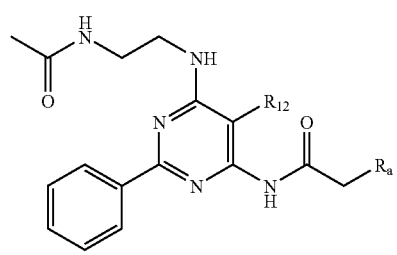

(VI)

wherein $R_a$ is Cl, Br or I; and $R_{12}$ is hydrogen, alkyl, halogen or cyano.

In one embodiment, $R_a$ is Cl.

In another embodiment, $R_a$ is Br.

The subject invention further provides compounds having the structure:

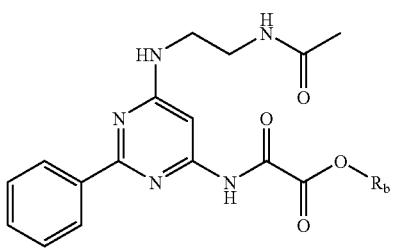

(VII)

wherein $R_b$ is hydrogen or methyl.

In one embodiment, $R_b$ is hydrogen.

In another embodiment, $R_b$ is methyl.

The subject invention further provides compounds having the structure:

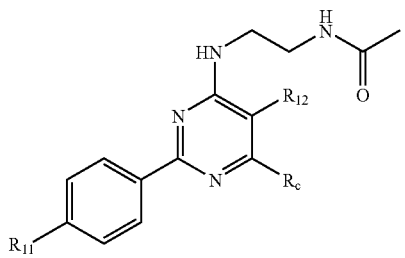

(VIII)

wherein,
$R_c$ is a halogen atom;
$R_{11}$ is a hydrogen or halogen atom; and
$R_{12}$ is hydrogen, alkyl, halogen or cyano.
In one embodiment, $R_c$ is Cl.
In a further embodiment, $R_{11}$ is hydrogen.
In another embodiment, $R_{12}$ is hydrogen.
In another embodiment, $R_{12}$ is methyl.
In another embodiment, $R_{11}$ is Cl.
In a further embodiment, $R_{12}$ is hydrogen.
In another embodiment, $R_{12}$ is methyl.
In a further embodiment of Structure I,
$R_1$ is unsubstituted phenyl or phenyl substituted with Cl;
$R_2$ is hydrogen;
$R_3$ is hydrogen or oxygen;
$R_4$, N, $R_5$ together form a piperidine ring substituted with —O($C_6H_5$), —O($C_6H_4$Cl), —O($C_6H_4$[OCH$_3$]), —($C_6H_5$), —CH$_2$($C_6H_4$[OCH$_3$]), —CH$_2$($C_6H_4$F), —CH$_2$($C_6H_4$Cl), —(OH)(CH$_2$)($C_6H_5$), —(CN)($C_6H_5$), —(CN)($C_6H_4$Cl); a 3,5-dimethyl piperazine ring substituted with —CH$_2$($C_6H_5$); a piperazine ring substituted with —CH$_2$($C_6H_5$), —($C_6H_5$), —CH$_2$($C_6H_4$[OCH$_3$]), —CH$_2$($C_6H_4$Cl), —CH$_2$($C_6H_4$F), —CH$_2$($C_6H_4$[CF$_3$]), —CH$_2$($C_5H_4$N), —CH$_2$($C_6H_{11}$), —(CH$_2$)$_2$($C_6H_5$); or a [1,4]diazepan ring substituted with —($C_6H_5$), —(CH$_2$)$_2$($C_6H_5$), —CH$_2$($C_6H_5$), —CH$_2$($C_6H_4$F), —CH$_2$($C_6H_4$[CF$_3$]), —CH$_2$($C_5H_4$N), —CH$_2$($C_6H_4$Cl), or —CH$_2$($C_5H_3$N[CH$_3$]); and
$R_{12}$ is hydrogen.

The subject invention also provides a method for treating a disease associated with the $A_{2b}$ adenosine receptor in a subject in need of such treatment comprising administering to the subject a therapeutically effective amount of the compound of Structure I so as to thereby treat the disease associated with the $A_{2b}$ adenosine receptor in the subject, wherein the disease associated with the $A_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor or is associated with mast cell degranulation, vasodilation, hypertension, hypersensitivity or the release of allergic mediators.

In one embodiment, the disease associated with the $A_{2b}$ adenosine receptor is diabetes.

In another embodiment, the disease associated with the $A_{2b}$ adenosine receptor is asthma.

In another embodiment, the disease associated with the $A_{2b}$ adenosine receptor is associated with mast cell degranulation.

In another embodiment, the disease associated with the $A_{2b}$ adenosine receptor is a proliferating tumor.

The subject invention also provides a pharmaceutical composition comprising the compound of any of Structures I-V and a pharmaceutically acceptable carrier.

In one embodiment, the pharmaceutical composition is formulated for oral, topical, parenteral or nasal administration.

The subject invention also provides a process for the manufacture of a pharmaceutical composition comprising admixing the compound of any of Structures I-V with a pharmaceutically acceptable carrier.

The subject invention also provides a package comprising the above pharmaceutical composition and instructions for use of the pharmaceutical composition in the treatment of a disease associated with the $A_{2b}$ adenosine receptor.

The subject invention also provides the pharmaceutically acceptable salt of Structure I, wherein the salt is a hydrochloride salt.

The subject invention also provides a process of manufacturing the compound of Structure VI, comprising the steps of:

(a) reacting

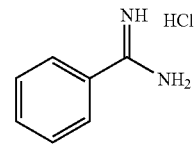

with a 2-substituted diethyl malonate in the presence of a base in a solvent under suitable conditions to provide:

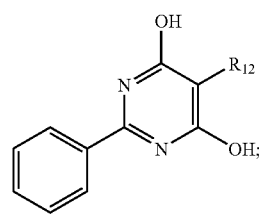

(b) reacting the product of step (a) with a chlorinating agent to provide:

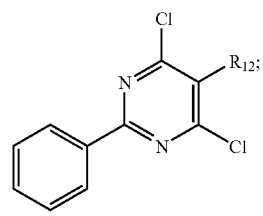

(c) reacting the product of step (b) with an aminating agent in the presence of solvent to provide:

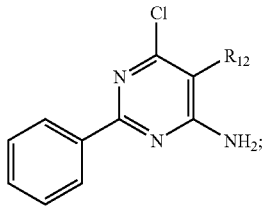

(d) reacting the product of step (c) with N-acetylethylenediamine to provide:

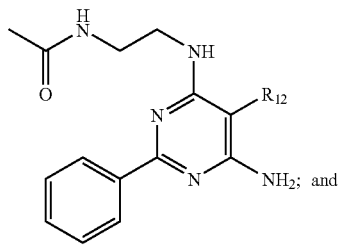

(e) reacting the product with

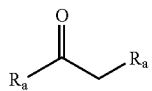

in the presence of base in solvent to provide:

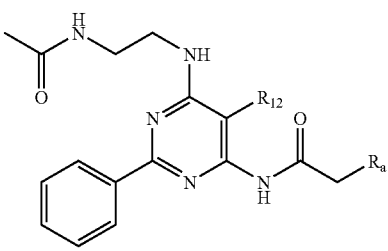

wherein $R_a$ is Cl or Br; and
$R_{12}$ is hydrogen, alkyl, halogen or cyano.

In one embodiment of the above process, the solvent in step (a) is DMF and the base is DBU.

In another embodiment, the chlorinating agent in step (b) is $POCl_3$.

In a further embodiment, the aminating agent of step (c) is ammonia and the solvent is DMSO.

In a further embodiment, the base is 2,6-lutidine and the solvent is $CH_2Cl_2$/DMF.

In a further embodiment, the subject invention provides a compound produced by the above process.

The subject invention also provides a process for manufacturing the compound of Structure II, comprising reacting a compound having the structure:

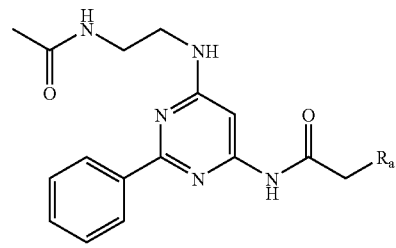

wherein $R_a$ is Cl or Br, with

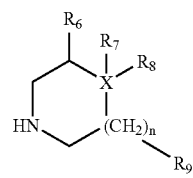

under suitable conditions to provide:

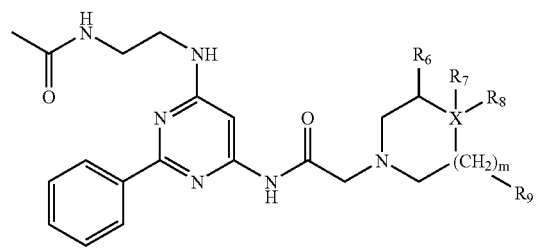

wherein,
$R_6$ and $R_9$ are each independently hydrogen or alkyl;
$R_7$ is hydrogen, OH, an alkoxy, an ester, an acetal, a ketal or CN;
$R_8$ is a substituted or unsubstituted aryl, aryloxy, or alkylaryl;
X is C or N;
wherein when X is N, $R_7$ or $R_8$ is absent;
wherein when X is C, $R_7XR_8$ may form a 3-8 membered carbocyclic or heterocyclic ring; and
m is 1 or 2.

The subject invention also provides a compound produced by the above process.

The subject invention also provides a compound having the structure:

(IX)

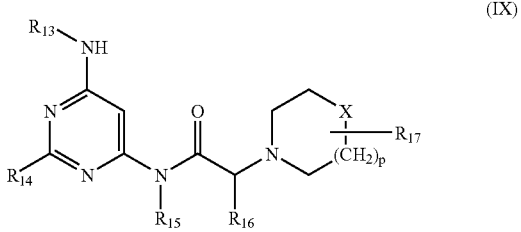

wherein, $R_{13}$ is a substituted or unsubstituted ($C_1$-$C_4$)alkyl, branched alkyl or ($C_3$-$C_7$)cycloalkyl, wherein the substituent is —OH, OR, —NH$_2$, —NR$_{18}$R$_{19}$, —R$_{20}$NOCR$_{21}$, R$_{22}$R$_{23}$NCO—, carboxyl, carbamoyl (—R$_{20}$NOCNR$_{22}$R$_{23}$), carbamate (—R$_{20}$NOCOR), or a heterocyclic ring; or a substituted or unsubstituted aryl or heterocyclic ring wherein any substituent, if present, is OH, OR, halogen, NH$_2$, or NHR; -wherein R is alkyl, cycloalkyl, aryl, heteroaryl, susbtituted alkyl, aryl, arylalkyl, or heterocyclic;

$R_{14}$ is substituted or unsubstituted phenyl, wherein the substituent, if present, is halogen, OH, NH$_2$, OR, NHR or a 5-6 membered heterocyclic ring;

$R_{15}$ is H, or alkyl;

$R_{16}$ is H, substituted or unsubstituted alkyl or aryl, or $R_{15}$ and $R_{16}$ are joined to form a heterocyclic ring;

X is CHR$_{17}$, CR$_{24}$R$_{25}$, O or NR;

$R_{17}$ is H, substituted or unsubstituted alkyl, aryl, arylalkyl, heterocyclic, heterocyclic alkyl, OH, OR, NH$_2$, NR$_{18}$R$_{19}$, R$_{20}$NOCR$_{21}$, R$_{22}$R$_{23}$NCO—, carboxyl, carbamoyl (—R$_{20}$NOCNR$_{22}$R$_{23}$), carbamate (—R$_{20}$NOCOR), or ($C_3$-$C_7$)cycloalkyl;

$R_{18}$ and $R_{19}$ are each independently hydrogen, substituted or unsubstituted alkyl or aryl or $R_{18}$NR$_{19}$ together form a heterocyclic ring of between 4 and 8 members;

$R_{20}$ and $R_{21}$ are each independently a substituted or unsubstituted alkyl, aryl, or alkylaryl moiety;

$R_{22}$ and $R_{23}$ are each independently hydrogen, substituted or unsubstituted alkyl, aryl or alkylaryl, or $R_{22}$NR$_{23}$ together form a heterocyclic ring of between 4 and 8 members;

$R_{24}$ and $R_{25}$ are each independently hydrogen, substituted or unsubstituted alkyl, cycloalkyl, aryl, heterocyclic or $R_{24}$ and $R_{25}$ together form a 3-7 membered ring system or a dioxalane or dioxane ring system; and p is 0, 1 or 2.

The subject invention also provides the use of the compound of any one of Structures I-VIII for manufacturing a medicament useful for treating a disease associated with the $A_{2b}$ adenosine receptor in a subject, wherein the disease associated with the $A_{2b}$ adenosine receptor is asthma, urticaria, scleroderm arthritis, myocardial infarction, myocardial reperfusion after ischemia, diabetic retinopathy, retinopathy of prematurity, diabetes, diarrhea, inflammatory bowel disease, proliferating tumor or is associated with mast cell degranulation, vasodilation, hypertension, hypersensitivity or the release of allergic mediators.

In one embodiment of the above use, the disease associated with the $A_{2b}$ adenosine receptor is diabetes.

In another embodiment, the disease associated with the $A_{2b}$ adenosine receptor is asthma.

In another embodiment, the disease associated with the $A_{2b}$ adenosine receptor is associated with mast cell degranulation.

In another embodiment, the disease associated with the $A_{2b}$ adenosine receptor is a proliferating tumor.

The compound of any one of Structures I-V or IX, wherein any alkyl is a straight chain ($C_1$-$C_{30}$)alkyl or a branched chain ($C_3$-$C_{30}$)alkyl, any cycloalkyl is ($C_3$-$C_{10}$)cycloalkyl, and any substituent, if present, is selected from halogen, hydroxyl, straight chain ($C_1$-$C_{30}$)alkyl, branched chain ($C_3$-$C_{30}$)alkyl, ($C_3$-$C_{10}$)cycloalkyl, straight chain($C_1$-$C_{30}$)alkylcarbonyloxy, branched chain ($C_3$-$C_{30}$)alkylcarbonyloxy, arylcarbonyloxy, straight chain($C_1$-$C_{30}$)alkoxycarbonyloxy, branched chain ($C_3$-$C_{30}$)alkoxycarbonyloxy, aryloxycarbonyloxy, carboxylate, straight chain($C_1$-$C_{30}$)alkylcarbonyl, branched chain ($C_3$-$C_{30}$)alkylcarbonyl, straight chain ($C_1$-$C_{30}$)alkoxycarbonyl, branched chain ($C_3$-$C_{30}$)alkoxycarbonyl, aminocarbonyl, straight chain ($C_1$-$C_{30}$)alkylthiocarbonyl, branched chain ($C_3$-$C_{30}$)alkylthiocarbonyl, straight chain ($C_1$-$C_{30}$)alkoxyl, branched chain ($C_1$-$C_{30}$)alkoxyl, phosphate, phosphonato, cyano, amino, straight chain ($C_1$-$C_{30}$)alkylamino, branched chain ($C_3$-$C_{30}$)alkylamino, straight chain ($C_1$-$C_{30}$)dialkylamino, branched chain ($C_3$-$C_{30}$)dialkylamino, arylamino, diarylamino, straight chain ($C_1$-$C_{30}$)alkylarylamino, branched chain ($C_3$-$C_{30}$)alkylarylamino, acylamino, straight chain ($C_1$-$C_{30}$)alkylcarbonylamino, branched chain ($C_3$-$C_{30}$)alkylcarbonylamino, arylcarbonylamino, carbamoyl, ureido, amidino, imino, sulfhydryl, straight chain ($C_1$-$C_{30}$)alkylthio, branched chain ($C_3$-$C_{30}$)alkylthio, arylthio, thiocarboxylate, sulfates, sulfonato, sulfamoyl, sulfonamido, nitro, trifluoromethyl, azido, 4-10 membered heterocyclyl, straight chain ($C_1$-$C_{30}$)alkylaryl, branched chain ($C_3$-$C_{30}$)alkylaryl, or an aromatic or 5-6 membered heteroaromatic moiety, which substituent may be further substituted by any of the above.

This invention also discloses compounds having the structure:

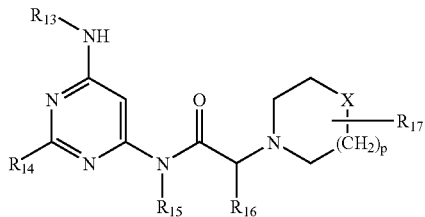

wherein $R_{13}$=Alkyl (1-4 carbons);

Branched alkyl substituted with —OH, OR, —NH$_2$, —NR$_{18}$R$_{19}$, —R$_{20}$NOCR$_{21}$, R$_{22}$R$_{23}$NCO—, carboxyl, carbamoyl (—R$_{20}$NOCNR$_{22}$R$_{23}$), carbamate (—R$_{20}$NOCOR), heterocyclic; Cycloalkyl (3-7 membered);

Aryl optionally substituted with OH, OR, halogen, NH$_2$, NHR; Heterocyclic (e.g. pyridynyl, imidazole, pyrazole, pyrrole); wherein R is alkyl, cycloalkyl, aryl, heteroaryl, susbtituted alkyl, aryl, arylalkyl, or heterocyclic;

$R_{14}$ is phenyl, optionally substituted with halogen, OH, NH$_2$, OR, NHR or a 5-6 membered heterocyclic ring;

$R_{15}$ is H, alkyl, $R_{15}$ joined to $R_{16}$;

$R_{16}$ is H, alkyl, substituted alkyl, aryl;

X is CHR$_{17}$, CR$_{24}$R$_{25}$, O or NR;

$R_{17}$ is H, alkyl, branched alkyl, substituted alkyl, aryl, substituted aryl, arylalkyl, heterocyclic, heterocyclic alkyl, OH, OR, NH$_2$, NR$_{18}$R$_{19}$, —R$_{20}$NOCR$_{21}$, R$_{22}$R$_{23}$NCO—, carboxyl, carbamoyl (—R$_{20}$NOCNR$_{22}$R$_{23}$), carbamate (—R$_{20}$NOCOR), cycloalkyl (3-7 membered);

$R_{18}$ and $R_{19}$ are each independently hydrogen, substituted or unsubstituted alkyl or aryl or $R_{18}$NR$_{19}$ together form a heterocyclic ring of between 4 and 8 members;

$R_{20}$ and $R_{21}$ are each independently a substituted or unsubstituted alkyl, aryl, or alkylaryl moiety;

$R_{22}$ and $R_{23}$ are each independently hydrogen, substituted or unsubstituted alkyl, aryl or alkylaryl, or $R_{22}$NR$_{23}$ together form a heterocyclic ring of between 4 and 8 members;

$R_{24}$ and $R_{25}$ are each independently hydrogen, substituted or unsubstituted alkyl, cycloalkyl, aryl, heterocyclic or $R_{24}$ and $R_{25}$ together form a 3-7 membered ring system or a dioxalane or dioxane ring system; and p is 0, 1 or 2.

The subject invention also includes the specific compounds that are included by Structure III, such as compounds 26.1-26.79 discussed in the examples.

The subject invention also includes the specific compounds that are included by Structure IV, such as compounds 29.1-29.146 and 34.1-34.155 discussed in the examples.

The subject invention also includes the specific compounds that are included by Structure V, such as compounds 36.1-36.141, 41.1-41.144 and 46.1-46.82 discussed in the examples.

The subject invention also includes the specific compounds that are included by Structure VI, such as compound 6 discussed in the examples.

The subject invention also includes the specific compounds that are included by Structure VII, such as compounds 24 and 25 discussed in the examples.

The subject invention also includes the specific compounds that are included by Structure VIII, such as compounds 39 and 44 discussed in the examples.

The number of carbons when represented as "$(C_1-C_{30})$" or "$(C_3-C_{30})$" is intended to mean any incremental whole number between 1 and 3 and 30, e.g. 1, 2, 3, 4, 5 . . . or 30.

The present invention is based on compounds which selectively bind to adenosine $A_{2b}$ receptor, thereby treating a disease associated with $A_{2b}$ adenosine receptor in a subject by administering to the subject a therapeutically effective amount of such compounds. The diseases to be treated are associated with, for example, asthma, mast cell degranulation, myocardial reperfusion injury, allergic reactions including but not limited to rhinitis, poison ivy induced responses, urticaria, scleroderm arthritis, autoimmune diseases, inflammatory bowel diseases, hypertension, myocardial infarction, myocardial reperfusion after ischemia, lymphocyte activation, vasodilation, growth, neural reflexes in the human gut, retinal angiogenesis, abberant neovascularization such as diabetic retinopathy and retinopathy of prematurity, modulation of intestinal tone and secretion and neurotransmission and neurosecretion.

$A_{2b}$ receptors have also been implicated in hypersensitivity, hay fever, serum sickness, allergic vasculitis, atopic dermatitis, dermatitis, eczema, idiopathic pulmonary fibrosis, eosinophilic chlorecystitis, chronic airway inflammation, hypereosinophilic syndromes, eosinophilic gastroenteritis, edema, eosinophilic myocardial disease, episodic angioedema with eosinophilia, ulcerative colitis, allergic granulomatosis, carcinomatosis, eosinophilic granuloma, familial histiocytosis, tumor, cardiac hypoxia, cerebral ischemia, diuresis, renal failure, neurological disorder, mental disorder, cognitive disorder, myocardial ischemia, bronchoconstriction, Crohn's disease, Grave's disease, diabetes, multiple sclerosis, anaemia, psoriasis, fertility disorders, lupus erthyematosus, brain arteriole diameter, the release of allergic mediators, scleroderma, stroke, global ischemia, central nervous system disorder, cardiovascular disorder, renal disorder, inflammatory disorder, gastrointestinal disorder, eye disorder, allergic disorder, respiratory disorder, or immunological disorder.

The invention further pertains to methods for treating $A_{2b}$ associated disorders in a mammal by administering to the mammal a therapeutically effective amount of the compounds of the present invention, such that treatment of the disorder in the mammal occurs.

The invention further pertains to methods for treating $A_{2b}$ associated disorders in a mammal by administering to the mammal a therapeutically effective amount of the compounds of the present invention, such that treatment of the disorder in the mammal occurs.

The present invention also pertains to packaged pharmaceutical compositions for treating $A_{2b}$ associated disorders. The packaged pharmaceutical composition includes a container holding a therapeutically effective amount of at least one of the compounds of the present invention and instructions for using the said compounds for treating an $A_{2b}$ associated disease.

The compounds of this invention may advantageously be selective $A_{2b}$ receptor antagonists.

In a particularly preferred embodiment, the compound is a water soluble prodrug that is capable of being metabolized in vivo to an active drug by, for example, esterase catalyzed hydrolysis.

In yet another embodiment, the invention features a method for inhibiting the activity of an adenosine receptor (e.g., $A_{2b}$) in a cell, by contacting the cell with a compound of the present invention (e.g., preferably, an adenosine receptor antagonist).

The invention also features a pharmaceutical composition comprising a compound of the present invention. Preferably, the pharmaceutical preparation is an ophthalmic formulation (e.g., an periocular, retrobulbar or intraocular injection formulation, a systemic formulation, or a surgical irrigating solution).

The present invention pertains to methods for treating an $A_{2b}$ associated disorder in a mammal. The methods include administration of a therapeutically effective amount of the compounds of the invention, described infra, to the mammal, such that treatment of the $A_{2b}$ associated disorder in the mammal occurs.

The language "treatment of an $A_{2b}$ associated disorder" refers to treatment which includes a significant diminishment of at least one symptom or effect of the disorder achieved with a compound of the invention. Typically such disorders are associated with an increase of adenosine within a host such that the host often experiences physiological symptoms which include, but are not limited to, urticaria, scleroderm arthritis, allergic rhinitis, asthma, inflammatory bowel diseases, hypertension, diabetic retinopathy and retinopathy of prematurity. (See for example, C. E. Muller and B. Stein "Adenosine Receptor Antagonists: Structures and Potential Therapeutic Applications," *Current Pharmaceutical Design*, 2:501 (1996) and C. E. Muller "$A_1$-Adenosine Receptor Antagonists," *Exp. Opin. Ther. Patents* 7(5):419 (1997) and I. Feoktistove, R. Polosa, S. T. Holgate and I. Biaggioni "Adenosine $A_{2B}$ receptors: a novel therapeutic target in asthma?" TiPS 19; 148 (1998)). The effects often associated with such symptoms include, but are not limited to, fever, shortness of breath, nausea, diarrhea, weakness, headache, and even death. In one embodiment, the disorder includes those disease states which are mediated by stimulation of adenosine receptors, e.g., $A_1$, $A_{2a}$, $A_{2b}$, $A_3$, etc., such that calcium concentrations in cells and/or activation of PLC (phospholipase C) is modulated. In a preferred embodiment, the disorder is associated with adenosine receptor(s), e.g., the compound of the invention acts as an antagonist. Examples of suitable responsive states which can be treated by the compounds of the invention, e.g., adenosine receptor subtypes which mediate biological effects, include central nervous system (CNS) effects, cardiovascular effects, renal effects, respiratory effects, immunological effects, gastro-intestinal effects and metabolic effects. The relative amount of adenosine in a subject can be associated with the effects listed below; that is increased levels of adenosine can trigger an effect, e.g., an undesired physiological response, e.g., an asthmatic attack.

Immunological effects include mast cell degranulation ($A_{2b}$). Therapeutic applications of antagonists include allergic and non allergic inflammation, e.g., release of histamine and other inflammatory mediators.

Gastrointestinal effects include colonic, intestinal and diarrheal disease, e.g., diarrheal disease associated with intestinal inflammation ($A_{2b}$).

The term "disease state" is intended to include those conditions caused by or associated with unwanted levels of adenosine, adenylyl cyclase activity, increased physiological activity associated with aberrant stimulation of adenosine receptors and/or an increase in cAMP. In one embodiment, the disease state is, for example, asthma, chronic obstructive pulmonary disease, allergic rhinitis, bronchitis, renal disorders, gastrointestinal disorders, or eye disorders. Additional examples include chronic bronchitis and cystic fibrosis. Suitable examples of inflammatory diseases include non-lymphocytic leukemia, myocardial ischaemia, angina, infarction, cerebrovascular ischaemia, intermittent claudication, critical limb ischemia, venous hypertension, varicose veins, venous ulceration and arteriosclerosis. Impaired reperfusion states include, for example, any post-surgical trauma, such as reconstructive surgery, thrombolysis or angioplasty.

This invention also provides a combination therapy for glaucoma, comprising one of the compounds of the invention, and a prostagladin agonist, beta-2 agonist, or a muscarinic antagonist.

The language "treating an $A_{2b}$ associated disorder" or "treating an $A_{2b}$ associated disease" is intended to include changes in a disease state or condition, as described above, such that physiological symptoms in a mammal can be significantly diminished or minimized. The language also includes control, prevention or inhibition of physiological symptoms or effects associated with an aberrant amount of adenosine. In one preferred embodiment, the control of the disease state or condition is such that the disease state or condition is eradicated. In another preferred embodiment, the control is selective such that aberrant levels of adenosine receptor activity are controlled while other physiologic systems and parameters are unaffected.

The language "therapeutically effective amount" of the compounds of the invention, described infra, refers to that amount of a therapeutic compound necessary or sufficient to perform its intended function within a mammal, e.g., treat an $A_{2b}$ associated disorder, or a disease state in a mammal. An effective amount of the therapeutic compound can vary according to factors such as the amount of the causative agent already present in the mammal, the age, sex, and weight of the mammal, and the ability of the therapeutic compounds of the present invention to affect the $A_{2b}$ associated disorder in the mammal. One of ordinary skill in the art would be able to study the aforementioned factors and make a determination regarding the effective amount of the therapeutic compound without undue experimentation.

An in vitro or in vivo assay also can be used to determine an "effective amount" of the therapeutic compounds described infra. The ordinarily skilled artisan would select an appropriate amount of the therapeutic compound for use in the aforementioned assay or as a therapeutic treatment.

A therapeutically effective amount preferably diminishes at least one symptom or effect associated with the $A_{2b}$ associated disorder being treated by at least about 20%, (more preferably by at least about 40%, even more preferably by at least about 60%, and still more preferably by at least about 80%) relative to untreated subjects. Assays can be designed by one skilled in the art to measure the diminishment of such symptoms and/or effects. Any art recognized assay capable of measuring such parameters are intended to be included as part of this invention. For example, if asthma is the state being treated, then the volume of air expended from the lungs of a subject can be measured before and after treatment for measurement of increase in the volume using an art recognized technique. Likewise, if inflammation is the state being treated, then the area which is inflamed can be measured before and after treatment for measurement of diminishment in the area inflamed using an art recognized technique.

The term "cell" includes both prokaryotic and eukaryotic cells.

The term "animal" includes any organism with adenosine receptors. Examples of animals include yeast, mammals, reptiles, and birds. It also includes transgenic animals.

The term "mammal" is art recognized and is intended to include an animal, more preferably a warm-blooded animal, most preferably cattle, sheep, pigs, horses, dogs, cats, rats, mice, and humans. Mammals susceptible to $A_{2b}$ associated disorders responsive state, inflammation, emphysema, asthma, central nervous system conditions, or acute respiratory distress syndrome, for example, are included as part of this invention.

In another aspect, the present invention pertains to methods for modulating an adenosine receptor(s) in a mammal by administering to the mammal a therapeutically effective amount of the compounds of the invention, such that modulation of the adenosine receptor in the mammal occurs. Suitable adenosine receptors include the families of $A_1$, $A_2$, or $A_3$. In a preferred embodiment, the compound is an adenosine receptor antagonist.

The language "modulating an adenosine receptor" is intended to include those instances where a compound interacts with an adenosine receptor(s), causing increased, decreased or abnormal physiological activity associated with an adenosine receptor or subsequent cascade effects resulting from the modulation of the adenosine receptor. Physiological activities associated with adenosine receptors include induction of sedation, vasodilation, suppression of cardiac rate and contractility, inhibition of platelet aggregbility, stimulation of gluconeogenesis, inhibition of lipolysis, opening of potassium channels, reducing flux of calcium channels, etc.

The terms "modulate", "modulating" and "modulation" are intended to include preventing, eradicating, or inhibiting the resulting increase of undesired physiological activity associated with abnormal stimulation of an adenosine receptor, e.g., in the context of the therapeutic methods of the invention. In another embodiment, the term modulate includes antagonistic effects, e.g., diminishment of the activity or production of mediators of allergy and allergic inflammation which results from the overstimulation of adenosine receptor(s). For example, the therapeutic deazapurines of the invention can interact with an adenosine receptor to inhibit, for example, adenylate cyclase activity.

The language "condition characterized by aberrant adenosine receptor activity" is intended to include those diseases, disorders or conditions which are associated with aberrant stimulation of an adenosine receptor, in that the stimulation of the receptor causes a biochemical and or physiological chain of events that is directly or indirectly associated with the disease, disorder or condition. This stimulation of an adenosine receptor does not have to be the sole causative agent of the disease, disorder or condition but merely be responsible for causing some of the symptoms typically associated with the disease, disorder, or condition being treated. The aberrant stimulation of the receptor can be the sole factor or at least one other agent can be involved in the state being treated. Examples of conditions include those disease states listed supra, and those symptoms manifested by the presence of increased adenosine receptor activity.

The language "treating or treatment of a condition characterized by aberrant adenosine receptor activity" is intended to include the alleviation of or diminishment of at least one symptom typically associated with the condition. The treatment also includes alleviation or diminishment of more than one symptom. Preferably, the treatment cures, e.g., substantially eliminates, the symptoms associated with the condition.

The invention further pertains to a method for inhibiting the activity of an adenosine receptor (e.g., an $A_{2b}$ adenosine receptor) in a cell by contacting the cell with a compound of the invention. Preferably, the compound is an antagonist of the receptor.

In another embodiment, the invention relates to a pharmaceutical composition containing a compound of the invention and a pharmaceutically acceptable carrier.

The invention also pertains to a method for treating an $A_{2b}$ associated disease in an animal, by administering to a mammal a therapeutically effective amount of a compound of the invention, such that treatment of the $A_{2b}$ associated disorder occurs. Advantageously, the disease state may be a disorder mediated by adenosine. Examples of preferred disease states include: central nervous system disorders, cardiovascular disorders, renal disorders, inflammatory disorders, allergic disorders, gastrointestinal disorders, eye disorders, and respiratory disorders.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 4-10 carbon atoms in their ring structure, and more preferably have 5, 6 or 7 carbons in the ring structure.

The term "substituted alkyls" refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively. For example, the invention contemplates cyano and propargyl groups.

Unless the number of carbons is otherwise specified, "lower alkyl" as used herein means an alkyl group, as defined above, but having from one to ten carbons, more preferably from one to six carbon atoms in its backbone structure, even more preferably one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more atoms are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "heterocycle" or "heterocyclic system" as used herein is intended to mean a stable 5, 6 or 7-membered monocyclic or 7, 8, 9, 10 or 11-membered bicyclic heterocyclic ring which is saturated or partially unsaturated.

The terms "carbocyclic" or "heterocyclic" further include spiro compounds, which denote a bicyclic compound in which the two rings have one atom in common and the atom may be carbon or a heteroatom.

The term "amino acids" includes naturally and unnaturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. Amino acid analogs include amino acids with lengthened or shortened side chains or variant side chains with appropriate functional groups. Amino acids also include D and L stereoisomers of an amino acid when the structure of the amino acid admits of stereoisomeric forms. The term "dipeptide" includes two or more amino acids linked together. Preferably, dipeptides are two amino acids linked via a peptide linkage. Particularly preferred dipeptides include, for example, alanine-alanine and glycine-alanine.

It will be noted that the structure of some of the compounds of this invention includes asymmetric carbon atoms and thus occur as racemates and racemic mixtures, single enantiomers, diastereomeric mixtures and individual diastereomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Each specific isomer can be obtained in substantially pure form by classical separation techniques and/or by stereochemically controlled synthesis.

The invention further pertains to pharmaceutical compositions for treating $A_{2b}$ associated disorders in a mammal. The pharmaceutical composition includes a therapeutically effective amount of a compound of the invention and a pharmaceutically acceptable carrier. It is to be understood, that all of the compounds described below are included for therapeutic treatment. It is to be further understood that the compounds of the invention can be used alone or in combination with other compounds of the invention or in combination with additional therapeutic compounds, such as antibiotics, antiinflammatories, or anticancer agents, for example.

The term "antibiotic" is art recognized and is intended to include those substances produced by growing microorganisms and synthetic derivatives thereof, which eliminate or inhibit growth of pathogens and are selectively toxic to the pathogen while producing minimal or no deleterious effects upon the infected host subject. Suitable examples of antibiotics include, but are not limited to, the principle classes of aminoglycosides, cephalosporins, chloramphenicols, fuscidic acids, macrolides, penicillins, polymixins, tetracyclines and streptomycins.

The term "antiinflammatory" is art recognized and is intended to include those agents which act on body mechanisms, without directly antagonizing the causative agent of the inflammation such as glucocorticoids, aspirin, ibuprofen, NSAIDS, etc.

The term "anticancer agent" is art recognized and is intended to include those agents which diminish, eradicate, or prevent growth of cancer cells without, preferably, adversely affecting other physiological functions. Representative examples include cisplatin and cyclophosphamide.

The term "cancer" as used herein is intended to mean a cellular malignancy whose unique trait—loss of normal controls—results in unregulated growth, lack of differentiation, and ability to invade local tissues and metastasize. The presence of a cellular malignancy is often indicated by the presence of a tumor. Local tissue invasion can result from local tumor pressure on normal tissues that can lead to inflammation, or the tumor may elaborate substances that lead to enzymatic destruction.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra.)

The invention further contemplates the use of prodrugs which are converted in vivo to the therapeutic compounds of the invention (see, e.g., R. B. Silverman, 1992, "The Organic Chemistry of Drug Design and Drug Action", Academic Press, Chapter 8). Such prodrugs can be used to alter the biodistribution (e.g., to allow compounds which would not typically enter the reactive site of the protease) or the pharmacokinetics of the therapeutic compound. For example, a carboxylic acid group, can be esterified, e.g., with a methyl group or an ethyl group to yield an ester. When the ester is administered to a subject, the ester is cleaved, enzymatically or non-enzymatically, reductively or hydrolytically, to reveal the anionic group. An anionic group can be esterified with moieties (e.g., acyloxymethyl esters) which are cleaved to reveal an intermediate compound which subsequently decomposes to yield the active compound. In another embodiment, the prodrug is a reduced form of a sulfate or sulfonate, e.g., a thiol, which is oxidized in vivo to the therapeutic compound. Furthermore, an anionic moiety can be esterified to a group which is actively transported in vivo, or which is selectively taken up by target organs. The ester can be selected to allow specific targeting of the therapeutic moieties to particular reactive sites, as described below for carrier moieties.

The compounds of the invention may comprise water-soluble prodrugs which are described in WO 99/33815, International Application No. PCT/US98/04595, filed Mar. 9, 1998 and published Jul. 8, 1999. The entire content of WO 99/33815 is expressly incorporated herein by reference. The water-soluble prodrugs are metabolized in vivo to an active drug, e.g., by esterase catalyzed hydrolysis.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, acetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Preferably, the pharmaceutical preparation is an ophthalmic formulation (e.g., an periocular, retrobulbar or intraocular injection formulation, a systemic formulation, or a surgical irrigating solution).

The ophthalmic formulations of the present invention may include one or more of the compounds of the invention and a pharmaceutically acceptable vehicle. Various types of vehicles may be used. The vehicles will generally be aqueous in nature. Aqueous solutions are generally preferred, based on case of formulation, as well as a patient's ability to easily administer such compositions by means of instilling one to two drops of the solutions in the affected eyes. However, the deazapurines of the present invention may also be readily incorporated into other types of compositions, such as suspensions, viscous or semi-viscous gels or other types of solid or semi-solid compositions. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

When the compounds of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth. W. B. Sanders Co., Philadelphia, Pa., U.S.A., pages 85-87 (1990).

As indicated above, use of the compounds of the present invention to prevent or reduce damage to retinal and optic nerve head tissues at the cellular level is a particularly important aspect of one embodiment of the invention. Ophthalmic conditions which may be treated include, but are not limited to, retinopathies and damage associated with injuries to ophthalmic tissues, such as ischemia reperfusion injuries. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 200 mg per kilogram of body weight per day, more preferably from about 0.01 to about 150 mg per kg per day, and still more preferably from about 0.2 to about 140 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The present invention also pertains to packaged pharmaceutical compositions for treating $A_{2b}$ associated disorders in a mammal. The packaged pharmaceutical compositions include a container holding a therapeutically effective amount of at least one compound of the invention, as described below, and instructions for using the compound for treating the $A_{2b}$ associated disorder in the mammal.

In another aspect, the invention features a method for treating damage to the eye of an animal (e.g., a human) by administering to the animal an effective amount of the compounds of the present invention. Preferably, the compound is an antagonist of $A_{2b}$ adenosine receptors in cells of the animal. The damage is to the retina or the optic nerve head and may be acute or chronic. The damage may be the result of, for example, glaucoma, edema, ischemia, hypoxia or trauma.

The invention further pertains to a method for inhibiting the activity of an adenosine receptor (e.g., an $A_{2b}$ adenosine receptor) in a cell by contacting the cell with a compound of the invention. Preferably, the compound is an antagonist of the receptor.

In another embodiment, the invention relates to a pharmaceutical composition containing a compound of the invention and a pharmaceutically acceptable carrier.

The invention also pertains to a method for treating an $A_{2b}$ associated disease state in an animal, by administering to a mammal a therapeutically effective amount of a compound of the invention, such that treatment of disorder in the animal occurs. Advantageously, the disease state may be a disorder mediated by adenosine. Examples of preferred disease states include: central nervous system disorders, cardiovascular disorders, renal disorders, inflammatory disorders, allergic disorders, gastrointestinal disorders, eye disorders, and respiratory disorders.

The invention further pertains to pharmaceutical compositions for treating an $A_{2b}$ associated disease state in a mammal, e.g., respiratory disorders (e.g., asthma, bronchitis, chronic obstructive pulmonary disorder, and allergic rhinitis), renal disorders, gastrointestinal disorders, and eye disorders. The pharmaceutical composition includes a therapeutically effective amount of a compound of the invention, described below, and a pharmaceutically acceptable carrier. It is to be understood, that all of the compounds described below are included for therapeutic treatment. It is to be further understood that the compounds of the invention can be used alone or in combination with other compounds of the invention or in combination with additional therapeutic compounds, such as antibiotics, antiinflammatories, or anticancer agents, for example.

As indicated above, use of the compounds of the invention to prevent or reduce damage to retinal and optic nerve head tissues at the cellular level is a particularly important aspect of one embodiment of the invention. Ophthalmic conditions which may be treated include, but are not limited to, retinopathies, macular degeneration, ocular ischemia, glaucoma, and damage associated with injuries to ophthalmic tissues, such as ischemia reperfusion injuries, photochemical injuries, and injuries associated with ocular surgery, particularly injuries to the retina or optic nerve head by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The features and other details of the invention will now be more particularly described and pointed out in the claims. It is to be understood that the particular embodiments of the invention are shown by way of illustration and not as limitations of the invention. The principal features of this invention can be employed in various embodiments without departing from the scope of the invention.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

General Information

LC/MS analysis was performed using a Gilson 215 autosampler and Gilson 819 autoinjector, attached to a Hewlett Packard HP110.

Mass spectra were obtained on a Micromass Platform II mass spectrometer, using positive electrospray ionization.

LC analysis was undertaken at 254 nm using a UV detector. Samples were eluted on a Phenomenex Luna C18(2) (5 microns, 4.6×150 mm) column using either a linear gradient of 15-99% solvent A in solvent B over 10 minutes (method A, non-polar) or 5-100% solvent A in solvent B over 15 minutes (method B, polar). The solvent A was 100% acetonitrile, solvent B was 0.01% formic acid, which was observed to have no noticeable effect on sample retention time, in water.

IR spectra were recorded on a Perkin-Elmer Spectrum 1000 FT-IR spectrometer as thin films using diffuse reflectance.

$^1$H NMR and $^{13}$C NMR spectra were recorded with Varian instruments (400 MHz or 200 MHz for $^1$H, 100.6 MHz or 50.3 MHz for $^{13}$C) at ambient temperature with TMS or the residual solvent peak as internal standards. The line positions or multiplets are given in ppm ($\delta$) and the coupling constants (J) are given as absolute values in Hertz, while the signal multiplicities are abbreviated as follows: s (singlet), d (doublet), t (triplet), q (quartet), quint (quintet), m (multiplet), $m_c$ (centered multiplet), br (broadened).

All melting points were determined with a Mel-Temp II apparatus and are uncorrected.

Elemental analyses were carried out at Atlantic Microlab, Inc., Norcross, Ga.

Commercially available anhydrous solvents and HPLC-grade solvents were used without further purification.

33

Abbreviations:

| | |
|---|---|
| DMSO | Dimethylsulfoxide |
| HATU | O-(7-Azabenzotriazolo-1-yl)-N,N,N',N'-tetramethyluronium hexafluorophosphate |
| HPLC | High Pressure Liquid Chromatography |
| LCMS | Liquid Chromatography/Mass Spectrometry |
| NMP | N-Methylpyrrolidinone |
| NMR | Nuclear Magnetic Resonance |
| PS-NCO | Polymer Supported Isocyanate |
| RT | Retention Time |
| SCX | Strong cation exchange silica |
| THF | Tetrahydrofuran |

DETAILS FOR EXPERIMENTAL PROCEDURES OF DISCRETE EXAMPLES

Reverse phase, high pressure liquid chromatography where mentioned below in the following preparations was effected according to the following general method. A Xterra column (C18 silica packing, 7 micron particle size, 19×150 mm) was previously equilibrated in a mixture of water, acetonitrile, and trifluoroacetic acid (90:10:0.1 v/v/v) at pH 3.0. Samples were eluted using a linear gradient of 10% to 90% acetonitrile in water, containing 0.1% trifluoroacetic acid, at pH 3.0, over 10 minutes, with a flow rate of 10 mLmin$^{-1}$. Analysis was undertaken at 220 nm using a diode array detector. Where a compound was purified in this manner it was assumed to be isolated as its trifluoroacetate salt.

Purification using benzenesulphonic acid functionalised strong cation exchange (SCX) silica in a 96 well format, where mentioned below in the following preparations, was effected according to the following general method. Approximately 70 mg of the silica per well was conditioned with 500 µl of a 1:1 v/v methanol water mixture. The impure material was loaded as a 4:1 mixture of 0.1M HCl:NMP then washed with 500 µl methanol. Purified material was eluted with 500 µl of a 3:97 v/v mixture of ammonium hydroxide:methanol.

Analytical Procedures $^1$H NMR analysis was conducted on a Varian Gemini instrument at 400 MHz, using standard procedures.

LCMS analysis was performed using a Gilson 215 autosampler and Gilson 819 autoinjector, attached to a Hewlett Packard HP110. Mass spectra were obtained on a Micromass Platform LC mass spectrometer, using positive and negative electrospray ionisation. Masses found refer to the most abundant MH$^+$ positive ion found corresponding to the title compound unless otherwise stated. Analysis was undertaken at 220 nm using a diode array detector.

The following general methods were used:

Method A: Waters Symmetry C18 (3.5 micron, 2.1×30 mm), 4.8 minute gradient or

Method B: Phenomenex Mercury MS Luna C18 (3 micron, 2.0×10 mm), 3.6 minute gradient Samples were eluted using a linear gradient of 0-100% Solvent B in Solvent A over either 4.8 or 3.6 minutes (see above). The buffer used was formic acid (0.1%) which was observed to have had no noticeable effect on sample retention time.

34

Mobile Phase (plus buffer)
Solvent A: Water (95%), acetonitrile (5%).
Solvent B: Acetonitrile (100%).

Example 1

Synthesis of Chloroacetamide Intermediate 6

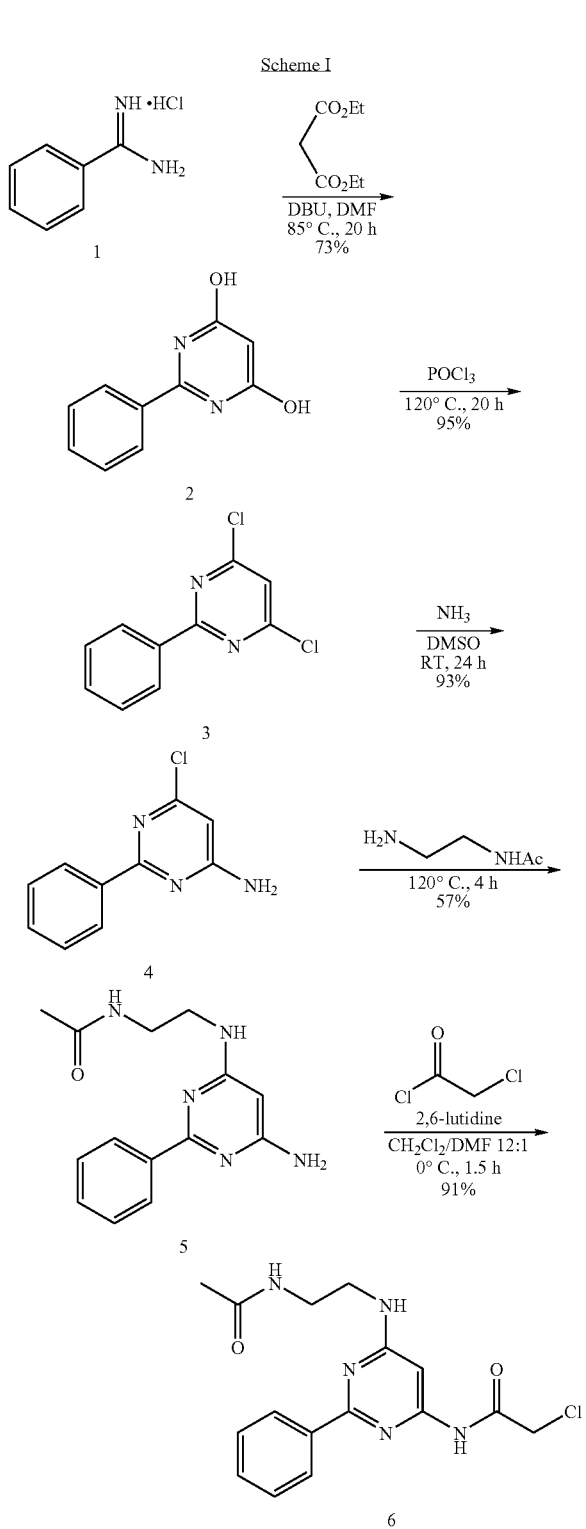

Scheme I

Condensation of benzamidine hydrochloride with diethyl malonate in DMF using DBU as base gave the diol 2, which was converted to the dichloride 3 by reaction with neat $POCl_3$. Selective, stepwise displacement of the chloro substituents with ammonia in DMSO and then with neat N-acetylethylenediamine yielded the diamine 5. Acylation with chloroacetyl chloride using 2,6-lutidine as base in $CH_2Cl_2$/DMF 12:1 gave the chloroacetamide 6.

2-Phenylpyrimidine-4,6-diol (2): A solution of benzamidine hydrochloride (44.41 g; 0.284 mol), diethyl malonate (45.51 g; 0.284 mol) and DBU (86.40 g; 0.568 mol) in DMF (250 mL) was heated at 85° C. for 20 h. After cooling to room temperature, the flask was placed in a refrigerator overnight. The crystalline product was collected by filtration and washed with DMF (300 mL), then dissolved in water (ca. 110 mL) and acidified with 2 M HCl (110 mL) with water added, as necessary, to maintain a suspension. The product was collected by filtration, washed with water (100 mL) and dried to a constant weight under high vacuum giving 39.09 g (73%) of an off-white solid. LC (method B) $t_R$=6.2 min; $^1$H NMR (200 MHz, DMSO-$d_6$) δ 8.08 (m, 2H), 7.54 (m, 3H), 5.34 (s, 1H); ESIMS 189.0 ([M+H]$^+$).

4,6-Dichloro-2-phenylpyrimidine (3): A slurry of diol 2 (39.08 g; 0.208 mol) in phosphorus oxychloride (124 mL; 1.33 mol) was heated from 75-120° C. over 45 min. After 20 h at 120° C. the volatiles were removed in vacuo. The resulting tan solid was added to crushed ice (600 mL) and this suspension was stirred for 2 h at rt, collected by filtration, washed with water and dried to a constant weight under high vacuum giving a tan solid (44.34 g; 95%). $^1$H NMR (200 MHz, CDCl$_3$) δ 8.44 (m, 2H), 7.51 (m, 3H), 7.27 (s, 1H).

6-Chloro-2-phenylpyrimidin-4-ylamine (4): An ice-cold suspension of pyrimidine 3 (44.34 g; 0.197 mol) in DMSO (366 mL) was saturated with ammonia, during which time a solution formed. After 24 h at rt, water (710 mL) was added dropwise. The suspension was cooled in an ice bath for 1 h then collected by filtration and washed with water (500 mL), yielding a light tan powder after drying in vacuo (37.84 g; 93%). LC (method B) $t_R$=16.0 min; $^1$H NMR (200 MHz, CDCl$_3$) δ 8.33 (m, 2H), 8.44 (m, 3H), 6.32 (s, 1H), 5.12 (brs, 2H); $^{13}$C NMR (50.3 MHz, CDCl$_3$) δ 165.1, 164.0, 160.5, 136.7, 131.0, 128.4, 128.4, 101.4; ESIMS 205.9/207.8 (100/34) [MH$^+$].

N-[2-(6-Amino-2-phenylpyrimidin-4-ylamino)-ethyl]-acetamide (5): A solution of chloroarene 4 (20.57 g; 0.100 mol) in N-(2-aminoethyl)-acetamide (71.05 g; 0.696 mol) was heated from 60 to 120° C. over 20 min then kept at 120° C. for 4.0 h. After cooling to rt, the reaction was diluted with EtOAc (500 mL) then washed with water (1×150 mL). The aq phase was extracted with EtOAc (3×25 mL) and the combined organic portions were washed with water (2×25 mL) and saturated NaCl (2×50 mL). The solution was dried (MgSO$_4$), filtered then concentrated in vacuo to 21.34 g of an off-white hard foam. The product was purified in two batches on silica gel (1.7 L total) using 15-8:1 DCM:MeOH yielding a hard white foam (15.36 g; 57%). LC (method B) $t_R$=5.5 min; $^1$H NMR (200 MHz, CDCl$_3$) δ 8.29 (m, 2H), 7.43 (m, 3H), 6.71 (brs, 1H), 5.41 (s, 1H), 5.12 (brt, J=5.4 Hz, 1H), 4.68 (brs, 2H), 3.53 (m, 1H), 3.45 (m, 1H), 1.83 (s, 3H); ESIMS 272.03 (100) [MH$^+$].

N-[6-(2-Acetylaminoethylamino)-2-phenylpyrimidin-4-yl]-2-chloroacetamide (6): A solution of amine 5 was titrated with chloroacetyl chloride with monitoring by TLC (SiO$_2$/8:1 and 14:1 DCM:MeOH) as follows: Neat chloroacetyl chloride (0.45 mL; 5.7 mmol) was slowly added down the side of a flask immersed in an ice-water bath into a solution of aminopyrimidine 5 (1.531 g; 5.64 mmol) and 2,6-lutidine (2.0 mL; 17 mmol) in DCM (30 mL) plus DMF (2.5 mL). Starting material remained so additional chloroacetyl chloride was added after 0.4 h (0.45 mL; 5.7 mmol) and again after an additional 0.5 h (90 µL; 1.1 mmol). After 0.5 h, EtOAc (150 mL) was added and the solution washed with saturated NaHCO$_3$ (40 mL), 50% saturated NaCl (5×40 mL), saturated NaCl (2×40 mL), dried (MgSO$_4$), filtered and concentrated to a yellow-orange crystalline solid. The crude material was triturated with hexanes (10 mL) then 1:1 hexanes:Et$_2$O (2×10 mL) then purified on silica gel (250 mL) with 18:1 DCM:MeOH yielding a hard yellow foam (1.78 g; 91%). LC (method B) $t_R$=13.5 min; $^1$H NMR (200 MHz, CDCl$_3$) δ 8.70 (brs, 1H), 8.35 (m, 2H), 7.47 (m, 3H), 7.16 (s, 1H), 6.48 (brs, 1H), 5.59 (brt, 1H), 4.19 (s, 2H), 3.68 (m, 2H), 3.54 (m, 2H), 1.88 (s, 3H); ESIMS 347.9/349.9 (100/32) [MH$^+$].

Example 2

Preparation of Not Commercially Available Amines 7

The syntheses of non-commercial amines 7 are shown in Scheme II. Benzyl piperidines were prepared by Horner-Wadsworth-Emmons reaction or from N-Boc-4-methylenepiperidine by hydroboration and Suzuki cross-coupling. Phenyl ethers were synthesized from N-Boc-4-hydroxypiperidine and the phenols by Mitsunobu reaction. Alkylation of the nitrile 17.15 with the protected nitrogen mustard 15 followed by Boc removal with HCl in dioxane gave amine 7.15. The piperazines and homopiperazines were prepared from the mono-Boc-protected derivatives by reductive amination with the appropriate aldehyde using NaBH(OAc)$_3$ as reducing agent followed by deprotection with TFA or HCl/MeOH.

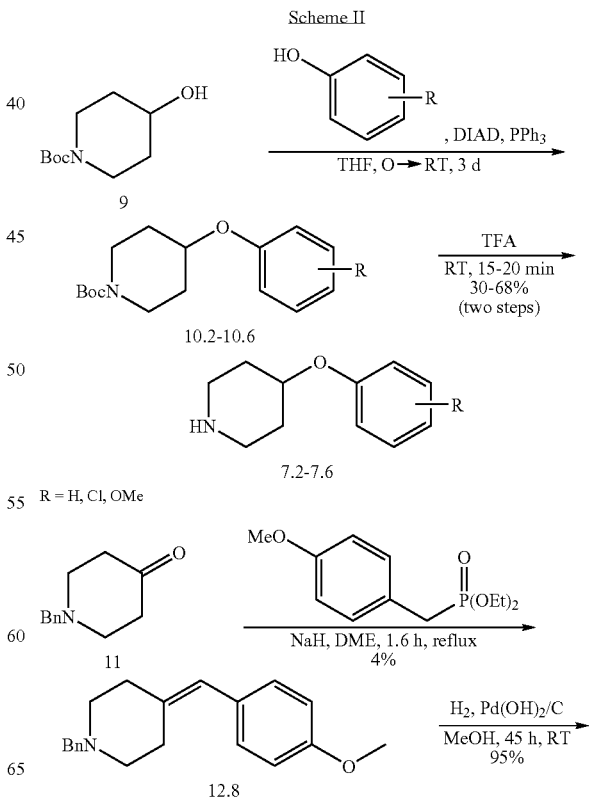

Scheme II

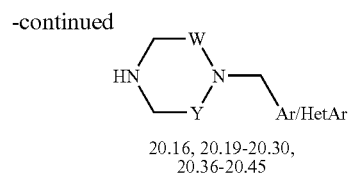
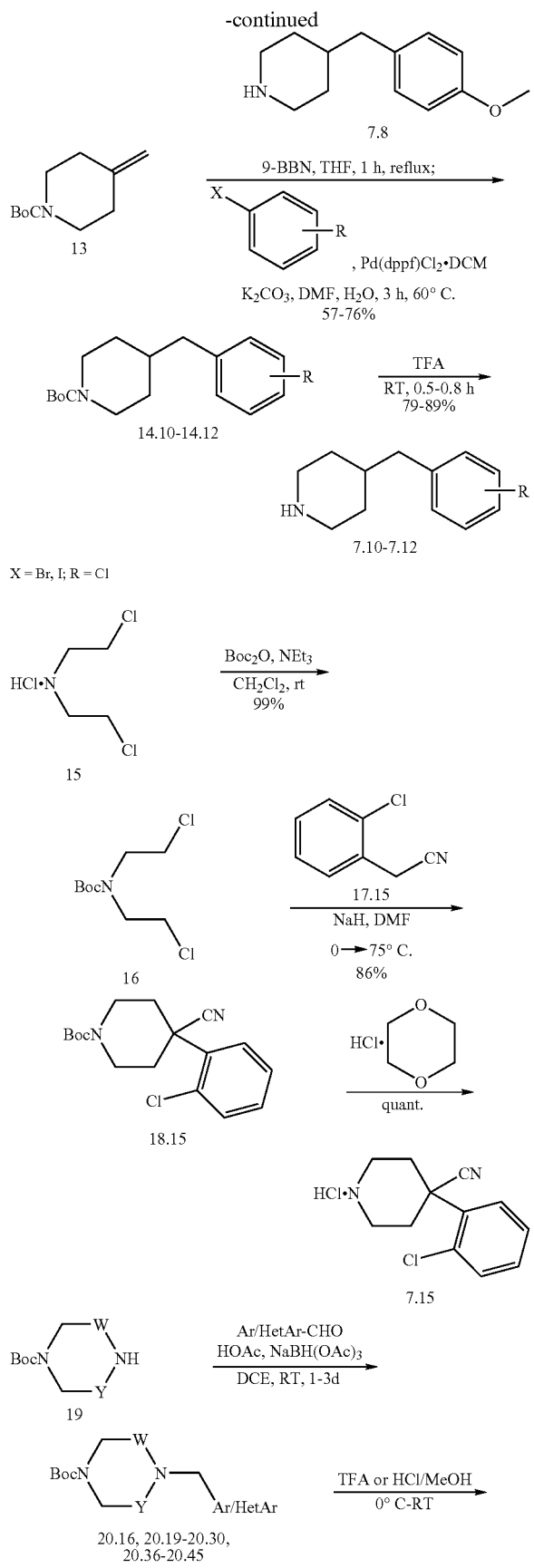

W = Y = CH₂: 7.19-7.30
W = CH₂, Y = CH₂CH₂: 7.36-7.45
W = Y = CHCH₃: 7.16

4-Methylenepiperidine-1-carboxylic acid tert-butyl ester (13) Methyltriphenyl-phosphonium bromide (1.870 g; 5.23 mmol) was added in one portion to a suspension of KOtBu (0.586 g; 5.22 mmol) in anhydrous ether (10 mL). After 30 min the yellow suspension was cooled to 0° C., then a solution of 4-oxo-piperidine-1-carboxylic acid tert-butyl ester (1.02 g; 5.12 mmol) was added. After 2.0 h water (10 mL) and EtOAc (10 mL) were added; the organic portion was washed with water (2×10 mL) and saturated NaCl (2×10 mL), dried (MgSO₄), filtered and concentrated to a white solid. The material soluble in 12:1 hexanes:EtOAc was purified on silica gel (60 mL) with this solvent system yielding a clear, colorless liquid (685 mg; 68%). ¹H NMR (200 MHz, CDCl₃) δ 4.74 (t, J=1.0 Hz, 2H), 3.42 (m, 4H), 2.18 (m, 4H), 1.47 (s, 9H).

4-(2-Chlorobenzyl)-piperidine-1-carboxylic acid tert-butyl ester (14.10) This compound was synthesized in a manner analogous to 14.12 from 1-chloro-2-iodobenzene (264 mg; 1.11 mmol) giving a clear, colorless oil (262 mg; 76%) after silica gel chromatography (40 mL, eluting with 10:1 hexanes:EtOAc). LC (method A) $t_R$=12.09 min; $R_f$=0.29 (SiO₂/8:1 hexanes:EtOAc); ¹H NMR (200 MHz, CDCl₃) δ 7.35 (m, 1H), 7.16 (m, 3H), 4.08 (m, 2H), 2.8-2.5 (m, 4H), 2.0-1.4 (m, 3H), 1.45 (s, 9H), 1.23 (m, 2H); ESIMS 294.9/296.9 (100/34) [MH⁺–C₄H₉+CH₃CN], 253.9/255.9 (40/12) [MH³⁰ –C₄H₉].

4-(3-Chlorobenzyl)-piperidine-1-carboxylic acid tert-butyl ester (14.11) This compound was synthesized in a manner analogous to 14.12 from 1-bromo-3-chlorobenzene (223 mg; 1.16 mmol) giving a clear, pale yellow oil (204 mg; 57%) after silica gel chromatography (40 mL, eluting with 9:1 hexanes:EtOAc). LC (method A) $t_R$=12.04 min; $R_f$=0.27 (SiO₂/9:1 hexanes:EtOAc); ¹H NMR (200 MHz, CDCl₃) δ 7.3-7.1 (m, 3H), 7.00 (m, 1H), 4.08 (m, 2H), 2.63 (m, 2H), 2.51 (m, 2H), 2.0-1.4 (m, 3H), 1.45 (s, 9H), 1.16 (m, 2H); ESIMS 294.9/296.9 (100/34) [MH⁺–C₄H₉+CH₃CN], 253.9/255.9 (32/10) [MH⁺–C₄H₉].

4-(4-Chlorobenzyl)-piperidine-1-carboxylic acid tert-butyl ester (14.12) A solution of alkene 13 (195 mg; 0.988 mmol) and 9-BBN (1.5 M in THF; 2.0 mL; 1.0 mmol) was immersed in an oil bath at rt, heated to reflux and kept at reflux for 1.0 h then cooled to rt. This solution was added to a suspension of 1-bromo-4-chlorobenzene (172 mg; 0.898 mmol), K₂CO₃ (163 mg; 1.18 mmol) and Pd(dppf)Cl₂·CH₂Cl₂ (37 mg; 0.045 mmol) in water (0.20 mL) and DMF (2.0 mL). The reaction was degassed (reduced pressure then nitrogen for three cycles) then heated at 60° C. for 3.0 h. Water (6 mL) and 1 M NaOH (6 mL) were added to the cooled solution and this was then extracted with EtOAc (15 mL). The organic portion was washed with 1 M NaOH (4 mL), water (2×2 mL) and saturated NaCl (2×4 mL), then dried (MgSO₄). filtered and concentrated to a brown oil. Pure product was obtained as a clear, colorless oil after chromatography on silica gel (40 mL), eluting with 8:1 hexanes:EtOAc (161 mg; 58%). LC (method A) $t_R$=12.10 min; $R_f$=0.30 (SiO₂/8:1 hexanes:EtOAc); ¹H NMR (200 MHz, CDCl₃) δ 7.24 (m, 2H), 7.06 (m, 2H), 4.07 (m, 2H), 2.63 (m, 2H), 2.50 (m, 2H), 2.0-1.4 (m, 3H), 1.45 (s, 9H), 1.15 (m, 2H); ESIMS 309.8/311.8 (1/0.4) [MH$^+$], 294.9/296.9 (100/34) [MH$^+$–C$_4$H$_9$+CH$_3$CN], 253.9/255.9 (32/10) [MH$^+$–C$_4$H$_9$], 210.0/212.0 (7/3) [MH$^+$–C$_4$H$_9$–CO$_2$].

4-(2-Chlorobenzyl)-piperidine (7.10) Trifluoroacetic acid (1 mL) was added to carbamate 14.10 (256 mg; 0.826 mmol). After 0.5 h the reaction was concentrated on a rotary evaporator. Ether (8 mL) was added and the solution was washed with 5 M NaOH (2×3 mL) and water (3 mL). The product was extracted into 1 M HCl (3×2 mL). After basification of the acidic portion with 5 M NaOH (4 mL), the product was extracted with DCM (3×2 mL). The organic portion was dried (MgSO$_4$), filtered and concentrated affording a clear, pale yellow liquid (137 mg; 79%). LC (method B) t$_R$=9.48 min; $^1$H NMR (200 MHz, CDCl$_3$) δ 7.34 (m, 1H), 7.2-7.0 (m, 3H), 3.05 (m, 2H), 2.66 (m, 2H), 2.54 (m, 2H), 1.9-1.5 (m, 3H), 1.21 (m, 2H); ESIMS 210.0/212.0 (100/35) [MH$^+$].

4-(3-Chlorobenzyl)-piperidine (7.11) This compound was synthesized in a manner analogous to 7.10 from carbamate 14.11 (200 mg; 0.646 mmol) giving a clear, pale yellow viscous liquid which solidified upon standing to a waxy solid (111 mg; 82%). LC (method B) t$_R$=9.84 min; $^1$H NMR (200 MHz, CDCl$_3$) δ 7.3-7.1 (m, 3H), 7.01 (m, 1H), 3.05 (m, 2H), 2.7-2.4 (m, 4H), 1.8-1.5 (m, 3H), 1.14 (m, 2H); ESIMS 210.0/212.0 (100/35) [MH$^+$].

4-(4-Chlorobenzyl)-piperidinium trifluoroacetate (7.12): Trifluoroacetic acid (1 mL) was added to carbamate 14.12 (153 mg; 0.494 mmol). After 0.8 h the reaction was concentrated on a rotary evaporator. Ether (8 mL) was added and the resulting solid was triturated with ether, collected by filtration and washed with ether leaving a white solid (143 mg; 89%). LC (method B) t$_R$=10.79 min; $^1$H NMR (200 MHz, CDCl$_3$) δ 9.57 (brs, 1H), 9.09 (brs, 1H), 7.27 (m, 2H), 7.06 (m, 2H), 3.38 (m, 2H), 2.82 (m, 2H), 2.57 (m, 2H), 1.9-1.4 (m, 5H); ESIMS 210.0/212.0 (100/33) [MH$^+$].

1-Benzyl-4-(4-methoxybenzylidene)-piperidine (12.8): A solution of 1-benzylpiperidin-4-one (11) (2.310 g; 12.2 mmol) and (4-methoxybenzyl)-phosphonic acid diethyl ester (3.100 g; 12.0 mmol) in DME (20 mL) was added to NaH (0.51 g; 21 mmol). The flask was immersed in a rt oil bath, heated to reflux and kept at this temperature for 1.6 h. The reaction was cooled, poured into water (200 mL) and extracted with EtOAc (4×60 mL). The organic portion was washed with saturated NaCl (4×25 mL), dried (MgSO$_4$), filtered and concentrated to an oil. The product was partially purified on silica gel (320 mL) with 25:1 DCM:MeOH giving an oil (0.5 g). This oil was dissolved in 1 M HCl (10 mL) and the product was extracted into DCM (5×3 mL). The organic portion was washed with saturated NaHCO$_3$, dried (MgSO$_4$), filtered and concentrated to an orange-brown liquid (0.46 g). This material was combined with crude material (2.41 g, unchromatographed) similarly prepared from ketone (1.535 g; 8.1 mmol), phosphonate (2.071 g; 8.02 mmol) and NaH (0.22 g; 8.8 mmol). The combined crude material was purified on silica gel (250 mL) with 2:1 hexanes:EtOAc giving a pale yellow solid (230 mg; 4%). mp 71.5-72.0° C. $^1$H NMR (200 MHz, CDCl$_3$) δ 7.4-7.2 (m, 5H), 7.12 (m, 2H), 6.84 (m, 2H), 6.21 (m, 1H), 3.80 (s, 3H), 3.52 (s, 2H), 2.62.3 (m, 8H).

4-(4-Methoxybenzyl)-piperidine (7.8) Palladium hydroxide (27 mg) was added to a solution of N-benzyl alkene 10 (204 mg; 0.695 mmol) in methanol (9 mL). The suspension was degassed then left under 1 atm hydrogen for 45 h. After filtration through a short pad of diatomaceous earth, the solution was concentrated in vacuo to a waxy solid (135 mg; 95% crude yield). LC (method "polar_short") t$_R$=3.01 min; ESIMS 206.0 ([M+H]$^+$).

4-(3-Chlorophenoxy)-piperidine-1-carboxylic acid tert-butyl ester (10.5) A solution of DIAD (11.4 mL; 55.0 mmol) in THF (15 mL) was added dropwise over 35 min to an ice-cold solution of 4-hydroxypiperidine-1-carboxylic acid tert-butyl ester (9) (10.06 g; 50.0 mmol), 3-chlorophenol (5.1 mL; 50.4 mmol) and triphenylphosphine (14.44 g; 55.1 mmol) in THF (40 mL). After 2.9 days at room temperature the solvent was removed on a rotary evaporator leaving a viscous liquid; hexanes was added then evaporated leaving a solid. Ether (25 mL), followed by hexanes (100 mL), was added and the solid was filtered and washed with hexanes. The filtrate was concentrated on a rotary evaporator leaving a golden, viscous liquid (19.6 g). The crude product was used as is. LC (method A) t$_R$=11.2 min; ESIMS 311.9/313.8 (25/10) [MH$^+$], 296.9/298.8 (100/34) [MH$^+$–C$_4$H$_9$+CH$_3$CN], 255.9/257.8 (94/32) [MH$^+$–C$_4$H$_9$], 212.0/214.0 (13/5) [MH$^+$–C$_4$H$_9$–CO$_2$].

4-(2-Chlorophenoxy)-piperidine-1-carboxylic acid tert-butyl ester (10.6) This compound was prepared from 4-hydroxypiperidine-1-carboxylic acid tert-butyl ester (9) (3.505 g; 17.4 mmol), 2-chloro-phenol (3.375 g; 26.3 mmol), triphenylphosphine (6.002 g; 22.9 mmol) and DIAD (4.30 mL; 21.8 mmol) in a manner analogous to 10.5. After 8 days, EtOAc (200 mL) was added to the crude reaction mixture and the solution washed with 50% saturated NaHCO$_3$ (50 mL), saturated NaHCO$_3$ (2×25 mL) and saturated NaCl (2×25 mL) then dried (MgSO$_4$), filtered and concentrated to a viscous liquid. Ether (50 mL) and hexanes (50 mL) were added and this was allowed to stand overnight; whereupon the precipitate was removed by filtration and the filtrate partially concentrated. More material precipitated, which was also removed by filtration, and the filtrate was concentrated to an oil. The product was partially purified on basic alumina (160 mL), eluting with 8:1 hexanes:EtOAc, giving a clear, colorless viscous liquid (5.12 g; 94% crude yield). LC (method A) t$_R$=11.50 min; ESIMS 312.1/314.1 (1/0.3) [MH$^+$], 296.9/298.9 (100/34) [MH$^+$–C$_4$H$_9$+CH$_3$CN], 255.9/257.8 (41/12) [MH$^+$–C$_4$H$_9$], 212.0/214.0 (4/1)[MH$^+$–C$_4$H$_9$–CO$_2$].

Compounds 10.2-10.4 were prepared in an analogous manner.

4-(3-Chlorophenoxy)-piperidinium chloride (7.5): Trifluoroacetic acid (40 mL) was added to crude carbamate 10.5 (18.6 g; 59.7 mmol) cooled in an ice-water bath. After 1 min the reaction was stirred at rt for 15 min, then concentrated on a rotary evaporator. Ether (200 mL) was added and this washed with 3 M NaOH (3×50 mL) and water (50 mL). The product was extracted into 1 M HCl (3×50 mL) and the aq phase was basified with 3 M NaOH (60 mL). The free base was extracted into DCM (1×50 mL then 2×25 mL), dried (MgSO$_4$), filtered and concentrated to an oil. The hydrochloride salt was precipitated from a methanolic (6 mL) solution of the free base by the dropwise addition of HCl in ether (200 mL of HCl-saturated ether plus 150 mL of ether). The salt was collected by filtration and washed with ether (100 mL) giving an off-white solid (7.97 g; 68% from 4-hydroxypiperidine-1-carboxylic acid tert-butyl ester). LC (method B) t$_R$=8.2 min; $^1$H NMR (200 MHz, DMSO-d$_6$) δ 8.94 (brs, 2H), 7.33 (m, 1H), 7.12 (m, 1H), 7.00 (m, 2H), 4.70 (m, 1H), 3.20 (m, 2H), 3.08 (m, 2H), 2.08 (m, 2H), 1.85 (m, 2H); ESIMS (free base) 212.0/213.9 (100/35) [MH$^+$].

4-(2-Chlorophenoxy)-piperidine (7.6): Trifluoroacetic acid (4 mL) was added to crude carbamate 10.6 (1.030 g). After 20 min at rt most of the volatiles were removed in vacuo and 1 M HCl (10 mL) was added, whereupon an oil separated. This was washed with DCM (3×3 mL). The aqueous portion was basified to pH>12 with 5 M NaOH, extracted with DCM (3×4 mL), dried (MgSO$_4$), filtered and concentrated to an oil (10 mg). The initial DCM washing was dried (MgSO$_4$), filtered and concentrated to a pale yellow oil (1.26 g), whose $^1$H NMR was consistent with being the piperidinium trifluoroacetate. This material, plus the initial collected free base (10 mg) was dissolved in ether (30 mL) and washed with 5 M NaOH (10 mL), 1 M NaOH (2×10 mL), water (10 mL) and saturated NaCl (2×10 mL), then dried (MgSO$_4$) and filtered. HCl-saturated ether (35 mL) was added and the turbid solution was extracted with 1 M HCl (3×10 mL). The acidic portion was basified with 5 M NaOH, extracted with DCM (3×8 mL) and the organic portion dried (MgSO$_4$), filtered and concentrated to a pale yellow oil (457 mg; 62% from 4-hydroxypiperidine-1-carboxylic acid tert-butyl ester). LC (method B) t$_R$=8.2 min; $^1$H NMR (200 MHz, CDCl$_3$) δ 7.37 (dd, J=1.6, 8.0 Hz, 1H), 7.19 (ddd, J=1.5, 7.3, 8.6 Hz, 1H), 7.0-6.8 (m, 2H), 4.42 (tt, J=3.9, 3.9 Hz, 1H), 3.18 (ddd, J=4.0, 6.3, 12.0 Hz, 2H), 2.73 (ddd, J=3.7, 8.6, 12.3 Hz, 2H), 2.00 (m, 2H), 1.77 (m, 2H); ESIMS (free base) 212.0/213.9 (100/37) [MH$^+$].

Compounds 7.2-7.4 were prepared in an analogous manner.

General Procedures for the Reductive Amination of Boc-Protected Piperazines and Homopiperazine with Aldehydes and Deprotection with TFA 4-(3-Chlorobenzyl)-piperazine-1-carboxylic acid tert-butyl ester (20.24): To a solution of piperazine-1-carboxylic acid tert-butyl ester (4.00 g, 21.5 mmol) in dry dichloroethane (70 mL) are added 3-chlorobenzaldehyde (2.49 mL, 3.08 g, 21.9 mmol), HOAc (2.58 mL, 2.71 g, 45.1 mmol) and NaBH (OAc)$_3$ (5.46 g, 25.8 mmol) at ambient temperature. After stirring at ambient temperature for 3d, 2N NaOH (40 mL) is added, the layers are separated, and the aqueous layer is extracted with CH$_2$Cl$_2$ (4×50 mL). The combined organic extracts are washed with water (3×50 mL) and brine (80 mL) and dried over MgSO$_4$. The crude material is purified by chromatography on silica gel, eluting with hexane:EtOAc mixtures, yielding 5.83 g (18.8 mmol, 87%) of the title compound as yellow oil. MS (ES): m/z 311.0/313.0 (50/18) [MH$^+$]. t$_R$ (method A)=5.0 min.

1-(3-Chlorobenzyl)-piperazine (7.24): To 4-(3-chlorobenzyl)-piperazine-1-carboxylic acid tert-butyl ester (20.24) (8.82 g, 28.4 mmol) is added TFA (45 mL) at ambient temperature over 5 min. After 1 h 50 min, TFA is evaporated, the residue is dissolved in 2N HCl (45 mL) and extracted with ether (2×45 mL). The aqueous layer is basified to pH 13 with 2N NaOH (60 mL) and extracted with CH$_2$Cl$_2$ (6×90 mL). The combined organic extracts are washed with brine (75 mL) and dried over MgSO$_4$. The crude material obtained after filtration and concentration (5.44 g, 25.8 mmol, 91%) is used without further purification. MS (ES): m/z 211.0/213.0 (100/35) [MH$^+$]. t$_R$ (method B)=5.1 min.

4-(3-Trifluoromethylbenzyl)-[1,4]diazepane-1-carboxylic acid tert-butyl ester (20.40): The procedure for the corresponding 3-chlorobenzyl piperazine was used. The title compound was obtained as yellow oil (87% yield). MS (ES): m/z 359.0 (81) [MH$^+$]. t$_R$ (method A)=4.9 min.

1-(3-Trifluoromethylbenzyl)-[1,4]diazepane (7.40): The procedure for the corresponding 3-chlorobenzyl piperazine was used. The title compound was obtained as yellow oil (93% yield) and is used without further purification. MS (ES): m/z 259.1 (100) [MH$^+$]. t$_R$ (method A)=3.4 min.

4-Benzyl-cis-3,5-dimethylpiperazine-1-carboxylic acid tert-butyl ester (20.16): The procedure for the corresponding 3-chlorobenzyl piperazine was used. The title compound was obtained as yellow oil (34% yield) after chromatography on silica gel. $^1$H NMR (200 MHz, CDCl$_3$) δ 7.40-7.18 (m, 5H), 3.90-3.80 (m, 2H), 3.81 (s, 2H), 2.72-2.50 (m, 4H), 1.45 (s, 9H), 1.04 (d, J=6.0 Hz, 6H).

General Procedure for the removal of Boc groups with HCl/MeOH: Acetyl chloride (1.5 ML, 21 mmol) is added dropwise into dry methanol (8 mL) at ambient temperature. After 10 min, this solution is added to a solution of the Boc-protected amine (0.9 mmol), and the reaction is stirred at ambient temperature. Upon complete consumption of starting material as judged by TLC, the solvents are evaporated. The residue (amine hydrochloride) is used directly for the amide formation.

1-Benzyl-cis-2,6-dimethylpiperazine dihydrochloride (7.16): Following the general procedure, the title compound was obtained from 4-benzyl-cis-3,5-dimethylpiperazine-1-carboxylic acid tert-butyl ester as beige solid (quant.). MS (ES, free base): m/z 205.1 (100) [MH$^+$]. t$_R$ (method B, free base)=5.8 min.

Bis-(2-chloroethyl)-carbamic acid tert-butyl ester (16): To a suspension of bis(2-chloroethyl)amine hydrochloride (10.05 g, 56.3 mmol) and Boc$_2$O (13.6 g, 62.3 mmol) in CH$_2$Cl$_2$ (70 mL), cooled by ice/water, was added triethylamine (9.5 mL, 68.2 mmol). After 45 min, the cooling bath was removed, and the reaction mixture was stirred at ambient temperature overnight. Water (50 mL) was added, and the mixture was extracted with ether:hexanes 1:1 (3×100 mL). The combined organic layers were washed with water (2×) and brine, dried over MgSO$_4$ and concentrated to give a pale yellow liquid, which was a 1:1 mixture of 16 and Boc$_2$O. The reaction was therefore repeated with this material twice, first with 5.89 g (33.0 mmol) of 15 and 4.8 mL of NEt$_3$ (34 mmol) and then with 2.5 g (14 mmol) of 15 and 2.3 mL of NEt$_3$ (17 mmol). This gave 14.887 g (61.5 mmol, 99%) of the known amine 16 as pale yellow liquid, pure by $^1$H NMR and TLC. $^1$H NMR (200 MHz, CDCl$_3$): δ=1.47 (s, 9H), 3.55-3.70 (brm, 8H).

4-(2-Chlorophenyl)-4-cyanopiperidine-1-carboxylic acid tert-butyl ester (18.15): To a suspension of NaH (60% oil suspension, 7.37 g, 184.4 mmol) in DMF (110 mL), cooled by ice/water, was added a solution of the nitrile 17.15 (9.782 g, 64.52 mmol) in DMF (20 mL) over 20 min. Hydrogen evolved, and the reaction mixture turned yellow. After 30 min, a solution of the chloroamine 16 (14.88 g, 61.45 mmol) in DMF (15 mL) was added. After 15 min the cooling bath was removed, and the reaction mixture was heated to 75° C. (bath temperature) for 5.5 h. TLC indicated the complete consumption of both 16 and 17.15. The DMF was evaporated. Upon addition of water and ether (200 mL each) a solid separated, which was filtered off, washed thoroughly with ether and EtOAc, and dried, yielding 8.018 g (24.99 mmol, 41%) of 18.15. The layers of the combined filtrate and washings were separated, and the aqueous layer was extracted with more ether (2×150 mL). The combined organic layers were washed with 5% HOAc, water, 1N NaOH, water, and brine and dried over MgSO$_4$. This solution was filtered through a pad of silica gel. Upon concentration a solid precipitated, which was filtered off, washed with ether and hexanes and dried, yielding 6.138 g (19.13 mmol, 31%) of 18.15. The mother liquor was concentrated and the residue purified by column chromatography on silica gel, yielding 2.885 g (8.99 mmol, 15%) of 18.15. The total yield was 17.04 g (53.12 mmol, 86%), mp 165-166° C. $^1$H NMR (200 MHz, CDCl$_3$): δ=1.48 (s, 9H), 2.00 (brdt, J=4.2, 13.0 Hz, 2H), 2.43-2.53 (m, 2H), 3.28 (brt, J=12.8 Hz, 2H), 4.28 (brd, J=13.2 Hz, 2H), 7.28-7.50 (m, 4H). C$_{17}$H$_{21}$ClN$_2$O$_2$ (320.82): calcd. C, 63.65, H, 6.60, Cl, 11.05, N, 8.73; found C, 63.82, H, 6.61, Cl, 10.90, N, 8.72.

4-(2-Chlorophenyl)-piperidine-4-carbonitrile hydrochloride (7.15): A solution of HCl in dioxane (4M, 200 mL, 800 mmol) was added to the Boc-protected amine 18.15 (18.4 g, 57.4 mmol). After 1.5 h the solvent was evaporated and the residue dried in vacuo, giving 14.8 g (57.4 mmol, 100%) of 7.15, colorless solid, mp 241-243° C. (decomp.). $^1$H NMR (200 MHz, CDCl$_3$): δ=2.5-2.8 (brm, 4H), 3.4-3.6 (brm, 2H), 3.6-3.8 (brm, 2H), 7.33-7.39 (m, 3H), 7.48-7.53 (m, 1H), 10.01 (brs, 2H). $C_{12}H_{14}Cl_2N_2$ (257.16): calcd. C, 56.05, H, 5.49, Cl, 27.57, N, 10.89; found C, 55.67, H, 5.48, Cl, 27.86, N, 10.61.

Example 3

Synthesis of Hydroxy-piperidines for Displacement Reactions

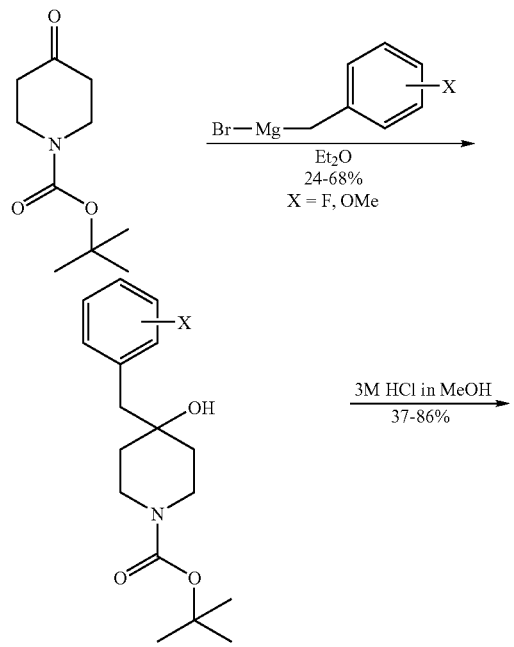

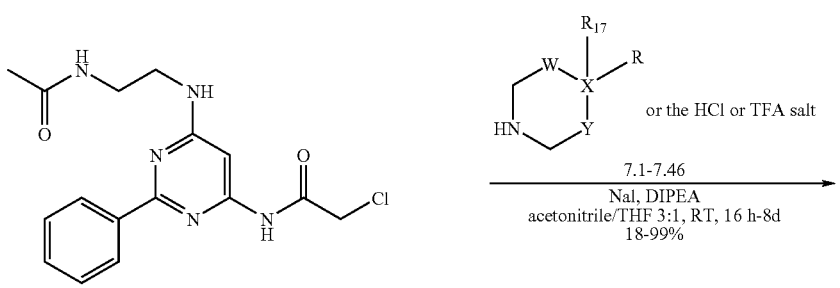

7.57, 7.66,
7.103, 7.126

Known amines 7.57, 7.66, 7.103 and 7.126 were prepared as described in *J. Med. Chem.* (1999), 42(12): 2087-2104 and in U.S. Pat. No. 5,889,026.

Example 4

Preparation of $A_{2B}$ Antagonists 8

The chloroacetamide 6 was reacted with amines 7 (free bases or HCl or TFA salts) to give the target compounds 8 (Scheme III); see Scheme IV for library-format synthesis and characterization data of 8.47-8.128. Selected compounds were converted to their HCl salts.

Scheme III

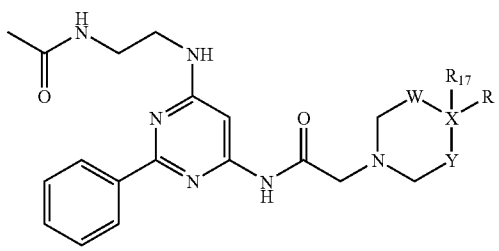

TABLE 1

A$_{2B}$ antagonists 8.1-8.46

| Comp. # | Structure | MW |
|---|---|---|
| 8.1 | 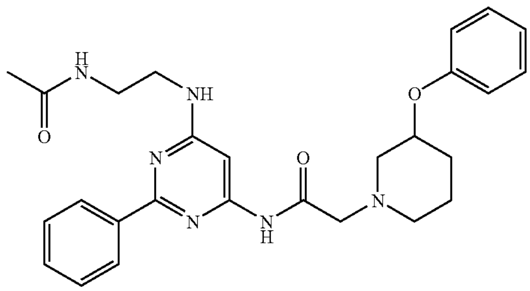 | 488.59 |
| 8.2 | 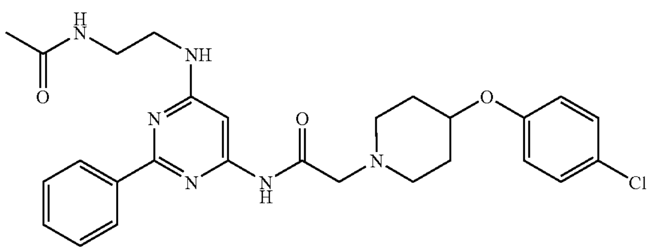 | 523.04 |
| 8.3 | 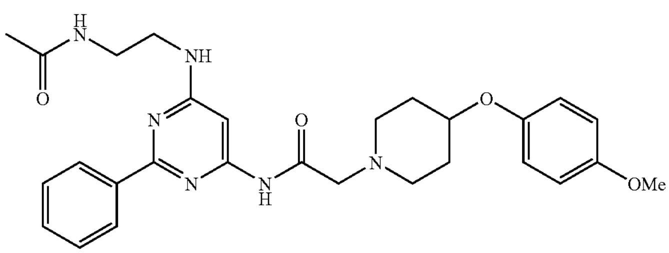 | 518.62 |
| 8.4 | 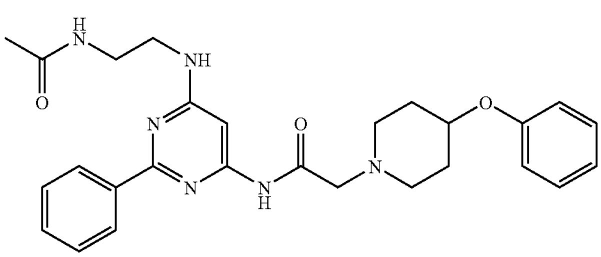 | 488.59 |
| 8.5 | 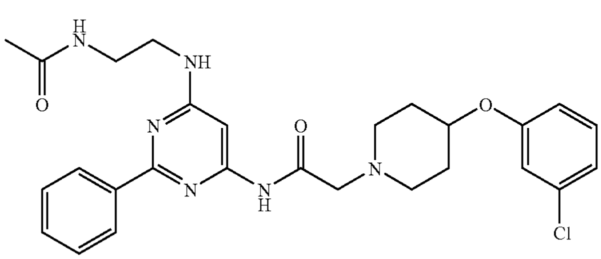 | 523.04 |

TABLE 1-continued
A$_{2B}$ antagonists 8.1-8.46
| Comp. # | Structure | MW |
|---|---|---|
| 8.6 | 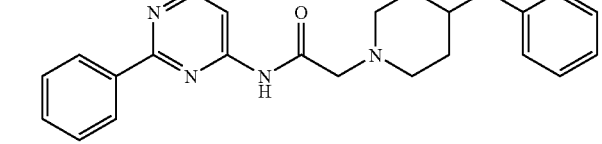 | 523.04 |
| 8.7 | 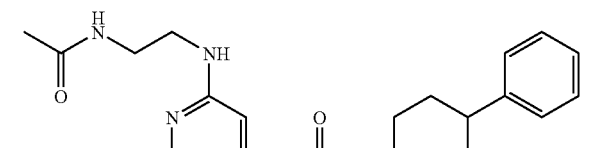 | 472.60 |
| 8.8 | 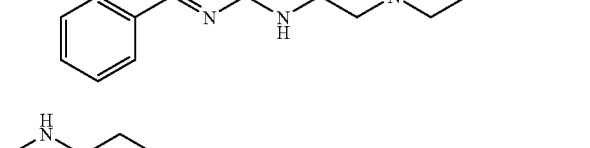 | 516.65 |
| 8.9 | 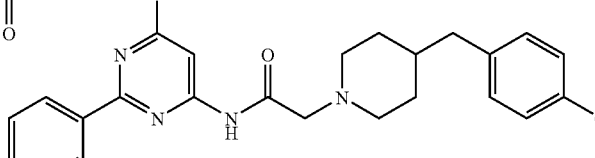 | 504.61 |
| 8.10 | 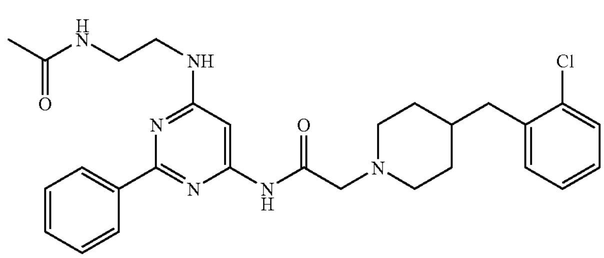 | 521.07 |
| 8.11 | 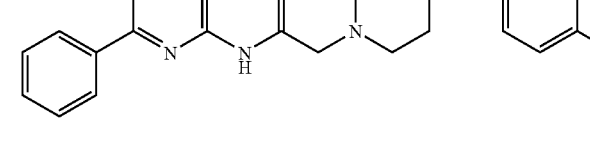 | 521.07 |

TABLE 1-continued

A$_{2B}$ antagonists 8.1-8.46

| Comp. # | Structure | MW |
|---|---|---|
| 8.12 | | 521.07 |
| 8.13 | | 502.62 |
| 8.14 | | 497.61 |
| 8.15 | | 532.05 |
| 8.16 | | 515.66 |

TABLE 1-continued

A$_{2B}$ antagonists 8.1-8.46

| Comp. # | Structure | MW |
|---|---|---|
| 8.17 | 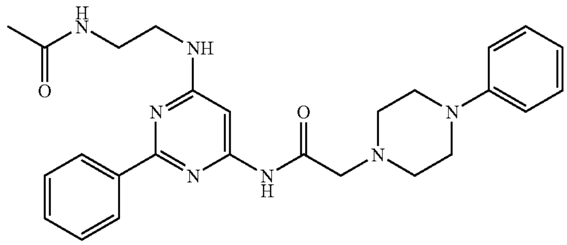 | 473.58 |
| 8.18 | 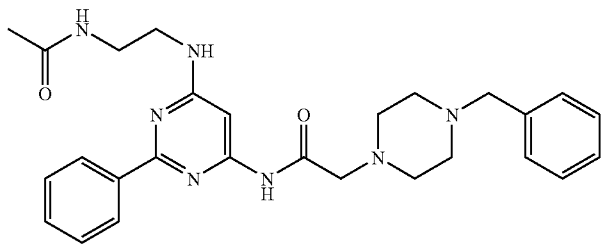 | 487.61 |
| 8.19 | 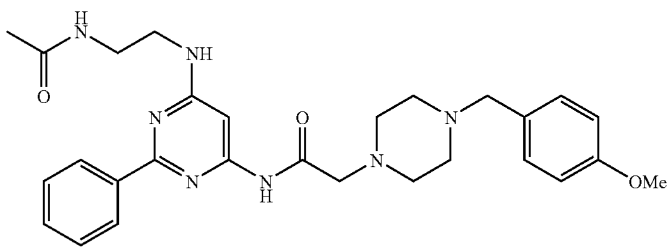 | 517.64 |
| 8.20 | 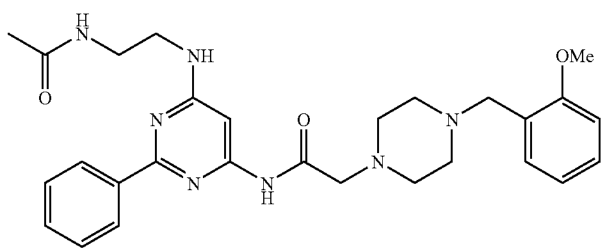 | 517.64 |
| 8.21 | 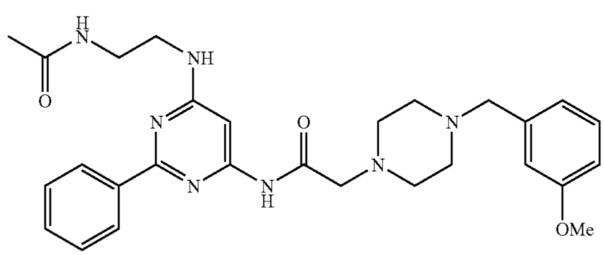 | 517.64 |
| 8.22 | 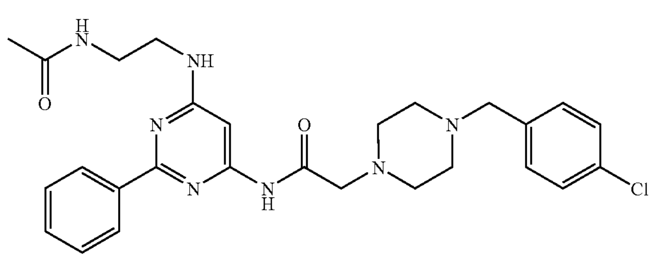 | 522.05 |

TABLE 1-continued

A$_{2B}$ antagonists 8.1-8.46

| Comp. # | Structure | MW |
|---|---|---|
| 8.23 | 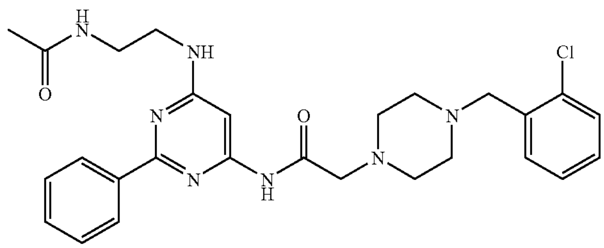 | 522.05 |
| 8.24 | 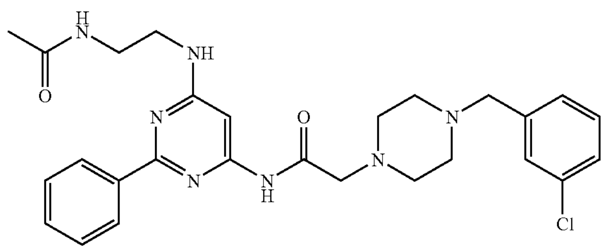 | 522.05 |
| 8.25 | 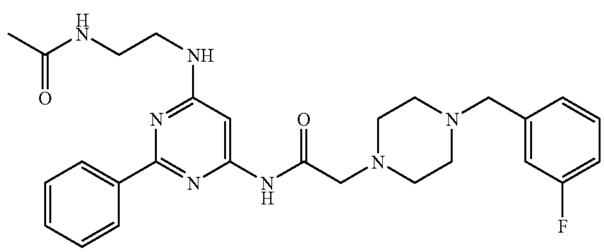 | 505.60 |
| 8.26 | 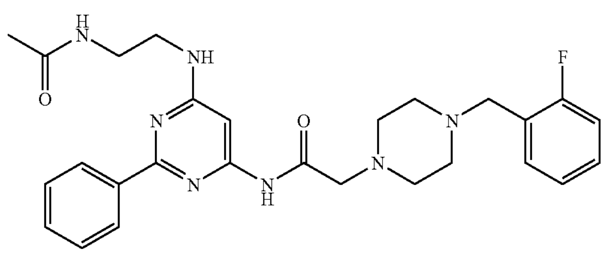 | 505.60 |
| 8.27 | 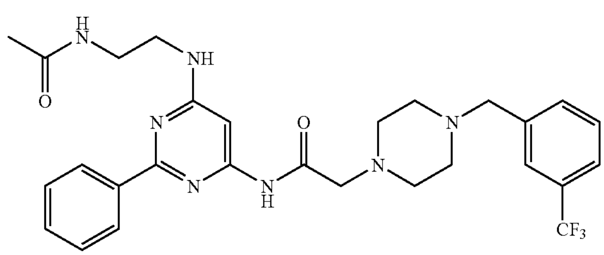 | 555.61 |

TABLE 1-continued

A$_{2B}$ antagonists 8.1-8.46

| Comp. # | Structure | MW |
|---|---|---|
| 8.28 | 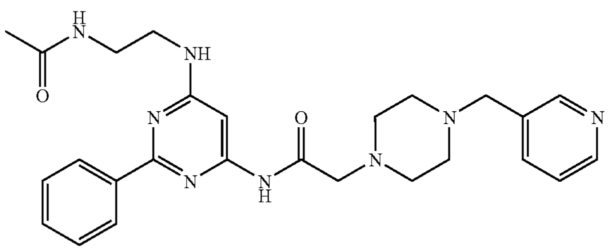 | 488.60 |
| 8.29 | 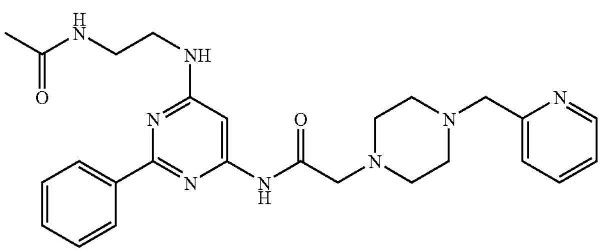 | 488.60 |
| 8.30 | 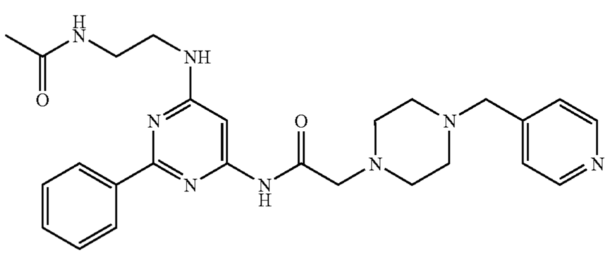 | 488.60 |
| 8.31 | 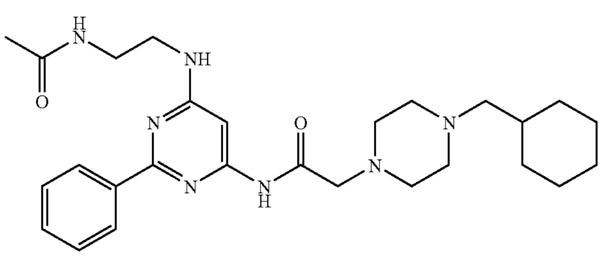 | 493.66 |
| 8.32 | 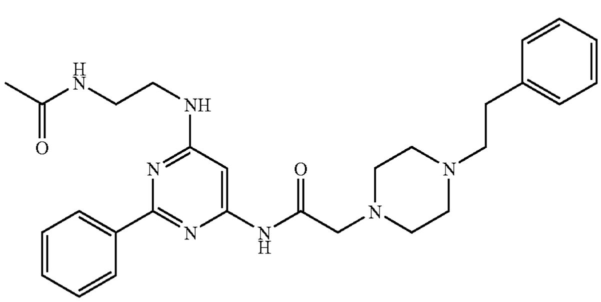 | 501.64 |

TABLE 1-continued

A$_{2B}$ antagonists 8.1-8.46

| Comp. # | Structure | MW |
|---|---|---|
| 8.33 | 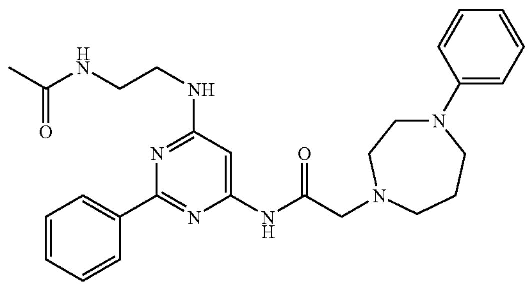 | 487.61 |
| 8.34 | 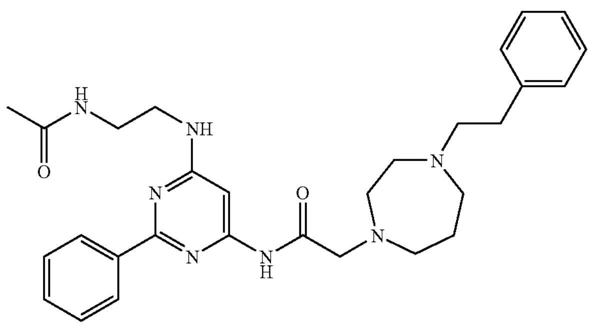 | 515.66 |
| 8.35 | 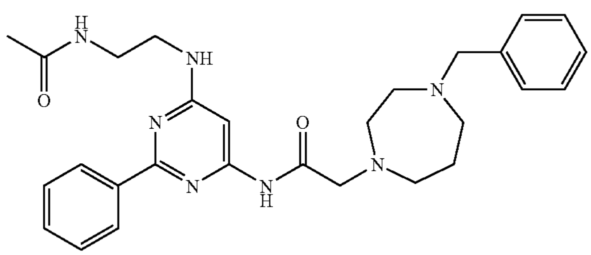 | 501.64 |
| 8.36 | 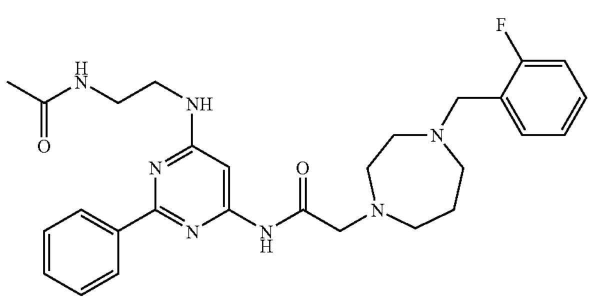 | 519.63 |
| 8.37 | 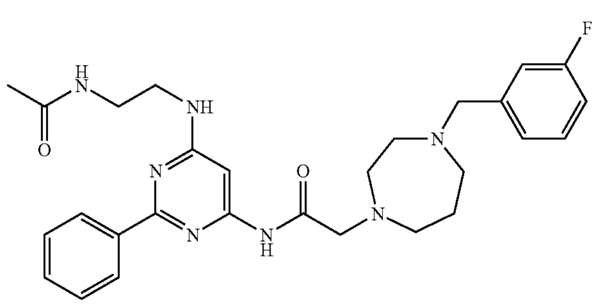 | 519.63 |

TABLE 1-continued
A$_{2B}$ antagonists 8.1-8.46
| Comp. # | Structure | MW |
|---|---|---|
| 8.38 | 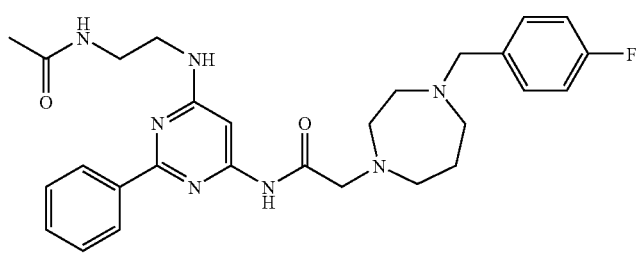 | 519.63 |
| 8.39 | 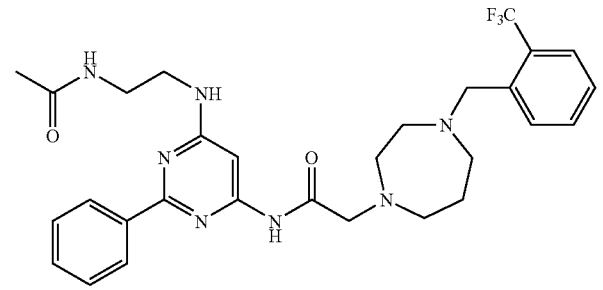 | 569.64 |
| 8.40 | 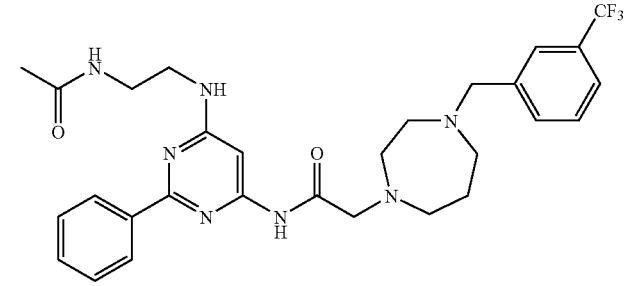 | 569.64 |
| 8.41 | 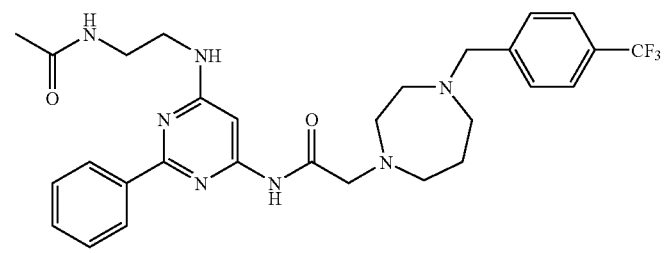 | 569.64 |
| 8.42 | 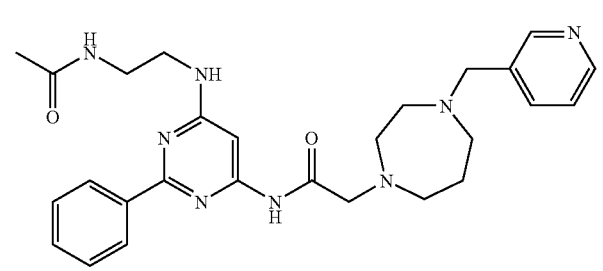 | 502.62 |

TABLE 1-continued

A$_{2B}$ antagonists 8.1-8.46

| Comp. # | Structure | MW |
|---|---|---|
| 8.43 | 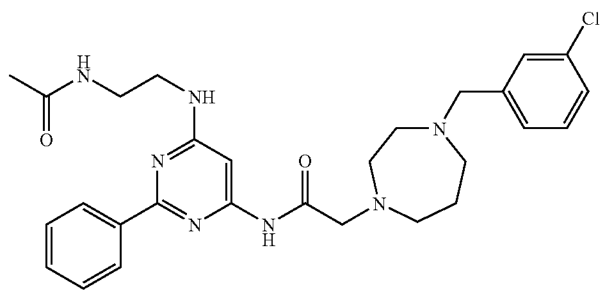 | 536.08 |
| 8.44 | 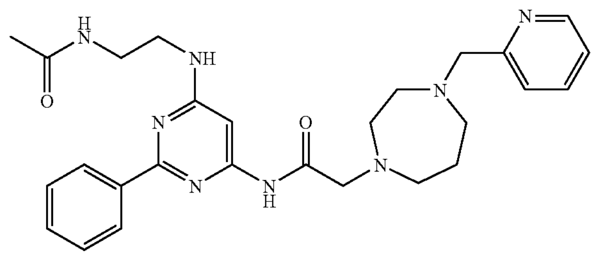 | 502.62 |
| 8.45 | 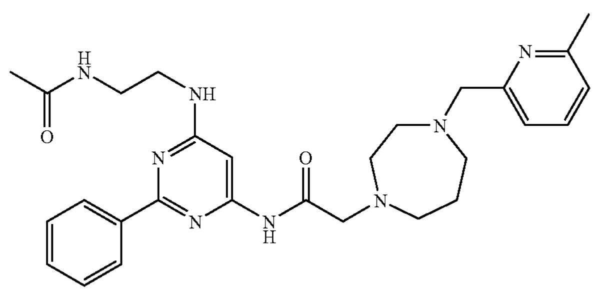 | 516.65 |
| 8.46 | 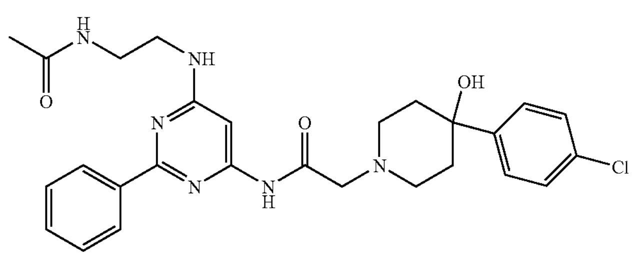 | 523.03 |

Preparation of the A$_{2B}$ antagonists 8 (when no details are given, then the preparation was carried analogously to 8.6):

N-[6-(2-Acetylaminoethylamino)-2-phenylpyrimidin-4-yl]-2-(3-phenoxypiperidin-1-yl)-acetamide (8.1): MS (ES) 489 (M$^+$); t$_R$ (method B)=14.1 min.

N-[6-(2-Acetylaminoethylamino)-2-phenylpyrimidin-4-yl]-2-[4-(4-chlorophenoxy)-piperidin-1-yl]-acetamide (8.2): MS (ES) 522.9/524.9 (92/32) [MH$^+$], 480.9/482.8 (88/29) [MH$^+$–CH$_2$=CO]; t$_R$ (method B)=14.3 min.

N-[6-(2-Acetylaminoethylamino)-2-phenylpyrimidin-4-yl]-2-[4-(4-methoxyphenoxy)-piperidin-1-yl]-acetamide (8.3): MS (ES) 519 (M$^+$); t$_R$ (method B)=12.6 min.

N-[6-(2-Acetylaminoethylamino)-2-phenylpyrimidin-4-yl]-2-(4-phenoxypiperidin-1-yl)-acetamide (8.4): MS (ES) 489 (M$^+$); t$_R$ (method B)=12.8 min.

N-[6-(2-Acetylaminoethylamino)-2-phenylpyrimidin-4-yl]-2-[4-(3-chlorophenoxy)-piperidin-1-yl]-acetamide (8.5): This compound was prepared from chloroacetamide 6 (37 mg; 0.11 mmol), piperidinium salt 7.5 (35 mg; 0.14 mmol), DIPEA (47 µL; 0.27 mmol) and sodium iodide (16 mg; 0.11 mmol) in a manner analogous to 8.6 yielding a hard white foam after silica gel chromatography (47.8 mg; 86%). LC (method B) t$_R$=13.6 min; $^1$H NMR (200 MHz, CDCl$_3$) δ 9.49 (s, 1H), 8.37 (m, 2H), 7.48 (m, 3H), 7.27-7.15 (m, 2H), 6.93 (m, 2H), 6.81 (m, 1H), 6.50 (brs, 1H), 5.39 (brt, J=5.0 Hz, 1H), 4.41 (m, 1H), 3.68 (m, 2H), 3.53 (m, 2H, 3.19 (s, 2H), 2.86 (m, 2H), 2.56 (m, 2H), 2.20-1.91 (m, 4H). 1.86 (s, 3H). ESIMS 523.0/525.0 (100/42) [MH$^+$], 262 (60), 198 (73).

Large scale reaction: Sodium iodide (2.45 g; 16.3 mmol) was added to a suspension of chloroacetamide 6 (5.67 g; 16.3 mmol), piperidinium chloride 7.5 (4.85 g; 19.5 mmol) and DIPEA (7.0 mL; 40.2 mmol) in 3:1 acetonitrile:THF (480 mL). After 19.5 h the reaction was concentrated on a rotary evaporator. EtOAc (250 mL) was added and the suspension was washed with 50% saturated NaHCO$_3$ (1×50 mL), water (2×25 mL) and saturated NaCl (2×35 mL). The orange-brown solution was dried over MgSO$_4$; charcoal (0.86 g) was added and this was filtered then concentrated leaving a light orange foam. The crude material was purified on silica gel (850 mL) with 12-9:1 EtOAc:i-PrOH. Product was obtained as a pale yellow/off-white hard foam (7.82 g; 92%).

N-[6-(2-Acetylaminoethylamino)-2-phenylpyrimidin-4-yl]-2-[4-(3-chlorophenoxy)-piperidin-1-yl]-acetamide dihydrochloride (8.5-2HCl): Hydrogen chloride in dioxane (4 M; 6.5 mL; 26 mmol) was added to a solution of free base 8.5 (3.38 g; 6.46 mmol) in methanol (34 mL). The slightly turbid solution was filtered through a plug of glass wool and the glassware rinsed with methanol (2×5 mL). Anhydrous ether was carefully added until a persistent precipitate just formed (56 mL). After 1 h at room temperature the flask was put into a refrigerator overnight. The white precipitate was collected on a Büchner funnel and rinsed with 4:1 ether:methanol (30 mL), 9:1 ether:methanol (30 mL) and ether (50 mL). Product was obtained as a white solid (2.88 g; 75%), mp. 195° C. (decomp.). ESIMS 522.9/524.9 (80/28) [MH$^+$], 262.0 (50), 198.0 (100). $^1$H NMR (D$_2$O) δ 8.14 (m, 2H), 7.83-7.62 (m, 4H), 7.40 (m, 1H), 7.22-7.01 (m, 3H), 4.87 (m, 1H), 4.43 (s, 2H), 3.82-3.46 (m, 8H), 2.31 (m, 4H), 1.94 (s, 3H). UV (MeOH): λ$_{max}$/nm (log ε)=237 (4.72), 205 (4.78).

N-[6-(2-Acetylaminoethylamino)-2-phenylpyrimidin-4-yl]-2-[4-(2-chlorophenoxy)-piperidin-1-yl]-acetamide (8.6): Sodium iodide (19 mg; 0.13 mmol) was added to a solution of chloroacetamide 6 (40 mg; 0.12 mmol), piperidine 7.6 (31 mg; 0.15 mmol) and DIPEA (30 μL; 0.17 mmol) in 3:1 acetonitrile:THF (2 mL). After 22 h the reaction was filtered through a short plug of silica gel with THF as a wash. The solution was concentrated in vacuo then purified on silica gel (20 mL) with 10:1 EtOAc:i-PrOH yielding a hard white foam (59.2 mg; 98%). LC (method B) t$_R$=12.9 min; $^1$H NMR (200 MHz, CDCl$_3$) δ 9.51 (s, 1H), 8.37 (m, 2H), 7.47 (m, 3H), 7.38 (m, 1H), 7.31-7.14 (m, 2H), 7.02-6.86 (m, 2H), 6.72 (brs, 1H), 5.69 (brt, J=5.6 Hz, 1H), 4.48 (m, 1H), 3.67 (m, 2H), 3.53 (m, 2H), 3.19 (s, 2H), 2.90 (m, 2H), 2.56 (m, 2H), 2.20-2.00 (m, 4H), 1.86 (s, 3H). ESIMS 523.0/525.0 (100/42) [MH$^+$], 262 (58), 198 (75).

N-[6-(2-Acetylaminoethylamino)-2-phenylpyrimidin-4-yl]-2-(4-phenylpiperidin-1-yl)acetamide (8.7): MS (ES) 473 (M$^+$); t$_R$ (method B)=4.1 min.

N-[6-(2-Acetylaminoethylamino)-2-phenylpyrimidin-4-yl]-2-[4-(4-methoxybenzyl)-piperidin-1-yl]-acetamide (8.8): A solution of chloroacetamide 6 (41 mg; 0.118 mmol), piperidine 7.8 (27 mg; 0.132 mmol) and DIPEA (30 μL; 0.172 mmol) in 2.5 mL of 3:2 acetonitrile:THF was reacted at rt for 8 days; whereupon the reaction was concentrated on a rotary evaporator then purified on silica gel (20 mL) with 12:1 EtOAc:i-PrOH yielding a glassy material. A solution of the product in DCM plus hexanes was evaporated leaving a white solid (23 mg; 38%). LC (method B) t$_R$=12.8 min; $^1$H NMR (200 MHz, CDCl$_3$) δ 9.53 (brs, 1H), 8.37 (m, 2H), 7.48 (m, 3H), 7.22 (s, 1H), 7.08 (m, 2H), 6.84 (m, 3H), 6.62 (brs, 1H), 5.50 (brt, J=5.5 Hz, 1H), 3.79 (s, 3H), 3.68 (m, 2H), 3.53 (m, 2H), 3.10 (s, 2H), 2.88 (m, 2H), 2.54 (m, 2H), 2.20 (m, 2H), 1.85 (s, 3H), 1.80-1.20 (m, 5H); ESIMS 517.0 (28) [MH$^+$], 259.1 (100).

N-[6-(2-Acetylaminoethylamino)-2-phenylpyrimidin-4-yl]-2-[4-(4-fluorobenzyl)-piperidin-1-yl]-acetamide (8.9): This compound was prepared from chloroacetamide 6 (77 mg; 0.221 mmol) and 4-(4-fluorobenzyl)-piperidine (7.9) (47 mg; 0.24 mmol) in a manner analogous to 8.8 yielding a white crystalline solid (80.5 mg; 72%) after silica gel chromatography (12-8:1 EtOAc:i-PrOH). LC (method B) t$_R$=13.1 min; $^1$H NMR (200 MHz, CDCl$_3$) δ 9.51 (brs, 1H), 8.37 (m, 2H), 7.48 (m, 3H), 7.22 (s, 1H), 7.11 (m, 2H), 6.98 (m, 2H), 6.58 (brs, 1H), 5.45 (brt, J=5.4 Hz, 1H), 3.68 (m, 2H), 3.53 (m, 2H), 3.11 (s, 2H), 2.89 (m, 2H), 2.57 (m, 2H), 2.20 (m, 2H), 1.86 (s, 3H), 1.80-1.30 (m, 5H); ESIMS 505.0 (42) [MH$^+$], 253.1 (100).

N-[6-(2-Acetylaminoethylamino)-2-phenylpyrimidin-4-yl]-2-[4-(2-chlorobenzyl)-piperidin-1-yl]-acetamide (8.10): This compound was prepared from chloroacetamide 6 (40 mg; 0.12 mmol) and piperidine 7.10 (29 mg; 0.14 mmol) in a manner analogous to 8.6, yielding a hard white foam after silica gel chromatography (33.9 mg; 57%). LC (method B) t$_R$=12.5 min; $^1$H NMR (200 MHz, CDCl$_3$) δ 9.52 (s, 1H), 8.38 (m, 2H), 7.49 (m, 3H), 7.40-7.08 (m, 5H), 6.83 (brs, 1H), 5.83 (brt, J=5.6 Hz, 1H), 3.66 (m, 2H), 3.52 (m, 2H), 3.11 (s, 2H), 2.88 (m, 2H), 2.73 (m, 2H), 2.20 (m, 2H), 1.85 (s, 3H), 1.80-1.35 (m, 5H). ESIMS 521.0/523.0 (41/18) [MH$^+$], 479.0/481.0 (50/20) [MH$^+$–CH$_2$═CO], 261 (100).

N-[6-(2-Acetylaminoethylamino)-2-phenylpyrimidin-4-yl]-2-[4-(3-chlorobenzyl)-piperidin-1-yl]-acetamide (8.11): This compound was prepared from chloroacetamide 6 (40 mg; 0.12 mmol) and piperidine 7.11 (29 mg; 0.14 mmol) in a manner analogous to 8.6 yielding a white solid after silica gel chromatography (54.0 mg; 90%). LC (method B) t$_R$=12.5 min; $^1$H NMR (200 MHz, CDCl$_3$) δ 9.49 (s, 1H), 8.37 (m, 2H), 7.48 (m, 3H), 7.26-7.11 (m, 4H), 7.04 (m, 1H), 6.56 (brs, 1H), 5.45 (brt, J=5.5 Hz, 1H), 3.68 (m, 2H), 3.52 (m, 2H), 3.11 (s, 2H), 2.89 (m, 2H), 2.58 (m, 2H), 2.21 (m, 2H), 1.86 (s, 3H), 1.79-1.34 (m, 5H). $^{13}$C NMR (50.3 MHz, CDCl$_3$) δ 171.0, 170.7, 164.5, 163.6, 156.0, 142.4, 137.7, 134.0, 130.5, 129.5, 129.1, 128.3, 127.9, 127.3, 126.1, 89.8, 62.6, 54.2, 42.6, 40.9, 37.1, 32.1, 23.1. ESIMS 521.0/523.0 (42/18) [MH$^+$], 479.0/481.0 (55/22) [MH$^+$–CH$_2$═CO], 261 (100).

N-[6-(2-Acetylaminoethylamino)-2-phenylpyrimidin-4-yl]-2-[4-(4-chlorobenzyl)-piperidin-1-yl]-acetamide (8.12): This compound was prepared from chloroacetamide 6 (40 mg; 0.12 mmol), piperidinium salt 7.12 (45 mg; 0.14 mmol), DIPEA (50 μL; 0.29 mmol) and sodium iodide (19 mg; 0.13 mmol) in a manner analogous to 8.6 yielding a white crystalline solid after silica gel chromatography (45.8 mg; 76%). LC (method B) t$_R$=12.6 min; $^1$H NMR (400 MHz, CDCl$_3$) δ 9.49 (s, 1H), 8.36 (m, 2H), 7.48 (m, 3H), 7.26 (m, 2H), 7.22 (s, 1H), 7.09 (m, 2H), 6.56 (brs, 1H), 5.41 (brs, 1H), 3.68 (m, 2H), 3.52 (m, 2H), 3.10 (s, 2H), 2.88 (m, 2H), 2.57 (m, 2H), 2.19 (m, 2H), 1.85 (s, 3H), 1.66 (m, 2H), 1.54 (m, 1H), 1.44 (m, 2H). ESIMS 521.0/523.0 (55/22) [MH$^+$], 479.0/481.0 (67/23) [MH$^+$–CH$_2$═CO], 261 (100).

N-[6-(2-Acetylaminoethylamino)-2-phenylpyrimidin-4-yl]-2-(4-benzyl-4-hydroxy-piperidin-1-yl)-acetamide (8.13): MS (ES) 503 (M$^+$); t$_R$ (method B)=3.8 min.

N-[6-(2-Acetylaminoethylamino)-2-phenylpyrimidn-4-yl]-2-(4-cyano-4-phenyl-piperidin-1-yl)-acetamide (8.14): MS (ES) 498 (M$^+$); t$_R$ (method B)=5.8 min.

N-[6-(2-Acetylaminoethylamino)-2-phenylpyrimidin-4-yl]-2-[4-(2-chlorophenyl)-4-cyanopiperidin-1-yl]-acetamide (8.15): MS (ES) 531.9/533.9 (100/39) [MH$^+$]; t$_R$ (method B)=6.1 min.

N-[6-(2-Acetylaminoethylamino)-2-phenylpyrimidin-4-yl]-2-(4-benzyl-cis-3,5-dimethylpiperazin-1-yl)-acetamide (8.16): MS (ES) 516 (M$^+$); t$_R$ (method B)=11.5 min.

N-[6-(2-Acetylaminoethylamino)-2-phenylpyrimidin-4-yl]-2-(4-phenylpiperazin-1-yl)-acetamide (8.17): MS (ES) 474 (M$^+$); t$_R$ (method B)=4.9 min.

N-[6-(2-Acetylaminoethylamino)-2-phenylpyrimidin-4-yl]-2-(4-benzylpiperazin-1-yl)-acetamide (8.18): MS (ES) 488 (M$^+$); t$_R$ (method B)=3.7 min.

N-[6-(2-Acetylaminoethylamino)-2-phenylpyrimidin-4-yl]-2-[4-(4-methoxybenzyl)-piperazin-1-yl]-acetamide (8.19): MS (ES) 518 (M$^+$); t$_R$ (method B)=4.0 min.

N-[6-(2-Acetylaminoethylamino)-2-phenylpyrimidin-4-yl]-2-[4-(2-methoxybenzyl)-piperazin-1-yl]-acetamide (8.20): MS (ES) 518 (M$^+$); t$_R$ (method B)=11.4 min.

N-[6-(2-Acetylaminoethylamino)-2-phenylpyrimidin-4-yl]-2-[4-(3-methoxybenzyl)-piperazin-1-yl]-acetamide (8.21): MS (ES) 518 (M$^+$); t$_R$ (method B)=11.2 min.

N-[6-(2-Acetylaminoethylamino)-2-phenylpyrimidin-4-yl]-2-[4-(4-chlorobenzyl)-piperazin-1-yl]-acetamide (8.22): MS (ES) 521.9/523.9 (100/38) [MH$^+$], 397.9 (69) [MH$^+$–3-ClPhCH$_2$]; t$_R$ (method B)=3.7 min.

N-[6-(2-Acetylaminoethylamino)-2-phenylpyrimidin-4-yl]-2-[4-(2-chlorobenzyl)-piperazin-1-yl]-acetamide (8.23): MS (ES) 522.0/524.0 (12/4) [MH$^+$], 397.9 (100) [MH$^+$–3-ClPhCH$_2$]; t$_R$ (method B)=11.8 min.

N-[6-(2-Acetylaminoethylamino)-2-phenylpyrimidin-4-yl]-2-[4-(3-chlorobenzyl)-piperazin-1-yl]-acetamide (8.24): MS (ES) 522.0/524.0 (14/5) [MH$^+$], 398.0 (100) [MH$^+$3-ClPhCH$_2$]; $^1$H NMR (200 MHz, CDCl$_3$) δ 9.45 (s, 1H), 8.41-8.32 (m, 2H), 7.55-7.42 (m, 3H), 7.36 (s, 1H), 7.27-7.18 (m, 4H), 6.46 (brs, 1H), 5.35 (brs, 1H), 3.75-3.62 (m, 2H), 3.58-3.47 (m, 2H), 3.55 (s, 2H), 3.17 (s, 2H), 2.71-2.52 (m, 8H), 1.86 (s, 3H); t$_R$ (method B)=12.1 min; t$_R$ (method A)=5.5 min.

N-[6-(2-Acetylaminoethylamino)-2-phenylpyrimidin-4-yl]-2-[4-(3-chlorobenzyl)-piperazin-1-yl]-acetamide trihydrochloride (8.24·3HCl): Prepared similarly to 8.40·3HCl and triturated with acetone. Off-white solid, mp. 192-194° C. (decomp.). MS (ES) 522.0/524.0 (38/13) [MH$^+$], 398.0 (100) [MH$^+$–3-ClPhCH$_2$]. $^1$H NMR (200 MHz, D$_2$O) δ 8.14-8.02 (m, 2H), 7.83-7.43 (m, 8H), 4.44 (s, 2H), 3.90-3.62 (m, 4H), 3.60-3.45 (m, 4H), 3.48 (s, 2H), 3.22 (brs, 4H), 1.88 (s, 3H). UV (MeOH): λ$_{max}$/nm (log ε)=238 (4.63), 209 (4.59).

N-[6-(2-Acetylaminoethylamino)-2-phenylpyrimidin-4-yl]-2-[4-(3-fluorobenzyl)-piperazine-1-yl]-acetamide (8.25): (20%) $^1$H NMR (200 MHz, CDCl$_3$) δ 9.44 (s, 1H), 8.36 (m, 2H), 7.46 (m, 3H), 7.21 (m, 2H), 7.11 (m, 3H), 6.95 (m, 1H), 6.60 (m, 1H), 5.55 (m, 1H), 3.66 (m, 2H), 3.56 (m, 4H), 3.16 (s, 2H), 2.63 (m, 8H), 1.85 (s, 3H). MS (ES) 506 (M$^+$). t$_R$ (method B)=9.5 min.

N-[6-(2-Acetylaminoethylamino)-2-phenylpyrimidin-4-yl]-2-[4-(2-fluorobenzyl)-piperazine-1-yl]-acetamide (8.26): (54%) $^1$H NMR (200 MHz, CDCl$_3$) δ 9.44 (s, 1H), 8.33 (m, 2H), 7.48 (m, 3H), 7.29-7.04 (m, 7H) 6.54 (m, 1H), 5.44 (m, 1H), 3.66 (m, 4H) 3.53 (m, 2H), 3.15 (s, 2H), 2.65 (m, 8H) 1.86 (s, 3H). MS (ES) 506 (M$^+$). t$_R$ (method B)=9.2 min.

N-[6-(2-Acetylaminoethylamino)-2-phenylpyrimidin-4-yl]-2-[4-(3-trifluoromethyl-benzyl)-piperazine-1-yl]-acetamide (8.27): (28%) $^1$H NMR (200 MHz, CDCl$_3$) δ 9.45 (s, 1H), 8.36 (m, 2H), 7.62-7.48 (m, 7H), 7.22 (s, 1H), 6.52 (m, 1H), 5.44 (m, 1H), 3.68 (m, 2H), 3.63 (s, 2H), 3.54 (m, 2H), 3.17 (s, 2H), 2.66 (m, 8H). MS (ES) 556 (M$^+$). t$_R$ (method A)=10.9 min.

N-[6-(2-Acetylaminoethylamino)-2-phenylpyrimidin-4-yl]-2-(4-pyridin-3-ylmethyl-piperazine-1-yl)-acetamide (8.28): (69%) $^1$H NMR (200 MHz, CDCl$_3$) δ 9.42 (s, 1H), 8.56 (s, 1H) 8.50 (d, 1H, J=4.0 Hz), 8.36 (m, 2H), 7.67 (d, 1H, J=8.0 Hz), 7.45 (m, 3H), 7.29-7.20 (m, 2H), 6.59 (m, 1H), 5.54 (m, 1H), 3.66 (m, 2H), 3.57-3.49 (m, 4H), 3.15 (s, 2H), 2.61 (m, 8H), 1.85 (s, 3H). MS (ES) 489 (M$^+$). t$_R$ (method B)=6.7 min.

N-[6-(2-Acetylaminoethylamino)-2-phenylpyrimidin-4-yl]-2-(4-pyridin-2-ylmethyl-piperazine-1-yl)-acetamide (8.29): (54%) $^1$H NMR (200 MHz, CDCl$_3$+CD$_3$OD) δ 8.52 (d, 1H, J=3.6 Hz) 8.31 (m, 2H), 7.74 (ddd, 1H, J=7.4 Hz, 5.8 Hz, 1.5 Hz) 7.48 (m, 4H), 7.24 (dd, 1H, J=6.6 Hz, 5.8 Hz), 7.16 (s, 1H), 3.74 (s, 2H), 3.64 (m, 2H) 3.41 (m, 4H), 3.18 (s, 2H), 2.69 (m, 8H), 1.86 (s, 3H). MS (ES) 489 (M$^+$). t$_R$ (method B)=7.4 min.

N-[6-(2-Acetlaminoethylamino)-2-phenylpyrimidin-4yl]-2-(4-pyridin-4-ylmethyl-piperazine-1-yl)-acetamide (8.30): (47%) $^1$H NMR (200 MHz, CDCl$_3$) δ 9.43 (s, 1H), 8.55 (d, 2H, J=5.8 Hz), 8.36 (m, 2H), 7.26 (m, 3H), 7.28 (d, 2H, J=6.0 Hz), 6.60 (m, 1H), 5.56 (m, 1H) 3.67 (m, 2H), 3.58 (m, 4H) 3.17 (s, 2H), 2.63 (m, 8H) 1.86 (s, 3H). MS (ES) 489 (M$^+$). t$_R$ (method B)=6.1 min.

N-[6-(2-Acetylaminoethylamino)-2-phenylpyrimidin-4-yl]-2-(4-cyclohexylmethyl-piperazin-1-yl)-acetamide (8.31): MS (ES) 494 (M$^+$); t$_R$ (method B)=3.9 min. yl)-acetamide (8.32): MS (ES) 502 (M$^+$); t$_R$ (method B)=3.9 min.

N-[6-(2-Acetylaminoethylamino)-2-phenylpyrimidin-4-yl]-2-(4-phenyl-[1,4]diazepan-1-yl)-acetamide (8.33): MS (ES) 489 (M$^+$); t$_R$ (method B)=4.6 min.

N-[6-(2-Acetylaminoethylamino)-2-phenylpyrimidin-4-yl]-2-(4-phenethyl-[1,4]diazepan-1-yl)-acetamide (8.34): MS (ES) 516 (M$^+$); t$_R$ (method B)=3.9 min.

N-[6-(2-Acetylaminoethylamino)-2-phenylpyrimidin-4-yl]-2-(4-benzyl-[1,4]diazepan-1-yl)-acetamide (8.35): MS (ES) 502 (M$^+$); t$_R$ (method B)=3.7 min.

N-[6-(2-Acetylaminoethylamino)-2-phenylpyrimidin-4yl]-2-[4-(2-fluorobenzyl)-[1,4]diazapan-1-yl]-acetamide (8.36): (60%). $^1$H NMR (200 MHz, CDCl$_3$) δ 9.69 (s, 1H) 8.42 (m, 2H), 7.53 (m, 3H), 7.32 (m, 3H), 7.14 (m, 2H), 6.74 (m, 1H), 5.68 (m, 1H) 3.85 (s, 2H), 3.74 (m, 2H), 3.60 (m, 2H), 3.38 (s, 2H), 2.91 (m, 8H), 1.93 (m, 5H). MS (ES) 520 (M$^+$). t$_R$ (method B)=9.1 min.

N-[6-(2-Acetylaminoethylamino)-2-phenylpyrimidin-4yl]-2-[4-(3-fluorobenzyl)-[1,4]diazapan-1-yl]-acetamide (8.37): (45%) $^1$H NMR (200 MHz, CDCl$_3$) δ 9.63 (s, 1H), 8.36 (m, 2H), 7.48 (m, 3H), 7.21 (m, 4H), 6.91 (m, 1H), 6.53 (m, 1H) 5.51 (m, 1H), 3.71 (m, 4H), 3.53 (m, 2H), 3.31 (s, 2H), 2.80 (m, 8H), 1.86 (m, 5H). MS (ES) 520 (M$^+$). t$_R$ (method A)=9.4 min.

N-[6-(2-Acetylaminoethylamino)-2-phenylpyrimidin-4yl]-2-[4-(4-fluorobenzyl)-[1,4]diazapan-1-yl]-acetamide (8.38): (64%) $^1$H NMR (200 MHz, CDCl$_3$) δ 9.64 (s, 1H), 8.36 (m, 2H), 7.48 (m, 3H), 7.37-7.26 (m, 3H) 6.99 (dd, 2H, J=8.6 Hz, 8.8 Hz) 6.53 (m, 1H), 5.39 (m, 1H), 3.67 (m, 4H), 3.54 (m, 2H), 3.31 (s, 2H) 2.83 (m, 8H), 1.86 (5H). MS (ES) 520 (M$^+$). t$_R$ (method A)=9.4 min.

N-[6-(2-Acetylaminoethylamino)-2-phenylpyrimidin-4yl]-2-[4-(2-trifluoromethylbenzyl)-[1,4]diazapan-1-yl]-acetamide (8.39): (54%) $^1$H NMR (200 MHz, CDCl$_3$) δ 9.67 (s, 1H), 8.36 (m, 2H), 7.87 (d, 1H, J=8.2 Hz) 7.62 (d, 1H, J=7.4 Hz) 7.48 (m, 4H), 7.26-7.22 (m, 2H), 6.60 (m, 1H), 5.45 (m, 1H) 3.85 (s, 2H), 3.68 (m, 2H), 3.53 (m, 2H), 3.49 (s, 2H), 2.81 (m, 8H), 1.85 (m, 5H). MS (ES) 570 (M$^+$). t$_R$ (method B)=10.9 min.

N-[6-(2-Acetylaminoethylamino)-2-phenylpyrimidin-4yl]-2-[4-(3-trifluoromethylbenzyl)-[1,4]diazepan-1-yl]-acetamide (8.40): Sodium iodide (903 mg; 6.02 mmol) was added to a solution of chloroacetamide 6 (2.088 g; 6.00 mmol), 1-(3-trifluoromethylbenzyl)-[1,4]diazepane (7.40) (1.863 g; 7.21 mmol) and DIPEA (1.45 mL; 8.32 mmol) in 3:1 acetonitrile:THF (30 mL). After 21 h the reaction was concentrated on a rotary evaporator. EtOAc (90 mL) was added and the suspension was washed with 50% saturated NaHCO$_3$ (25 mL), water (3×25 mL) and saturated NaCl (2×25 mL). The solution was dried (MgSO$_4$), filtered, concentrated to an oil then purified on silica gel (340 mL), eluting with 9:1 EtOAc:methanol. Pure product was obtained as a hard white foam (3.10 g; 91%). LC (method B) $t_R$=12.6 min; $^1$H NMR (200 MHz, CDCl$_3$) δ 9.64 (s, 1H), 8.36 (m, 2H), 7.7-7.3 (m, 7H), 7.22 (s, 1H), 6.56 (brs, 1H), 5.42 (brt, J=5.8 Hz, 1H), 3.75 (s, 2H), 3.68 (m, 2H), 3.54 (m, 2H), 3.32 (s, 2H), 3.0-2.7 (m, 8H), 1.93 (m, 2H), 1.65 (s, 3H). ESIMS 570 (12) [MH$^+$], 286 (100).

N-[6-(2-Acetylaminoethylamino)-2-phenylpyrimidin-4-yl]-2-[4-(3-trifluoromethylbenzyl)-[1,4]diazepan-1-yl]-acetamide trihydrochloride (8.40.3HCl): HCl-saturated methanol (10 mL) was added to a solution (10 mL) of free base 8.40 (2.88 g; 5.06 mmol) in methanol (10 mL). The solution was filtered then concentrated in vacuo affording product as an off-white hard foam (3.30 g; 96%), mp. 160° C. (decomp.). LC (method B) $t_R$=12.5 min; $^1$H NMR (D$_2$O) δ 8.08 (m, 2H), 7.87 (m, 2H), 7.79 (m, 1H), 7.70 (m, 2H), 7.61 (m, 2H), 4.55 (s, 2H), 4.14 (brs, 2H), 3.8-3.4 (m, 12H), 2.27 (m, 2H), 1.86 (brs, 3H); ESIMS 569.9 (23) [MH$^+$], 285.6 (100). ESIMS 570.0 (24) [MH$^+$], 285.5 (100). UV (MeOH): $\lambda_{max}$/nm (log ε)=238 (4.62), 205 (4.60).

N-[6-(2-Acetylaminoethylamino)-2-phenylpyrimidin-4yl]-2-[4-(4-trifluoromethylbenzyl)-[1,4]diazapan-1-yl]-acetamide (8.41): (18%) $^1$H NMR (200 MHz, CDCl$_3$) δ 9.63 (s, 1H), 8.36 (m, 2H), 7.51 (m, 7H), 7.21 (s, 1H), 6.62 (m, 1H), 5.53 (m, 1H), 3.75 (s, 2H), 3.67 (m, 2H), 3.53 (m, 2H), 3.32 (s, 2H), 2.95-2.76 (m, 8H), 1.86 (m, 5H). MS (ES) 570 (M$^+$). $t_R$ (method B)=11.0 min N-[6-(2-Acetylaminoethylamino)-2-phenylpyrimidin-4yl]-2-(4-pyridin-3-ylmethyl-[1,4]diazapan-1-yl)-acetamide (8.42): (82%) $^1$H NMR (200 MHz, CDCl$_3$) δ 9.62 (s, 1H) 8.57 (s, 1H) 8.50 (d, 1H, J=3 Hz) 8.35 (m, 2H), 7.73 (d, 1H, J=8 Hz) 7.47 (m, 3H) 7.21 (s, 1H) 6.58 (m, 1H) 5.46 (m, 1H) 3.71 (m, 4H), 3.53 (m, 2H) 3.31 (s, 2H), 2.90-2.76 (m, 8H), 1.86 (m, 5H). MS (ES) 503 (M$^+$). $t_R$ (method B)=6.8 min.

N-[5-(2-Acetylaminoethylamino)-biphenyl-3-yl]-2-[4-(3-chlorobenzyl)-[1,4]diazepan-1-yl]-acetamide (8.43): Yield 99%. MS (ES): m/z 535.9/538.0 (57/19) [MH$^+$]. $^1$H NMR (200 MHz, CDCl$_3$) δ 9.64 (s, 1H), 8.40-8.32 (m, 2H), 7.50-7.42 (m, 3H), 7.37 (s, 1H), 7.26-7.20 (m, 4H), 6.52 (brs, 1H), 5.36 (brs, 1H), 3.75-3.62 (m, 2H), 3.67 (s, 2H), 3.58-3.47 (m, 2H) 3.32 (s, 2H), 2.95-2.72 (m, 8H), 1.96-1.85 (m, 2H), 1.86 (s, 3H). $t_R$ (method A)=5.6 min.

N-[5-(2-Acetylaminoethylamino)-biphenyl-3-yl]-2-(4-pyridin-2-ylmethyl-[1,4]diazepan-1-yl)-acetamide (8.44): Yield 70%. MS (ES): m/z 502.9 (32) [MH$^+$]. $^1$H NMR (200 MHz, CDCl$_3$) δ 9.63 (s, 1H), 8.50 (dd, 1H, J=1.8, 4.8 Hz), 8.40-8.32 (m, 2H), 7.66 (dt, 1H, J=1.8, 7.6 Hz), 7.55-7.44 (m, 4H), 7.24-7.12 (m, 1H), 7.21 (s, 1H), 6.52 (brs, 1H) 5.34 (brs, 1H) 3.88 (s, 2H), 3.75-3.62 (m, 2H), 3.58-3.47 (m, 2H) 3.32 (s, 2H), 2.95-2.80 (m, 8H), 2.00-1.85 (m, 2H), 1.86 (s, 3H). $t_R$ (method B)=9.4 min.

N-[5-(2-Acetylaminoethylamino)-biphenyl-3-yl]-2-[4-(6-methylpyridin-2-ylmethyl)-[1,4]diazepan-1-yl]-acetamide (8.45): Yield 93%. MS (ES): m/z 516.9 (23) [M$^+$]. $^1$H NMR (200 MHz, CDCl$_3$, 200 MHz) δ 9.64 (s, 1H), 8.40-8.33 (m, 2H), 7.55 (t, 1H, J=7.9 Hz), 7.50-7.42 (m, 3H), 7.34 (d, 1H, J=7.8 Hz), 7.22 (s, 1H), 7.02 (d, 1H, J=8.0 Hz), 6.52 (brs, 1H) 5.34 (brs, 1H) 3.85 (s, 2H), 3.75-3.62 (m, 2H), 3.58-3.47 (m, 2H) 3.32 (s, 2H), 2.95-2.80 (m, 8H), 2.54 (s, 3H), 2.00-1.85 (m, 2H), 1.86 (s, 3H). $t_R$ (method B)=9.9 min.

N-[6-(2-Acetylaminoethylamino)-2-phenylpyrimidin-4-yl]-2-[4-(4-chlorophenyl)-4-hydroxypiperidin-1-yl]-acetamide (8.46): MS (ES) 523.3/525.3 (70/25) [MH$^+$].

Example 5

Synthesis of Compounds 8.47-8.128 (for Library Format)

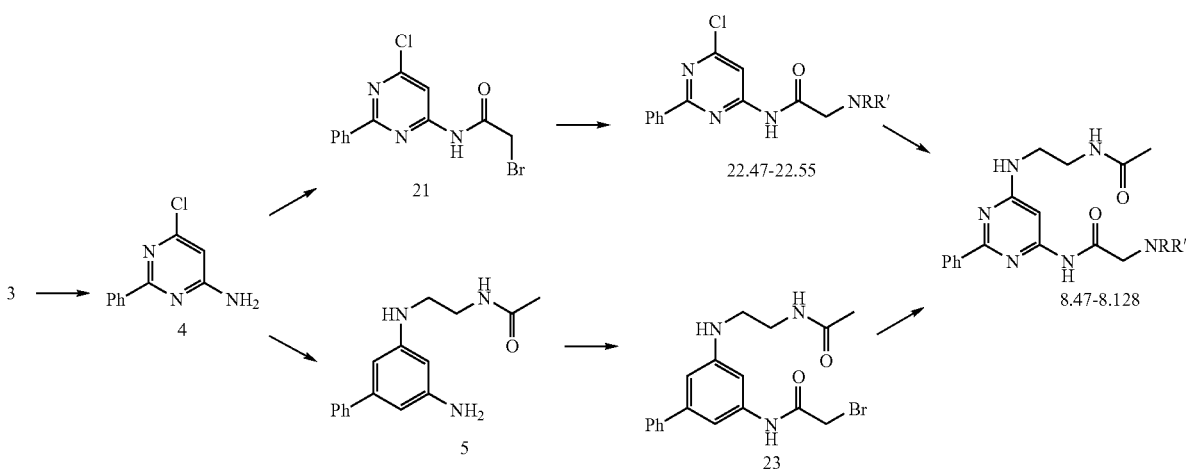

Scheme IV 6-chloro-2-phenylpyrimidin-4-amine (4)

4,6-dichloro-2-phenylpyrimidine (3) (5.0 g) (literature reference: Biagi, Giuliana: Giorgi, Irene; Livi, Oreste; Scartoni, Valerio; Lucacchini, Antonio; *Farmaco:* 52; 1; 1997; 61-66) was dissolved in DMSO (50ml) in a sealable vessel. Ammonia gas was then bubbled through the solution for 15 minutes, the vessel sealed and the reaction left to stir for 24 hr. The solution was partitioned between ethyl acetate (200 ml) and water (200 ml) and the aqueous phase extracted with ethyl acetate (2×100 ml). The combined organic phases were washed with brine (100 ml), dried over anhydrous magnesium sulfate and concentrated in vacuo, affording the title compound (3.87 g).

$\delta_H$ (CDCl$_3$): 5.0 (2H, s), 6.38 (1H, s), 7.41-7.48 (3H, m), 8.35-8.38 (2H, d); m/z (ES$^+$) 206 (MH)$^+$ 2-Bromo-N-(6-chloro-2-phenylpyrimidin-4-yl)acetamide (21)

6-chloro-2-phenylpyrimidin-4-amine (4) (830 mg) was dissolved in anhydrous DCM (50 ml). To this was added dropwise a solution of bromoacetylbromide (1.05 ml in 10 ml DCM), forming a precipitate after 10 min. To this was then added dropwise a solution of N,N-diisopropylethylamine (1.06 ml in 10 ml DCM) and the solution left for 1 hr. The solvent was removed in vacuo, then the crude solid purified by flash chromatography on silica gel eluting with a mixture of ethyl acetate and petroleum ether (1:9 then 1:1 v/v), furnishing the title compound as a solid (1.09 g).

$\delta_H$ (CDCl$_3$): 4.02 (2H, s), 7.42-7.52 (3H, m), 8.05 (1H, s), 8.35-8.42 (2H, d), 8.75-8.80 (1H, s); m/z (ES$^+$) 328 (MH)$^+$ N-(6-chloro-2-phenylpyrimidin-4-yl)-2-piperidin-1-ylacetamide (22.47)

2-Bromo-N-(6-chloro-2-phenylpyrimidin-4-yl)acetamide (28 mg) was dissolved in acetonitrile (2 ml) and piperidine added (23 µl in 500 µl acetonitrile). The mixture was left to stir for 1.5 hr after which time the solvent was removed in vacuo. Purification using a short silica plug, eluting with a mixture of ethyl acetate and petroleum ether (1:1 v/v) furnished the title compound (25 mg).

$\delta_H$ (CDCl$_3$): 1.48-1.52 (2H, m), 1.63-1.78 (4H, m), 2.50-2.60 (4H, m), 3.15 (2H, s), 7.42-7.51 (3H, m), 8.14 (1H, s), 8.38-8.42 (2H, d); m/z (ES$^+$) 331 (MH)$^+$ N-(6-chloro-2-phenylpyrimidin-4-yl)-2-[4-(4-trifluromethyl-2-nitrophenyl)piperazin-1-yl]acetamide (22.48)

2-Bromo-N-(6-chloro-2-phenylpyrimidin-4-yl)acetamide (100 mg) was dissolved in acetonitrile (5 ml) and (4-trifluromethyl-2-nitrophenyl)piperazine (253 mg) added. The solution was stirred overnight at room temperature. After this time the solvent was removed in vacuo. Purification by flash chromatography on silica gel eluting with a mixture of dichloromethane and methanol (98:2, then 93:7 v/v) afforded the title compound. m/z (ES$^+$) 521 (MH)$^+$ Compounds 22.49-22.53 were synthesized in an analogous manner:

2-[4-(3-Chloro-5-trifluoromethylpyridin-2-yl)piperazin-1-yl]-N-(6-chloro-2-phenylpyrimidin-4-yl)acetamide (22.49): m/z (ES$^+$) 511 (MH)$^+$.

N-(6-Chloro-2-phenylpyrimidin-4-yl)-2-[4-(3-phenylpropyl)piperazin-1-yl]acetamide (22.50): m/z (ES$^+$) 450 (MH)$^+$.

2-[4-(4-tert-Butylbenzyl)piperazin-1-yl]-N-(6-chloro-2-phenylpyrimidin-4-yl)acetamide (22.51): m/z (ES$^+$) 478 (MH)$^+$.

N-(6-Chloro-2-phenylpyrimidin-4-yl)-2-(4-pyrrolidin-1-ylpiperidin-1-yl)acetamide (22.52): m/z (ES$^+$) 400 (MH)$^+$.

N-(6-Chloro-2-phenylpyrimidin-4-yl)-2-(4-hydroxy-4-thien-2-ylpiperidin-1-yl)acetamide (22.53): m/z (ES$^+$) 411 (M+H–H$_2$O)$^+$.

N-(6-Chloro-2-phenylpyrimidin-4-yl)-2-{4-[(2E)-3-phenylprop-2-enyl]piperazin-1-yl}acetamide (22.54).

To a stirred solution of 2-bromo-N-(6-chloro-2-phenylpyrimidin-4-yl)acetamide (0.80 g in 40 ml acetonitrile) was added [(2E)-3-phenylprop-2-enyl]piperazine (0.50 g in 10 ml acetonitrile). After 3 hrs, N,N-diisopropylethylamine was added (428 µl in 10 ml acetonitrile) and the reaction stirred for a further 2 hrs after which time a precipitate of the title compound appeared. This was used crude in the next step.

m/z (ES$^+$) 448 (MH)$^+$

Compound 22.55 was synthesised in an analogous manner:

N-(6-chloro-2-phenylpyrimidin-4-yl)-2-(4-benzylpiperidin-1-yl)acetamide (22.55): m/z (ES$^+$) 421 (MH)$^+$.

N-(6-{([2-(acetylamino)ethyl]amino}-2-phenylpyrimidin-4-yl)-2-piperidin-1-ylacetamide (8.47)

N-(6-Chloro-2-phenylpyrimidin-4-yl)-2-piperidin-1-ylacetamide (25 mg) was dissolved in DMSO (1 ml) and N-acetylethylenediamine (78 mg) added. A reflux condenser was fitted and the mixture heated to 130° C. with stirring for 16 hrs. The reaction was cooled to room temperature and the solvent removed in vacuo. Purification via flash chromatography on silica gel, eluting with a mixture of dichloromethane and methanol (95:5, then 93:7 v/v) yielded the title compound (18 mg).

$\delta_H$ (CDCl$_3$): 1.50-1.58 (2H, m), 1.69-1.78 (4H, m), 1.89 (3H, s), 2.50-2.60 (4H, m), 3.12 (2H, s), 3.51-3.58 (2H, m); 3.67-3.75 (2H, m), 5.35-5.43 (1H, br s), 7.27 (1H, s), 7.48-7.52 (3H, m), 8.36-8.42 (2H, m), 9.61 (1H, s); m/z$^-$(ES$^+$) 397 (MH)$^+$ Compounds 8.48-8.55 were synthesised in an analogous manner apart from where otherwise indicated:

N-(6-{[2-(acetylamino)ethyl]amino}-2-phenylpyrimidin-4-yl)-2-{4-[2-nitro-4-(trifluoromethyl)phenyl]piperazin-1-yl}acetamide (8.48): 59 mg over 2 steps from 100 mg 2-bromo-N-(6-chloro-2-phenylpyrimidin-4-yl)acetamide.

$\delta_H$ (CDCl$_3$): 1.86 (3H, s), 2.75-2.80 (4H, m), 3.20-3.28 (6H, m), 3.48-3.52 (2H, m), 3.61-3.69 (2H, br m), 5.90-5.98 (1H, br s), 6.68-6.83 (1H, br s), 7.20 (2H, s), 7.41-7.47 (3H, m), 7.65-7.70 (1H, d), 8.05 (1H, s), 8.30-8.35 (2H, m), 9.33 (1H, s); m/z (ES$^+$) 587 (MH)$^+$ N-(6-{[2-(acetylamino)ethyl]amino}-2-phenylpyrimidin-4-yl)-2-{4-[3-chloro-5-(trifluoromethyl)pyridin-2-yl]piperazin-1-yl}acetamide (8.49): 47 mg over 2 steps from 100 mg 2-bromo-N-(6-chloro-2-phenylpyrimidin-4-yl)acetamide.

$\delta_H$ (CDCl$_3$): 1.85 (3H, s), 2.73-2.81 (4H, m), 3.22 (2H, s), 3.49-3.55 (2H, m), 3.59-3.71 (6H, m), 5.75-5.79 (1H, m), 6.64-6.78 (1H, br s), 7.20 (1H, s), 7.42-7.47 (3H, m), 7.77 (1H, s), 8.30-8.37 (2H, m), 8.40 (1H, s), 9.45 (1H, s); m/z (ES$^+$) 577 (MH)$^+$ N-(6-{[2-(acetylamino)ethyl]amino}-2-phenylpyrimidin-4-yl)-2-[4-(3-phenylpropyl)piperazin-1-yl]acetamide (8.50): Purification via reverse phase HPLC (6 mg over 2 steps from 100 mg 2-bromo-N-(6-chloro-2-phenylpyrimidin-4-yl)acetamide.)

$\delta_H$ (CDCl$_3$): 2.12 (3H, s), 2.08-2.16 (2H, m), 2.66-2.74 (2H, m), 2.98-3.10 (6H, m), 3.42-3.66 (m, 8H), 3.81-3.88 (2H, m), 6.78-6.84 (1H, br s), 7.12-7.16 (2H, d), 7.20-7.26 (2H, m), 7.28-7.32 (2H, t), 7.56-7.62 (2H, m), 7.64-7.72 (1H, m), 8.06-8.12 (2H, d), 8.28-8.32 (1H, br s), 8.58-8.62 (1H, br s); m/z (ES$^-$) 514 (M–H)$^-$ N-(6-{[2-(acetylamino)ethyl]amino}-2-phenylpyrimidin-4-yl)-2-[4-(4-tert-butylbenzyl)piperazin-1-yl]acetamide (8.51): 19 mg over 2 steps from 100 mg 2-bromo-N-(6-chloro-2-phenylpyrimidin-4-yl)acetamide.

δ$_H$(CDCl$_3$): 1.30 (9H, s), 1.85 (3H, s), 2.50-2.68 (11H, m), 3.14 (2H, s), 3.48-3.52 (4H, m), 3.62-3.70 (2H, m), 5.50-5.60 (1H, m), 6.55-6.70 (1H, br s), 7.20 (1H, s), 7.21-7.27 (2H, d), 7.32-7.37 (2H, d), 7.43-7.48 (3H, m), 8.32-8.38 (2H, m), 9.45 (1H, s); m/z (ES$^-$) 542 (M–H)$^-$

N-(6-{[2-(acetylamino)ethyl]amino}-2-phenylpyrimidin-4-yl)-2-(4-pyrrolidin-1-yl-piperidin-1-yl)acetamide (8.52): Reaction conducted at 100° C. (27 mg over 2 steps from 100 mg 2-bromo-N-(6-chloro-2-phenylpyrimidin-4-yl)acetamide.

δ$_H$ (CDCl$_3$): 1.72-1.87 (7H, m), 1.92-2.10 (4H, m), 2.24-2.32 (2H, t), 2.58-2.65 (4H, br, s), 2.87-2.95 (2H, d), 3.10 (2H, s), 3.33 (1H, s), 3.46-3.52 (2H, m), 3.61-3.70 (2H, m), 5.68-5.72 (1H, m), 6.73-6.83 (1H, br s), 7.18 (1H, s), 7.40-7.48 (3H, m), 8.32-8.38 (2H, m), 9.50 (1H, s); m/z (ES$^+$) 466 (MH)$^+$

N-(6-{[2-(acetylamino)ethyl]amino}-2-phenylpyrimidin-4-yl)-2-(4-hydroxy-4-thien-2-ylpiperidin-1-yl)acetamide (8.53): 9 mg over 2 steps from 100 mg 2-bromo-N-(6-chloro-2-phenylpyrimidin-4-yl)acetamide.

δ$_H$ (CDCl$_3$): 1.74-1.89 (4H, m), 2.03-2.11 (2H, d), 2.25-2.35 (2H, m), 2.73-2.85 (4H, m), 3.21 (2H, s), 3.48-3.55 (2H, m), 3.61-3.72 (2H, m), 5.62 (1H, s), 6.57-6.71 (1H, br s), 7.00 (1H, m), 7.04-7.07 (1H, m), 7.22 (1H, s), 7.25 (1H, s), 7.42-7.47 (3H, m), 8.31-8.37 (2H, m), 9.47 (1H, s); m/z (ES$^+$) 495 (MH)$^+$

N-(6-{[2-(acetylamino)ethyl]amino}-2-phenylpyrimidin-4-yl)-2-{4-[(2E)-3-phenylprop-2-enyl]piperazin-1-yl}acetamide (8.54): Reaction conducted at 100° C. for 3 hrs. Sample recrystallized from methanol (354 mg over 2 steps from 0.80 g 2-bromo-N-(6-chloro-2-phenylpyrimidin-4-yl)acetamide).

δ$_H$(CDCl$_3$): 1.83 (3H, s), 2.59-2.75 (8H, br s), 3.17 (2H, s), 3.22 (2H, d), 3.45-3.54 (2H, m), 3.62-3.70 (2H, m), 5.38-5.42 (1H, m), 6.23-6.32 (1H, m), 6.40-6.52 (1H, br s), 6.52-6.59 (1H, d), 7.21-7.24 (2H, m), 7.28-7.34 (2H, t), 7.35-7.40 (2H, d), 7.43-7.49 (3H, m), 8.38-8.40 (2H, m), 9.43 (1H, s); m/z (ES$^+$) 514 (MH)$^+$

N-(6-{[2-(acetylamino)ethyl]amino}-2-phenylpyrimidin-4-yl)-2-(4-benzylpiperidin-1-yl)acetamide (8.55): Reaction conducted at 100° C. for 3 hrs. (546 mg over 2 steps from 0.80 g 2-bromo-N-(6-chloro-2-phenylpyrimidin-4-yl)acetamide).

δ$_H$(CDCl$_3$): 1.42-1.50 (2H, t), 1.56 (1H, s), 1.66-1.74 (2H, br d), 1.84-1.86 (3H, s), 2.18-2.24 (2H, t), 2.58-2.62 (2H, d), 2.84-2.91 (2H, d), 3.10 (2H, s), 3.50-3.56 (2H, m), 3.64-3.72 (2H, m), 5.36-5.40 (1H, m), 7.14-7.21 (3H, m), 7.22 (1H, s), 7.28-7.32 (2H, t), 7.46-7.50 (3H, m), 8.35-8.40 (2H, m), 9.50 (1H, s); m/z (ES$^+$) 487 (MH)$^+$

N-{2-[(6-amino-2-phenylpyrimidin-4-yl)amino]ethyl}acetamide (5):

6-Chloro-2-phenylpyrimidin-4-amine (2.87 g) was dissolved in DMSO (50 ml) and N-acetylethylenediamine (14.28 g) added. The stirred solution was heated at 130° C. for 8 hrs then partitioned between ethyl acetate (500 ml) and saturated brine solution (400 ml). The organic phase was dried over magnesium sulfate, filtered and the solvent removed in vacuo. Purification by flash chromatography on silica gel eluting with first ethyl acetate then a mixture of ethyl acetate and methanol (9:1 then 8:2 v/v) yielded the title compound (2.50 g).

δ$_H$ (CDCl$_3$): 1.82 (3H, s), 3.41-3.44 (2H, m), 3.52-3.59 (2H, m), 4.62 (2H, s), 4.98-5.04 (1H, m), 6.57-6.65 (1H, br s), 7.41-7.43 (3H, m), 8.29-8.34 (2H, m); m/z (ES$^+$) 272 (MH)$^+$

N-(6-{[2-(acetylamino)ethyl]amino}-2-phenylpyrimidin-4-yl)-2-bromoacetamide (23)

To N-{2-[(6-amino-2-phenylpyrimidin-4-yl)amino]ethyl}acetamide (5) (1.20 g) in anhydrous dichloromethane (100 ml) was added triethylamine (1.23 ml), then bromoacetylbromide (768 μl) in 2 aliquots. The mixture was left to stir at room temperature for 10 mins then was partitioned between dichloromethane (50 ml) and water (50 ml). The aqueous layer was extracted with dichloromethane (3×50 ml) and the organic layers combined, dried over magnesium sulfate and filtered. The solvent was removed in vacuo and the resulting solid purified via column chromatography on silica gel eluting with a mixture of ethyl acetate and petrol ether (1:1 v/v), then ethyl acetate, then a mixture of ethyl acetate and methanol (95:5 v/v) to furnish the title compound (195 mg).

δ$_H$(d$^6$-acetone): 1.84 (3H, s), 3.35-3.44 (2H, m), 3.50-3.60 (2H, m), 4.04 (2H, s), 6.18-6.23 (1H, br s), 6.68-6.75 (1H, br s), 7.11 (1H, s), 7.48-7.51 (3H, m), 8.35-8.40 (2H, m), 8.97-9.04 (1H, br s); m/z (ES$^+$) 392 (MH)$^+$ Example of Library Method:

N-(6-{[2-(acetylamino)ethyl]amino}-2-phenylpyrimidin-4-yl)-2-[4-(4-bromophenyl)-4-hydroxypiperidin-1-yl]acetamide (8.56):

N-(6-{[2-(Acetylamino)ethyl]amino}-2-phenylpyrimidin-4-yl)-2-bromoacetamide (23) (30 μl of a 0.167M solution) was dispensed to a well of a 96 well microtitre plate, followed by [4-(4-bromophenyl)-4-hydroxypiperidine] (30 μl of a 0.167M solution) and N,N-diisopropylethylamine (30 μl of a 0.167M solution). The plate was placed in an oven at 63° C. for 5 hrs. The solvent was removed in vacuo yielding the title compound.

LCMS (Method A) RT=2.43 min, m/z (ES$^+$) 569 (MH)$^+$

The following compounds 8.57-8.128 were synthesized in an analogous manner:

| Name | Retention time (min) | Mass ion (ES$^+$) (MH)$^+$ |
| --- | --- | --- |
| N-(6-{[2-(acetylamino)ethyl]amino}-2-phenylpyrimidin-4-yl)-2-[4-hydroxy-4-(4-methoxybenzyl)piperidin-1-yl]acetamide | 2.32 | 533 |
| N-(6-{[2-(acetylamino)ethyl]amino}-2-phenylpyrimidin-4-yl)-2-[4-(2-methoxyphenyl)piperazin-1-yl]acetamide | 2.36 | 504 |
| tert-butyl 4-{2-[(6-{[2-(acetylamino)ethyl]amino}-2-phenylpyrimidin-4-yl)amino]-2-oxoethyl}piperazine-1-carboxylate | 2.47 | 498 |
| N-(6-{[2-(acetylamino)ethyl]amino}-2-phenylpyrimidin-4-yl)-2-[4-(2-hydroxyethyl)piperazin-1-yl]acetamide | 1.93 | 442 |
| N-(6-{[2-(acetylamino)ethyl]amino}-2-phenylpyrimidin-4-yl)-2-[4-(2,4-dimethoxyphenyl)piperazin-1-yl]acetamide | 2.37 | 534 |
| N-(6-{[2-(acetylamino)ethyl]amino}-2-phenylpyrimidin-4-yl)-2-(3-hydroxypiperidin-1-yl)acetamide | 1.96 | 413 |

| Name | Retention time (min) | Mass ion (ES⁺) (MH)⁺ |
|---|---|---|
| N-(6-{[2-(acetylamino)ethyl]amino}-2-phenylpyrimidin-4-yl)-2-{4-[2-(2-hydroxyethoxy)ethyl]piperazin-1-yl}acetamide | 2.00 | 486 |
| N-(6-{[2-(acetylamino)ethyl]amino}-2-phenylpyrimidin-4-yl)-2-(4-pyrimidin-2-ylpiperazin-1-yl)acetamide | 2.26 | 476 |
| N-(6-{[2-(acetylamino)ethyl]amino}-2-phenylpyrimidin-4-yl)-2-[4-(3-hydroxypropyl)piperazin-1-yl]acetamide | 1.97 | 456 |
| N-(6-{[2-(acetylamino)ethyl]amino}-2-phenylpyrimidin-4-yl)-2-[4-hydroxy-4-(3-methoxybenzyl)piperidin-1-yl]acetamide | 2.33 | 533 |
| N-(6-{[2-(acetylamino)ethyl]amino}-2-phenylpyrimidin-4-yl)-2-[3-(hydroxymethyl)piperidin-1-yl]acetamide | 2.01 | 427 |
| N-(6-{[2-(acetylamino)ethyl]amino}-2-phenylpyrimidin-4-yl)-2-(4-phenylpiperazin-1-yl)acetamide | 2.47 | 474 |
| N-(6-{[2-(acetylamino)ethyl]amino}-2-phenylpyrimidin-4-yl)-2-[4-(4-fluorophenyl)piperazin-1-yl]acetamide | 2.52 | 492 |
| N-(6-{[2-(acetylamino)ethyl]amino}-2-phenylpyrimidin-4-yl)-2-[4-(4-nitrophenyl)piperazin-1-yl]acetamide | 2.60 | 519 |
| N-(6-{[2-(acetylamino)ethyl]amino}-2-phenylpyrimidin-4-yl)-2-[4-(4-acetylphenyl)piperazin-1-yl]acetamide | 2.40 | 516 |
| N-(6-{[2-(acetylamino)ethyl]amino}-2-phenylpyrimidin-4-yl)-2-(4-pyridin-2-ylpiperazin-1-yl)acetamide | 2.08 | 475 |
| N-(6-{[2-(acetylamino)ethyl]amino}-2-phenylpyrimidin-4-yl)-2-[4-(2-fluorophenyl)piperazin-1-yl]acetamide | 2.50 | 492 |
| N-(6-{[2-(acetylamino)ethyl]amino}-2-phenylpyrimidin-4-yl)-2-{4-[3-(trifluoromethyl)pyridin-2-yl]piperazin-1-yl}acetamide | 2.45 | 543 |
| N-(6-{[2-(acetylamino)ethyl]amino}-2-phenylpyrimidin-4-yl)-2-[4-(hydroxymethyl)piperidin-1-yl]acetamide | 2.00 | 427 |
| N-(6-{[2-(acetylamino)ethyl]amino}-2-phenylpyrimidin-4-yl)-2-[4-(4-fluorobenzoyl)piperidin-1-yl]acetamide | 2.41 | 519 |
| N-(6-{[2-(acetylamino)ethyl]amino}-2-phenylpyrimidin-4-yl)-2-[4-(3,5-dichloropyridin-4-yl)piperazin-1-yl]acetamide | 2.49 | 543 |
| N-(6-{[2-(acetylamino)ethyl]amino}-2-phenylpyrimidin-4-yl)-2-[4-(2-methoxyphenyl)piperidin-1-yl]acetamide | 2.45 | 503 |
| 1-{2-[(6-{[2-(acetylamino)ethyl]amino}-2-phenylpyrimidin-4-yl)amino]-2-oxoethyl}piperidine-4-carboxamide | 1.95 | 440 |
| N-(6-{[2-(acetylamino)ethyl]amino}-2-phenylpyrimidin-4-yl)-2-[4-(3-methoxyphenyl)piperazin-1-yl]acetamide | 2.49 | 504 |
| N-(6-{[2-(acetylamino)ethyl]amino}-2-phenylpyrimidin-4-yl)-2-[4-(4-methoxyphenyl)piperazin-1-yl]acetamide | 2.40 | 504 |
| N-(6-{[2-(acetylamino)ethyl]amino}-2-phenylpyrimidin-4-yl)-2-[4-(4-chlorophenyl)piperazin-1-yl]acetamide | 2.68 | 508 |
| N-(6-{[2-(acetylamino)ethyl]amino}-2-phenylpyrimidin-4-yl)-2-[4-(2,4-dimethylphenyl)piperazin-1-yl]acetamide | 2.66 | 502 |
| N-(6-{[2-(acetylamino)ethyl]amino}-2-phenylpyrimidin-4-yl)-2-(4-pyrimidin-2-ylpiperazin-1-yl)acetamide | 2.25 | 476 |
| N-(6-{[2-(acetylamino)ethyl]amino}-2-phenylpyrimidin-4-yl)-2-[4-(3,4-dichlorophenyl)piperazin-1-yl]acetamide | 2.86 | 542 |
| N-(6{[2-(acetylamino)ethyl]amino}-2-phenylpyrimidin-4-yl)-2-[4-(4-hydroxyphenyl)piperazin-1-yl]acetamide | 2.24 | 490 |
| N-(6-{[2-(acetylamino)ethyl]amino}-2-phenylpyrimidin-4-yl)-2-[4-(3-chlorophenyl)piperazin-1-yl]acetamide | 2.67 | 508 |
| N-(6-{[2-(acetylamino)ethyl]amino}-2-phenylpyrimidin-4-yl)-2-[4-(3,4-dimethylphenyl)piperazin-1-yl]acetamide | 2.55 | 502 |
| 1-{2-[(6-{[2-(acetylamino)ethyl]amino}-2-phenylpyrimidin-4-yl)amino]-2-oxoethyl}-piperidine-3-carboxylic acid diethyl amide | 2.22 | 496 |
| N-(6-{[2-(acetylamino)ethyl]amino}-2-phenylpyrimidin-4-yl)-2-[4-(2-furoyl)piperazin-1-yl]acetamide | 2.30 | 492 |
| N-(6-{[2-(acetylamino)ethyl]amino}-2-phenylpyrimidin-4-yl)-2-[4-(2,5-dimethylphenyl)piperazin-1-yl]acetamide | 2.63 | 502 |
| N-(6-{[2-(acetylamino)ethyl]amino}-2-phenylpyrimidin-4-yl)-2-(4-cycloheptylpiperazin-1-yl)acetamide | 2.32 | 494 |
| N-(6-{[2-(acetylamino)ethyl]amino}-2-phenylpyrimidin-4-yl)-2-(4-ethylpiperazin-1-yl)acetamide | 2.02 | 426 |
| N-(6-{[2-(acetylamino)ethyl]amino}-2-phenylpyrimidin-4-yl)-2-[4-(1,3-benzodioxol-5-ylmethyl)piperazin-1-yl]acetamide | 2.28 | 532 |
| N-(6-{[2-(acetylamino)ethyl]amino}-2-phenylpyrimidin-4-yl)-2-(4-acetylpiperazin-1-yl)acetamide | 2.07 | 440 |
| N-(6-{[2-(acetylamino)ethyl]amino}-2-phenylpyrimidin-4-yl)-2-{4-[bis(4-fluorophenyl)methyl]piperazin-1-yl}acetamide | 2.68 | 600 |
| N-(6-{[2-(acetylamino)ethyl]amino}-2-phenylpyrimidin-4-yl)-2-(4-benzhydrylpiperazin-1-yl)acetamide | 2.57 | 564 |
| N-(6-{[2-(acetylamino)ethyl]amino}-2-phenylpyrimidin-4-yl)-2-{4-[(4-chlorophenyl)(phenyl)methyl]piperazin-1-yl}acetamide | 2.73 | 598 |
| N-(6-{[2-(acetylamino)ethyl]amino}-2-phenylpyrimidin-4-yl)-2-[4-(2-phenylethyl)-1,4-diazepan-1-yl]acetamide | 2.32 | 516 |

-continued

| Name | Retention time (min) | Mass ion (ES+) (MH)+ |
|---|---|---|
| N-(6-{[2-(acetylamino)ethyl]amino}-2-phenylpyrimidin-4-yl)-2-(2-methylpiperidin-1-yl)acetamide | 2.16 | 411 |
| N-(6-{[2-(acetylamino)ethyl]amino}-2-phenylpyrimidin-4-yl)-2-(4-allylpiperazin-1-yl)acetamide | 2.06 | 438 |
| N-(6-{[2-(acetylamino)ethyl]amino}-2-phenylpyrimidin-4-yl)-2-(4-cyclopentylpiperazin-1-yl)acetamide | 2.19 | 466 |
| N-(6-{[2-(acetylamino)ethyl]amino}-2-phenylpyrimidin-4-yl)-2-[4-(4-fluorobenzyl)-4-hydroxypiperidin-1-yl]acetamide | 2.36 | 521 |
| N-(6-{[2-(acetylamino)ethyl]amino}-2-phenylpyrimidin-4-yl)-2-[4-(2-phenylethyl)piperazin-1-yl]acetamide | 2.37 | 502 |
| N-(6-{[2-(acetylamino)ethyl]amino}-2-phenylpyrimidin-4-yl)-2-[4-(2-methoxyethyl)piperazin-1-yl]acetamide | 2.06 | 456 |
| N-(6-{[2-(acetylamino)ethyl]amino}-2-phenylpyrimidin-4-yl)-2-[4-(4-chlorobenzyl)piperazin-1-yl]acetamide | 2.37 | 522 |
| N-(6-{[2-(acetylamino)ethyl]amino}2-phenylpyrimidin-4-yl)-2-[4-(2-oxo-2-pyrrolidin-1-ylethyl)piperazin-1-yl]acetamide | 2.07 | 509 |
| N-(6-{[2-(acetylamino)ethyl]amino}-2-phenylpyrimidin-4-yl)-2-(4-benzylpiperidin-1-yl)acetamide | 2.43 | 487 |
| N-(6-{[2-(acetylamino)ethyl]amino}-2-phenylpyrimidin-4-yl)-2-(4-cyano-4-phenylpiperidin-1-yl)acetamide | 2.59 | 498 |
| N-(6-{[2-(acetylamino)ethyl]amino}-2-phenylpyrimidin-4-yl)-2-(3,4-dihydroisoquinolin-2(1H)-yl)acetamide | 2.32 | 445 |
| ethyl 4-{2-[(6-{[2-(acetylamino)ethyl]amino}-2-phenylpyrimidin-4-yl)amino]-2-oxoethyl}piperazine-1-carboxylate | 2.30 | 470 |
| N-(6-{[2-(acetylamino)ethyl]amino}-2-phenylpyrimidin-4-yl)-2-(4-hydroxy-4-phenylpiperidin-1-yl)acetamide | 2.26 | 498 |
| N-(6-{[2-(acetylamino)ethyl]amino}-2-phenylpyrimidin-4-yl)-2-(4-pyrazin-2-ylpiperazin-1-yl)acetamide | 2.20 | 476 |
| N-(6-{[2-(acetylamino)ethyl]amino}-2-phenylpyrimidin-4-yl)-2-{4-hydroxy-4-[3-(trifluoromethyl)phenyl]piperidin-1-yl}acetamide | 2.42 | 557 |
| N-(6-{[2-(acetylamino)ethyl]amino}-2-phenylpyrimidin-4-yl)-2-(4-acetyl-4-phenylpiperidin-1-yl)acetamide | 2.37 | 515 |
| N-(6-{[2-(acetylamino)ethyl]amino}-2-phenylpyrimidin-4-yl)-2-{4-[hydroxy(diphenyl)methyl]piperidin-1-yl}acetamide | 2.50 | 579 |
| N-(6-{[2-(acetylamino)ethyl]amino}-2-phenylpyrimidin-4-yl)-2-(4-oxo-1-phenyl-1,3,8-triazaspiro[4.5]dec-8-yl)acetamide | 2.32 | 543 |
| N-(6-{[2-(acetylamino)ethyl]amino}-2-phenylpyrimidin-4-yl)-2-{4-[4-chloro-3-(trifluoromethyl)phenyl]-4-hydroxypiperidin-1-yl}acetamide | 2.56 | 591 |
| N-(6-{[2-(acetylamino)ethyl]amino}-2-phenylpyrimidin-4-yl)-2-morpholin-4-ylacetamide | 2.04 | 399 |
| N-(6-{[2-(acetylamino)ethyl]amino}-2-phenylpyrimidin-4-yl)-2-[4-(4-methoxyphenyl)-3-methylpiperazin-1-yl]acetamide | 2.40 | 517 |
| N-(6-{[2-(acetylamino)ethyl]amino}-2-phenylpyrimidin-4-yl)-2-{4-[2-(diallylamino)ethyl]piperazin-1-yl}acetamide | 1.96 | 521 |
| N-(6-{[2-(acetylamino)ethyl]amino}-2-phenylpyrimidin-4-yl)-2-(4-cyclohexylpiperazin-1-yl)acetamide | 2.26 | 480 |
| N-(6-{[2-(acetylamino)ethyl]amino}-2-phenylpyrimidin-4-yl)-2-[4-(2-hydroxyphenyl)piperazin-1-yl]acetamide | 2.31 | 490 |
| N-(6-{[2-(acetylamino)ethyl]amino}-2-phenylpyrimidin-4-yl)-2-[3-methyl-4-(3-methylphenyl)piperazin-1-yl]acetamide | 2.57 | 502 |
| N-(6-{[2-(acetylamino)ethyl]amino}-2-phenylpyrimidin-4-yl)-2-azepan-1-ylacetamide | 2.18 | 411 |
| N-(6-{[2-(acetylamino)ethyl]amino}-2-phenylpyrimidin-4-yl)-2-[4-(3-fluorobenzyl)-4-hydroxypiperidin-1-yl]acetamide | 2.32 | 520 |
| N-(6-{[2-(acetylamino)ethyl]amino}-2-phenylpyrimidin-4-yl)-2-[3-methyl-4-(4-methylphenyl)piperazin-1-yl]acetamide | 2.50 | 502 |
| N-(6-{[2-(acetylamino)ethyl]amino}-2-phenylpyrimidin-4-yl)-2-[4-(2-cyanophenyl)piperazin-1-yl]acetamide | 2.48 | 499 |

Example 6

Synthesis of Oxalamides 26.1-26.79

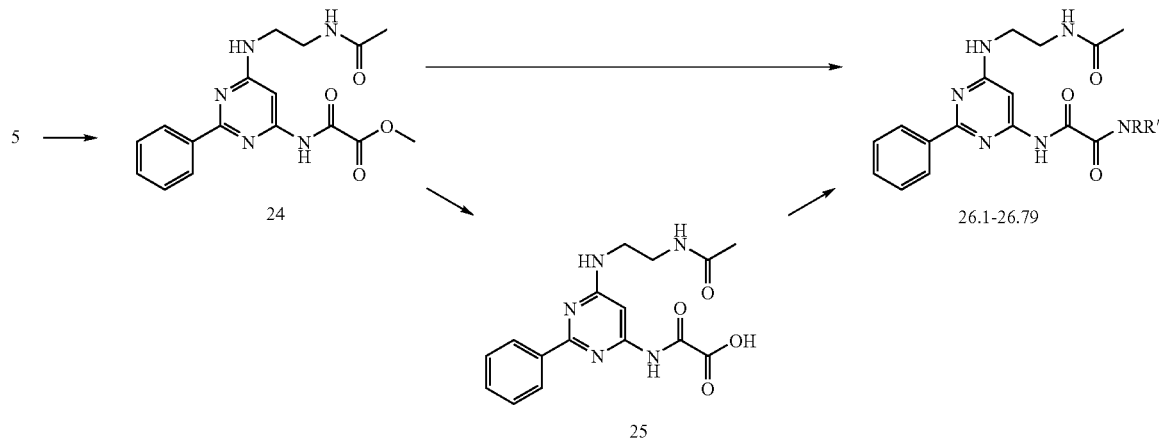

Methyl [(6-{[2-(acetylamino)ethyl]amino}-2-phenylpyrimidin-4-yl)amino](oxo)acetate (24)

N-{2-[(6-Amino-2-phenylpyrimidin-4-yl)amino]ethyl}acetamide (5) (500 mg) was dissolved in anhydrous dichloromethane (10 ml) with stirring and cooled to 0° C. using an ice bath. To this was added dropwise a solution of methyl oxalyl chloride (170 µl in 5 ml anhydrous dichloromethane) and the reaction left to warm to room temperature over 3 hrs. The solvent was removed in vacuo and the mixture purified via column chromatography on silica gel eluting with a mixture of dichloromethane and methanol (95:5 v/v) to reveal the title compound (247 mg).

$\delta_H$ (d$^6$-DMSO): 1.87 (3H, s), 3.50-3.58 (2H, m), 3.63-3.77 (2H, m), 3.98 (3H, s), 5.58-5.62 (1H, br s), 7.20 (1H, s), 7.42-7.48 (3H, m), 8.32-8.37 (2H, m), 9.21 (1H, s); m/z (ES$^+$) 358 (MH)$^+$

[(6-{[2-(Acetylamino)ethyl]amino}-2-phenylpyrimidin-4-yl)amino](oxo)acetic acid (25)

Methyl [(6-{[2-(acetylamino)ethyl]amino}-2-phenylpyrimidin-4-yl)amino](oxo)acetate (10 mg) was dissolved in anhydrous THF (1.5 ml) and potassium trimethylsilanate (4 mg) added. The reaction was left for 3 hrs after which time a precipitate of the title compound was visible which was filtered (10 mg).

m/z (ES$^+$) 344 (MH)$^+$

N-(6-{[2-(acetylamino)ethyl]amino}-2-phenylpyrimidin-4-yl)-2-oxo-2-piperidin-1-ylacetamide (26.1)

To a stirred solution of [(6-{[2-(acetylamino)ethyl]amino}-2-phenylpyrimidin-4-yl)amino](oxo)acetic acid (50 mg) in NMP (2.5 ml) were added HATU (51 mg) and N,N-diisopropylethylamine (25 µl). The mixture was stirred at room temperature for 15 min then piperidine (90 µl) added and the solution left for 16 hrs. After this time, the solvent was removed in vacuo. Purification via flash chromatography on silica gel using ethyl acetate as the eluent furnished the correct material (10 mg).

$\delta_H$ (CD$_3$CN): 1.52-1.70 (6H, m), 1.79 (3H, s), 3.33-3.39 (2H, q), 3.42-3.68 (6H, br m), 6.10-6.18 (1H, br s), 6.58-6.62 (1H, br s), 7.05-7.15 (1H, br s), 7.42-7.48 (3H, m), 8.35-8.40 (2H, m), 9.11-9.20 (1H, br s); m/z (ES$^+$) 411 (MH)$^+$ N-(6-{[2-(acetylamino)ethyl]amino}-2-phenylpyrimidin-4-yl)-2-(4-benzylpiperidin-1-yl)-2-oxoacetamide (26.2)

Methyl [(6-{[2-(acetylamino)ethyl]amino}-2-phenylpyrimidin-4-yl)amino](oxo)acetate (50 mg) was dissolved in DMSO (420 µl) with stirring. To this were added 4-benzylpiperidine (74 µl) and activated powdered 4 angstrom molecular sieves and the mixture left to stir at room temperature for 5 hrs. After this time the reaction was filtered and first dichloromethane (1.6 ml) then PS-NCO (0.58 g) were added and the mixture left to stir for 1 hr. The resulting slurry was filtered, then partitioned between dichloromethane (20 ml) and water (20 ml), and the aqueous layer extracted with dichloromethane (2×20 ml). The combined organics were dried over magnesium sulfate, filtered and the solvent removed in vacuo. Further purification via column chromatography on silica gel eluting with a mixture of dichloromethane and methanol (94:6 v/v) furnished the title compound (33 mg).

$\delta_H$ (CDCl$_3$): 1.20-1.40 (2H, m), 1.57 (1H, s), 1.72-1.90 (5H, m), 2.54-2.60 (2H, m), 2.66-2.76 (1H, t), 3.01-3.10 (1H, t), 3.48-3.56 (2H, m), 3.63-3.72 (2H, m), 4.52-4.59 (1H, d), 4.81-4.90 (1H, d), 5.38-5.42 (1H, br s), 7.10-7.16 (3H, m), 7.18-7.24 (1H, m), 7.24-7.32 (2H, m), 7.41-7.48 (3H, m), 8.30-8.36 (2H, m), 9.30-9.36 (1H, br s); m/z (ES$^+$) 501 (MH)$^+$ Library Example:

N-(6-{[2-(acetylamino)ethyl]amino}-2-phenylpyrimidin-4-yl)-2—Oxo-2-(4-phenylpiperazin-1-yl)acetamide (26.3)

To a well of a 96 well microtitre plate were added methyl [(6-{[2-(acetylamino)ethyl]amino}-2-phenylpyrimidin-4-yl)amino](oxo)acetate (30 µl of a 0.3M solution in anhydrous DMSO) and 4-phenylpiperazine (30 µl of a 1.5M solution). This solution was left to shake on a plate shaker for 16 hrs. After this time 800 µl of dichloromethane were added, then 100 mg of PS-NCO. The plate was sealed, then mixed for 48 hrs. The slurry was filtered and the solvents removed in vacuo, to furnish the title compound.

LCMS (Method B) RT=2.04 min, m/z (ES+) 488 (MH)+
The following compounds 26.4-26.79 were synthesized in an analogous manner:

| Name | Retention time (min) | Mass Ion (ES+) (MH)+ |
|---|---|---|
| N-(6-{[2-(acetylamino)ethyl]amino}-2-phenylpyrimidin-4-yl)-2-[4-(4-fluorophenyl)piperazin-1-yl]-2-oxoacetamide | 2.10 | 506 |
| N-(6-{[2-(acetylamino)ethyl]amino}-2-phenylpyrimidin-4-yl)-2-[4-(4-acetylphenyl)piperazin-1-yl]-2-oxoacetamide | 1.99 | 530 |
| N-(6-{[2-(acetylamino)ethyl]amino}-2-phenylpyrimidin-4-yl)-2-[4-(2-fluorophenyl)piperazin-1-yl]-2-oxoacetamide | 2.08 | 506 |
| N-(6-{[2-(acetylamino)ethyl]amino}-2-phenylpyrimidin-4-yl)-2-(4-hydroxy-4-phenylpiperidin-1-yl)-2-oxoacetamide | 1.88 | 503 |
| N-(6-{[2-(acetylamino)ethyl]amino}-2-phenylpyrimidin-4-yl)-2-oxo-2-{4-[3-(trifluoromethyl)phenyl]piperazin-1-yl}acetamide | 2.28 | 556 |
| N-(6-{[2-(acetylamino)ethyl]amino}-2-phenylpyrimidin-4-yl)-2-oxo-2-{4-[3-(trifluoromethyl)pyridin-2-yl]piperazin-1-yl}acetamide | 2.14 | 557 |
| N-(6-{[2-(acetylamino)ethyl]amino}-2-phenylpyrimidin-4-yl)-2-[4-(3,5-dichloropyridin-4-yl)piperazin-1-yl]-2-oxoacetamide | 2.02 | 557 |
| N-(6-{[2-(acetylamino)ethyl]amino}-2-phenylpyrimidin-4-yl)-2-[4-(2,5-dimethylphenyl)piperazin-1-yl]-2-oxoacetamide | 2.26 | 516 |
| N-(6-{[2-(acetylamino)ethyl]amino}-2-phenylpyrimidin-4-yl)-2-[4-(4-methoxyphenyl)piperazin-1-yl]-2-oxoacetamide | 1.97 | 518 |
| N-(6-{[2-(acetylamino)ethyl]amino}-2-phenylpyrimidin-4-yl)-2-(4-methylpiperazin-1-yl)-2-oxoacetamide | 1.37 | 426 |
| N-(6-{[2-(acetylamino)ethyl]amino}-2-phenylpyrimidin-4-yl)-2-[4-(2-methoxyphenyl)piperazin-1-yl]-2-oxoacetamide | 1.98 | 518 |
| N-(6-{[2-(acetylamino)ethyl]amino}-2-phenylpyrimidin-4-yl)-2-[4-(2-hydroxyethyl)piperazin-1-yl]-2-oxoacetamide | 1.35 | 456 |
| N-(6-{[2-(acetylamino)ethyl]amino}-2-phenylpyrimidin-4-yl)-2-[4-(1,3-benzothiazol-2-yl)piperidin-1-yl]-2-oxoacetamide | 2.09 | 544 |
| N-(6-{[2-(acetylamino)ethyl]amino}-2-phenylpyrimidin-4-yl)-2-[4-(3-hydroxypropyl)piperazin-1-yl]-2-oxoacetamide | 1.40 | 470 |
| N-(6-{[2-(acetylamino)ethyl]amino}-2-phenylpyrimidin-4-yl)-2-[4-(3,4-dimethylphenyl)piperazin-1-yl]-2-oxoacetamide | 2.14 | 516 |
| N-(6-{[2-(acetylamino)ethyl]amino}-2-phenylpyrimidin-4-yl)-2-(4-benzylpiperazin-1-yl)-2-oxoacetamide | 2.21 | 501 |
| N-(6-{[2-(acetylamino)ethyl]amino}-2-phenylpyrimidin-4-yl)-2-(4-ethylpiperazin-1-yl)-2-oxoacetamide | 1.44 | 440 |
| N-(6-{[2-(acetylamino)ethyl]amino}-2-phenylpyrimidin-4-yl)-2-(4-acetylpiperazin-1-yl)-2-oxoacetamide | 1.67 | 454 |
| N-(6-{[2-(acetylamino)ethyl]amino}-2-phenylpyrimidin-4-yl)-2-oxo-2-{4-[(2E)-3-phenylprop-2-enyl]piperazin-1-yl}acetamide | 1.65 | 528 |
| N-(6-{[2-(acetylamino)ethyl]amino}-2-phenylpyrimidin-4-yl)-2-(4-allylpiperazin-1-yl)-2-oxoacetamide | 1.42 | 452 |
| N-(6-{[2-(acetylamino)ethyl]amino}-2-phenylpyrimidin-4-yl)-2-(4-cyclopentylpiperazin-1-yl)-2-oxoacetamide | 1.50 | 480 |
| N-(6-{[2-(acetylamino)ethyl]amino}-2-phenylpyrimidin-4-yl)-2-(4-cycloheptylpiperazin-1-yl)-2-oxoacetamide | 1.62 | 508 |
| N-(6-{[2-(acetylamino)ethyl]amino}-2-phenylpyrimidin-4-yl)-2-oxo-2-[4-(2-phenylethyl)piperazin-1-yl]acetamide | 1.60 | 516 |
| N-(6-{[2-(acetylamino)ethyl]amino}-2-phenylpyrimidin-4-yl)-2-[4-(2-methoxyethyl)piperazin-1-yl]-2-oxoacetamide | 1.42 | 470 |
| N-(6-{[2-(acetylamino)ethyl]amino}-2-phenylpyrimidin-4-yl)-2-[4-(4-chlorobenzyl)piperazin-1-yl]-2-oxoacetamide | 1.68 | 536 |
| N-(6-{[2-(acetylamino)ethyl]amino}-2-phenylpyrimidin-4-yl)-2-{4-[2-(dimethylamino)ethyl]piperazin-1-yl}-2-oxoacetamide | 1.41 | 483 |
| N-(6-{[2-(acetylamino)ethyl]amino}-2-phenylpyrimidin-4-yl)-2-(4-benzyl-4-hydroxypiperidin-1-yl)-2-oxoacetamide | 1.93 | 517 |
| N-(6-{[2-(acetylamino)ethyl]amino}-2-phenylpyrimidin-4-yl)-2-[4-(4-methoxyphenyl)-3-methylpiperazin-1-yl]-2-oxoacetamide | 1.86 | 532 |
| N-(6-{[2-(acetylamino)ethyl]amino}-2-phenylpyrimidin-4-yl)-2-oxo-2-(4-pyridin-4-ylpiperazin-1-yl)acetamide | 1.46 | 489 |
| N-(6-{[2-(acetylamino)ethyl]amino}-2-phenylpyrimidin-4-yl)-2-[4-(3-hydroxyphenyl)piperazin-1-yl]-2-oxoacetamide | 1.85 | 504 |
| N-(6-{[2-(acetylamino)ethyl]amino}-2-phenylpyrimidin-4-yl)-2-[4-(2-hydroxyphenyl)piperazin-1-yl]-2-oxoacetamide | 1.92 | 504 |
| N-(6-{[2-(acetylamino)ethyl]amino}-2-phenylpyrimidin-4-yl)-2-oxo-2-[4-(2-oxo-2-pyrrolidin-1-ylethyl)piperazin-1-yl]acetamide | 1.48 | 523 |
| N-(6-{[2-(acetylamino)ethyl]amino}-2-phenylpyrimidin-4-yl)-2-[4-(2-cyanophenyl)piperazin-1-yl]-2-oxoacetamide | 2.08 | 513 |
| N-(6-{[(2-(acetylamino)ethyl]amino}-2-phenylpyrimidin-4-yl)-2-[4-(hydroxymethyl)piperidin-1-yl]-2-oxoacetamide | 1.64 | 441 |
| N-(6-{[2-(acetylamino)ethyl]amino}-2-phenylpyrimidin-4-yl)-2-(4-hydroxypiperidin-1-yl)-2-oxoacetamide | 1.62 | 427 |

| Name | Retention time (min) | Mass Ion (ES+) (MH)+ |
|---|---|---|
| N-(6-{[2-(acetylamino)ethyl]amino}-2-phenylpyrimidin-4-yl)-2-[2-(2-hydroxyethyl)piperidin-1-yl]-2-oxoacetamide | 1.77 | 455 |
| ethyl 1-[[(6-{[2-(acetylamino)ethyl]amino}-2-phenylpyrimidin-4-yl)amino](oxo)acetyl]piperidine-4-carboxylate | 1.94 | 483 |
| N-(6-{[2-(acetylamino)ethyl]amino}-2-phenylpyrimidin-4-yl)-2-oxo-2-(4-pyrrolidin-1-ylpiperidin-1-yl)acetamide | 1.42 | 480 |
| 1-[[(6-{[2-(acetylamino)ethyl]amino}-2-phenylpyrimidin-4-yl)amino](oxo)acetyl]piperidine-4-carboxamide | 1.57 | 454 |
| 1-[[(6-{[2-(acetylamino)ethyl]amino}-2-phenylpyrimidin-4-yl)amino](oxo)acetyl]-piperidine-3-carboxylic acid diethylamide | 1.85 | 510 |
| ethyl 1-[[(6-{[2-(acetylamino)ethyl]amino}-2-phenylpyrimidin-4-yl)amino](oxo)acetyl]piperidine-3-carboxylate | 1.96 | 483 |
| 1-[[(6-{[2-(acetylamino)ethyl]amino}-2-phenylpyrimidin-4-yl)amino](oxo)acetyl]piperidine-3-carboxamide | 1.66 | 454 |
| N-(6-{[2-(acetylamino)ethyl]amino}-2-phenylpyrimidin-4-yl)-2-[3-(hydroxymethyl)piperidin-1-yl]-2-oxoacetamide | 1.69 | 441 |
| N-(6-{[2-(acetylamino)ethyl]amino}-2-phenylpyrimidin-4-yl)-2-(3-hydroxypiperidin-1-yl)-2-oxoacetamide | 1.67 | 427 |
| N-(6-{[2-(acetylamino)ethyl]amino}-2-phenylpyrimidin-4-yl)-2-morpholin-4-yl-2-oxoacetamide | 1.72 | 413 |
| N-(6-{[2-(acetylamino)ethyl]amino}-2-phenylpyrimidin-4-yl)-2-azepan-1-yl-2-oxoacetamide | 1.93 | 425 |
| N1-(6-{[2-(acetylamino)ethyl]amino}-2-phenylpyrimidin-4-yl)-N2-benzyl-N2-methylethanediamide | 2.02 | 447 |
| N-(6-{[2-(acetylamino)ethyl]amino}-2-phenylpyrimidin-4-yl)-2-(3,4-dihydroisoquinolin-2(1H)-yl)-2-oxoacetamide | 2.06 | 459 |
| N-(6-{[2-(acetylamino)ethyl]amino}-2-phenylpyrimidin-4-yl)-2-[4-(2,4-difluorophenyl)piperazin-1-yl]-2-oxoacetamide | 2.17 | 524 |
| N-(6-{[2-(acetylamino)ethyl]amino}-2-phenylpyrimidin-4-yl)-2-[4-(6-methylpyridin-2-yl)piperazin-1-yl]-2-oxoacetamide | 1.53 | 503 |
| N-(6-{[2-(acetylamino)ethyl]amino}-2-phenylpyrimidin-4-yl)-2-[4-(4-methylphenyl)piperazin-1-yl]-2-oxoacetamide | 2.11 | 502 |
| N-(6-{[2-(acetylamino)ethyl]amino}-2-phenylpyrimidin-4-yl)-2-[4-(4-cyanophenyl)piperazin-1-yl]-2-oxoacetamide | 2.03 | 513 |
| N1-(6-{[2-(acetylamino)ethyl]amino}-2-phenylpyrimidin-4-yl)-N2-methyl-N2-(2-phenylethyl)ethanediamide | 2.03 | 461 |
| N-(6-{[2-(acetylamino)ethyl]amino}-2-phenylpyrimidin-4-yl)-2-oxo-2-pyrrolidin-1-ylacetamide | 1.82 | 397 |
| N-(6-{[2-(acetylamino)ethyl]amino}-2-phenylpyrimidin-4-yl)-2-(4-cyano-4-phenylpiperidin-1-yl)-2-oxoacetamide | 2.09 | 512 |
| N1-(6-{[2-(acetylamino)ethyl]amino}-2-phenylpyrimidin-4-yl)-N2-(2-cyanoethyl)-N2-methylethanediamide | 1.71 | 410 |
| N-(6-{[2-(acetylamino)ethyl]amino}-2-phenylpyrimidin-4-yl)-2-[4-(2,4-dimethoxyphenyl)piperazin-1-yl]-2-oxoacetamide | 1.92 | 548 |
| N1-(6-{[2-(acetylamino)ethyl]amino}-2-phenylpyrimidin-4-yl)-N2-methyl-N2-(1-methylpiperidin-4-yl)ethanediamide | 1.36 | 454 |
| N1-(6-{[2-(acetylamino)ethyl]amino}-2-phenylpyrimidin-4-yl)-N2,N2-diallylethanediamide | 2.03 | 423 |
| N-(6-{[2-(acetylamino)ethyl]amino}-2-phenylpyrimidin-4-yl)-2-oxo-2-[2-(pyrrolidin-1-ylmethyl)pyrrolidin-1-yl]acetamide | 1.56 | 480 |
| N1-(6-{[2-(acetylamino)ethyl]amino}-2-phenylpyrimidin-4-yl)-N2-[2-(dimethylamino)ethyl]-N2-methylethanediamide | 1.38 | 428 |
| N-(6-{[2-(acetylamino)ethyl]amino}-2-phenylpyrimidin-4-yl)-2-[4-(2,6-dimethylphenyl)piperazin-1-yl]-2-oxoacetamide | 2.30 | 516 |
| N-(6-{[2-(acetylamino)ethyl]amino}-2-phenylpyrimidin-4-yl)-2-oxo-2-(1,3-thiazolidin-3-yl)acetamide | 1.90 | 415 |
| N-(6-{[2-(acetylamino)ethyl]amino}-2-phenylpyrimidin-4-yl)-2-(2,6-dimethylmorpholin-4-yl)-2-oxoacetamide | 1.84 | 441 |
| N-(6-{[2-(acetylamino)ethyl]amino}-2-phenylpyrimidin-4-yl)-2-[4-(4-ethoxyphenyl)piperazin-1-yl]-2-oxoacetamide | 2.06 | 532 |
| N-(6-{[2-(acetylamino)ethyl]amino}-2-phenylpyrimidin-4-yl)-2-[4-(3-fluorobenzyl)-4-hydroxypiperidin-1-yl]-2-oxoacetamide | 1.96 | 535 |
| N-(6-{[2-(acetylamino)ethyl]amino}-2-phenylpyrimidin-4-yl)-2-[4-(2-ethylphenyl)piperazin-1-yl]-2-oxoacetamide | 2.27 | 516 |
| N-(6-{[2-(acetylamino)ethyl]amino}-2-phenylpyrimidin-4-yl)-2-oxo-2-[4-(3-phenylpropyl)piperazin-1-yl]acetamide | 1.66 | 530 |
| N-(6-{[2-(acetylamino)ethyl]amino}-2-phenylpyrimidin-4-yl)-2-oxo-2-[4-(2-pyrrolidin-1-ylethyl)piperazin-1-yl]acetamide | 1.42 | 509 |
| N-(6-{[2-(acetylamino)ethyl]amino}-2-phenylpyrimidin-4-yl)-2-oxo-2-[4-(2-phenylethyl)-1,4-diazepan-1-yl]acetamide | 1.61 | 530 |
| N-(6-{[2-(acetylamino)ethyl]amino}-2-phenylpyrimidin-4-yl)-2-[3-methyl-4-(3-methylphenyl)piperazin-1-yl]-2-oxoacetamide | 2.07 | 516 |
| N-(6-{[2-(acetylamino)ethyl]amino}-2-phenylpyrimidin-4-yl)-2-[4-(1,3-benzodioxol-5-ylmethyl)piperazin-1-yl]-2-oxoacetamide | 1.60 | 546 |
| N-(6-{[2-(acetylamino)ethyl]amino}-2-phenylpyrimidin-4-yl)-2-[4-(3,5-dimethoxyphenyl)piperazin-1-yl]-2-oxoacetamide | 2.10 | 548 |

| Name | Retention time (min) | Mass Ion (ES+) (MH)+ |
|---|---|---|
| N-(6-{[2-(acetylamino)ethyl]amino}-2-phenylpyrimidin-4-yl)-2-oxo-2-[4-(tetrahydrofuran-2-ylcarbonyl)piperazin-1-yl]acetamide | 1.68 | 510 |
| N-(6-{[2-(acetylamino)ethyl]amino}-2-phenylpyrimidin-4-yl)-2-oxo-2-(4-pyridin-2-ylpiperazin-1-yl)acetamide | 1.52 | 489 |
| N-(1-{2-[(6-{[2-(acetylamino)ethyl]amino}-2-phenylpyrimidin-4-yl)amino]-2-oxoacetyl}piperidin-4-yl)benzamide | 1.88 | 530 |

Example 7

Synthesis of Compounds 29.1-29.146

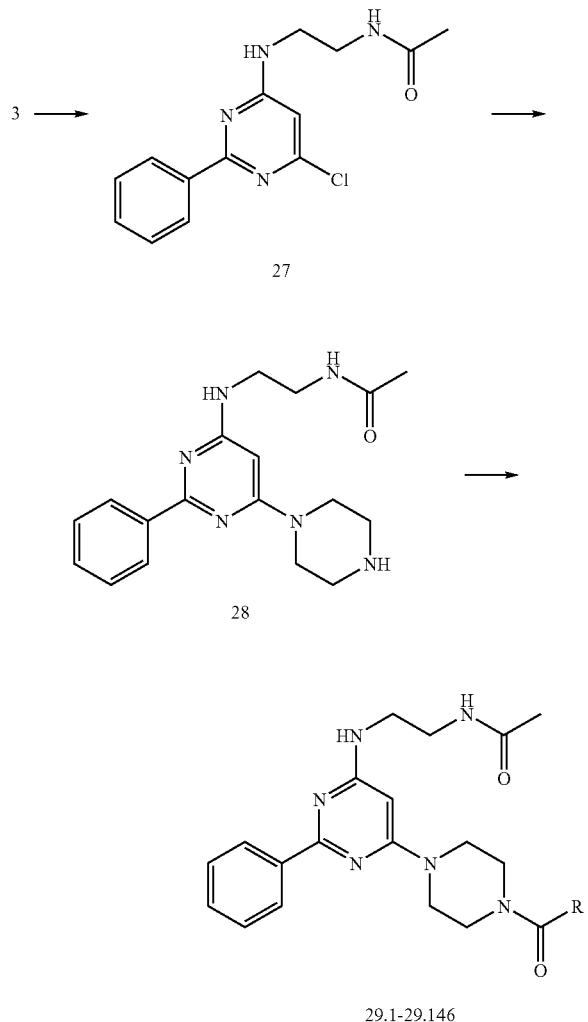

N-{2-[(6-Chloro-2-phenylpyrimidin-4-yl)amino]ethyl}acetamide (27)

4,6-Dichloro-2-phenylpyrimidine (3) (5.59 g), N-acetylethylenediamine (2.79 g) and N,N-diisopropylethylamine (3.53 g) were added to propan-1-ol (50 ml). A calcium drying tube was fitted and the resulting suspension heated to reflux for 34 hrs, then left to cool to ambient temperature. The resulting solution was evaporated in vacuo onto silica gel (40 g) and purified by flash chromatography eluting with ethyl acetate then a mixture of ethyl acetate and methanol (10:1 v/v) to furnish the title compound (6.79 g).

$\delta_H$ (CDCl$_3$): 1.92 (3H, s), 3.43-3.52 (2H, m), 3.54-3.64 (2H, br s), 5.70-5.78 (1H, br s), 6.28 (1H, s), 7.41-7.46 (3H, m), 8.37-8.40 (2H, d); m/z (ES+) 291 (MH)+

N-{2-[(2-Phenyl-6-piperazin-1-ylpyrimidin-4-yl)amino]ethyl}acetamide (28)

N-{2-[(6-Chloro-2-phenylpyrimidin-4-yl)amino]ethyl}acetamide (27) (1.5 g) and piperazine (4.44 g) were dissolved in DMSO. To this was added sodium hydrogencarbonate (2.16 g) and the mixture heated to 110° C. for 3 hrs. The reaction mixture was cooled to ambient temperature then partitioned between ethyl acetate (150 ml) and water (150 ml). The aqueous layer was washed with ethyl acetate (2×200 ml) and the combined organics washed with brine (100 ml), dried over magnesium sulfate then filtered. Removal of the solvent in vacuo furnished the title compound (0.865 g).

$\delta_H$ (CDCl$_3$): 1.81 (3H, s), 2.92-2.98 (4H, m), 3.42-3.48 (2H, m), 3.58-3.63 (6H, m), 4.90-4.95 (1H, m), 5.43 (1H, s), 6.80-6.85 (1H br s), 7.40-7.43 (3H, m), 8.33-8.38 (2H, m); m/z (ES+) 341 (MH)+

N-(2-{[6-(4-Benzoylpiperazin-1-yl)-2-phenylpyrimidin-4-yl]amino}ethyl)acetamide (29.1)

A solution of benzoic acid (18 mg), HATU (51 mg) and diisopropylethylamine (26 μl) in NMP (2 ml) was stirred at ambient temperature for 5 min then N-{2-[(2-phenyl-6-piperazin-1-ylpyrimidin-4-yl)amino]ethyl}acetamide (50 mg in 1 ml NMP) was added and the mixture stirred for a further 1.5 hr. Purification via ion exchange silica (SCX) yields the title compound on evaporation of the solvent (25 mg).

LC retention time: 2.55 min; m/z (ES+) 445 (MH)+

Library Example:

N-[2-({2-Phenyl-6-[4-(quinolin-2-ylcarbonyl)piperazin-1-yl]pyrimidin-4-yl}amino)ethyl]acetamide (29.2)

A solution of quinaldic acid (30 μl of a 0.3M solution in NMP), HATU (30 μl of a 0.3M solution in NMP) and diisopropylethylamine (30 μl of a 0.3M solution in NMP) was shaken at ambient temperature in a well of a 96 position microtitre plate for 10 min. N-{2-[(2-phenyl-6-piperazin-1-ylpyrimidin-4-yl)amino]ethyl}acetamide (30 μl of a 0.3M solution in NMP) was then added and the mixture shaken for a further 12 hr. Purification via ion exchange silica (SCX) yields the title compound.

LCMS (Method A) RT=2.45 min; m/z (ES$^+$) 497 (MH)$^+$

The following compounds 29.3-29.146 were made in an analogous manner:

| Name | Retention Time (min) | Mass ion (ES$^+$) (MH)$^+$ |
|---|---|---|
| N-[2-({6-[4-(isoquinolin-3-ylcarbonyl)piperazin-1-yl]-2-phenylpyrimidin-4-yl}amino)ethyl]acetamide | 2.42 | 496 |
| N-[2-({2-phenyl-6-[4-(quinoxalin-2-ylcarbonyl)piperazin-1-yl]pyrimidin-4-yl}amino)ethyl]acetamide | 2.43 | 497 |
| N-[2-({6-[4-(isoquinolin-1-ylcarbonyl)piperazin-1-yl]-2-phenylpyrimidin-4-yl}amino)ethyl]acetamide | 2.41 | 496 |
| N-[2-({6-[4-(2-hydroxy-5-nitrobenzoyl)piperazin-1-yl]-2-phenylpyrimidin-4-yl}amino)ethyl]acetamide | 2.39 | 506 |
| N-[2-({6-[4-(2,5-dihydroxybenzoyl)piperazin-1-yl]-2-phenylpyrimidin-4-yl}amino)ethyl]acetamide | 2.32 | 477 |
| N-[2-({2-phenyl-6-[4-(pyrazin-2-ylcarbonyl)piperazin-1-yl]pyrimidin-4-yl}amino)ethyl]acetamide | 2.17 | 447 |
| N-(2-{[6-(4-isonicotinoylpiperazin-1-yl)-2-phenylpyrimidin-4-yl]amino}ethyl)acetamide | 2.10 | 446 |
| N-{2-[(6-{4-[(2-hydroxypyridin-3-yl)carbonyl]piperazin-1-yl}-2-phenylpyrimidin-4-yl)amino]ethyl}acetamide | 2.41 | 462 |
| N-[2-({6-[4-(1H-indol-2-ylcarbony)piperazin-1-yl]-2-phenylpyrimidin-4-yl}amino)ethyl]acetamide | 2.58 | 484 |
| N-[2-({6-[4-(1H-indol-3-ylcarbonyl)piperazin-1-yl]-2-phenylpyrimidin-4-yl}amino)ethyl]acetamide | 2.40 | 484 |
| N-[2-({6-[4-(3-nitrobenzoyl)piperazin-1-yl]-2-phenylpyrimidin-4-yl}amino)ethyl]acetamide | 2.46 | 490 |
| N-{2-[(6-{4-[(4-acetyl-5-methyl-2-oxo-2,3-dihydro-1H-pyrrol-3-yl)acetyl]piperazin-1-yl}-2-phenylpyrimidin-4-yl)amino]ethyl}acetamide | 2.24 | 520 |
| N-{2-[(6-{4-[(3-hydroxy-4-methoxyphenyl)acetyl]piperazin-1-yl}-2-phenylpyrimidin-4-yl)amino]ethyl}acetamide | 2.41 | 505 |
| N-{2-[(6-{4-[(2E)-3-(1H-indol-3-yl)prop-2-enoyl]piperazin-1-yl}-2-phenylpyrimidin-4-yl)amino]ethyl}acetamide | 2.52 | 510 |
| N-{2-[(6-{4-[(2E)-3-(3-nitrophenyl)prop-2-enoyl]piperazin-1-yl}-2-phenylpyrimidin-4-yl)amino]ethyl}acetamide | 2.55 | 516 |
| N-[2-({6-[4-(2-hydroxy-4-methylbenzoyl)piperazin-1-yl]-2-phenylpyrimidin-4-yl}amino)ethyl]acetamide | 2.42 | 475 |
| N-[2-({6-[4-(2-hydroxy-3-methoxybenzoyl)piperazin-1-yl]-2-phenylpyrimidin-4-yl}amino)ethyl]acetamide | 2.36 | 492 |
| N-[2-({6-[4-(2-hydroxy-3-methylbenzoyl)piperazin-1-yl]-2-phenylpyrimidin-4-yl}amino)ethyl]acetamide | 2.48 | 475 |
| N-[2-({6-[4-(1H-indol-3-ylacetyl)piperazin-1-yl]-2-phenylpyrimidin-4-yl}amino)ethyl]acetamide | 2.45 | 498 |
| N-{2-[(6-{4-[3-(1H-indol-3-yl)propanoyl]piperazin-1-yl}-2-phenylpyrimidin-4-yl)amino]ethyl}acetamide | 2.49 | 512 |
| N-[2-({2-phenyl-6-[4-(pyridin-2-ylcarbonyl)piperazin-1-yl]pyrimidin-4-yl}amino)ethyl]acetamide | 2.48 | 446 |
| N-{2-[(6-{4-[4-(1H-indol-3-yl)butanoyl]piperazin-1-yl}-2-phenylpyrimidin-4-yl)amino]ethyl}acetamide | 2.59 | 526 |
| N-{2-[(6-{4-[(5-methylpyrazin-2-yl)carbonyl]piperazin-1-yl}-2-phenylpyrimidin-4-yl)amino]ethyl}acetamide | 2.24 | 461 |
| N-{2-[(6-{4-[(5-methyl-2-phenyl-2H-1,2,3-triazol-4-yl)carbonyl]piperazin-1-yl}-2-phenylpyrimidin-4-yl)amino]ethyl}acetamide | 2.71 | 526 |
| N-{2-[(6-{4-[(4-oxo-4,5,6,7-tetrahydro-1-benzofuran-3-yl)carbonyl]piperazin-1-yl}-2-phenylpyrimidin-4-yl)amino]ethyl}acetamide | 2.28 | 503 |
| N-(2-{[6-(4-{[2-(methylsulfanyl)pyridin-3-yl]carbonyl}piperazin-1-yl)-2-phenylpyrimidin-4-yl]amino}ethyl)acetamide | 2.37 | 492 |
| N-{2-[(6-{4-[(1-tert-butyl-3-methyl-1H-pyrazol-5-yl)carbonyl]piperazin-1-yl}-2-phenylpyrimidin-4-yl)amino]ethyl}acetamide | 2.45 | 505 |
| N-[2-({6-[4-(1-benzothien-2-ylcarbonyl)piperazin-1-yl]-2-phenylpyrimidin-4-yl}amino)ethyl]acetamide | 2.62 | 501 |
| N-{2-[(2-phenyl-6-{4-[4-(trifluoromethoxy)benzoyl]piperazin-1-yl}pyrimidin-4-yl)amino]ethyl}acetamide | 2.64 | 529 |
| N-{2-[(6-{4-[(5-chloro-2-hydroxypyridin-3-yl)carbonyl]piperazin-1-yl}-2-phenylpyrimidin-4-yl)amino]ethyl}acetamide | 2.39 | 496 |
| N-{2-[(6-{4-[(2E)-4-oxo-4-(2,3,4,5,6-pentamethylphenyl)but-2-enoyl]piperazin-1-yl}-2-phenylpyrimidin-4-yl)amino]ethyl}acetamide | 2.81 | 569 |
| N-{2-[(2-phenyl-6-{4-[4-(trifluoroacetyl)benzoyl]piperazin-1-yl}pyrimidin-4-yl)amino]ethyl}acetamide | 2.39 | 541 |
| N-{2-[4-(6-{[2-(acetylamino)ethyl]amino}-2-phenylpyrimidin-4-yl)piperazin-1-yl]-2-oxoethyl}-4-chlorobenzamide | 2.46 | 536 |
| N-{2-[(6-{4-[(2,4-dihydroxypyrimidin-5-yl)carbonyl]piperazin-1-yl}-2-phenylpyrimidin-4-yl)amino]ethyl}acetamide | 2.01 | 479 |

-continued

| Name | Retention Time (min) | Mass ion (ES+) (MH)+ |
|---|---|---|
| N-[2-({2-phenyl-6-[4-(1,2,3-thiadiazol-4-ylcarbonyl)piperazin-1-yl]pyrimidin-4-yl}amino)ethyl]acetamide | 2.44 | 453 |
| N-(2-{[6-(4-{[5-chloro-2-(methylsulfanyl)pyrimidin-4-yl]carbonyl}piperazin-1-yl)-2-phenylpyrimidin-4-yl]amino}ethyl)acetamide | 2.52 | 527 |
| N-(2-{[6-(4-{[1-(2-furylmethyl)-5-oxopyrrolidin-3-yl]carbonyl}piperazin-1-yl)-2-phenylpyrimidin-4-yl]amino}ethyl)acetamide | 2.33 | 532 |
| N-{2-[(6-{4-[(3-tert-butyl-1-methyl-1H-pyrazol-5-yl)carbonyl]piperazin-1-yl}-2-phenylpyrimidin-4-yl)amino]ethyl}acetamide | 2.55 | 505 |
| N-{2-[(6-{4-[(4-nitrophenyl)acetyl]piperazin-1-yl}-2-phenylpyrimidin-4-yl)amino]ethyl}acetamide | 2.49 | 504 |
| N-{2-[(6-{4-[(2,5-dimethoxyphenyl)acetyl]piperazin-1-yl}-2-phenylpyrimidin-4-yl)amino]ethyl}acetamide | 2.48 | 519 |
| N-{2-[(6-{4-[(3-methoxyphenyl)acetyl]piperazin-1-yl}-2-phenylpyrimidin-4-yl)amino]ethyl}acetamide | 2.45 | 489 |
| N-{2-[(6-{4-[(4-methoxyphenyl)acetyl]piperazin-1-yl}-2-phenylpyrimidin-4-yl)amino]ethyl}acetamide | 2.44 | 490 |
| N-{2-[(6-{4-[(2-methoxyphenyl)acetyl]piperazin-1-yl}-2-phenylpyrimidin-4-yl)amino]ethyl}acetamide | 2.47 | 489 |
| N-{2-({2-phenyl-6-[4-(1,2,3,4-tetrahydronaphthalen-2-ylcarbonyl)piperazin-1-yl]pyrimidin-4-yl}amino)ethyl]acetamide | 2.65 | 499 |
| N-{2-[(6-{4-[(2R)-2-hydroxy-3-phenylpropanoyl]piperazin-1-yl}-2-phenylpyrimidin-4-yl)amino]ethyl}acetamide | 2.40 | 489 |
| N-[2-({2-phenyl-6-[4-(1H-pyrrol-2-ylcarbonyl)piperazin-1-yl]pyrimidin-4-yl}amino)ethyl]acetamide | 2.54 | 434 |
| N-[2-({2-phenyl-6-[4-(4-vinylbenzoyl)piperazin-1-yl]pyrimidin-4-yl}amino)ethyl]acetamide | 2.54 | 471 |
| N-[2-({6-[4-(cyclohexylacetyl)piperazin-1-yl]-2-phenylpyrimidin-4-yl}amino)ethyl]acetamide | 2.61 | 465 |
| N-{2-[(2-phenyl-6-{4-[4-(1H-pyrrol-1-yl)benzoyl]piperazin-1-yl}pyrimidin-4-yl)amino]ethyl}acetamide | 2.63 | 510 |
| N-{2-[(6-{4-[2-(1,3-dioxo-1,3-dihydro-2H-isoindol-2-yl)propanoyl]piperazin-1-yl}-2-phenylpyrimidin-4-yl)amino]ethyl}acetamide | 2.47 | 542 |
| N-{2-({6-[4-([1,1'-biphenyl]-4-ylacetyl)piperazin-1-yl]-2-phenylpyrimidin-4-yl}amino)ethyl]acetamide | 2.78 | 536 |
| N-{2-[(6-{4-[(6-methoxy-3-oxo-2,3-dihydro-1H-inden-1-yl)acetyl]piperazin-1-yl}-2-phenylpyrimidin-4-yl)amino]ethyl}acetamide | 2.41 | 543 |
| N-{2-[(6-{4-[(3-nitrophenyl)acetyl]piperazin-1-yl}-2-phenylpyrimidin-4-yl)amino]ethyl}acetamide | 2.51 | 504 |
| N-{2-[(6-{4-[(2-methylphenyl)acetyl]piperazin-1-yl}-2-phenylpyrimidin-4-yl)amino]ethyl}acetamide | 2.53 | 473 |
| N-{2-[(6-{4-[(4-methylphenyl)acetyl]piperazin-1-yl}-2-phenylpyrimidin-4-yl)amino]ethyl}acetamide | 2.55 | 473 |
| N-[2-({6-[4-(3-methylbenzoyl)piperazin-1-yl]-2-phenylpyrimidin-4-yl}amino)ethyl]acetamide | 2.69 | 459 |
| N-[2-({6-[4-(4-methylbenzoyl)piperazin-1-yl]-2-phenylpyrimidin-4-yl}amino)ethyl]acetamide | 2.50 | 459 |
| N-[2-({6-[4-(2-methylbenzoyl)piperazin-1-yl]-2-phenylpyrimidin-4-yl}amino)ethyl]acetamide | 2.45 | 459 |
| N-{2-[(6-{4-[(3-methylphenyl)acetyl]piperazin-1-yl}-2-phenylpyrimidin-4-yl)amino]ethyl}acetamide | 2.53 | 473 |
| N-[2-({6-[4-(4-butylbenzoyl)piperazin-1-yl]-2-phenylpyrimidin-4-yl}amino)ethyl]acetamide | 2.81 | 501 |
| N-[2-({6-[4-(4-nitrobenzoyl)piperazin-1-yl]-2--phenylpyrimidin-4-yl}amino)ehyl]acetamide | 2.45 | 490 |
| N-[2-({6-[4-(2-phenoxypropanoyl)piperazin-1-yl]-2-phenylpyrimidin-4-yl}amino)ethyl]acetamide | 2.50 | 489 |
| N-{2-[(6-{4-[(3,4-dihydroxyphenyl)acetyl]piperazin-1-yl}-2-phenylpyrimidin-4-yl)amino]ethyl}acetamide | 2.40 | 491 |
| N-[2-({6-[4-(1,3-benzodioxol-5-ylcarbonyl)piperazin-1-yl]-2-phenylpyrimidin-4-yl}amino)ethyl]acetamide | 2.39 | 489 |
| N-[2-({2-phenyl-6-[4-(phenylacetyl)piperazin-1-yl]pyrimidin-4-yl}amino)ethyl]acetamide | 2.42 | 459 |
| N-[2-({6-[4-(bicyclo[2.2.1]hept-5-en-2-ylcarbonyl)piperazin-1-yl]-2-phenylpyrimidin-4-yl}amino)ethyl]acetamide | 2.45 | 461 |
| N-{2-[(6-{4-[hydroxy(phenyl)acetyl]piperazin-1-yl}-2-phenylpyrimidin-4-yl)amino]ethyl}acetamide | 2.33 | 475 |
| N-{2-[(6-{4-[(2-naphthyloxy)acetyl]piperazin-1-yl}-2-phenylpyrimidin-4-yl)amino]ethyl}acetamide | 2.69 | 525 |
| N-[2-({2-phenyl-6-{4-[(1-phenylcyclopentyl)carbonyl]piperazin-1-yl}pyrimidin-4-yl)amino]ethyl}acetamide | 2.76 | 513 |
| N-[2-({2-phenyl-6-[4-(2-sulfanylbenzoyl)piperazin-1-yl]pyrimidin-4-yl}amino)ethyl]acetamide | 2.68 | 477 |

-continued

| Name | Retention Time (min) | Mass ion (ES+) (MH)+ |
|---|---|---|
| N-{2-[(6-{4-[cyclopentyl(phenyl)acetyl]piperazin-1-yl}-2-phenylpyrimidin-4-yl)amino]ethyl}acetamide | 2.84 | 527 |
| N-[2-({6-[4-(4-tert-butylbenzoyl)piperazin-1-yl]-2-phenylpyrimidin-4-yl}amino)ethyl]acetamide | 2.74 | 501 |
| N-[2-({6-[4-(1-adamantylcarbonyl)piperazin-1-yl]-2-phenylpyrimidin-4-yl}amino)ethyl]acetamide | 2.76 | 503 |
| N-[2-({6-[4-(4-methoxybenzoyl)piperazin-1-yl]-2-phenylpyrimidin-4-yl}amino)ethyl]acetamide | 2.43 | 475 |
| N-[2-({6-[4-(4-cyclohexylbenzoyl)piperazin-1-yl]-2-phenylpyrimidin-4-yl}amino)ethyl]acetamide | 2.96 | 527 |
| N-[2-({6-[4-(1-naphthoyl)piperazin-1-yl]-2-phenylpyrimidin-4-yl}amino)ethyl]acetamide | 2.59 | 495 |
| N-[2-({6-[4-(4-bromo-3-methylbenzoyl)piperazin-1-yl]-2-phenylpyrimidin-4-yl}amino)ethyl]acetamide | 2.68 | 539 |
| N-[2-({6-[4-(5-chloro-2-hydroxybenzoyl)piperazin-1-yl]-2-phenylpyrimidin-4-yl}amino)ethyl]acetamide | 2.48 | 495 |
| N-{2-[(6-{4-[(4-(dimethylamino)benzoyl]piperazin-1-yl}-2-phenylpyrimidin-4-yl)amino]ethyl}acetamide | 2.44 | 488 |
| N-{2-[(6-{4-[(acetylamino)acetyl]piperazin-1-yl}-2-phenylpyrimidin-4-yl)amino]ethyl}acetamide | 2.41 | 440 |
| N-{2-[(6-{4-[[4-hydroxy-3-methoxyphenyl)acetyl]piperazin-1-yl}-2-phenylpyrimidin-4-yl)amino]ethyl}acetamide | 2.30 | 505 |
| N-[2-({6-[4-(3-hydroxy-4-methylbenzoyl)piperazin-1-yl]-2-phenylpyrimidin-4-yl}amino)ethyl]acetamide | 2.41 | 475 |
| N-[2-({6-[4-(4-fluoro-1-naphthoyl)piperazin-1-yl]-2-phenylpyrimidin-4-yl}amino)ethyl]acetamide | 2.65 | 513 |
| N-[2-({6-[4-(5-formyl-2-hydroxybenzoyl)piperazin-1-yl]-2-phenylpyrimidin-4-yl}amino)ethyl]acetamide | 2.37 | 489 |
| N-[2-({6-[4-(cyclohex-1-en-1-ylcarbonyl)piperazin-1-yl]-2-phenylpyrimidin-4-yl}amino)ethyl]acetamide | 2.46 | 449 |
| N-[2-({6-[4-([1,1'-biphenyl]-4-ylcarbonyl)piperazin-1-yl]-2-phenylpyrimidin-4-yl}amino)ethyl]acetamide | 2.74 | 521 |
| N-{2-[(6-{4-[(4-bromophenyl)acetyl]piperazin-1-yl}-2-phenylpyrimidin-4-yl)amino]ethyl}acetamide | 2.60 | 537 |
| N-{2-[(6-{4-[2-(methylsulfanyl)benzoyl]piperazin-1-yl}-2-phenylpyrimidin-4-yl)amino]ethyl}acetamide | 2.48 | 491 |
| N-[2-({6-[4-(4-benzoylbenzoyl)piperazin-1-yl]-2-phenylpyrimidin-4-yl}amino)ethyl]acetamide | 2.63 | 550 |
| N-{2-[(2-phenyl-6-{4-[4-(trifluoromethyl)benzoyl]piperazin-1-yl}pyrimidin-4-yl)amino]ethyl}acetamide | 2.63 | 513 |
| N-[2-({6-[4-(4-acetylbenzoyl)piperazin-1-yl]-2-phenylpyrimidin-4-yl}amino)ethyl]acetamide | 2.36 | 487 |
| N-[2-({6-[4-(4-cyanobenzoyl)piperazin-1-yl]-2-phenylpyrimidin-4-yl}amino)ethyl]acetamide | 2.59 | 470 |
| N-[2-[(2-phenyl-6-{4-[3-(trifluoromethyl)benzoyl]piperazin-1-yl}pyrimidin-4-yl)amino]ethyl}acetamide | 2.60 | 513 |
| N-[2-({6-[4-(3-cyanobenzoyl)piperazin-1-yl]-2-phenylpyrimidin-4-yl}amino)ethyl]acetamide | 2.37 | 470 |
| N-[2-({6-[4-(diphenylacetyl)piperazin-1-yl]-2-phenylpyrimidin-4-yl}amino)ethyl]acetamide | 2.70 | 535 |
| N-[2-({6-[4-(4-ethylbenzoyl)piperazin-1-yl]-2-phenylpyrimidin-4-yl}amino)ethyl]acetamide | 2.57 | 473 |
| N-[2-({6-[4-(2-hydroxybenzoyl)piperazin-1-yl]-2-phenylpyrimidin-4-yl}amino)ethyl]acetamide | 2.30 | 461 |
| N-[2-({6-[4-(3-bromobenzoyl)piperazin-1-yl]-2-phenylpyrimidin-4-yl}amino)ethyl]acetamide | 2.54 | 525 |
| N-(2-{[6-(4-{[(4-chlorophenyl)sulfanyl]acetyl}piperazin-1-yl)-2-phenylpyrimidin-4-yl]amino}ethyl)acetamide | 2.68 | 525 |
| N-{2-[(6-{4-[(4-acetyl-3,5-dimethyl-1H-pyrrol-2-yl)carbonyl]piperazin-1-yl}-2-phenylpyrimidin-4-yl)amino]ethyl}acetamide | 2.34 | 504 |
| N-{2-[(2-phenyl-6-{4-[(2E)-3-thien-3-ylprop-2-enoyl]piperazin-1-yl}pyrimidin-4-yl)amino]ethyl}acetamide | 2.51 | 477 |
| N-{2-[(6-{4-[2-furyl(morpholin-4-yl)acetyl]piperazin-1-yl}-2-phenylpyrimidin-4-yl)amino]ethyl}acetamide | 2.02 | 534 |
| N-{2-[(6-{4-[(2-methyl-1H-benzimidazol-5-yl)carbonyl]piperazin-1-yl}-2-phenylpyrimidin-4-yl)amino]ethyl}acetamide | 2.40 | 499 |
| N-(2-{[6-(4-isobutyrylpiperazin-1-yl)-2-phenylpyrimidin-4-yl]amino}ethyl)acetamide | 2.27 | 411 |
| N-{2-[(6-{4-[(1H-benzimidazol-2-ylsulfanyl)acetyl]piperazin-1-yl}-2-phenylpyrimidin-4-yl)amino]ethyl}acetamide | 2.27 | 531 |
| N-{2-[(6-{4-[(2-hydroxyquinolin-4-yl)carbonyl]piperazin-1-yl}-2-phenylpyrimidin-4-yl)amino]ethyl}acetamide | 2.30 | 512 |
| N-{2-[(6-{4-[(5-chlorothien-2-yl)carbonyl]piperazin-1-yl}-2-phenylpyrimidin-4-yl)amino]ethyl}acetamide | 2.54 | 485 |

-continued

| Name | Retention Time (min) | Mass ion (ES+) (MH)+ |
|---|---|---|
| N-{2-[(6-{4-[(2E)-3-(3-cyanophenyl)prop-2-enoyl]piperazin-1-yl}-2-phenylpyrimidin-4-yl)amino]ethyl}acetamide | 2.53 | 496 |
| N-{2-[(6-{4-[(5-nitrothien-3-yl)carbonyl]piperazin-1-yl}-2-phenylpyrimidin-4-yl)amino]ethyl}acetamide | 2.41 | 496 |
| N-(2-{[6-(4-{[5-(methylsulfonyl)thien-2-yl]carbonyl}piperazin-1-yl)-2-phenylpyrimidin-4-yl]amino}ethyl)acetamide | 2.33 | 529 |
| N-{2-{[2-phenyl-6-(4-{[4-(trifluoromethyl)cyclohexyl]carbonyl}piperazin-1-yl)pyrimidin-4-yl]amino}ethyl}acetamide | 2.64 | 519 |
| N-{2-[(6-{4-[(3-ethoxythien-2-yl)carbonyl]piperazin-1-yl}-2-phenylpyrimidin-4-yl)amino]ethyl}acetamide | 2.60 | 495 |
| N-{2-[(6-{4-[(2E)-3-(2-furyl)prop-2-enoyl]piperazin-1-yl}-2-phenylpyrimidin-4-yl)amino]ethyl}acetamide | 2.45 | 461 |
| N-[2-({2-phenyl-6-[4-(2,3,5,6-tetrafluoro-4-methylbenzoyl)piperazin-1-yl]pyrimidin-4-yl}amino)ethyl]acetamide | 2.68 | 531 |
| N-[2-({6-[4-(5-bromo-2-furoyl)piperazin-1-yl]-2-phenylpyrimidin-4-yl}amino)ethyl]acetamide | 2.46 | 515 |
| N-[2-({2-phenyl-6-[4-(4,4,4-trifluoro-3-hydroxy-3-methylbutanoyl)piperazin-1-yl]pyrimidin-4-yl}amino)ethyl]acetamide | 2.38 | 495 |
| N-{2-[(2-phenyl-6-{4-[(2E)-3-(2,3,4-trifluorophenyl)prop-2-enoyl]piperazin-1-yl}pyrimidin-4-yl)amino]ethyl}acetamide | 2.66 | 525 |
| N-{2-[(6-{4-[(8-hydroxyquinolin-2-yl)carbonyl]piperazin-1-yl}-2-phenylpyrimidin-4-yl)amino]ethyl}acetamide | 2.49 | 512 |
| N-[2-({6-[4-(6-hydroxy-2-naphthoyl)piperazin-1-yl]-2-phenylpyrimidin-4-yl}amino)ethyl]acetamide | 2.41 | 511 |
| N-{2-[(6-{4-[(2E)-3-(4-isopropylphenyl)prop-2-enoyl]piperazin-1-yl}-2-phenylpyrimidin-4-yl)amino]ethyl}acetamide | 2.80 | 513 |
| N-{2-[(2-phenyl-6-{4-[(2E)-3-thien-2-ylprop-2-enoyl]piperazin-1-yl}pyrimidin-4-yl)amino]ethyl}acetamide | 2.49 | 477 |
| N-{2-[(2-phenyl-6-{4-[(3E)-4-phenylbut-3-enoyl]piperazin-1-yl}pyrimidin-4-yl)amino]ethyl}acetamide | 2.58 | 485 |
| N-{2-[(6-{4-[(1-benzoylpiperidin-4-yl)carbonyl]piperazin-1-yl}-2-phenylpyrimidin-4-yl)amino]ethyl}acetamide | 2.39 | 556 |
| N-(2-{[6-(4-{4-[(aminocarbothioyl)amino]benzoyl}piperazin-1-yl)-2-phenylpyrimidin-4-yl]amino}ethyl)acetamide | 2.46 | 519 |
| methyl 3-{[4-(6-{[2-(acetylamino)ethyl]amino}-2-phenylpyrimidin-4-yl)piperazin-1-yl]carbonyl}isonicotinate | 2.21 | 504 |
| N-[2-({6-[4-(2-oxo-3-phenylpropanoyl)piperazin-1-yl]-2-phenylpyrimidin-4-yl}amino)ethyl]acetamide | 2.58 | 487 |
| N-{2-[(6-{4-[5-(1,2-dithiolan-3-yl)pentanoyl]piperazin-1-yl}-2-phenylpyrimidin-4-yl)amino]ethyl}acetamide | 2.75 | 529 |
| N-{2-[(6-{4-[(2-methyl-5,6-dihydro-1,4-oxathiin-3-yl)carbonyl]piperazin-1-yl}-2-phenylpyrimidin-4-yl)amino]ethyl}acetamide | 2.33 | 483 |
| N-[2-({2-phenyl-6-[4-(1H-tetraazol-1-ylacetyl)piperazin-1-yl]pyrimidin-4-yl}amino)ethyl]acetamide | 2.39 | 451 |
| N-{2-[(6-{4-[3-(2-furyl)propanoyl]piperazin-1-yl}-2-phenylpyrimidin-4-yl)amino]ethyl}acetamide | 2.45 | 465 |
| N-{2-[(2-phenyl-6-{4-[(2E,4E)-5-phenylpenta-2,4-dienoyl]piperazin-1-yl}pyrimidin-4-yl)amino]ethyl}acetamide | 2.69 | 497 |
| N-(2-{[6-(4-{[2-(4-methylphenoxy)pyridin-3-yl]carbonyl}piperazin-1-yl)-2-phenylpyrimidin-4-yl]amino}ethyl)acetamide | 2.57 | 552 |
| N-{2-[(2-phenyl-6-{4-[(2E)-3-pyridin-2-ylprop-2-enoyl]piperazin-1-yl}pyrimidin-4-yl)amino]ethyl}acetamide | 2.23 | 472 |
| N-[2-({6-[4-(3-methyl-2-nitrobenzoyl)piperazin-1-yl]-2-phenylpyrimidin-4-yl}amino)ethyl]acetamide | 2.51 | 504 |
| N-[2-({2-phenyl-6-[4-(3-thien-2-ylpropanoyl)piperazin-1-yl]pyrimidin-4-yl}amino)ethyl]acetamide | 2.49 | 479 |
| N-{2-[(6-{4-[(5-methyl-2,4-dioxo-3,4-dihydropyrimidin-1(2H)-yl)acetyl]piperazin-1-yl}-2-phenylpyrimidin-4-yl)amino]ethyl}acetamide | 2.46 | 507 |
| N-[2-[(6-{4-[(4'-hydroxy[1,1'-biphenyl]-4-yl)carbonyl]piperazin-1-yl}-2-phenylpyrimidin-4-yl)amino]ethyl}acetamide | 2.50 | 537 |
| N-[2-({6-[4-(cyclohex-3-en-1-ylcarbonyl)piperazin-1-yl]-2-phenylpyrimidin-4-yl}amino)ethyl]acetamide | 2.58 | 449 |
| N-{2-[(6-{4-[3-(4-hydroxyphenyl)propanoyl]piperazin-1-yl}-2-phenylpyrimidin-4-yl)amino]ethyl}acetamide | 2.30 | 489 |
| N-{2-[(2-phenyl-6-{4-[(2E)-3-phenylprop-2-enoyl]piperazin-1-yl}pyrimidin-4-yl)amino]ethyl}acetamide | 2.53 | 471 |
| N-{2-[(2-phenyl-6-{4-[3-(3,4,5-trimethoxyphenyl)propanoyl]piperazin-1-yl}pyrimidin-4-yl)amino]ethyl}acetamide | 2.40 | 563 |
| N-(2-{[6-(4-acetylpiperazin-1-yl)-2-phenylpyrimidin-4-yl]amino}ethyl)acetamide | 2.44 | 383 |
| N-(2-{[2-phenyl-6-(4-propionylpiperazin-1-yl)pyrimidin-4-yl]amino}ethyl)acetamide | 2.19 | 397 |
| N-{2-[(6-{4-[2-hydroxy-5-(1H-pyrrol-1-yl)benzoyl]piperazin-1-yl}-2-phenylpyrimidin-4-yl)amino]ethyl}acetamide | 2.56 | 526 |

Example 8

Synthesis of Compounds 34.1-34.155

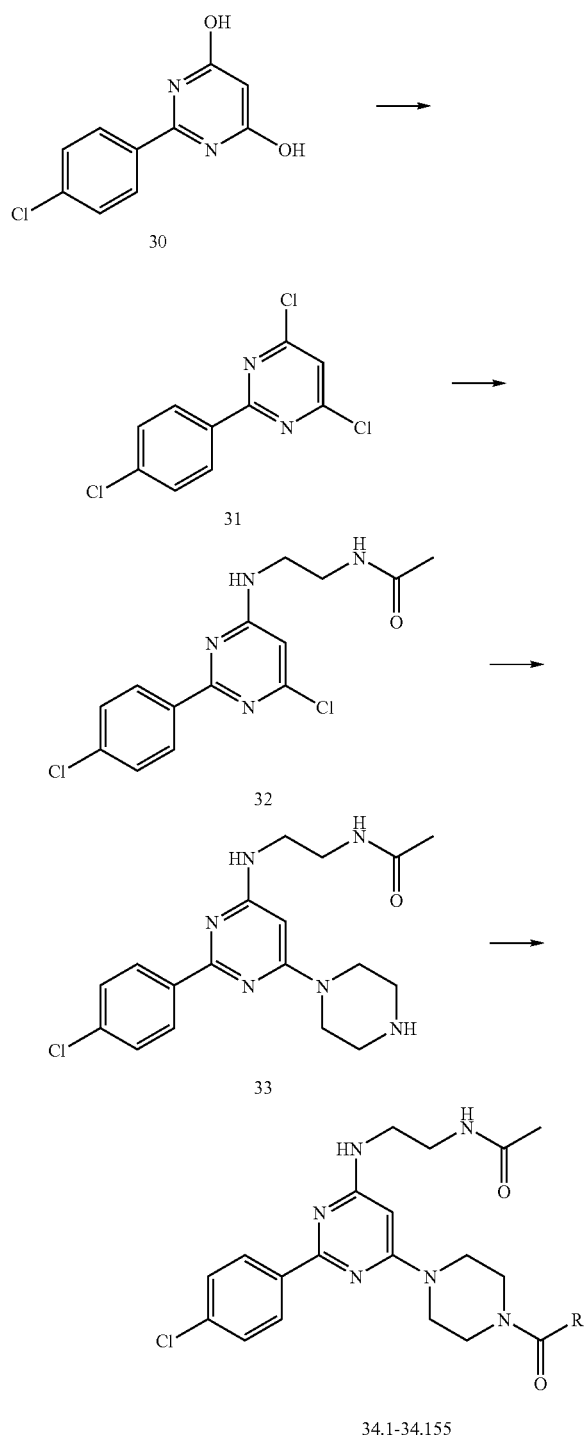

34.1-34.155

2-(4-Chlorophenyl)pyrimidine-4,6-diol (30)

To sodium ethoxide (48 ml of a 21% wt solution in ethanol diluted with a further 130 ml ethanol) was added 4-chlorobenzamidine (8 g) and diethyl malonate (6.67 ml) and the solution left to stir at 40° C. for 96 hrs. The reaction mixture was subsequently cooled to 5° C. and acidified cautiously to pH 2 using concentrated hydrochloric acid. The solid thus precipitated was filtered, washed with excess cold water, then 50 ml diethyl ether and dried in vacuo yielding the title compound (7.51 g).

$\delta_H$ (d$^6$-DMSO): 5.36 (1H, s), 7.53-7.58 (2H, d), 8.05-8.10 (2H, d); m/z (ES$^+$) 223 (MH)$^+$ 4,6-Dichloro-2-(4-chlorophenyl)pyrimidine (31)

To 2-(4-chlorophenyl)pyrimidine-4,6-diol (6.43 g) in phosphorous oxychloride (50 ml) was added N,N-dimethylformamide (10 drops) and the mixture heated to reflux for 16 hrs. After this time, the phosphorous oxychloride was removed in vacuo yielding a crude sample of the title compound. Cold water was cautiously added to remove traces of phosphorous oxychloride, then the solid filtered and dried in vacuo (6.81 g).

$\delta_H$ (d$^6$-DMSO): 7.68-7.72 (2H, d), 8.05 (1H, s), 8.36-8.40 (2H, d); m/z (ES$^+$) 258 (MH)$^+$ N-(2-{[6-Chloro-2-(4-chlorophenyl)pyrimidin-4-yl]amino}ethyl)acetamide (32)

N-Acetylethylenediamine (1.02 g) was dissolved in ethanol (250 ml) and 4,6-dichloro-2-(4-chlorophenyl)pyrimidine (2.5 g) then triethylamine (1.35 ml) added. The mixture was heated to 85° C. with stirring for 48 hrs. The solvent was then removed in vacuo and purified by column chromatography on silica gel eluting first with ethyl acetate then a mixture of ethyl acetate and methanol (9:1 v/v) to furnish the title compound (1.29 g).

$\delta_H$ (CDCl$_3$): 1.95 (3H, s), 3.51-3.56 (2H, m), 3.56-3.67 (2H, br s), 5.70-5.75 (1H, br s), 5.95-6.02 (1H, br s), 6.30 (1H, s), 7.38-7.42 (2H, d), 8.28-8.33 (2H, d)

N-(2-{[2-(4-Chlorophenyl)-6-piperazin-1-ylpyrimidin-4-yl]amino}ethyl)acetamide (33)

N-(2-{[6-Chloro-2-(4-chlorophenyl)pyrimidin-4-yl]amino}ethyl)acetamide (1.00 g) and piperazine (2.66 g) were dissolved in DMSO (40 ml) and sodium hydrogencarbonate added (1.29 g). The mixture was heated to 110° C. for 6 hrs. The solvent was removed in vacuo and the residue partitioned between ethyl acetate (100 ml) and water (100 ml). The aqueous phase was washed further with ethyl acetate (2×100 ml) and the combined organics subsequently washed with saturated brine solution (50 ml), dried over magnesium sulphate, filtered and the solvent removed in vacuo to afford the title compound (1.18 g).

$\delta_H$ (CDCl$_3$): 1.86 (3H, s), 2.93-2.98 (4H, m), 3.43-3.50 (2H, m), 3.55-3.64 (6H, m), 4.92-4.95 (1H, m), 5.43 (1H, s), 6.52-6.59 (1H, br s), 7.37-7.40 (2H, d), 8.28-8.32 (2H, d)

Library Compound:

N-[2-({2-(4-Chlorophenyl)-6-[4-(quinolin-2-ylcarbonyl)piperazin-1-yl]pyrimidin-4-yl}amino)ethyl]acetamide (34.1)

A solution of quinaldic acid (60 μl of a 0.3M solution in NMP), HATU (60 μl of a 0.3M solution in NMP) and diisopropylethylamine (60 μl of a 0.3M solution in NMP) was shaken at ambient temperature in a well of a 96 position microtitre plate for 5 min. N-(2-{[2-(4-chlorophenyl)-6-piperazin-1-ylpyrimidin-4-yl]amino}ethyl)acetamide (30 μl of a 0.3M solution in NMP) was then added and the mixture shaken for a further 12 hr. Purification via ion exchange silica (SCX) yields the title compound.

LCMS (Method A) RT=2.80 min; m/z (ES⁺) 530 (MH)⁺

The following compounds 34.2-34.155 were synthesised in an analogous manner:

| Name | Retention Time (min) | Mass Ion (ES⁺) (MH)⁺ |
|---|---|---|
| N-[2-({2-(4-chlorophenyl)-6-[4-(isoquinolin-3-ylcarbonyl)piperazin-1-yl]pyrimidin-4-yl}amino)ethyl]acetamide | 2.75 | 530 |
| N-[2-({2-(4-chlorophenyl)-6-[4-(quinoxalin-2-ylcarbonyl)piperazin-1-yl]pyrimidin-4-yl}amino)ethyl]acetamide | 2.75 | 531 |
| N-[2-({2-(4-chlorophenyl)-6-[4-(isoquinolin-1-ylcarbonyl)piperazin-1-yl]pyrimidin-4-yl}amino)ethyl]acetamide | 2.74 | 530 |
| N-[2-({2-(4-chlorophenyl)-6-[4-(2-hydroxy-5-nitrobenzoyl)piperazin-1-yl]pyrimidin-4-yl}amino)ethyl]acetamide | 2.71 | 540 |
| N-[2-({2-(4-chlorophenyl)-6-[4-(2,5-dihydroxybenzoyl)piperazin-1-yl]pyrimidin-4-yl}amino)ethyl]acetamide | 2.54 | 511 |
| N-[2-({2-(4-chlorophenyl)-6-[4-(pyrazin-2-ylcarbonyl)piperazin-1-yl]pyrimidin-4-yl}amino)ethyl]acetamide | 2.49 | 481 |
| N-[2-({2-(4-chlorophenyl)-6-[4-(pyridin-3-ylcarbonyl)piperazin-1-yl]pyrimidin-4-yl}amino)ethyl]acetamide | 2.44 | 480 |
| N-(2-{[2-(4-chlorophenyl)-6-(4-isonicotinoylpiperazin-1-yl)pyrimidin-4-yl]amino}ethyl)acetamide | 2.38 | 480 |
| N-{2-[(2-(4-chlorophenyl)-6-{4-[(2-hydroxypyridin-3-yl)carbonyl]piperazin-1-yl}pyrimidin-4-yl)amino]ethyl}acetamide | 2.37 | 496 |
| N-[2-({2-(4-chlorophenyl)-6-[4-(1H-indol-2-ylcarbonyl)piperazin-1-yl]pyrimidin-4-yl}amino)ethyl]acetamide | 2.92 | 518 |
| N-[2-({2-(4-chlorophenyl)-6-[4-(1H-indol-3-ylcarbonyl)piperazin-1-yl]pyrimidin-4-yl}amino)ethyl]acetamide | 2.73 | 518 |
| N-[2-({2-(4-chlorophenyl)-6-[4-(3-nitrobenzoyl)piperazin-1-yl]pyrimidin-4-yl}amino)ethyl]acetamide | 2.79 | 524 |
| N-{2-[(2-(4-chlorophenyl)-6-{4-[(1-methyl-6-oxo-1,4,5,6-tetrahydropyridazin-3-yl)carbonyl]piperazin-1-yl}pyrimidin-4-yl)amino]ethyl}acetamide | 2.45 | 514 |
| N-{2-[(2-(4-chlorophenyl)-6-{4-[1-(2,7-dimethylpyrazolo[1,5-a]pyrimidin-6-yl)vinyl]piperazin-1-yl}pyrimidin-4-yl)amino]ethyl}acetamide | 2.65 | 548 |
| N-{2-[(2-(4-chlorophenyl)-6-{4-[(3-hydroxy-4-methoxyphenyl)acetyl]piperazin-1-yl}pyrimidin-4-yl)amino]ethyl}acetamide | 2.59 | 539 |
| N-{2-[(2-(4-chlorophenyl)-6-{4-[(2E)-3-(3-nitrophenyl)prop-2-enoyl]piperazin-1-yl}pyrimidin-4-yl)amino]ethyl}acetamide | 2.91 | 550 |
| N-(2-{[6-{4-[3-(1H-benzimidazol-2-yl)propanoyl]piperazin-1-yl}-2-(4-chlorophenyl)pyrimidin-4-yl]amino}ethyl)acetamide | 2.30 | 547 |
| N-[2-({2-(4-chlorophenyl)-6-[4-(2-hydroxy-4-methylbenzoyl)piperazin-1-yl]pyrimidin-4-yl}amino)ethyl]acetamide | 2.70 | 509 |
| N-[2-({2-(4-chlorophenyl)-6-[4-(2-hydroxy-3-methoxybenzoyl)piperazin-1-yl]pyrimidin-4-yl}amino)ethyl]acetamide | 2.62 | 525 |
| N-[2-({2-(4-chlorophenyl)-6-[4-(2-hydroxy-3-methylbenzoyl)piperazin-1-yl]pyrimidin-4-yl}amino)ethyl]acetamide | 2.79 | 509 |
| N-[2-({2-(4-chlorophenyl)-6-[4-(1H-indol-3-ylacetyl)piperazin-1-yl]pyrimidin-4-yl}amino)ethyl]acetamide | 2.73 | 532 |
| N-{2-[(2-(4-chlorophenyl)-6-{4-[3-(1H-indol-3-yl)propanoyl]piperazin-1-yl}pyrimidin-4-yl)amino]ethyl}acetamide | 2.80 | 546 |
| N-[2-({2-(4-chlorophenyl)-6-[4-(pyridin-2-ylcarbonyl)piperazin-1-yl]pyrimidin-4-yl}amino)ethyl]acetamide | 2.53 | 480 |
| N-{2-[(2-(4-chlorophenyl)-6-{4-[4-(1H-indol-3-yl)butanoyl]piperazin-1-yl}pyrimidin-4-yl)amino]ethyl}acetamide | 2.91 | 560 |
| N-{2-[(2-(4-chlorophenyl)-6-{4-[(5-methylpyrazin-2-yl)carbonyl]piperazin-1-yl}pyrimidin-4-yl)amino]ethyl}acetamide | 2.54 | 495 |
| N-{2-[(2-(4-chlorophenyl)-6-{4-[(5-methyl-2-phenyl-2H-1,2,3-triazol-4-yl)carbonyl]piperazin-1-yl}pyrimidin-4-yl)amino]ethyl}acetamide | 3.07 | 560 |
| N-{2-[(2-(4-chlorophenyl)-6-{4-[(4-oxo-4,5,6,7-tetrahydro-1-benzofuran-3-yl)carbonyl]piperazin-1-yl}pyrimidin-4-yl)amino]ethyl}acetamide | 2.61 | 537 |
| N-{2-{[2-(4-chlorophenyl)-6-(4-{[2-(methylsulfanyl)pyridin-3-yl]carbonyl}piperazin-1-yl)pyrimidin-4-yl]amino}ethyl}acetamide | 2.72 | 526 |
| N-(2-{[6-{4-[(1-tert-butyl-3-methyl-1H-pyrazol-5-yl)carbonyl]piperazin-1-yl}-2-(4-chlorophenyl)pyrimidin-4-yl]amino}ethyl)acetamide | 2.81 | 539 |
| N-{2-[(2-(4-chlorophenyl)-6-{4-[(2Z)-2-(3-oxo-2-benzofuran-1(3H)-ylidene)ethanoyl]piperazin-1-yl}pyrimidin-4-yl)amino]ethyl}acetamide | 2.59 | 546 |
| N-(2-{[6-{4-(1-benzothien-2-ylcarbonyl)piperazin-1-yl]-2-(4-chlorophenyl)pyrimidin-4-yl]amino}ethyl)acetamide | 3.01 | 535 |
| N-{2-[(2-(4-chlorophenyl)-6-{4-[4-(trifluoromethoxy)benzoyl]piperazin-1-yl}pyrimidin-4-yl)amino]ethyl}acetamide | 3.01 | 563 |
| N-(2-{[6-{4-[(5-chloro-2-hydroxypyridin-3-yl)carbonyl]piperazin-1-yl}-2-(4-chlorophenyl)pyrimidin-4-yl]amino}ethyl)acetamide | 2.51 | 530 |

-continued

| Name | Retention Time (min) | Mass Ion (ES+) (MH)+ |
|---|---|---|
| N-{2-[(2-(4-chlorophenyl)-6-{4-[(2E)-4-oxo-4-(2,3,4,5,6-pentamethylphenyl)but-2-enoyl]piperazin-1-yl}pyrimidin-4-yl)amino]ethyl}acetamide | 3.24 | 603 |
| N-{2-[(2-(4-chlorophenyl)-6-{4-[4-(trifluoroacetyl)benzoyl]piperazin-1-yl}pyrimidin-4-yl)amino]ethyl}acetamide | 2.69 | 575 |
| N-(2-{4-[6-{[2-(acetylamino)ethyl]amino}-2-(4-chlorophenyl)pyrimidin-4-yl]piperazin-1-yl}-2-oxoethyl)-4-chlorobenzamide | 2.75 | 570 |
| N-{2-[(2-(4-chlorophenyl)-6-{4-[(2,4-dihydroxypyrimidin-5-yl)carbonyl]piperazin-1-yl}pyrimidin-4-yl)amino]ethyl}acetamide | 2.31 | 513 |
| N-[2-({2-(4-chlorophenyl)-6-[4-(1,2,3-thiadiazol-4-ylcarbonyl)piperazin-1-yl]pyrimidin-4-yl}amino)ethyl]acetamide | 2.58 | 487 |
| N-(2-{[6-(4-{[5-chloro-2-(methylsulfanyl)pyrimidin-4-yl]carbonyl}piperazin-1-yl)-2-(4-chlorophenyl)pyrimidin-4-yl]amino}ethyl)acetamide | 2.85 | 561 |
| N-(2-{[2-(4-chlorophenyl)-6-(4-{[1-(2-furylmethyl)-5-oxopyrrolidin-3-yl]carbonyl}piperazin-1-yl)pyrimidin-4-yl]amino}ethyl)acetamide | 2.61 | 566 |
| N-(2-{[6-{4-[(3-tert-butyl-1-methyl-1H-pyrazol-5-yl)carbonyl]piperazin-1-yl}-2-(4-chlorophenyl)pyrimidin-4-yl]amino}ethyl)acetamide | 2.91 | 539 |
| N-{2-[(2-(4-chlorophenyl)-6-{4-[(4-nitrophenyl)acetyl]piperazin-1-yl}pyrimidin-4-yl)amino]ethyl}acetamide | 2.82 | 538 |
| N-{2-[(2-(4-chlorophenyl)-6-{4-[(2,5-dimethoxyphenyl)acetyl]piperazin-1-yl}pyrimidin-4-yl)amino]ethyl}acetamide | 2.82 | 553 |
| N-{2-[(2-(4-chlorophenyl)-6-{4-[(3-methoxyphenyl)acetyl]piperazin-1-yl}pyrimidin-4-yl)amino]ethyl}acetamide | 2.78 | 523 |
| N-{2-[(2-(4-chlorophenyl)-6-{4-[(4-methoxyphenyl)acetyl]piperazin-1-yl}pyrimidin-4-yl)amino]ethyl}acetamide | 2.77 | 523 |
| N-{2-[(2-(4-chlorophenyl)-6-{4-[(2-methoxyphennyl)acetyl]piperazin-1-yl}pyrmidin-4-yl)amino]ethyl}acetamide | 2.81 | 523 |
| N-[2-({2-(4-chlorophenyl)-6-[4-(1,2,3,4-tetrahydronaphthalen-2-ylcarbonyl)piperazin-1-yl]pyrimidin-4-yl}amino)ethyl]acetamide | 3.04 | 533 |
| N-{2-[(2-(4-chlorophenyl)-6-{4-[(2R)-2-hydroxy-3-phenylpropanoyl]piperazin-1-yl}pyrimidin-4-yl)amino]ethyl}acetamide | 2.75 | 523 |
| N-[2-({2-(4-chlorophenyl)-6-[4-(1H-pyrrol-2-ylcarbonyl)piperazin-1-yl]pyrimidin-4-yl}amino)ethyl]acetamide | 2.68 | 468 |
| N-[2-({2-(4-chlorophenyl)-6-[4-(4-vinylbenzoyl)piperazin-1-yl]pyrimidin-4-yl}amino)ethyl]acetamide | 2.93 | 505 |
| N-[2-({2-(4-chlorophenyl)-6-[4-(cyclohexylacetyl)piperazin-1-yl]pyrimidin-4-yl}amino)ethyl]acetamide | 2.98 | 499 |
| N-{2-[(2-(4-chlorophenyl)-6-{4-[4-(1H-pyrrol-1-yl)benzoyl]piperazin-1-yl}pyrimidin-4-yl)amino]ethyl}acetamide | 2.98 | 544 |
| N-{2-[(2-(4-chlorophenyl)-6-{4-[2-(1,3-dioxo-1,3-dihydro-2H-isoindol-2-yl)propanoyl]piperazin-1-yl}pyrimidin-4-yl)amino]ethyl}acetamide | 2.78 | 576 |
| N-(2-{[6-{4-([1,1'-biphenyl]-4-ylacetyl)piperazin-1-yl}-2-(4-chlorophenyl)pyrimidin-4-yl]amino}ethyl)acetamide | 3.09 | 569 |
| N-{2-[(2-(4-chlorophenyl)-6-{4-[(6-methoxy-3-oxo-2,3-dihydro-1H-inden-1-yl)acetyl]piperazin-1-yl}pyrimidin-4-yl)amino]ethyl}acetamide | 2.75 | 577 |
| N-{2-[(2-(4-chlorophenyl)-6-{4-[(3-nitrophenyl)acetyl]piperazin-1-yl}pyrimidin-4-yl)amino]ethyl}acetamide | 2.83 | 538 |
| N-{2-[(2-(4-chlorophenyl)-6-{4-[(2-methylphenyl)acetyl]piperazin-1-yl}pyrimidin-4-yl)amino]ethyl}acetamide | 2.85 | 507 |
| N-{2-[(2-(4-chlorophenyl)-6-{4-[(4-methylphenyl)acetyl]piperazin-1-yl}pyrimidin-4-yl)amino]ethyl}acetamide | 2.89 | 507 |
| N-[2-({2-(4-chlorophenyl)-6-[4-(3-methylbenzoyl)piperazin-1-yl]pyrimidin-4-yl}amino)ethyl]acetamide | 2.86 | 493 |
| N-[2-({2-(4-chlorophenyl)-6-[4-(4-methylbenzoyl)piperazin-1-yl]pyrimidin-4-yl}amino)ethyl]acetamide | 2.87 | 493 |
| N-[2-({2-(4-chlorophenyl)-6-[4-(2-methylbenzoyl)piperazin-1-yl]pyrimidin-4-yl}amino)ethyl]acetamide | 2.85 | 493 |
| N-{2-[(2-(4-chlorophenyl)-6-{4-[(3-methylphenyl)acetyl]piperazin-1-yl}pyrimidin-4-yl)amino]ethyl}acetamide | 2.88 | 507 |
| N-(2-{[6-[4-(4-butylbenzoyl)piperazin-1-yl]-2-(4-chlorophenyl)pyrimidin-4-yl]amino}ethyl)acetamide | 3.26 | 535 |
| N-[2-({2-(4-chlorophenyl)-6-[4-(4-nitrobenzoyl)piperazin-1-yl]pyrimidin-4-yl}amino)ethyl]acetamide | 2.83 | 524 |
| N-[2-({2-(4-chlorophenyl)-6-[4-(2-phenoxypropanoyl)piperazin-1-yl]pyrimidin-4-yl}amino)ethyl]acetamide | 2.86 | 523 |
| N-(2-{[6-[4-(1,3-benzodioxol-5-ylcarbonyl)piperazin-1-yl]-2-(4-chlorophenyl)pyrimidin-4-yl]amino}ethyl)acetamide | 2.73 | 523 |
| N-[2-({2-(4-chlorophenyl)-6-[4-(phenylacetyl)piperazin-1-yl]pyrimidin-4-yl}amino)ethyl]acetamide | 2.84 | 493 |
| N-(2-{[6-[4-(bicyclo[2.2.1]hept-5-en-2-ylcarbonyl)piperazin-1-yl]-2-(4-chlorophenyl)pyrimidin-4-yl]amino}ethyl)acetamide | 2.80 | 495 |
| N-{2-[(2-(4-chlorophenyl)-6-{4-[hydroxy(phenyl)acetyl]piperazin-1-yl}pyrimidin-4-yl)amino]ethyl}acetamide | 2.68 | 509 |

-continued

| Name | Retention Time (min) | Mass Ion (ES+) (MH)+ |
|---|---|---|
| N-{2-[(2-(4-chlorophenyl)-6-{4-[(2-naphthyloxy)acetyl]piperazin-1-yl}pyrimidin-4-yl)amino]ethyl}acetamide | 3.02 | 559 |
| N-{2-[(2-(4-chlorophenyl)-6-{4-[(1-phenylcyclopentyl)carbonyl]piperazin-1-yl}pyrimidin-4-yl)amino]ethyl}acetamide | 3.12 | 547 |
| N-[2-({2-(4-chlorophenyl)-6-[4-(2-sulfanylbenzoyl)piperazin-1-yl]pyrimidin-4-yl}amino)ethyl]acetamide | 2.99 | 511 |
| N-[2-({2-(4-chlorophenyl)-6-[4-(tetrahydrofuran-2-ylcarbonyl)piperazin-1-yl]pyrimidin-4-yl}amino)ethyl]acetamide | 2.51 | 473 |
| N-{2-[(2-(4-chlorophenyl)-6-{4-[cyclopentyl(phenyl)acetyl]piperazin-1-yl}pyrimidin-4-yl)amino]ethyl}acetamide | 3.24 | 561 |
| N-(2-{[6-[4-(4-tert-butylbenzoyl)piperazin-1-yl]-2-(4-chlorophenyl)pyrimidin-4-yl]amino}ethyl)acetamide | 3.16 | 535 |
| N-(2-{[6-[4-(1-adamantylcarbonyl)piperazin-1-yl]-2-(4-chlorophenyl)pyrimidin-4-yl]amino}ethyl)acetamide | 3.17 | 537 |
| N-[2-({2-(4-chlorophenyl)-6-[4-(4-methoxybenzoyl)piperazin-1-yl]pyrimidin-4-yl}amino)ethyl]acetamide | 2.77 | 509 |
| N-[2-({2-(4-chlorophenyl)-6-[4-(4-cyclohexylbenzoyl)piperazin-1-yl]pyrimidin-4-yl}amino)ethyl]acetamide | 3.37 | 561 |
| N-[2-({2-(4-chlorophenyl)-6-[4-(1-naphthoyl)piperazin-1-yl]pyrimidin-4-yl}amino)ethyl]acetamide | 2.97 | 529 |
| N-(2-{[6-(4-benzoylpiperazin-1-yl)-2-(4-chlorophenyl)pyrimidin-4-yl]amino}ethyl)acetamide | 2.73 | 479 |
| N-{2-[(2-(4-chlorophenyl)-6-{4-[3-(2,4-dihydroxyphenyl)propanoyl]piperazin-1-yl}pyrimidin-4-yl)amino]ethyl}acetamide | 2.56 | 539 |
| N-(2-{[6-[4-(4-bromo-3-methylbenzoyl)piperazin-1-yl]-2-(4-chlorophenyl)pyrimidin-4-yl]amino}ethyl)acetamide | 3.06 | 573 |
| N-(2-{[6-[4-(5-chloro-2-hydroxybenzoyl)piperazin-1-yl]-2-(4-chlorophenyl)pyrimidin-4-yl]amino}ethyl)acetamide | 2.78 | 529 |
| N-{2-[(2-(4-chlorophenyl)-6-{4-[4-(dimethylamino)benzoyl]piperazin-1-yl}pyrimidin-4-yl)amino]ethyl}acetamide | 2.78 | 522 |
| N-(2-{[6-{4-[(acetylamino)acetyl]piperazin-1-yl}-2-(4-chlorophenyl)pyrimidin-4-yl]amino}ethyl)acetamide | 2.37 | 474 |
| N-{2-[(2-(4-chlorophenyl)-6-{4-[(4-hydroxy-3-methoxyphenyl)acetyl]piperazin-1-yl}pyrimidin-4-yl)amino]ethyl}acetamide | 2.59 | 539 |
| N-[2-({2-(4-chlorophenyl)-6-[4-(3-hydroxy-4-methylbenzoyl)piperazin-1-yl]pyrimidin-4-yl}amino)ethyl]acetamide | 2.75 | 509 |
| N-[2-({2-(4-chlorophenyl)-6-[4-(3-phenylprop-2-ynoyl)piperazin-1-yl]pyrimidin-4-yl}amino)ethyl]acetamide | 2.96 | 503 |
| N-[2-({2-(4-chlorophenyl)-6-[4-(4-fluoro-1-naphthoyl)piperazin-1-yl]pyrimidin-4-yl}amino)ethyl]acetamide | 3.01 | 547 |
| N-[2-({2-(4-chlorophenyl)-6-[4-(5-formyl-2-hydroxybenzoyl)piperazin-1-yl]pyrimidin-4-yl}amino)ethyl]acetamide | 2.55 | 523 |
| N-[2-({2-(4-chlorophenyl)-6-[4-(cyclohex-1-en-1-ylcarbonyl)piperazin-1-yl]pyrimidin-4-yl}amino)ethyl]acetamide | 2.78 | 483 |
| N-(2-{[6-[4-([1,1'-biphenyl]-4-ylcarbonyl)piperazin-1-yl]-2-(4-chlorophenyl)pyrimidin-4-yl]amino}ethyl)acetamide | 3.09 | 555 |
| N-(2-{[6-{4-[(4-bromophenyl)acetyl]piperazin-1-yl}-2-(4-chlorophenyl)pyrimidin-4-yl]amino}ethyl)acetamide | 2.93 | 573 |
| N-{2-[(2-(4-chlorophenyl)-6-{4-[2-(methylsulfanyl)benzoyl]piperazin-1-yl}pyrimidin-4-yl)amino]ethyl}acetamide | 2.81 | 525 |
| N-{2-[(2-(4-chlorophenyl)-6-{4-[4-(methylsulfonyl)benzoyl]piperazin-1-yl}pyrimidin-4-yl)amino]ethyl}acetamide | 2.62 | 557 |
| N-(2-{[6-[4-(4-benzoylbenzoyl)piperazin-1-yl]-2-(4-chlorophenyl)pyrimidin-4-yl]amino}ethyl)acetamide | 3.00 | 583 |
| N-{2-[(2-(4-chlorophenyl)-6-{4-[4-(trifluoromethyl)benzoyl]piperazin-1-yl}pyrimidin-4-yl)amino]ethyl}acetamide | 3.00 | 547 |
| N-(2-{[6-[4-(4-acetylbenzoyl)piperazin-1-yl]-2-(4-chlorophenyl)pyrimidin-4-yl]amino}ethyl)acetamide | 2.70 | 521 |
| N-[2-({2-(4-chlorophenyl)-6-[4-(4-cyanobenzoyl)piperazin-1-yl]pyrimidin-4-yl}amino)ethyl]acetamide | 2.73 | 504 |
| N-{2-[(2-(4-chlorophenyl)-6-{4-[3-(trifluoromethyl)benzoyl]piperazin-1-yl}pyrimidin-4-yl)amino]ethyl}acetamide | 2.98 | 547 |
| N-[2-({2-(4-chlorophenyl)-6-[4-(3-cyanobenzoyl)piperazin-1-yl]pyrimidin-4-yl}amino)ethyl]acetamide | 2.76 | 504 |
| N-(2-{[6-[4-(1H-benzimidazol-5-ylcarbonyl)piperazin-1-yl]-2-(4-chlorophenyl)pyrimidin-4-yl]amino}ethyl)acetamide | 2.26 | 519 |
| N-[2-({2-(4-chlorophenyl)-6-[4-(diphenylacetyl)piperazin-1-yl]pyrimidin-4-yl}amino)ethyl]acetamide | 3.11 | 569 |
| N-[2-({2-(4-chlorophenyl)-6-[4-(4-ethylbenzoyl)piperazin-1-yl]pyrimidin-4-yl}amino)ethyl]acetamide | 3.00 | 507 |
| N-[2-({2-(4-chlorophenyl)-6-[4-(2-hydroxybenzoyl)piperazin-1-yl]pyrimidin-4-yl}amino)ethyl]acetamide | 2.62 | 495 |

-continued

| Name | Retention Time (min) | Mass Ion (ES+) (MH)+ |
|---|---|---|
| N-(2-{[6-[4-(3-bromobenzoyl)piperazin-1-yl]-2-(4-chlorophenyl)pyrimidin-4-yl]amino}ethyl)acetamide | 2.93 | 559 |
| N-[2-({2-(4-chlorophenyl)-6-[4-(4-oxopentanoyl)piperazin-1-yl]pyrimidin-4-yl}amino)ethyl]acetamide | 2.47 | 473 |
| N-(2-{[2-(4-chlorophenyl)-6-(4-{[(4-chlorophenyl)sulfanyl]acetyl}piperazin-1-yl)pyrimidin-4-yl]amino}ethyl)acetamide | 3.05 | 559 |
| N-(2-{[6-{4-[(4-acetyl-3,5-dimethyl-1H-pyrrol-2-yl)carbonyl]piperazin-1-yl}-2-(4-chlorophenyl)pyrimidin-4-yl]amino}ethyl)acetamide | 2.62 | 538 |
| N-{2-[(2-(4-chlorophenyl)-6-{4-[(2E)-3-thien-3-ylprop-2-enoyl]piperazin-1-yl}pyrimidin-4-yl)amino]ethyl}acetamide | 2.81 | 511 |
| N-{2-[(2-(4-chlorophenyl)-6-{4-[2-furyl(4-phenylpiperazin-1-yl)acetyl]piperazin-1-yl}pyrimidin-4-yl)amino]ethyl}acetamide | 2.60 | 643 |
| N-{2-[(2-(4-chlorophenyl)-6-{4-[2-furyl(morpholin-4-yl)acetyl]piperazin-1-yl}pyrimidin-4-yl)amino]ethyl}acetamide | 2.31 | 568 |
| N-{2-[(2-(4-chlorophenyl)-6-{4-[(2-methyl-1H-benzimidazol-5-yl)carbonyl]piperazin-1-yl}pyrimidin-4-yl)amino]ethyl}acetamide | 2.26 | 533 |
| N-(2-{[2-(4-chlorophenyl)-6-(4-isobutyrylpiperazin-1-yl)pyrimidin-4-yl]amino}ethyl)acetamide | 2.61 | 445 |
| N-(2-{[6-{4-[(1H-benzimidazol-2-ylsulfanyl)acetyl]piperazin-1-yl}-2-(4-chlorophenyl)pyrimidin-4-yl]amino}ethyl)acetamide | 2.54 | 565 |
| N-{2-[(2-(4-chlorophenyl)-6-{4-[(2-hydroxyquinolin-4-yl)carbonyl]piperazin-1-yl}pyrimidin-4-yl)amino]ethyl}acetamide | 2.61 | 546 |
| N-{2-[(2-(4-chlorophenyl)-6-{4-[(5-chlorothien-2-yl)carbonyl]piperazin-1-yl}pyrimidin-4-yl)amino]ethyl}acetamide | 2.92 | 519 |
| N-{2-[(2-(4-chlorophenyl)-6-{4-[(2E)-3-(3-cyanophenyl)prop-2-enoyl]piperazin-1-yl}pyrimidin-4-yl)amino]ethyl}acetamide | 2.88 | 530 |
| N-{2-[(2-(4-chlorophenyl)-6-{4-[(5-nitrothien-3-yl)carbonyl]piperazin-1-yl}pyrimidin-4-yl)amino]ethyl}acetamide | 2.79 | 530 |
| N-(2-{[2-(4-chlorophenyl)-6-(4-{[4-(trifluoromethyl)cyclohexyl]carbonyl}piperazin-1-yl)pyrimidin-4-yl]amino}ethyl)acetamide | 2.97 | 553 |
| N-{2-[(2-(4-chlorophenyl)-6-{4-[(3-ethoxythien-2-yl)carbonyl]piperazin-1-yl}pyrimidin-4-yl)amino]ethyl}acetamide | 2.78 | 529 |
| N-{2-[(2-(4-chlorophenyl)-6-{4-[(2E)-3-(2-furyl)prop-2-enoyl]piperazin-1-yl}pyrimidin-4-yl)amino]ethyl}acetamide | 2.74 | 495 |
| N-[2-({2-(4-chlorophenyl)-6-[4-(2,3,5,6-tetrafluoro-4-methylbenzoyl)piperazin-1-yl]pyrimidin-4-yl}amino)ethyl]acetamide | 3.11 | 565 |
| N-(2-{[6-[4-(5-bromo-2-furoyl)piperazin-1-yl]-2-(4-chlorophenyl)pyrimidin-4-yl]amino}ethyl)acetamide | 2.85 | 549 |
| N-[2-({2-(4-chlorophenyl)-6-[4-(4,4,4-trifluoro-3-hydroxy-3-methylbutanoyl)piperazin-1-yl]pyrimidin-4-yl}amino)ethyl]acetamide | 2.72 | 529 |
| N-{2-[(2-(4-chlorophenyl)-6-{4-[(2E)-3-(2,3,4-trifluorophenyl)prop-2-enoyl]piperazin-1-yl}pyrimidin-4-yl)amino]ethyl}acetamide | 3.04 | 559 |
| N-{2-[(2-(4-chlorophenyl)-6-{4-[(8-hydroxyquinolin-2-yl)carbonyl]piperazin-1-yl}pyrimidin-4-yl)amino]ethyl}acetamide | 2.82 | 546 |
| N-[2-({2-(4-chlorophenyl)-6-[4-(6-hydroxy-2-naphthoyl)piperazin-1-yl]pyrimidin-4-yl}amino)ethyl]acetamide | 2.73 | 545 |
| N-{2-[(2-(4-chlorophenyl)-6-{4-[(2E)-3-(4-isopropylphenyl)prop-2-enoyl]piperazin-1-yl}pyrimidin-4-yl)amino]ethyl}acetamide | 3.20 | 547 |
| N-{2-[(2-(4-chlorophenyl)-6-{4-[(2E)-3-thien-2-ylprop-2-enoyl]piperazin-1-yl}pyrimidin-4-yl)amino]ethyl}acetamide | 2.85 | 511 |
| N-{2-[(2-(4-chlorophenyl)-6-{4-[(3E)-4-phenylbut-3-enoyl]piperazin-1-yl}pyrimidin-4-yl)amino]ethyl}acetamide | 2.92 | 519 |
| N-(2-{[6-{4-[(1-benzoylpiperidin-4-yl)carbonyl]piperazin-1-yl}-2-(4-chlorophenyl)pyrimidin-4-yl]amino}ethyl)acetamide | 2.73 | 590 |
| N-(2-{[6-(4-{4-[(aminocarbothioyl)amino]benzoyl}piperazin-1-yl)-2-(4-chlorophenyl)pyrimidin-4-yl]amino}ethyl)acetamide | 2.52 | 553 |
| methyl 3-({4-[6-{[2-(acetylamino)ethyl]amino}-2-(4-chlorophenyl)pyrimidin-4-yl]piperazin-1-yl}carbonyl)isonicotinate | 2.57 | 538 |
| N-[2-({2-(4-chlorophenyl)-6-[4-(2-oxo-3-phenylpropanoyl)piperazin-1-yl]pyrimidin-4-yl}amino)ethyl]acetamide | 2.94 | 521 |
| N-{2-[(2-(4-chlorophenyl)-6-{4-[5-(1,2-dithiolan-3-yl)pentanoyl]piperazin-1-yl}pyrimidin-4-yl)amino]ethyl}acetamide | 2.96 | 563 |
| N-{2-[(2-(4-chlorophenyl)-6-{4-[(2-methyl-5,6-dihydro-1,4-oxathiin-3-yl)carbonyl]piperazin-1-yl}pyrimidin-4-yl)amino]ethyl}acetamide | 2.67 | 517 |
| N-[2-({2-(4-chlorophenyl)-6-[4-(1H-tetraazol-1-ylacetyl)piperazin-1-yl]pyrimidin-4-yl}amino)ethyl]acetamide | 2.43 | 485 |
| N-{2-[(2-(4-chlorophenyl)-6-{4-[3-(2-furyl)propanoyl]piperazin-1-yl}pyrimidin-4-yl)amino]ethyl}acetamide | 2.75 | 497 |
| N-{2-[(2-(4-chlorophenyl)-6-{4-[(2E,4E)-5-phenylpenta-2,4-dienoyl]piperazin-1-yl}pyrimidin-4-yl)amino]ethyl}acetamide | 3.00 | 531 |
| N-[2-({2-(4-chlorophenyl)-6-[4-(3-nitropropanoyl)piperazin-1-yl]pyrimidin-4-yl}amino)ethyl]acetamide | 2.56 | 476 |

-continued

| Name | Retention Time (min) | Mass Ion (ES+) (MH)+ |
|---|---|---|
| N-(2-{[2-(4-chlorophenyl)-6-(4-{[2-(4-methylphenoxy)pyridin-3-yl]carbonyl}piperazin-1-yl)pyrimidin-4-yl]amino}ethyl)acetamide | 2.97 | 586 |
| N-{2-[(2-(4-chlorophenyl)-6-{4-[(2E)-3-pyridin-2-ylprop-2-enoyl]piperazin-1-yl}pyrimidin-4-yl)amino]ethyl}acetamide | 2.51 | 506 |
| N-[2-({2-(4-chlorophenyl)-6-[4-(3-methyl-2-nitrobenzoyl)piperazin-1-yl]pyrimidin-4-yl}amino)ethyl]acetamide | 2.87 | 538 |
| N-[2-({2-(4-chlorophenyl)-6-[4-(3-thien-2-ylpropanoyl)piperazin-1-yl]pyrimidin-4-yl}amino)ethyl]acetamide | 2.82 | 513 |
| N-{2-[(2-(4-chlorophenyl)-6-{4-[(5-methyl-2,4-dioxo-3,4-dihydropyrimidin-1(2H)-yl)acetyl]piperazin-1-yl}pyrimidin-4-yl)amino]ethyl}acetamide | 2.41 | 541 |
| N-{2-[(2-(4-chlorophenyl)-6-{4-[(4'-hydroxy[1,1'-biphenyl]-4-yl)carbonyl]piperazin-1-yl}pyrimidin-4-yl)amino]ethyl}acetamide | 2.82 | 571 |
| N-[2-({2-(4-chlorophenyl)-6-[4-(cyclohex-3-en-1-ylcarbonyl)piperazin-1-yl]pyrimidin-4-yl}amino)ethyl]acetamide | 2.81 | 483 |
| N-{2-[(2-(4-chlorophenyl)-6-{4-[3-(4-hydroxyphenyl)propanoyl]piperazin-1-yl}pyrimidin-4-yl)amino]ethyl}acetamide | 2.60 | 523 |
| N-{2-[(2-(4-chlorophenyl)-6-{4-[3-(3,4,5-trimethoxyphenyl)propanoyl]piperazin-1-yl}pyrimidin-4-yl)amino]ethyl}acetamide | 2.71 | 597 |
| N-(2-{[6-(4-acetylpiperazin-1-yl)-2-(4-chlorophenyl)pyrimidin-4-yl]amino}ethyl)acetamide | 2.45 | 417 |
| N-(2-{[2-(4-chlorophenyl)-6-(4-propionylpiperazin-1-yl)pyrimidin-4-yl]amino}ethyl)acetamide | 2.52 | 431 |
| N-{2-[(2-(4-chlorophenyl)-6-{4-[2-hydroxy-5-(1H-pyrrol-1-yl)benzoyl]piperazin-1-yl}pyrimidin-4-yl)amino]ethyl}acetamide | 2.86 | 560 |
| N-[2-({2-(4-chlorophenyl)-6-[4-(2-hydroxy-3-nitrobenzoyl)piperazin-1-yl]pyrimidin-4-yl}amino)ethyl]acetamide | 2.76 | 540 |

Example 9

Synthesis of Compounds 36.1-36.141

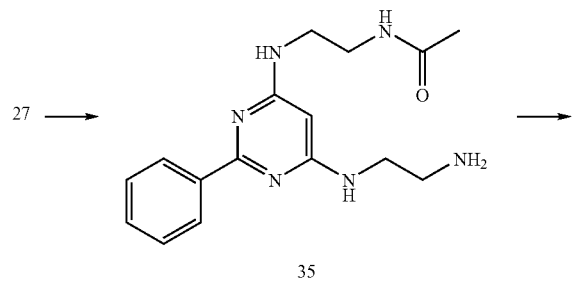

35

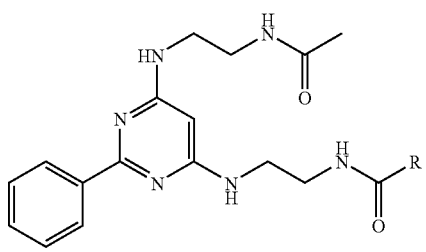

36.1-36.141

N-[2-({6-[(2-Aminoethyl)amino]-2-phenylpyrimidin-4-yl}amino)ethyl]acetamide (35)

N-{2-[(6-Chloro-2-phenylpyrimidin-4-yl)amino]ethyl}acetamide (100 mg) was dissolved in ethylenediamine (5 ml) and the stirred under reflux for 4 hrs. The reaction mixture was then cooled to ambient temperature and the solvent removed in vacuo. Purification via flash chromatography on silica gel eluting first with a mixture of ethyl acetate and methanol (9:1 v/v) then a mixture of ethyl acetate, methanol and ammonium hydroxide (80:20:2 v/v/v) to furnish the title compound (89 mg).

$\delta_H$ (d$^6$-DMSO): 1.80 (3H, s), 2.63-2.70 (2H, t), 3.18-3.36 (6H, m), 5.35 (1H, s), 6.50-6.61 (2H, m), 7.38-7.40 (3H, m), 7.90-7.95 (1H, m), 8.22-8.25 (2H, m); m/z (ES+) 315 (MH)+

Library Example:

N-{2-[(6-{[2-(acetylamino)ethyl]amino}-2-phenylpyrimidin-4-yl)amino]ethyl}quinoline-2-carboxamide (36.1)

A solution of quinaldic acid (30 μl of a 0.3M solution in NMP), HATU (30 μl of a 0.3M solution in NMP) and diisopropylethylamine (30 μl of a 0.3M solution in NMP) was shaken at ambient temperature in a well of a 96 position microtitre plate for 2 hrs. N-[2-({6-[(2-aminoethyl)amino]-2-phenylpyrimidin-4-yl}amino)ethyl]acetamide (30 μl of a 0.3M solution in NMP) was then added and the mixture shaken for a further 12 hrs. Purification via ion exchange silica (SCX) yields the title compound.

LCMS (Method A) RT=2.67 min; m/z (ES+) 470 (MH)+

The following compounds 36.2-36.141 were synthesized in an analogous manner:

| Name | Retention Time (min) | Mass ion (ES+) (MH)+ |
|---|---|---|
| N-{2-[(6-{[2-(acetylamino)ethyl]amino}-2-phenylpyrimidin-4-yl)amino]ethyl}isoquinoline-3-carboxamide | 2.67 | 470 |
| N-{2-[(6-{[2-(acetylamino)ethyl]amino}-2-phenylpyrimidin-4-yl)amino]ethyl}isoquinoline-1-carboxamide | 2.58 | 470 |
| N-{2-[(6-{[2-(acetylamino)ethyl]amino}-2-phenylpyrimidin-4-yl)amino]ethyl}indoline-2-carboxamide | 2.74 | 458 |
| N-{2-[(6-{[2-(acetylamino)ethyl]amino}-2-phenylpyrimidin-4-yl)amino]ethyl}pyrazine-2-carboxamide | 2.41 | 421 |
| N-{2-[(6-{[2-(acetylamino)ethyl]amino}-2-phenylpyrimidin-4-yl)amino]ethyl}nicotinamide | 2.32 | 420 |
| N-{2-[(6-{[2-(acetylamino)ethyl]amino}-2-phenylpyrimidin-4-yl)amino]ethyl}isonicotinamide | 2.31 | 420 |
| N-{2-[(6-{[2-(acetylamino)ethyl]amino}-2-phenylpyrimidin-4-yl)amino]ethyl}-2-hydroxynicotinamide | 2.38 | 436 |
| N-{2-[(6-{[2-(acetylamino)ethyl]amino}-2-phenylpyrimidin-4-yl)amino]ethyl}-1H-indole-2-carboxamide | 2.68 | 458 |
| N-{2-[(6-{[2-(acetylamino)ethyl]amino}-2-phenylpyrimidin-4-yl)amino]ethyl}-1H-indole-3-carboxamide | 2.58 | 458 |
| N-{2-[(6-{[2-(acetylamino)ethyl]amino}-2-phenylpyrimidin-4-yl)amino]ethyl}-2-(3-hydroxy-4-methoxyphenyl)acetamide | 2.43 | 479 |
| (2E)-N-{2-[(6-{[2-(acetylamino)ethyl]amino}-2-phenylpyrimidin-4-yl)amino]ethyl}-3-(1H-indol-3-yl)prop-2-enamide | 2.67 | 484 |
| (2E)-N-{2-[(6-{[2-(acetylamino)ethyl]amino}-2-phenylpyrimidin-4-yl)amino]ethyl}-3-(3-nitrophenyl)prop-2-enamide | 2.71 | 490 |
| N-{2-[(6-{[2-(acetylamino)ethyl]amino}-2-phenylpyrimidin-4-yl)amino]ethyl}-3-(1H-benzimidazol-2-yl)propanamide | 2.27 | 487 |
| N-{2-[(6-{[2-(acetylamino)ethyl]amino}-2-phenylpyrimidin-4-yl)amino]ethyl}-2-hydroxy-4-methylbenzamide | 2.73 | 449 |
| N-{2-[(6-{[2-(acetylamino)ethyl]amino}-2-phenylpyrimidin-4-yl)amino]ethyl}-2-hydroxy-3-methoxybenzamide | 2.59 | 465 |
| N-{2-[(6-{[2-(acetylamino)ethyl]amino}-2-phenylpyrimidin-4-yl)amino]ethyl}-2-hydroxy-3-methylbenzamide | 2.80 | 449 |
| N-{2-[(6-{[2-(acetylamino)ethyl]amino}-2-phenylpyrimidin-4-yl)amino]ethyl}-2-(1H-indol-3-yl)acetamide | 2.53 | 472 |
| N-{2-[(6-{[2-(acetylamino)ethyl]amino}-2-phenylpyrimidin-4-yl)amino]ethyl}-3-(1H-indol-3-yl)propanamide | 2.64 | 486 |
| N-{2-[(6-{[2-(acetylamino)ethyl]amino}-2-phenylpyrimidin-4-yl)amino]ethyl}pyridine-2-carboxamide | 2.48 | 420 |
| N-{2-[(6-{[2-(acetylamino)ethyl]amino}-2-phenylpyrimidin-4-yl)amino]ethyl}-4-(1H-indol-3-yl)butanamide | 2.69 | 500 |
| N-{2-[(6-{[2-(acetylamino)ethyl]amino}-2-phenylpyrimidin-4-yl)amino]ethyl}-5-methylpyrazine-2-carboxamide | 2.45 | 435 |
| N-{2-[(6-{[2-(acetylamino)ethyl]amino}-2-phenylpyrimidin-4-yl)amino]ethyl}-5-methyl-2-phenyl-2H-1,2,3-triazole-4-carboxamide | 2.81 | 500 |
| N-{2-[(6-{[2-(acetylamino)ethyl]amino}-2-phenylpyrimidin-4-yl)amino]ethyl}-4-oxo-4,5,6,7-tetrahydro-1-benzofuran-3-carboxamide | 2.54 | 477 |
| N-{2-[(6-{[2-(acetylamino)ethyl]amino}-2-phenylpyrimidin-4-yl)amino]ethyl}-2-(methylsulfanyl)nicotinamide | 2.48 | 466 |
| N-{2-[(6-{[2-(acetylamino)ethyl]amino}-2-phenylpyrimidin-4-yl)amino]ethyl}-1-tert-butyl-3-methyl-1H-pyrazole-5-carboxamide | 2.59 | 479 |
| N-{2-[(6-{[2-(acetylamino)ethyl]amino}-2-phenylpyrimidin-4-yl)amino]ethyl}-1-benzothiophene-2-carboxamide | 2.75 | 475 |
| N-{2-[(6-{[2-(acetylamino)ethyl]amino}-2-phenylpyrimidin-4-yl)amino]ethyl}-4-(trifluoromethoxy)benzamide | 2.80 | 503 |
| N-{2-[(6-{[2-(acetylamino)ethyl]amino}-2-phenylpyrimidin-4-yl)amino]ethyl}-5-chloro-2-hydroxynicotinamide | 2.51 | 470 |
| N-{2-[(6-{[2-(acetylamino)ethyl]amino}-2-phenylpyrimidin-4-yl)amino]ethyl}-4-(trifluoroacetyl)benzamide | 2.56 | 515 |
| N-[2-({2-[(6-{[2-(acetylamino)ethyl]amino}-2-phenylpyrimidin-4-yl)amino]ethyl}amino)-2-oxoethyl]-4-chlorobenzamide | 2.65 | 510 |
| N-{2-[(6-{[2-(acetylamino)ethyl]amino}-2-phenylpyrimidin-4-yl)amino]ethyl}-1,2,3-thiadiazole-4-carboxamide | 2.44 | 427 |
| N-{2-[(6-{[2-(acetylamino)ethyl]amino}-2-phenylpyrimidin-4-yl)amino]ethyl}-5-chloro-2-(methylsulfanyl)pyrimidine-4-carboxamide | 2.65 | 501 |
| N-{2-[(6-{[2-(acetylamino)ethyl]amino}-2-phenylpyrimidin-4-yl)amino]ethyl}-1-(2-furylmethyl)-5-oxopyrrolidine-3-carboxamide | 2.53 | 506 |
| N-{2-[(6-{[2-(acetylamino)ethyl]amino}-2-phenylpyrimidin-4-yl)amino]ethyl}-3-tert-butyl-1-methyl-1H-pyrazole-5-carboxamide | 2.66 | 479 |
| N-{2-[(6-{[2-(acetylamino)ethyl]amino}-2-phenylpyrimidin-4-yl)amino]ethyl}-2-(2,5-dimethoxyphenyl)acetamide | 2.59 | 493 |

| Name | Retention Time (min) | Mass ion (ES+) (MH)+ |
|---|---|---|
| N-{2-[(6-{[2-(acetylamino)ethyl]amino}-2-phenylpyrimidin-4-yl)amino]ethyl}-2-(3-methoxyphenyl)acetamide | 2.55 | 463 |
| N-{2-[(6-{[2-(acetylamino)ethyl]amino}-2-phenylpyrimidin-4-yl)amino]ethyl}-2-(4-methoxyphenyl)acetamide | 2.54 | 463 |
| N-{2-[(6-{[2-(acetylamino)ethyl]amino}-2-phenylpyrimidin-4-yl)amino]ethyl}-2-(2-methoxyphenyl)acetamide | 2.59 | 463 |
| N-{2-[(6-{[2-(acetylamino)ethyl]amino}-2-phenylpyrimidin-4-yl)amino]ethyl}-1,2,3,4-tetrahydronaphthalene-2-carboxamide | 2.74 | 473 |
| N-{2-[(6-{[2-(acetylamino)ethyl]amino}-2-phenylpyrimidin-4-yl)amino]ethyl}-2-hydroxy-3-phenylpropanamide | 2.59 | 463 |
| N-{2-[(6-{[2-(acetylamino)ethyl]amino}-2-phenylpyrimidin-4-yl)amino]ethyl}-1H-pyrrole-2-carboxamide | 2.45 | 408 |
| (3S,4R,5S)-N-{2-[(6-{[2-(acetylamino)ethyl]amino}-2-phenylpyrimidin-4-yl)amino]ethyl}-3,4,5-trihydroxycyclohex-1-ene-1-carboxamide | 2.15 | 471 |
| N-{2-[(6-{[2-(acetylamino)ethyl]amino}-2-phenylpyrimidin-4-yl)amino]ethyl}-2-cyclohexylacetamide | 2.67 | 439 |
| N-{2-[(6-{[2-(acetylamino)ethyl]amino}-2-phenylpyrimidin-4-yl)amino]ethyl}-4-(1H-pyrrol-1-yl)benzamide | 2.76 | 484 |
| N-{2-[(6-{[2-(acetylamino)ethyl]amino}-2-phenylpyrimidin-4-yl)amino]ethyl}-2-(4-oxo-2-thioxo-1,3-thiazolidin-3-yl)acetamide | 2.45 | 488 |
| N-{2-[(6-{[2-(acetylamino)ethyl]amino}-2-phenylpyrimidin-4-yl)amino]ethyl}-2-[1,1'-biphenyl]-4-ylacetamide | 2.86 | 509 |
| N-{2-[(6-{[2-(acetylamino)ethyl]amino}-2-phenylpyrimidin-4-yl)amino]ethyl}-2-(6-methoxy-3-oxo-2,3-dihydro-1H-inden-1-yl)acetamide | 2.56 | 517 |
| N-{2-[(6-{[2-(acetylamino)ethyl]amino}-2-phenylpyrimidin-4-yl)amino]ethyl}-2-(2-methylphenyl)acetamide | 2.61 | 447 |
| N-{2-[(6-{[2-(acetylamino)ethyl]amino}-2-phenylpyrimidin-4-yl)amino]ethyl}-2-(4-methylphenyl)acetamide | 2.61 | 447 |
| N-{2-[(6-{[2-(acetylamino)ethyl]amino}-2-phenylpyrimidin-4-yl)amino]ethyl}-3-methylbenzamide | 2.62 | 433 |
| N-{2-[(6-{[2-(acetylamino)ethyl]amino}-2-phenylpyrimidin-4-yl)amino]ethyl}-4-methylbenzamide | 2.62 | 433 |
| N-{2-[(6-{[2-(acetylamino)ethyl]amino}-2-phenylpyrimidin-4-yl)amino]ethyl}-2-methylbenzamide | 2.56 | 433 |
| N-{2-[(6-{[2-(acetylamino)ethyl]amino}-2-phenylpyrimidin-4-yl)amino]ethyl}-2-(3-methylphenyl)acetamide | 2.62 | 447 |
| N-{2-[(6-{[2-(acetylamino)ethyl]amino}-2-phenylpyrimidin-4-yl)amino]ethyl}-2-phenoxypropanamide | 2.67 | 463 |
| N-{2-[(6-{[2-(acetylamino)ethyl]amino}-2-phenylpyrimidin-4-yl)amino]ethyl}-1,3-benzodioxole-5-carboxamide | 2.55 | 463 |
| N-{2-[(6-{[2-(acetylamino)ethyl]amino}-2-phenylpyrimidin-4-yl)amino]ethyl}-2-phenylacetamide | 2.54 | 433 |
| N-{2-[(6-{[2-(acetylamino)ethyl]amino}-2-phenylpyrimidin-4-yl)amino]ethyl}bicyclo[2.2.1]hept-5-ene-2-carboxamide | 2.61 | 435 |
| N-{2-[(6-{[2-(acetylamino)ethyl]amino}-2-phenylpyrimidin-4-yl)amino]ethyl}-2-hydroxy-2-phenylacetamide | 2.46 | 449 |
| N-{2-[(6-{[2-(acetylamino)ethyl]amino}-2-phenylpyrimidin-4-yl)amino]ethyl}-1-phenylcyclopentanecarboxamide | 2.78 | 487 |
| N-{2-[(6-{[2-(acetylamino)ethyl]amino}-2-phenylpyrimidin-4-yl)amino]ethyl}-2-sulfanylbenzamide | 2.58 | 449 |
| N-{2-[(6-{[2-(acetylamino)ethyl]amino}-2-phenylpyrimidin-4-yl)amino]ethyl}tetrahydrofuran-2-carboxamide | 2.37 | 413 |
| N-{2-[(6-{[2-(acetylamino)ethyl]amino}-2-phenylpyrimidin-4-yl)amino]ethyl}-2-cyclopentyl-2-phenylacetamide | 2.85 | 501 |
| N-{2-[(6-{[2-(acetylamino)ethyl]amino}-2-phenylpyrimidin-4-yl)amino]ethyl}-4-tert-butylbenzamide | 2.87 | 475 |
| N-{2-[(6-{[2-(acetylamino)ethyl]amino}-2-phenylpyrimidin-4-yl)amino]ethyl}adamantane-1-carboxamide | 2.79 | 477 |
| N-{2-[(6-{[2-(acetylamino)ethyl]amino}-2-phenylpyrimidin-4-yl)amino]ethyl}-4-methoxybenzamide | 2.57 | 449 |
| N-{2-[(6-{[2-(acetylamino)ethyl]amino}-2-phenylpyrimidin-4-yl)amino]ethyl}-4-cyclohexylbenzamide | 3.04 | 501 |
| N-{2-[(6-{[2-(acetylamino)ethyl]amino}-2-phenylpyrimidin-4-yl)amino]ethyl}-1-naphthamide | 2.66 | 469 |
| N-{2-[(6-{[2-(acetylamino)ethyl]amino}-2-phenylpyrimidin-4-yl)amino]ethyl}benzamide | 2.55 | 419 |
| N-{2-[(6-{[2-(acetylamino)ethyl]amino}-2-phenylpyrimidin-4-yl)amino]ethyl}-4-bromo-3-methylbenzamide | 2.80 | 511 |
| N-{2-[(6-{[2-(acetylamino)ethyl]amino}-2-phenylpyrimidin-4-yl)amino]ethyl}-5-chloro-2-hydroxybenzamide | 2.77 | 469 |
| N-{2-[(6-{[2-(acetylamino)ethyl]amino}-2-phenylpyrimidin-4-yl)amino]ethyl}-4-(dimethylamino)benzamide | 2.62 | 462 |
| 2-(acetylamino)-N-{2-[(6-{[2-(acetylamino)ethyl]amino}-2-phenylpyrimidin-4yl)amino]ethyl}acetamide | 2.16 | 414 |

-continued

| Name | Retention Time (min) | Mass ion (ES+) (MH)+ |
|---|---|---|
| N-{2-[(6-{[2-(acetylamino)ethyl]amino}-2-phenylpyrimidin-4-yl)amino]ethyl}-2-(4-hydroxy-3-methoxyphenyl)acetamide | 2.40 | 479 |
| N-{2-[(6-{[2-(acetylamino)ethyl]amino}-2-phenylpyrimidin-4-yl)amino]ethyl}-3-hydroxy-4-methylbenzamide | 2.56 | 449 |
| N-{2-[(6-{[2-(acetylamino)ethyl]amino}-2-phenylpyrimidin-4-yl)amino]ethyl}-3-phenylprop-2-ynamide | 2.70 | 443 |
| N-{2-[(6-{[2-(acetylamino)ethyl]amino}-2-phenylpyrimidin-4-yl)amino]ethyl}-4-fluoro-1-naphthamide | 2.72 | 487 |
| N-{2-[(6-{[2-(acetylamino)ethyl]amino}-2-phenylpyrimidin-4-yl)amino]ethyl}-5-formyl-2-hydroxybenzamide | 2.64 | 463 |
| N-{2-[(6-{[2-(acetylamino)ethyl]amino}-2-phenylpyrimidin-4-yl)amino]ethyl}cyclohex-1-ene-1-carboxamide | 2.60 | 423 |
| N-{2-[(6-{[2-(acetylamino)ethyl]amino}-2-phenylpyrimidin-4-yl)amino]ethyl}-2-(4-bromophenyl)acetamide | 2.71 | 513 |
| N-{2-[(6-{[2-(acetylamino)ethyl]amino}-2-phenylpyrimidin-4-yl)amino]ethyl}-2-(methylsulfanyl)benzamide | 2.57 | 465 |
| N-{2-[(6-{[2-(acetylamino)ethyl]amino}-2-phenylpyrimidin-4-yl)amino]ethyl}-4-(methylsulfonyl)benzamide | 2.49 | 497 |
| N-{2-[(6-{[2-(acetylamino)ethyl]amino}-2-phenylpyrimidin-4-yl)amino]ethyl}-4-benzoylbenzamide | 2.81 | 523 |
| N-{2-[(6-{[2-(acetylamino)ethyl]amino}-2-phenylpyrimidin-4-yl)amino]ethyl}-4-(trifluoromethyl)benzamide | 2.78 | 487 |
| 4-acetyl-N-{2-[(6-{[2-(acetylamino)ethyl]amino}-2-phenylpyrimidin-4-yl)amino]ethyl}benzamide | 2.55 | 461 |
| N-{2-[(6-{[2-(acetylamino)ethyl]amino}-2-phenylpyrimidin-4-yl)amino]ethyl}-4-cyanobenzamide | 2.60 | 444 |
| N-{2-[(6-{[2-(acetylamino)ethyl]amino}-2-phenylpyrimidin-4-yl)amino]ethyl}-3-(trifluoromethyl)benzamide | 2.76 | 487 |
| N-{2-[(6-{[2-(acetylamino)ethyl]amino}-2-phenylpyrimidin-4-yl)amino]ethyl}-3-cyanobenzamide | 2.57 | 444 |
| N-{2-[(6-{[2-(acetylamino)ethyl]amino}-2-phenylpyrimidin-4-yl)amino]ethyl}-1H-benzimidazole-5-carboxamide | 2.22 | 459 |
| N-{2-[(6-{[2-(acetylamino)ethyl]amino}-2-phenylpyrimidin-4-yl)amino]ethyl}-2,2-diphenylacetamide | 2.83 | 509 |
| 2-[({2-[(6-{[2-(acetylamino)ethyl]amino}-2-phenylpyrimidin-4-yl)amino]ethyl}amino)carbonyl]phenyl acetate | 2.53 | 477 |
| N-{2-[(6-{[2-(acetylamino)ethyl]amino}-2-phenylpyrimidin-4-yl)amino]ethyl}-4-ethylbenzamide | 2.73 | 447 |
| N-{2-[(6-{[2-(acetylamino)ethyl]amino}-2-phenylpyrimidin-4-yl)amino]ethyl}-2-hydroxybenzamide | 2.64 | 435 |
| N-{2-[(6-{[2-(acetylamino)ethyl]amino}-2-phenylpyrimidin-4-yl)amino]ethyl}-3-bromobenzamide | 2.71 | 499 |
| N-{2-[(6-{[2-(acetylamino)ethyl]amino}-2-phenylpyrimidin-4-yl)amino]ethyl}-4-oxopentanamide | 2.36 | 413 |
| N-{2-[(6-{[2-(acetylamino)ethyl]amino}-2-phenylpyrimidin-4-yl)amino]ethyl}-2-[(4-chlorophenyl)sulfanyl]acetamide | 2.79 | 499 |
| 4-acetyl-N-{2-[(6-{[2-(acetylamino)ethyl]amino}-2-phenylpyrimidin-4-yl)amino]ethyl}-3,5-dimethyl-1H-pyrrole-2-carboxamide | 2.51 | 478 |
| (2E)-N-{2-[(6-{[2-(acetylamino)ethyl]amino}-2-phenylpyrimidin-4-yl)amino]ethyl}-3-thien-3-ylprop-2-enamide | 2.64 | 451 |
| N-{2-[(6-{[2-(acetylamino)ethyl]amino}-2-phenylpyrimidin-4-yl)amino]ethyl}-2-(2-furyl)-2-(4-phenylpiperazin-1-yl)acetamide | 2.64 | 583 |
| N-{2-[(6-{[2-(acetylamino)ethyl]amino}-2-phenylpyrimidin-4-yl)amino]ethyl}-2-(2-furyl)-2-morpholin-4-ylacetamide | 2.27 | 508 |
| N-{2-[(6-{[2-(acetylamino)ethyl]amino}-2-phenylpyrimidin-4-yl)amino]ethyl}-2-methyl-1H-benzimidazole-5-carboxamide | 2.22 | 473 |
| N-{2-[(6-{[2-(acetylamino)ethyl]amino}-2-phenylpyrimidin-4-yl)amino]ethyl}-2-methylpropanamide | 2.41 | 385 |
| N-{2-[(6-{[2-(acetylamino)ethyl]amino}-2-phenylpyrimidin-4-yl)amino]ethyl}-2-(1H-benzimidazol-2-ylsulfanyl)acetamide | 2.50 | 505 |
| N-{2-[(6-{[2-(acetylamino)ethyl]amino}-2-phenylpyrimidin-4-yl)amino]ethyl}-2-hydroxyquinoline-4-carboxamide | 2.46 | 486 |
| N-{2-[(6-{[2-(acetylamino)ethyl]amino}-2-phenylpyrimidin-4-yl)amino]ethyl}-5-chlorothiophene-2-carboxamide | 2.70 | 459 |
| (2E)-N-{2-[(6-{[2-(acetylamino)ethyl]amino}-2-phenylpyrimidin-4-yl)amino]ethyl}-3-(3-cyanophenyl)prop-2-enamide | 2.67 | 470 |
| N-{2-[(6-{[2-(acetylamino)ethyl]amino}-2-phenylpyrimidin-4-yl)amino]ethyl}-5-nitrothiophene-3-carboxamide | 2.64 | 470 |
| N-{2-[(6-{[2-(acetylamino)ethyl]amino}-2-phenyylpyrimidin-4-yl)amino]ethyl}5-(methylsulfonyl)thiophene-2-carboxamide | 2.52 | 503 |
| N-{2-[(6-{[2-(acetylamino)ethyl]amino}-2-phenylpyrimidin-4-yl)amino]ethyl}-4-(trifluoromethyl)cyclohexanecarboxamide | 2.74 | 493 |

-continued

| Name | Retention Time (min) | Mass ion (ES+) (MH)+ |
|---|---|---|
| N-{2-[(6-{[2-(acetylamino)ethyl]amino}-2-phenylpyrimidin-4-yl)amino]ethyl}-3-ethoxythiophene-2-carboxamide | 2.62 | 469 |
| (2E)-N-{2-[(6-{[2-(acetylamino)ethyl]amino}-2-phenylpyrimidin-4-yl)amino]ethyl}-3-(2-furyl)prop-2-enamide | 2.59 | 435 |
| N-{2-[(6-{[2-(acetylamino)ethyl]amino}-2-phenylpyrimidin-4-yl)amino]ethyl}2,3,5,6-tetrafluoro-4-methylbenzamide | 2.71 | 505 |
| N-{2-[(6-{[2-(acetylamino)ethyl]amino}-2-phenylpyrimidin-4-yl)amino]ethyl}-4,4,4-trifluoro-3-hydroxy-3-methylbutanamide | 2.52 | 469 |
| (2E)-N-{2-[(6-{[2-(acetylamino)ethyl]amino}-2-phenylpyrimidin-4-yl)amino]ethyl}-3-(2,3,4-trifluorophenyl)prop-2-enamide | 2.81 | 499 |
| N-{2-[(6-{[2-(acetylamino)ethyl]amino}-2-phenylpyrimidin-4-yl)amino]ethyl}-8-hydroxyquinoline-2-carboxamide | 2.71 | 486 |
| N-{2-[(6-{[2-(acetylamino)ethyl]amino}-2-phenylpyrimidin-4-yl)amino]ethyl}-6-hydroxy-2-naphthamide | 2.61 | 485 |
| (2E)-N-{2-[(6-{[2-(acetylamino)ethyl]amino}-2-phenylpyrimidin-4-yl)amino]ethyl}-3-(4-isopropylphenyl)prop-2-enamide | 2.96 | 487 |
| (2E)-N-{2-[(6-{[2-(acetylamino)ethyl]amino}-2-phenylpyrimidin-4-yl)amino]ethyl}-3-thien-2-ylprop-2-enamide | 2.64 | 451 |
| (3E)-N-{2-[(6-{[2-(acetylamino)ethyl]amino}-2-phenylpyrimidin-4-yl)amino]ethyl}-4-phenylbut-3-enamide | 2.72 | 459 |
| N-{2-[(6-{[2-(acetylamino)ethyl]amino}-2-phenylpyrimidin-4-yl)amino]ethyl}-1-benzoylpiperidine-4-carboxamide | 2.57 | 530 |
| N-{2-[(6-{[2-(acetylamino)ethyl]amino}-2-phenylpyrimidin-4-yl)amino]ethyl}-4-nitro-1H-pyrazole-3-carboxamide | 2.42 | 454 |
| methyl 3-[({2-[(6-{[2-(acetylamino)ethyl]amino}-2-phenylpyrimidin-4-yl)amino]ethyl}amino)carbonyl]isonicotinate | 2.45 | 478 |
| N-{2-[(6-{[2-(acetylamino)ethyl]amino}-2-phenylpyrimidin-4-yl)amino]ethyl}-5-(1,2-dithiolan-3-yl)pentanamide | 2.74 | 503 |
| N-{2-[(6-{[2-(acetylamino)ethyl]amino}-2-phenylpyrimidin-4-yl)amino]ethyl}-2-methyl-5,6-dihydro-1,4-oxathiine-3-carboxamide | 2.51 | 457 |
| N-{2-[(6-{[2-(acetylamino)ethyl]amino}-2-phenylpyrimidin-4-yl)amino]ethyl}-3-(2-furyl)propanamide | 2.55 | 437 |
| (2E,4E)-N-{2-[(6-{[2-(acetylamino)ethyl]amino}-2-phenylpyrimidin-4-yl)amino]ethyl}-5-phenylpenta-2,4-dienamide | 2.82 | 471 |
| N-{2-[(6-{[2-(acetylamino)ethyl]amino}-2-phenylpyrimidin-4-yl)amino]ethyl}-3-nitropropanamide | 2.35 | 416 |
| N-{2-[(6-{[2-(acetylamino)ethyl]amino}-2-phenylpyrimidin-4-yl)amino]ethyl}-2-oxo-2-thien-2-ylacetamide | 2.65 | 453 |
| (2E)-N-{2-[(6-{[2-(acetylamino)ethyl]amino}-2-phenylpyrimidin-4-yl)amino]ethyl}-3-pyridin-2-ylprop-2-enamide | 2.40 | 446 |
| N-{2-[(6-{[2-(acetylamino)ethyl]amino}-2-phenylpyrimidin-4-yl)amino]ethyl}-3-methyl-2-nitrobenzamide | 2.65 | 478 |
| N-{2-[(6-{[2-(acetylamino)ethyl]amino}-2-phenylpyrimidin-4-yl)amino]ethyl}-3-thien-2-ylpropanamide | 2.60 | 453 |
| N-{2-[(6-{[2-(acetylamino)ethyl]amino}-2-phenylpyrimidin-4-yl)amino]ethyl}-2-(5-methyl-2,4-dioxo-3,4-dihydropyrimidin-1(2H)-yl)acetamide | 2.29 | 481 |
| N-{2-[(6-{[2-(acetylamino)ethyl]amino}-2-phenylpyrimidin-4-yl)amino]ethyl}-4'-hydroxy[1,1'-biphenyl]-4-carboxamide | 2.65 | 511 |
| (4R)-N-{2-[(6-{[2-(acetylamino)ethyl]amino}-2-phenylpyrimidin-4-yl)amino]ethyl}-2-oxo-1,3-thiazolidine-4-carboxamide | 2.32 | 444 |
| N-{2-[(6-{[2-(acetylamino)ethyl]amino}-2-phenylpyrimidin-4-yl)amino]ethyl}cyclohex-3-ene-1-carboxamide | 2.58 | 423 |
| ethyl (2E)-4-({2-[(6-{[2-(acetylamino)ethyl]amino}-2-phenylpyrimidin-4-yl)amino]ethyl}amino)-4-oxobut-2-enoate | 2.54 | 441 |
| N-{2-[(6-{[2-(acetylamino)ethyl]amino}-2-phenylpyrimidin-4-yl)amino]ethyl}-3-(4-hydroxyphenyl)propanamide | 2.41 | 463 |
| (2E)-N-{2-[(6-{[2-(acetylamino)ethyl]amino}-2-phenylpyrimidin-4-yl)amino]ethyl}-3-phenylprop-2-enamide | 2.65 | 445 |
| N-{2-[(6-{[2-(acetylamino)ethyl]amino}-2-phenylpyrimidin-4-yl)amino]ethyl}acetamide | 2.31 | 357 |
| N-{2-[(6-{[2-(acetylamino)ethyl]amino}-2-phenylpyrimidin-4-yl)amino]ethyl}propanamide | 2.30 | 371 |
| N-{2-[(6-{[2-(formylamino)ethyl]amino}-2-phenylpyrimidin-4-yl)amino]ethyl}acetamide | 2.73 | 480 |

Example 10

Synthesis of Compounds 41.1-41.144

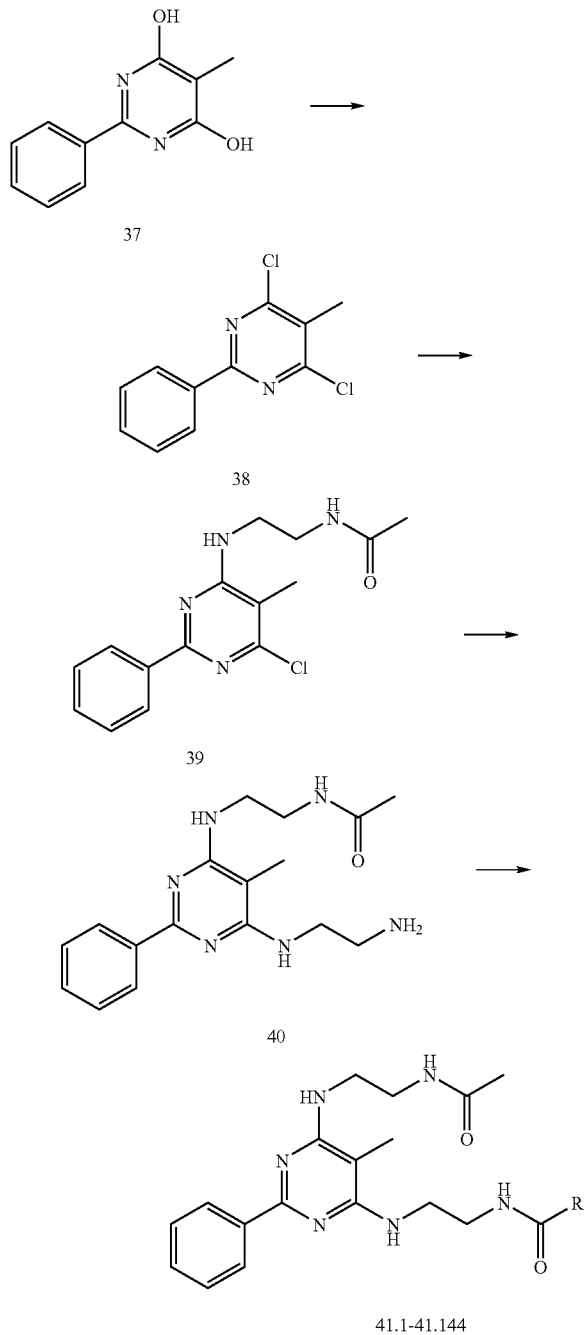

41.1-41.144

5-Methyl-2-phenyl-pyrimidine-4,6-diol (37)

To ethanol (180 ml) was added sodium ethoxide solution (38 ml of a 21% wt solution in ethanol), benzamidine hydrochloride (5.0 g) and diethylmethylmalonate (4.91 ml). The suspension was stirred at 40° C. in an inert atmosphere for 22 hrs after which time it was cooled to 5° C. (ice bath) and treated dropwise with concentrated hydrochloric acid to a pH of 2.5. The resulting pink suspension was filtered and washed with excess water. Purification by recrystallisation from boiling acetic acid (300 ml) afforded the title compound (4.22 g) after filtration and washing with ethanol (20 ml) and diethyl ether (20 ml).

$\delta_H$ (d$^6$-DMSO): 1.80 (3H, s), 7.45-7.55 (3H, m), 8.05-8.07 (2H, d); m/z (ES$^+$) 203 (MH)$^+$

4,6-Dichloro-5-methyl-2-phenylpyrimidine (38)

5-Methyl-2-phenylpyrimidine-4,6-diol (2.81 g) was added to a mixture of phosphorous oxychloride (30 ml) and N,N-dimethylformamide (5 drops). The resulting suspension became a solution on heating to reflux for 36 hrs. After this time the solvent was removed in vacuo. Iced water was cautiously added with stirring to reveal the title compound as a beige solid (1.83 g) after filtration and washing with ethanol (20 ml) and diethyl ether (20 ml).

$\delta_H$ (CDCl$_3$): 2.43-2.49 (3H, br s), 7.40-7.51 (3H, m), 8.33-8.40 (2H, m); m/z (ES$^+$) 239 (MH)$^+$

N-{2-[(6-Chloro-5-methyl-2-phenylpyrimidin-4-yl)amino]ethyl}acetamide (39)

4,6-Dichloro-5-methyl-2-phenylpyrimidine (3.45 g), N-acetyethylenediamine (1.62 g) and N,N-diisopropylethylamine (2.05 g) were added to propan-2-ol (60 ml) with stirring. The resulting solution was heated to reflux for 46 hrs then cooled to 5° C. Precipitated salt impurities were removed by filtration and the mother liquor evaporated onto silica gel. Purification by column chromatography on silica gel eluting with a mixture of ethyl acetate and methanol (9:1 v/v) furnished the title compound (3.28 g).

$\delta_H$ (d$^6$-DMSO): 1.79 (3H, s), 2.11 (3H, s), 3.23-3.33 (2H, m), 3.50-3.58 (2H, m), 7.23-7.28 (1H, m), 7.42-7.47 (3H, m), 7.92-8.00 (1H, m), 8.23-8.30 (2H, m); m/z (ES$^+$) 305 (MH)$^+$

N-[2-({6-[(2-Aminoethyl)amino]-5-methyl-2-phenylpyrimidin-4-yl}amino)ethyl]-acetamide (40)

N-{2-[(6-Chloro-5-methyl-2-phenylpyrimidin-4-yl)amino]ethyl}acetamide (2.0 g) was dissolved in ethylenediamine (40 ml) and heated with stirring to reflux for 21 hrs. After cooling to ambient temperature the solution was evaporated onto silica gel (50 g). Purification via flash chromatography on silica gel eluting with a mixture of ethyl acetate, methanol and ammonium hydroxide (80:20:5 v/v/v) furnished the title compound (1.83 g).

$\delta_H$ (d6-DMSO): 1.78 (3H, s), 1.81 (3H, s), 2.50-2.53 (1H, t), 2.70-2.75 (2H, t), 2.97-3.02 (1H, q), 3.23-3.29 (2H, m), 3.40-3.50 (2H, m), 6.00-6.04 (1H, m), 6.11-6.16 (1H, m), 7.07-7.25 (2H, m), 7.36-7.41 (3H, m), 7.91-7.97 (1H, m), 8.28-8.33 (2H, m); m/z (ES$^+$) 329 (MH)$^+$

N-{2-[(6-{([2-(Acetylamino)ethyl]amino}-5-methyl-2-phenylpyrimidin-4-yl)-amino]ethyl}benzamide (41.1)

Benzoic acid (55.8 mg), N,N-diisopropylethylamine (80 μl) and HATU (160 mg) were stirred in NMP (685 μl) for 30 min. After this time N-[2-({6-[(2-aminoethyl)amino]-5-methyl-2-phenylpyrimidin-4-yl}amino)ethyl]acetamide (150 mg) was added and the mixture stirred for 16 hrs at room temperature. Purification via SCX resin furnished the title compound (54 mg).

$\delta_H$ (CDCl$_3$): 1.69 (3H, s), 1.80 (3H, s), 3.38-3.43 (2H, m), 3.60-3.73 (4H, m), 3.83-3.90 (2H, m), 5.15-5.20 (2H, m), 6.90-6.95 (2H, t), 7.18-7.22 (1H, t), 7.37-7.42 (2H, m), 7.42-7.48 (3H, m), 8.16-8.20 (1H, m), 8.30-8.37 (2H, m); m/z (ES$^+$) 433 (MH)$^+$ Library Example:

N-{2-[(6-{[2-(Acetylamino)ethyl]amino}-5-methyl-2-phenylpyrimidin-4-yl)amino]ethyl}quinoline-2-carboxamide (41.2)

A solution of quinaldic acid (30 μl of a 0.3M solution in NMP), HATU (30 μl of a 0.3M solution in NMP) and diisopropylethylamine (30 μl of a 0.3M solution in NMP) was shaken at ambient temperature in a well of a 96 position microtitre plate for 45 min. N-[2-({6-[(2-aminoethyl)amino]-5-methyl-2-phenylpyrimidin-4-yl}amino)ethyl]acetamide (30 μl of a 0.3M solution in NMP) was then added and the mixture shaken for a further 12 hrs. Purification via ion exchange silica (SCX) yields the title compound.

LCMS (Method A) RT=2.67 min; m/z (ES$^+$) 484 (MH)$^+$

The following compounds 41.3-41.144 were synthesized in an analogous manner:

| Name | Retention Time (min) | Mass Ion (ES$^+$) (MH)$^+$ |
|---|---|---|
| N-{2-[(6-{[2-(acetylamino)ethyl]amino}-5-methyl-2-phenylpyrimidin-4-yl)amino]ethyl}isoquinoline-3-carboxamide | 2.57 | 484 |
| N-{2-[(6-{[2-(acetylamino)ethyl]amino}-5-methyl-2-phenylpyrimidin-4-yl)amino]ethyl}quinoxaline-2-carboxamide | 2.50 | 485 |
| N-{2-[(6-{[2-(acetylamino)ethyl]amino}-5-methyl-2-phenylpyrimidin-4-yl)amino]ethyl}isoquinoline-1-carboxamide | 2.57 | 484 |
| N-{2-[(6-{[2-(acetylamino)ethyl]amino}-5-methyl-2-phenylpyrimidin-4-yl)amino]ethyl}pyrazine-2-carboxamide | 2.30 | 435 |
| N-{2-[(6-{[2-(acetylamino)ethyl]amino}-5-methyl-2-phenylpyrimidin-4-yl)amino]ethyl}nicotinamide | 2.19 | 434 |
| N-{2-[(6-{[2-(acetylamino)ethyl]amino}-5-methyl-2-phenylpyrimidin-4-yl)amino]ethyl}isonicotinamide | 2.17 | 434 |
| N-{2-[(6-{[2-(acetylamino)ethyl]amino}-5-methyl-2-phenylpyrimidin-4-yl)amino]ethyl}-2-hydroxynicotinamide | 2.23 | 450 |
| N-{2-[(6-{[2-(acetylamino)ethyl]amino}-5-methyl-2-phenylpyrimidin-4-yl)amino]ethyl}-1H-indole-2-carboxamide | 2.58 | 472 |
| N-{2-[(6-{[2-(acetylamino)ethyl]amino}-5-methyl-2-phenylpyrimidin-4-yl)amino]ethyl}-1H-indole-3-carboxamide | 2.48 | 469 |
| N-{2-[(6-{[2-(acetylamino)ethyl]amino}-5-methyl-2-phenylpyrimidin-4-yl)amino]ethyl}-2-(3-hydroxy-4-methoxyphenyl)acetamide | 2.33 | 492 |
| (2E)-N-{2-[(6-{[2-(acetylamino)ethyl]amino}-5-methyl-2-phenylpyrimidin-4-yl)amino]ethyl}-3-(1H-indol-3-yl)prop-2-enamide | 2.58 | 498 |
| (2E)-N-{2-[(6-{[2-(acetylamino)ethyl]amino}-5-methyl-2-phenylpyrimidin-4-yl)amino]ethyl}-3-(3-nitrophenyl)prop-2-enamide | 2.64 | 504 |
| N-{2-[(6-{[2-(acetylamino)ethyl]amino}-5-methyl-2-phenylpyrimidin-4-yl)amino]ethyl}-3-(1H-benzimidazol-2-yl)propanamide | 2.14 | 501 |
| N-{2-[(6-{[2-(acetylamino)ethyl]amino}-5-methyl-2-phenylpyrimidin-4-yl)amino]ethyl}-2-hydroxy-4-methylbenzamide | 2.65 | 463 |
| N-{2-[(6-{[2-(acetylamino)ethyl]amino}-5-methyl-2-phenylpyrimidin-4-yl)amino]ethyl}-2-hydroxy-3-methoxybenzamide | 2.50 | 479 |
| N-{2-[(6-{[2-(acetylamino)ethyl]amino}-5-methyl-2-phenylpyrimidin-4-yl)amino]ethyl}-2-hydroxy-3-methylbenzamide | 2.75 | 463 |
| N-{2-[(6-{[2-(acetylamino)ethyl]amino}-5-methyl-2-phenylpyrimidin-4-yl)amino]ethyl}-2-(1H-indol-3-yl)acetamide | 2.42 | 486 |
| N-{2-[(6-{[2-(acetylamino)ethyl]amino}-5-methyl-2-phenylpyrimidin-4-yl)amino]ethyl}-3-(1H-indol-3-yl)propanamide | 2.55 | 500 |
| N-{2-[(6-{[2-(acetylamino)ethyl]amino}-5-methyl-2-phenylpyrimidin-4-yl)amino]ethyl}pyridine-2-carboxamide | 2.39 | 434 |
| N-{2-[(6-{[2-(acetylamino)ethyl]amino}-5-methyl-2-phenylpyrimidin-4-yl)amino]ethyl}-4-(1H-indol-3-yl)butanamide | 2.62 | 514 |
| N-{2-[(6-{[2-(acetylamino)ethyl]amino}-5-methyl-2-phenylpyrimidin-4-yl)amino]ethyl}-5-methylpyrazine-2-carboxamide | 2.34 | 449 |
| N-{2-[(6-{[2-(acetylamino)ethyl]amino}-5-methyl-2-phenylpyrimidin-4-yl)amino]ethyl}-5-methyl-2-phenyl-2H-1,2,3-triazole-4-carboxamide | 2.74 | 514 |
| N-{2-[(6-{[2-(acetylamino)ethyl]amino}-5-methyl-2-phenylpyrimidin-4-yl)amino]ethyl}-4-oxo-4,5,6,7-tetrahydro-1-benzofuran-3-carboxamide | 2.42 | 491 |
| N-{2-[(6-{[2-(acetylamino)ethyl]amino}-5-methyl-2-phenylpyrimidin-4-yl)amino]ethyl}-2-(methylsulfanyl)nicotinamide | 2.44 | 480 |
| N-{2-[(6-{[2-(acetylamino)ethyl]amino}-5-methyl-2-phenylpyrimidin-4-yl)amino]ethyl}-1-tert-butyl-3-methyl-1H-pyrazole-5-carboxamide | 2.57 | 493 |
| N-{2-[(6-{[2-(acetylamino)ethyl]amino}-5-methyl-2-phenylpyrimidin-4-yl)amino]ethyl}-1-benzothiophene-2-carboxamide | 2.70 | 489 |
| N-{2-[(6-{[2-(acetylamino)ethyl]amino}-5-methyl-2-phenylpyrimidin-4-yl)amino]ethyl}-4-(trifluoromethoxy)benzamide | 2.75 | 517 |
| N-{2-[(6-{[2-(acetylamino)ethyl]amino}-5-methyl-2-phenylpyrimidin-4-yl)amino]ethyl}-5-chloro-2-hydroxynicotinamide | 2.34 | 484 |
| N-{2-[(6-{[2-(acetylamino)ethyl]amino}-5-methyl-2-phenylpyrimidin-4-yl)amino]ethyl}-4-(trifluoroacetyl)benzamide | 2.47 | 529 |
| N-[2-({2-[(6-{[2-(acetylamino)ethyl]amino}-5-methyl-2-phenylpyrimidin-4-yl)amino]ethyl}amino)-2-oxoethyl]-4-chlorobenzamide | 2.49 | 524 |
| N-{2-[(6-{[2-(acetylamino)ethyl]amino}-5-methyl-2-phenylpyrimidin-4-yl)amino]ethyl}-4-phenyl-1,2,3-thiadiazole-5-carboxamide | 2.66 | 517 |
| N-{2-[(6-{[2-(acetylamino)ethyl]amino}-5-methyl-2-phenylpyrimidin-4-yl)amino]ethyl}-1,2,3-thiadiazole-4-carboxamide | 2.31 | 441 |
| N-{2-[(6-{[2-(acetylamino)ethyl]amino}-5-methyl-2-phenylpyrimidin-4-yl)amino]ethyl}-5-chloro-2-(methylsulfanyl)pyrimidine-4-carboxamide | 2.54 | 515 |

-continued

| Name | Retention Time (min) | Mass Ion (ES+) (MH)+ |
|---|---|---|
| N-{2-[(6-{[2-(acetylamino)ethyl]amino}-5-methyl-2-phenylpyrimidin-4-yl)amino]ethyl}-1-(2-furylmethyl)-5-oxopyrrolidine-3-carboxamide | 2.37 | 520 |
| N-{2-[(6-{[2-(acetylamino)ethyl]amino}-5-methyl-2-phenylpyrimidin-4-yl)amino]ethyl}-3-tert-butyl-1-methyl-1H-pyrazole-5-carboxamide | 2.60 | 493 |
| N-{2-[(6-{[2-(acetylamino)ethyl]amino}-5-methyl-2-phenylpyrimidin-4-yl)amino]ethyl}-5-oxopyrrolidine-2-carboxamide | 2.14 | 440 |
| N-{2-[(6-{[2-(acetylamino)ethyl]amino}-5-methyl-2-phenylpyrimidin-4-yl)amino]ethyl}-2-(2,5-dimethoxyphenyl)acetamide | 2.48 | 507 |
| N-{2-[(6-{[2-(acetylamino)ethyl]amino}-5-methyl-2-phenylpyrimidin-4-yl)amino]ethyl}-2-(3-methoxyphenyl)acetamide | 2.46 | 477 |
| N-{2-[(6-{[2-(acetylamino)ethyl]amino}-5-methyl-2-phenylpyrimidin-4-yl)amino]ethyl}-2-(4-methoxyphenyl)acetamide | 2.45 | 477 |
| N-{2-[(6-{[2-(acetylamino)ethyl]amino}-5-methyl-2-phenylpyrimidin-4-yl)amino]ethyl}-2-(2-methoxyphenyl)acetamide | 2.50 | 477 |
| N-{2-[(6-{[2-(acetylamino)ethyl]amino}-5-methyl-2-phenylpyrimidin-4-yl)amino]ethyl}-1,2,3,4-tetrahydronaphthalene-2-carboxamide | 2.70 | 487 |
| N-{2-[(6-{[2-(acetylamino)ethyl]amino}-5-methyl-2-phenylpyrimidin-4-yl)amino]ethyl}-1H-pyrrole-2-carboxamide | 2.36 | 422 |
| (2S)-N-{2-[(6-{[2-(acetylamino)ethyl]amino}-5-methyl-2-phenylpyrimidin-4-yl)amino]ethyl}-5-oxopyrrolidine-2-carboxamide | 2.16 | 440 |
| (3S,4R,5S)-N-{2-[(6-{[2-(acetylamino)ethyl]amino}-5-methyl-2-phenylpyrimidin-4-yl)amino]ethyl}-3,4,5-trihydroxycyclohex-1-ene-1-carboxamide | 2.06 | 485 |
| N-{2-[(6-{[2-(acetylamino)ethyl]amino}-5-methyl-2-phenylpyrimidin-4-yl)amino]ethyl}-2-cyclohexylacetamide | 2.62 | 453 |
| N-{2-[(6-{[2-(acetylamino)ethyl]amino}-5-methyl-2-phenylpyrimidin-4-yl)amino]ethyl}-4-(1H-pyrrol-1-yl)benzamide | 2.70 | 498 |
| N-{2-[(6-{[2-(acetylamino)ethyl]amino}-5-methyl-2-phenylpyrimidin-4-yl)amino]ethyl}-2-(1,3-dioxo-1,3-dihydro-2H-isoindol-2-yl)propanamide | 2.50 | 530 |
| N-{2-[(6-{[2-(acetylamino)ethyl]amino}-5-methyl-2-phenylpyrimidin-4-yl)amino]ethyl}-2-[1,1'-biphenyl]-4-ylacetamide | 2.77 | 523 |
| N-{2-[(6-{[2-(acetylamino)ethyl]amino}-5-methyl-2-phenylpyrimidin-4-yl)amino]ethyl}-2-(6-methoxy-3-oxo-2,3-dihydro-1H-inden-1-yl)acetamide | 2.47 | 531 |
| N-{2-[(6-{[2-(acetylamino)ethyl]amino}-5-methyl-2-phenylpyrimidin-4-yl)amino]ethyl}-2-(2-nitrophenyl)acetamide | 2.49 | 492 |
| N-{2-[(6-{[2-(acetylamino)ethyl]amino}-5-methyl-2-phenylpyrimidin-4-yl)amino]ethyl}-2-(2-methylphenyl)acetamide | 2.55 | 461 |
| N-{2-[(6-{[2-(acetylamino)ethyl]amino}-5-methyl-2-phenylpyrimidin-4-yl)amino]ethyl}-2-(4-methylphenyl)acetamide | 2.55 | 461 |
| N-{2-[(6-{[2-(acetylamino)ethyl]amino}-5-methyl-2-phenylpyrimidin-4-yl)amino]ethyl}-3-methylbenzamide | 2.57 | 447 |
| N-{2-[(6-{[2-(acetylamino)ethyl]amino}-5-methyl-2-phenylpyrimidin-4-yl)amino]ethyl}-4-methylbenzamide | 2.58 | 447 |
| N-{2-[(6-{[2-(acetylamino)ethyl]amino}-5-methyl-2-phenylpyrimidin-4-yl)amino]ethyl}-2-methylbenzamide | 2.53 | 447 |
| N-{2-[(6-{[2-(acetylamino)ethyl]amino}-5-methyl-2-phenylpyrimidin-4-yl)amino]ethyl}-2-(3-methylphenyl)acetamide | 2.54 | 461 |
| N-{2-[(6-{[2-(acetylamino)ethyl]amino}-5-methyl-2-phenylpyrimidin-4-yl)amino]ethyl}-2-phenoxypropanamide | 2.52 | 477 |
| N-{2-[(6-{[2-(acetylamino)ethyl]amino}-5-methyl-2-phenylpyrimidin-4-yl)amino]ethyl}-1,3-benzodioxole-5-carboxamide | 2.47 | 477 |
| N-{2-[(6-{[2-(acetylamino)ethyl]amino}-5-methyl-2-phenylpyrimidin-4-yl)amino]ethyl}-2-phenylacetamide | 2.45 | 447 |
| N-{2-[(6-{[2-(acetylamino)ethyl]amino}-5-methyl-2-phenylpyrimidin-4-yl)amino]ethyl}bicyclo[2.2.1]hept-5-ene-2-carboxamide | 2.52 | 449 |
| N-{2-[(6-{[2-(acetylamino)ethyl]amino}-5-methyl-2-phenylpyrimidin-4-yl)amino]ethyl}-2-hydroxy-2-phenylacetamide | 2.35 | 463 |
| N-{2-[(6-{[2-(acetylamino)ethyl]amino}-5-methyl-2-phenylpyrimidin-4-yl)amino]ethyl}-2-(2-naphthyloxy)acetamide | 2.69 | 513 |
| N-{2-[(6-{[2-(acetylamino)ethyl]amino}-5-methyl-2-phenylpyrimidin-4-yl)amino]ethyl}-1-phenylcyclopentanecarboxamide | 2.75 | 501 |
| N-{2-[(6-{[2-(acetylamino)ethyl]amino}-5-methyl-2-phenylpyrimidin-4-yl)amino]ethyl}-2-sulfanylbenzamide | 2.50 | 463 |
| N-{2-[(6-{[2-(acetylamino)ethyl]amino}-5-methyl-2-phenylpyrimidin-4-yl)amino]ethyl}tetrahydrofuran-2-carboxamide | 2.30 | 427 |
| N-{2-[(6-{[2-(acetylamino)ethyl]amino}-5-methyl-2-phenylpyrimidin-4-yl)amino]ethyl}-2-cyclopentyl-2-phenylacetamide | 2.87 | 515 |
| N-{2-[(6-{[2-(acetylamino)ethyl]amino}-5-methyl-2-phenylpyrimidin-4-yl)amino]ethyl}-4-tert-butylbenzamide | 2.86 | 489 |
| N-{2-[(6-{[2-(acetylamino)ethyl]amino}-5-methyl-2-phenylpyrimidin-4-yl)amino]ethyl}adamantane-1-carboxamide | 2.79 | 491 |
| N-{2-[(6-{[2-(acetylamino)ethyl]amino}-5-methyl-2-phenylpyrimidin-4-yl)amino]ethyl}-4-methoxybenzamide | 2.48 | 463 |

-continued

| Name | Retention Time (min) | Mass Ion (ES+) (MH)+ |
|---|---|---|
| N-{2-[(6-{[2-(acetylamino)ethyl]amino}-5-methyl-2-phenylpyrimidin-4-yl)amino]ethyl}-4-cyclohexylbenzamide | 3.07 | 515 |
| N-{2-[(6-{[2-(acetylamino)ethyl]amino}-5-methyl-2-phenylpyrimidin-4-yl)amino]ethyl}-1-naphthamide | 2.63 | 483 |
| N-{2-[(6-{[2-(acetylamino)ethyl]amino}-5-methyl-2-phenylpyrimidin-4-yl)amino]ethyl}benzamide | 2.49 | 433 |
| N-{2-[(6-{[2-(acetylamino)ethyl]amino}-5-methyl-2-phenylpyrimidin-4-yl)amino]ethyl}-4-bromo-3-methylbenzamide | 2.77 | 525 |
| N-{2-[(6-{[2-(acetylamino)ethyl]amino}-5-methyl-2-phenylpyrimidin-4-yl)amino]ethyl}-5-chloro-2-hydroxybenzamide | 2.73 | 482 |
| N-{2-[(6-{[2-(acetylamino)ethyl]amino}-5-methyl-2-phenylpyrimidin-4-yl)amino]ethyl}-4-(dimethylamino)benzamide | 2.56 | 476 |
| 2-(acetylamino)-N-{2-[(6-{[2-(acetylamino)ethyl]amino}-5-methyl-2-phenylpyrimidin-4-yl)amino]ethyl}acetamide | 2.12 | 428 |
| N-{2-[(6-{[2-(acetylamino)ethyl]amino}-5-methyl-2-phenylpyrimidin-4-yl)amino]ethyl}-2-(4-hydroxy-3-methoxyphenyl)acetamide | 2.32 | 493 |
| N-{2-[(6-{[2-(acetylamino)ethyl]amino}-5-methyl-2-phenylpyrimidin-4-yl)amino]ethyl}-3-hydroxy-4-methylbenzamide | 2.48 | 463 |
| N-{2-[(6-{[2-(acetylamino)ethyl]amino}-5-methyl-2-phenylpyrimidin-4-yl)amino]ethyl}-3-phenylprop-2-ynamide | 2.67 | 457 |
| N-{2-[(6-{[2-(acetylamino)ethyl]amino}-5-methyl-2-phenylpyrimidin-4-yl)amino]ethyl}-4-fluoro-1-naphthamide | 2.73 | 501 |
| N-{2-[(6-{[2-(acetylamino)ethyl]amino}-5-methyl-2-phenylpyrimidin-4-yl)amino]ethyl}-5-formyl-2-hydroxybenzamide | 2.56 | 477 |
| N-{2-[(6-{[2-(acetylamino)ethyl]amino}-5-methyl-2-phenylpyrimidin-4-yl)amino]ethyl}cyclohex-1-ene-1-carboxamide | 2.56 | 437 |
| N-{2-[(6-{[2-(acetylamino)ethyl]amino}-5-methyl-2-phenylpyrimidin-4-yl)amino]ethyl}-2-(4-bromophenyl)acetamide | 2.61 | 525 |
| N-{2-[(6-{[2-(acetylamino)ethyl]amino}-5-methyl-2-phenylpyrimidin-4-yl)amino]ethyl}-2-(methylsulfanyl)benzamide | 2.52 | 479 |
| N-{2-[(6-{[2-(acetylamino)ethyl]amino}-5-methyl-2-phenylpyrimidin-4-yl)amino]ethyl}-4-(methylsulfonyl)benzamide | 2.37 | 511 |
| N-{2-[(6-{[2-(acetylamino)ethyl]amino}-5-methyl-2-phenylpyrimidin-4-yl)amino]ethyl}-4-benzoylbenzamide | 2.75 | 537 |
| N-{2-[(6-{[2-(acetylamino)ethyl]amino}-5-methyl-2-phenylpyrimidin-4-yl)amino]ethyl}-4-(trifluoromethyl)benzamide | 2.75 | 501 |
| 4-acetyl-N-{2-[(6-{[2-(acetylamino)ethyl]amino}-5-methyl-2-phenylpyrimidin-4-yl)amino]ethyl}benzamide | 2.46 | 475 |
| N-{2-[(6-{[2-(acetylamino)ethyl]amino}-5-methyl-2-phenylpyrimidin-4-yl)amino]ethyl}-4-cyanobenzamide | 2.51 | 458 |
| N-{2-[(6-{[2-(acetylamino)ethyl]amino}-5-methyl-2-phenylpyrimidin-4-yl)amino]ethyl}-3-(trifluoromethyl)benzamide | 2.72 | 501 |
| N-{2-[(6-{[2-(acetylamino)ethyl]amino}-5-methyl-2-phenylpyrimidin-4-yl)amino]ethyl}-3-cyanobenzamide | 2.49 | 458 |
| N-{2-[(6-{[2-(acetylamino)ethyl]amino}-5-methyl-2-phenylpyrimidin-4-yl)amino]ethyl}-1H-benzimidazole-5-carboxamide | 2.12 | 473 |
| N-{2-[(6-{[2-(acetylamino)ethyl]amino}-5-methyl-2-phenylpyrimidin-4-yl)amino]ethyl}-2,2-diphenylacetamide | 2.79 | 523 |
| N-{2-[(6-{[2-(acetylamino)ethyl]amino}-5-methyl-2-phenylpyrimidin-4-yl)amino]ethyl}-4-ethylbenzamide | 2.70 | 461 |
| N-{2-[(6-{[2-(acetylamino)ethyl]amino}-5-methyl-2-phenylpyrimidin-4-yl)amino]ethyl}-2-hydroxybenzamide | 2.60 | 449 |
| N-{2-[(6-{[2-(acetylamino)ethyl]amino}-5-methyl-2-phenylpyrimidin-4-yl)amino]ethyl}-3-bromobenzamide | 2.67 | 513 |
| N-{2-[(6-{[2-(acetylamino)ethyl]amino}-5-methyl-2-phenylpyrimidin-4-yl)amino]ethyl}-4-oxopentanamide | 2.28 | 427 |
| N-{2-[(6-{[2-(acetylamino)ethyl]amino}-5-methyl-2-phenylpyrimidin-4-yl)amino]ethyl}-2-[(4-chlorophenyl)sulfanyl]acetamide | 2.67 | 513 |
| 4-acetyl-N-{2-[(6-{[2-(acetylamino)ethyl]amino}-5-methyl-2-phenylpyrimidin-4-yl)amino]ethyl}-3,5-dimethyl-1H-pyrrole-2-carboxamide | 2.39 | 492 |
| (2E)-N-{2-[(6-{[2-(acetylamino)ethyl]amino}-5-methyl-2-phenylpyrimidin-4-yl)amino]ethyl}-3-thien-3-ylprop-2-enamide | 2.58 | 465 |
| N-{2-[(6-{[2-(acetylamino)ethyl]amino}-5-methyl-2-phenylpyrimidin-4-yl)amino]ethyl}-2-(2-furyl)-2-(4-phenylpiperazin-1-yl)acetamide | 2.59 | 596 |
| N-{2-[(6-{[2-(acetylamino)ethyl]amino}-5-methyl-2-phenylpyrimidin-4-yl)amino]ethyl}-2-(2-furyl)-2-morpholin-4-ylacetamide | 2.23 | 522 |
| N-{2-[(6-{[2-(acetylamino)ethyl]amino}-5-methyl-2-phenylpyrimidin-4-yl)amino]ethyl}-2-methyl-1H-benzimidazole-5-carboxamide | 2.13 | 487 |
| N-{2-[(6-{[2-(acetylamino)ethyl]amino}-5-methyl-2-phenylpyrimidin-4-yl)amino]ethyl}-2-methylpropanamide | 2.35 | 399 |
| N-{2-[(6-{[2-(acetylamino)ethyl]amino}-5-methyl-2-phenylpyrimidin-4-yl)amino]ethyl}-2-(1H-benzimidazol-2-ylsulfanyl)acetamide | 2.33 | 519 |
| N-{2-[(6-{[2-(acetylamino)ethyl]amino}-5-methyl-2-phenylpyrimidin-4-yl)amino]ethyl}-2-hydroxyquinoline-4-carboxamide | 2.36 | 500 |

-continued

| Name | Retention Time (min) | Mass Ion (ES+) (MH)+ |
|---|---|---|
| N-{2-[(6-{[2-(acetylamino)ethyl]amino}-5-methyl-2-phenylpyrimidin-4-yl)amino]ethyl}-5-chlorothiophene-2-carboxamide | 2.63 | 473 |
| (2E)-N-{2-[(6-{[2-(acetylamino)ethyl]amino}-5-methyl-2-phenylpyrimidin-4-yl)amino]ethyl}-3-(3-cyanophenyl)prop-2-enamide | 2.61 | 484 |
| N-{2-[(6-{[2-(acetylamino)ethyl]amino}-5-methyl-2-phenylpyrimidin-4-yl)amino]ethyl}-5-nitrothiophene-3-carboxamide | 2.54 | 484 |
| N-{2-[(6-{[2-(acetylamino)ethyl]amino}-5-methyl-2-phenylpyrimidin-4-yl)amino]ethyl}-5-(methylsulfonyl)thiophene-2-carboxamide | 2.41 | 517 |
| N-{2-[(6-{[2-(acetylamino)ethyl]amino}-5-methyl-2-phenylpyrimidin-4-yl)amino]ethyl}-4-(trifluoromethyl)cyclohexanecarboxamide | 2.69 | 507 |
| N-{2-[(6-{[2-(acetylamino)ethyl]amino}-5-methyl-2-phenylpyrimidin-4-yl)amino]ethyl}-3-ethoxythiophene-2-carboxamide | 2.54 | 483 |
| (2E)-N-{2-[(6-{[2-(acetylamino)ethyl]amino}-5-methyl-2-phenylpyrimidin-4-yl)amino]ethyl}-3-(2-furyl)prop-2-enamide | 2.51 | 449 |
| N-{2-[(6-{[2-(acetylamino)ethyl]amino}-5-methyl-2-phenylpyrimidin-4-yl)amino]ethyl}-2,3,5,6-tetrafluoro-4-methylbenzamide | 2.81 | 519 |
| N-{2-[(6-{[2-(acetylamino)ethyl]amino}-5-methyl-2-phenylpyrimidin-4-yl)amino]ethyl}-4,4,4-trifluoro-3-hydroxy-3-methylbutanamide | 2.46 | 483 |
| (2E)-N-{2-[(6-{[2-(acetylamino)ethyl]amino}-5-methyl-2-phenylpyrimidin-4-yl)amino]ethyl}-3-(2,3,4-trifluorophenyl)prop-2-enamide | 2.77 | 513 |
| N-{2-[(6-{[2-(acetylamino)ethyl]amino}-5-methyl-2-phenylpyrimidin-4-yl)amino]ethyl}-8-hydroxyquinoline-2-carboxamide | 2.58 | 500 |
| N-{2-[(6-{[2-(acetylamino)ethyl]amino}-5-methyl-2-phenylpyrimidin-4-yl)amino]ethyl}-6-hydroxy-2-naphthamide | 2.52 | 499 |
| (2E)-N-{2-[(6-{[2-(acetylamino)ethyl]amino}-5-methyl-2-phenylpyrimidin-4-yl)amino]ethyl}-3-(4-isopropylphenyl)prop-2-enamide | 2.93 | 501 |
| (2E)-N-{2-[(6-{[2-(acetylamino)ethyl]amino}-5-methyl-2-phenylpyrimidin-4-yl)amino]ethyl}-3-thien-2-ylprop-2-enamide | 2.59 | 465 |
| (3E)-N-{2-[(6-{[2-(acetylamino)ethyl]amino}-5-methyl-2-phenylpyrimidin-4-yl)amino]ethyl}-4-phenylbut-3-enamide | 2.64 | 473 |
| N-{2-[(6-{[2-(acetylamino)ethyl]amino}-5-methyl-2-phenylpyrimidin-4-yl)amino]ethyl}-1-benzoylpiperidine-4-carboxamide | 2.47 | 544 |
| N-{2-[(6-{[2-(acetylamino)ethyl]amino}-5-methyl-2-phenylpyrimidin-4-yl)amino]ethyl}-4-nitro-1H-pyrazole-3-carboxamide | 2.34 | 468 |
| N-{2-[(6-{[2-(acetylamino)ethyl]amino}-5-methyl-2-phenylpyrimidin-4-yl)amino]ethyl}-2-[(4-methyl-4H-1,2,4-triazol-3-yl)sulfanyl]acetamide | 2.23 | 484 |
| N-{2-[(6-{[2-(acetylamino)ethyl]amino}-5-methyl-2-phenylpyrimidin-4-yl)amino]ethyl}-5-(1,2-dithiolan-3-yl)pentanamide | 2.66 | 517 |
| N-{2-[(6-{[2-(acetylamino)ethyl]amino}-5-methyl-2-phenylpyrimidin-4-yl)amino]ethyl}-2-methyl-5,6-dihydro-1,4-oxathiine-3-carboxamide | 2.44 | 471 |
| N-{2-[(6-{[2-(acetylamino)ethyl]amino}-5-methyl-2-phenylpyrimidin-4-yl)amino]ethyl}-3-(2-furyl)propanamide | 2.47 | 451 |
| (2E,4E)-N-{2-[(6-{[2-(acetylamino)ethyl]amino}-5-methyl-2-phenylpyrimidin-4-yl)amino]ethyl}-5-phenylpenta-2,4-dienamide | 2.75 | 485 |
| N-{2-[(6-{[2-(acetylamino)ethyl]amino}-5-methyl-2-phenylpyrimidin-4-yl)amino]ethyl}-3-nitropropanamide | 2.29 | 430 |
| N-{2-[(6-{[2-(acetylamino)ethyl]amino}-5-methyl-2-phenylpyrimidin-4-yl)amino]ethyl}-2-oxo-2-thien-2-ylacetamide | 2.58 | 467 |
| (2E)-N-{2-[(6-{[2-(acetylamino)ethyl]amino}-5-methyl-2-phenylpyrimidin-4-yl)amino]ethyl}-3-pyridin-2-ylprop-2-enamide | 2.30 | 460 |
| N-{2-[(6-{[2-(acetylamino)ethyl]amino}-5-methyl-2-phenylpyrimidin-4-yl)amino]ethyl}-3-methyl-2-nitrobenzamide | 2.61 | 492 |
| N-{2-[(6-{[2-(acetylamino)ethyl]amino}-5-methyl-2-phenylpyrimidin-4-yl)amino]ethyl}-3-thien-2-ylpropanamide | 2.54 | 467 |
| N-{2-[(6-{[2-(acetylamino)ethyl]amino}-5-methyl-2-phenylpyrimidin-4-yl)amino]ethyl}-2-(5-methyl-2,4-dioxo-3,4-dihydropyrimidin-1(2H)-yl)acetamide | 2.21 | 495 |
| N-{2-[(6-{[2-(acetylamino)ethyl]amino}-5-methyl-2-phenylpyrimidin-4-yl)amino]ethyl}-4'-hydroxy[1,1'-biphenyl]-4-carboxamide | 2.60 | 525 |
| (4R)-N-{2-[(6-{[2-(acetylamino)ethyl]amino}-5-methyl-2-phenylpyrimidin-4-yl)amino]ethyl}-2-oxo-1,3-thiazolidine-4-carboxamide | 2.24 | 458 |
| N-{2-[(6-{[2-(acetylamino)ethyl]amino}-5-methyl-2-phenylpyrimidin-4-yl)amino]ethyl}cyclohex-3-ene-1-carboxamide | 2.53 | 437 |
| ethyl (2E)-4-({2-[(6-{[2-(acetylamino)ethyl]amino}-5-methyl-2-phenylpyrimidin-4-yl)amino]ethyl}amino)-4-oxobut-2-enoate | 2.46 | 455 |
| N-{2-[(6-{[2-(acetylamino)ethyl]amino}-5-methyl-2-phenylpyrimidin-4-yl)amino]ethyl}-3-(4-hydroxyphenyl)propanamide | 2.40 | 477 |
| (2E)-N-{2-[(6-{[2-(acetylamino)ethyl]amino}-5-methyl-2-phenylpyrimidin-4-yl)amino]ethyl}-3-phenylprop-2-enamide | 2.63 | 459 |
| N-{2-[(6-{[2-(acetylamino)ethyl]amino}-5-methyl-2-phenylpyrimidin-4-yl)amino]ethyl}acetamide | 2.20 | 371 |

| Name | Retention Time (min) | Mass Ion (ES⁺) (MH)⁺ |
|---|---|---|
| N-{2-[(6-{[2-(acetylamino)ethyl]amino}-5-methyl-2-phenylpyrimidin-4-yl)amino]ethyl}propanamide | 2.28 | 385 |

Example 11

Synthesis of Compounds 46.1-46.82

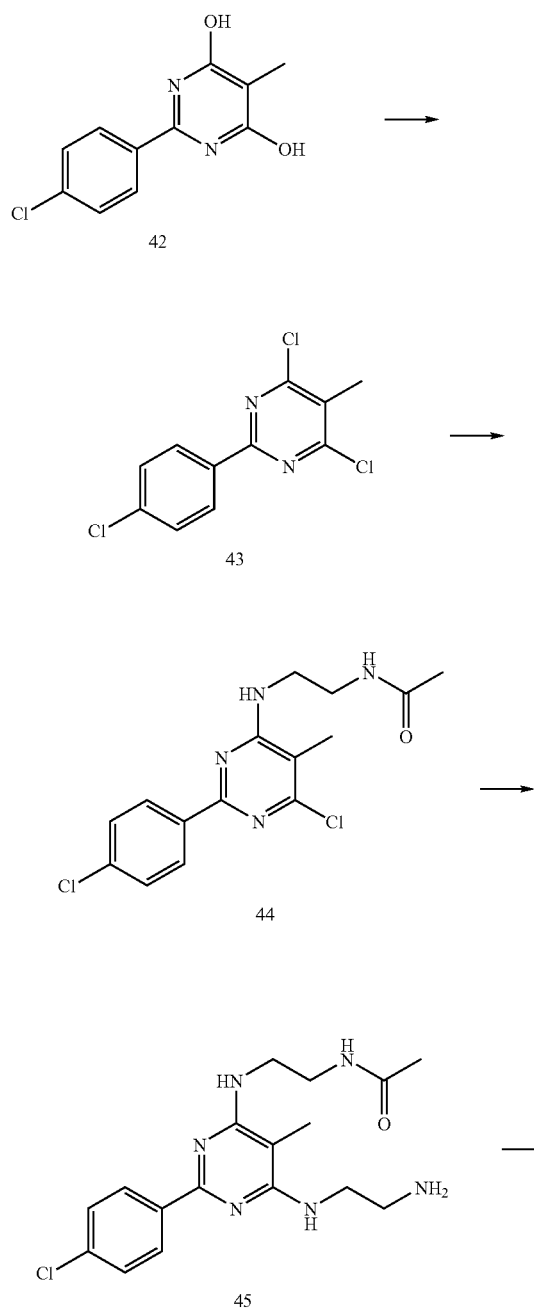

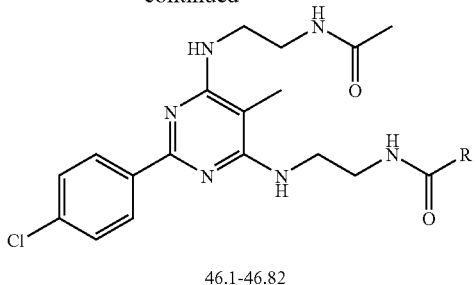

46.1-46.82

2-(4-Chlorophenyl)-5-methylpyrimidine-4,6-diol (42)

To ethanol (20 ml) was added sodium ethoxide solution (7.76 ml of a 21% wt solution in ethanol), 4-chlorobenzamidine hydrochloride (1.0 g) and diethylmethylmalonate (0.89 ml). The suspension was stirred at 40° C. in an inert atmosphere for 44 hrs after which time it was cooled to 5° C. and treated dropwise with concentrated hydrochloric acid to a pH of 2. The resulting suspension was filtered and washed with excess water, then ethanol (20 ml) and diethyl ether (20 ml) affording the title compound as a solid (1.71 g).

$\delta_H$ (d⁶-DMSO): 1.80 (3H, s), 7.56-7.6 (2H, d), 8.05-8.10 (2H, d); m/z (ES⁺) 237 (MH)⁺

4,6-Dichloro-2-(4-chlorophenyl)-5-methylpyrimidine (43)

2-(4-Chlorophenyl)-5-methylpyrimidine-4,6-diol was added to a mixture of phosphorous oxychloride (4 ml) and N,N-dimethylformamide (5 drops) and the mixture heated to reflux for 6 hrs. After this time the solvent was removed in vacuo. Iced water was cautiously added with stirring to reveal the title compound as a beige solid (1.83 g) after filtration and drying in vacuo.

$\delta_H$ (CDCl₃): 2.43 (3H, s), 7.58-7.62 (2H, d), 8.23-8.28 (2H, m)

N-{2-[(6-Chloro-5-methyl-2-(4-chlorophenylpyrimidin-4-yl)amino]ethyl}acetamide (44)

4,6-Dichloro-2-(4-chlorophenyl)-5-methylpyrimidine (1.0 g), N-acetyethylenediamine (0.39 g) and triethylamine (0.52 ml) were added to ethanol (100 ml) with stirring. The resulting solution was heated to reflux for 40 hrs then cooled to ambient temperature. The mother liquor was evaporated onto silica gel and purified by column chromatography on silica gel eluting with ethyl acetate furnishing the title compound (0.783 g).

$\delta_H$ (CDCl₃): 1.94 (3H, s), 2.19 (3H, s), 3.55-3.62 (2H, m), 3.68-3.75 (2H, m), 5.95-6.00 (1H, br s), 6.03-6.12 (1H, br s), 7.37-7.42 (2H, d), 8.28-8.32 (2H, d); m/z (ES⁺) 339 (MH)⁺

N-{2-[6-(2-Aminoethylamino)-2-(4-chlorophenyl)-5-methylpyrimidin-4-ylamino]-ethyl}acetamide (45)

N-{2-[(6-Chloro-5-methyl-2-(4-chlorophenylpyrimidin-4-yl)amino]ethyl}acetamide (0.78 g) was dissolved in ethylenediamine (20 ml) and heated with stirring to reflux for 18 hrs. After cooling to ambient temperature the solution was evaporated onto silica gel. Purification via flash chromatography on silica gel eluting with a mixture of ethyl acetate and methanol (30:70 v/v) then methanol, then a mixture of methanol and ammonium hydroxide (95:5 v/v) furnished the title compound (0.44 g).

$\delta_H$ (d$^6$-DMSO, trace of water): 1.78 (3H, s), 1.81 (3H, s), 2.50-2.53 (1H, t), 2.70-2.75 (2H, t), 2.97-3.02 (1H, q), 3.23-3.29 (2H, m, under water peak), 3.40-3.50 (2H, m), 6.05-6.10 (1H, m), 6.15-6.20 (1H, m), 7.40-7.43 (2H, d), 7.70-7.78 (1H, m), 7.88-7.95 (1H, m), 8.27-8.32 (2H, d); m/z (ES$^+$) 363 (MH)$^+$ Library Example:
N-(2-{[6-{[2-(Acetylamino)ethyl]amino}-2-(4-chlorophenyl)-5-methylpyrimidin-4-yl]amino}ethyl)isoquinoline-3-carboxamide (46.1)

A solution of 3-isoquinoline carboxylic acid (60 µl of a 0.3M solution in NMP), HATU (60 µl of a 0.3M solution in NMP) and diisopropylethylamine (60 µl of a 0.3M solution in NMP) was shaken at ambient temperature in a well of a 96 position microtitre plate for 20 min. N-{2-[6-(2-Aminoethylamino)-2-(4-chlorophenyl)-5-methylpyrimidin-4-ylamino]-ethyl}acetamide (30 µl of a 0.3M solution in NMP) was then added and the mixture shaken for a further 12 hrs. Purification via ion exchange silica (SCX) yields the title compound.

LCMS (Method A) RT=2.98 min; m/z (ES$^+$) 518 (MH)$^+$

The following compounds 46.2-46.82 were synthesised in an analogous manner:

| Name | Retention Time (min) | Mass Ion (ES$^+$) (MH)$^+$ |
|---|---|---|
| N-(2-{[6-{[2-(acetylamino)ethyl]amino}-2-(4-chlorophenyl)-5-methylpyrimidin-4-yl]amino}ethyl)-1H-indole-2-carboxamide | 2.75 | 506 |
| N-(2-{[6-{[2-(acetylamino)ethyl]amino}-2-(4-chlorophenyl)-5-methylpyrimidin-4-yl]amino}ethyl)-1H-indole-3-carboxamide | 2.57 | 506 |
| N-(2-{[6-{[2-(acetylamino)ethyl]amino}-2-(4-chlorophenyl)-5-methylpyrimidin-4-yl]amino}ethyl)-2-(3-hydroxy-4-methoxyphenyl)acetamide | 2.42 | 527 |
| (2E)-N-(2-{[6-{[2-(acetylamino)ethyl]amino}-2-(4-chlorophenyl)-5-methylpyrimidin-4-yl]amino}ethyl)-3-(1H-indol-3-yl)prop-2-enamide | 2.68 | 532 |
| (2E)-N-(2-{[6-{[2-(acetylamino)ethyl]amino}-2-(4-chlorophenyl)-5-methylpyrimidin-4-yl]amino}ethyl)-3-(3-nitrophenyl)prop-2-enamide | 2.77 | 538 |
| N-(2-{[6-{[2-(acetylamino)ethyl]amino}-2-(4-chlorophenyl)-5-methylpyrimidin-4-yl]amino}ethyl)-2-hydroxy-4-methylbenzamide | 2.86 | 497 |
| N-(2-{[6-{[2-(acetylamino)ethyl]amino}-2-(4-chlorophenyl)-5-methylpyrimidin-4-yl]amino}ethyl)-2-hydroxy-3-methylbenzamide | 2.96 | 497 |
| N-(2-{[6-{[2-(acetylamino)ethyl]amino}-2-(4-chlorophenyl)-5-methylpyrimidin-4-yl]amino}ethyl)-3-(1H-indol-3-yl)propanamide | 2.54 | 468 |
| N-(2-{[6-{[2-(acetylamino)ethyl]amino}-2-(4-chlorophenyl)-5-methylpyrimidin-4-yl]amino}ethyl)-4-oxo-4,5,6,7-tetrahydro-1-benzofuran-3-carboxamide | 2.59 | 525 |
| N-(2-{[6-{[2-(acetylamino)ethyl]amino}-2-(4-chlorophenyl)-5-methylpyrimidin-4-yl]amino}ethyl)-2-(methylsulfanyl)nicotinamide | 2.58 | 514 |
| N-(2-{[6-{[2-(acetylamino)ethyl]amino}-2-(4-chlorophenyl)-5-methylpyrimidin-4-yl]amino}ethyl)-1-tert-butyl-3-methyl-1H-pyrazole-5-carboxamide | 2.75 | 527 |
| N-(2-{[6-{[2-(acetylamino)ethyl]amino}-2-(4-chlorophenyl)-5-methylpyrimidin-4-yl]amino}ethyl)-4-(trifluoromethoxy)benzamide | 2.97 | 551 |
| N-(2-{[6-{[2-(acetylamino)ethyl]amino}-2-(4-chlorophenyl)-5-methylpyrimidin-4-yl]amino}ethyl)-2-(2,5-dimethoxyphenyl)acetamide | 2.59 | 541 |
| N-(2-{[6-{[2-(acetylamino)ethyl]amino}-2-(4-chlorophenyl)-5-methylpyrimidin-4-yl]amino}ethyl)-2-(3-methoxyphenyl)acetamide | 2.67 | 511 |
| N-(2-{[6-{[2-(acetylamino)ethyl]amino}-2-(4-chlorophenyl)-5-methylpyrimidin-4-yl]amino}ethyl)-2-(4-methoxyphenyl)acetamide | 2.59 | 511 |
| N-(2-{[6-{[2-(acetylamino)ethyl]amino}-2-(4-chlorophenyl)-5-methylpyrimidin-4-yl]amino}ethyl)-1,2,3,4-tetrahydronaphthalene-2-carboxamide | 2.87 | 521 |
| N-(2-{[6-{[2-(acetylamino)ethyl]amino}-2-(4-chlorophenyl)-5-methylpyrimidin-4-yl]amino}ethyl)-1H-pyrrole-2-carboxamide | 2.49 | 456 |
| (3S,4R,5S)-N-(2-{[6-{[2-(acetylamino)ethyl]amino}-2-(4-chlorophenyl)-5-methylpyrimidin-4-yl]amino}ethyl)-3,4,5-trihydroxycyclohex-1-ene-1-carboxamide | 2.19 | 519 |
| N-(2-{[6-{[2-(acetylamino)ethyl]amino}-2-(4-chlorophenyl)-5-methylpyrimidin-4-yl]amino}ethyl)-2-(2-methylphenyl)acetamide | 2.69 | 495 |
| N-(2-{[6-{[2-(acetylamino)ethyl]amino}-2-(4-chlorophenyl)-5-methylpyrimidin-4-yl]amino}ethyl)-2-methylbenzamide | 2.71 | 481 |
| N-(2-{[6-{[2-(acetylamino)ethyl]amino}-2-(4-chlorophenyl)-5-methylpyrimidin-4-yl]amino}ethyl)-2-sulfanylbenzamide | 2.70 | 497 |
| N-(2-{[6-{[2-(acetylamino)ethyl]amino}-2-(4-chlorophenyl)-5-methylpyrimidin-4-yl]amino}ethyl)-2-cyclopentyl-2-phenylacetamide | 3.04 | 549 |
| N-(2-{[6-{[2-(acetylamino)ethyl]amino}-2-(4-chlorophenyl)-5-methylpyrimidin-4-yl]amino}ethyl)-4-benzoylbenzamide | 3.15 | 571 |
| N-(2-{[6-{[2-(acetylamino)ethyl]amino}-2-(4-chlorophenyl)-5-methylpyrimidin-4-yl]amino}ethyl)-5-chlorothiophene-2-carboxamide | 2.99 | 507 |
| (2E)-N-(2-{[6-{[2-(acetylamino)ethyl]amino}-2-(4-chlorophenyl)-5-methylpyrimidin-4-yl]amino}ethyl)-3-(2-furyl)prop-2-enamide | 2.85 | 483 |

-continued

| Name | Retention Time (min) | Mass Ion (ES+) (MH)+ |
|---|---|---|
| (2E)-N-(2-{[6-{[2-(acetylamino)ethyl]amino}-2-(4-chlorophenyl)-5-methylpyrimidin-4-yl]amino}ethyl)-3-(2,3,4-trifluorophenyl)prop-2-enamide | 3.16 | 547 |
| (2E)-N-(2-{[6-{[2-(acetylamino)ethyl]amino}-2-(4-chlorophenyl)-5-methylpyrimidin-4-yl]amino}ethyl)-3-thien-2-ylprop-2-enamide | 2.99 | 499 |
| (2E,4E)-N-(2-{[6-{[2-(acetylamino)ethyl]amino}-2-(4-chlorophenyl)-5-methylpyrimidin-4-yl]amino}ethyl)-5-phenylpenta-2,4-dienamide | 3.15 | 519 |
| N-(2-{[6-{[2-(acetylamino)ethyl]amino}-2-(4-chlorophenyl)-5-methylpyrimidin-4-yl]amino}ethyl)propanamide | 2.64 | 419 |
| N-(2-{[6-{[2-(acetylamino)ethyl]amino}-2-(4-chlorophenyl)-5-methylpyrimidin-4-yl]amino}ethyl)quinoline-2-carboxamide | 3.05 | 518 |
| N-(2-{[6-{[2-(acetylamino)ethyl]amino}-2-(4-chlorophenyl)-5-methylpyrimidin-4-yl]amino}ethyl)-2-(1H-indol-3-yl)acetamide | 2.79 | 520 |
| N-(2-{[6-{[2-(acetylamino)ethyl]amino}-2-(4-chlorophenyl)-5-methylpyrimidin-4-yl]amino}ethyl)-4-(1H-indol-3-yl)butanamide | 3.01 | 548 |
| N-(2-{[6-{[2-(acetylamino)ethyl]amino}-2-(4-chlorophenyl)-5-methylpyrimidin-4-yl]amino}ethyl)-5-methyl-2-phenyl-2H-1,2,3-triazole-4-carboxamide | 3.23 | 548 |
| N-(2-{[6-{[2-(acetylamino)ethyl]amino}-2-(4-chlorophenyl)-5-methylpyrimidin-4-yl]amino}ethyl)-1-benzothiophene-2-carboxamide | 3.13 | 523 |
| N-(2-{[6-{[2-(acetylamino)ethyl]amino}-2-(4-chlorophenyl)-5-methylpyrimidin-4-yl]amino}ethyl)-4-(trifluoroacetyl)benzamide | 2.60 | 563 |
| N-(2-{[6-{[2-(acetylamino)ethyl]amino}-2-(4-chlorophenyl)-5-methylpyrimidin-4-yl]amino}ethyl)-3-tert-butyl-1-methyl-1H-pyrazole-5-carboxamide | 2.83 | 527 |
| N-(2-{[6-{[2-(acetylamino)ethyl]amino}-2-(4-chlorophenyl)-5-methylpyrimidin-4-yl]amino}ethyl)-2-(2-methoxyphenyl)acetamide | 2.69 | 511 |
| N-(2-{[6-{[2-(acetylamino)ethyl]amino}-2-(4-chlorophenyl)-5-methylpyrimidin-4-yl]amino}ethyl)-2-cyclohexylacetamide | 2.81 | 487 |
| N-(2-{[6-{[2-(acetylamino)ethyl]amino}-2-(4-chlorophenyl)-5-methylpyrimidin-4-yl]amino}ethyl)-4-(1H-pyrrol-1-yl)benzamide | 2.87 | 532 |
| N-(2-{[6-{[2-(acetylamino)ethyl]amino}-2-(4-chlorophenyl)-5-methylpyrimidin-4-yl]amino}ethyl)-3-methylbenzamide | 2.76 | 481 |
| N-(2-{[6-{[2-(acetylamino)ethyl]amino}-2-(4-chlorophenyl)-5-methylpyrimidin-4-yl]amino}ethyl)-4-methylbenzamide | 2.72 | 481 |
| N-(2-{[6-{[2-(acetylamino)ethyl]amino}-2-(4-chlorophenyl)-5-methylpyrimidin-4-yl]amino}ethyl)-1,3-benzodioxole-5-carboxamide | 2.61 | 511 |
| N-(2-{[6-{[2-(acetylamino)ethyl]amino}-2-(4-chlorophenyl)-5-methylpyrimidin-4-yl]amino}ethyl)-2-phenylacetamide | 2.60 | 481 |
| N-(2-{[6-{[2-(acetylamino)ethyl]amino}-2-(4-chlorophenyl)-5-methylpyrimidin-4-yl]amino}ethyl)bicyclo[2.2.1]hept-5-ene-2-carboxamide | 2.64 | 483 |
| N-(2-{[6-{[2-(acetylamino)ethyl]amino}-2-(4-chlorophenyl)-5-methylpyrimidin-4-yl]amino}ethyl)-1-phenylcyclopentanecarboxamide | 2.97 | 535 |
| N-(2-{[6-{[2-(acetylamino)ethyl]amino}-2-(4-chlorophenyl)-5-methylpyrimidin-4-yl]amino}ethyl)-4-tert-butylbenzamide | 3.02 | 523 |
| N-(2-{[6-{[2-(acetylamino)ethyl]amino}-2-(4-chlorophenyl)-5-methylpyrimidin-4-yl]amino}ethyl)adamantane-1-carboxamide | 2.95 | 525 |
| N-(2-{[6-{[2-(acetylamino)ethyl]amino}-2-(4-chlorophenyl)-5-methylpyrimidin-4-yl]amino}ethyl)-4-methoxybenzamide | 2.66 | 497 |
| N-(2-{[6-{[2-(acetylamino)ethyl]amino}-2-(4-chlorophenyl)-5-methylpyrimidin-4-yl]amino}ethyl)-4-cyclohexylbenzamide | 3.24 | 549 |
| N-(2-{[6-{[2-(acetylamino)ethyl]amino}-2-(4-chlorophenyl)-5-methylpyrimidin-4-yl]amino}ethyl)benzamide | 2.65 | 467 |
| N-(2-{[6-{[2-(acetylamino)ethyl]amino}-2-(4-chlorophenyl)-5-methylpyrimidin-4-yl]amino}ethyl)-4-ethylbenzamide | 2.87 | 495 |
| N-(2-{[6-{[2-(acetylamino)ethyl]amino}-2-(4-chlorophenyl)-5-methylpyrimidin-4-yl]amino}ethyl)-8-hydroxyquinoline-2-carboxamide | 2.57 | 578 |
| N-(2-{[6-{[2-(acetylamino)ethyl]amino}-2-(4-chlorophenyl)-5-methylpyrimidin-4-yl]amino}ethyl)-3-(4-hydroxyphenyl)propanamide | 2.51 | 511 |
| (2E)-N-(2-{[6-{[2-(acetylamino)ethyl]amino}-2-(4-chlorophenyl)-5-methylpyrimidin-4-yl]amino}ethyl)-3-phenylprop-2-enamide | 2.79 | 493 |
| N-(2-{[6-{[2-(acetylamino)ethyl]amino}-2-(4-chlorophenyl)-5-methylpyrimidin-4-yl]amino}ethyl)acetamide | 2.32 | 405 |
| N-(2-{[6-{[2-(acetylamino)ethyl]amino}-2-(4-chlorophenyl)-5-methylpyrimidin-4-yl]amino}ethyl)-1-naphthamide | 2.85 | 517 |
| N-(2-{[6-{[2-(acetylamino)ethyl]amino}-2-(4-chlorophenyl)-5-methylpyrimidin-4-yl]amino}ethyl)-4-bromo-3-methylbenzamide | 2.94 | 561 |
| N-(2-{[6-{[2-(acetylamino)ethyl]amino}-2-(4-chlorophenyl)-5-methylpyrimidin-4-yl]amino}ethyl)-4-(dimethylamino)benzamide | 2.69 | 510 |
| 2-(acetylamino)-N-(2-{[6-{[2-(acetylamino)ethyl]amino}-2-(4-chlorophenyl)-5-methylpyrimidin-4-yl]amino}ethyl)acetamide | 2.22 | 462 |
| N-(2-{[6-{[2-(acetylamino)ethyl]amino}-2-(4-chlorophenyl)-5-methylpyrimidin-4-yl]amino}ethyl)-2-(4-hydroxy-3-methoxyphenyl)acetamide | 2.40 | 527 |

| Name | Retention Time (min) | Mass Ion (ES+) (MH)+ |
|---|---|---|
| N-(2-{[6-{[2-(acetylamino)ethyl]amino}-2-(4-chlorophenyl)-5-methylpyrimidin-4-yl]amino}ethyl)-3-hydroxy-4-methylbenzamide | 2.58 | 497 |
| N-(2-{[6-{[2-(acetylamino)ethyl]amino}-2-(4-chlorophenyl)-5-methylpyrimidin-4-yl]amino}ethyl)cyclohex-1-ene-1-carboxamide | 2.69 | 471 |
| N-(2-{[6-{[2-(acetylamino)ethyl]amino}-2-(4-chlorophenyl)-5-methylpyrimidin-4-yl]amino}ethyl)-2-(methylsulfanyl)benzamide | 2.69 | 513 |
| 4-acetyl-N-(2-{[6-{[2-(acetylamino)ethyl]amino}-2-(4-chlorophenyl)-5-methylpyrimidin-4-yl]amino}ethyl)benzamide | 2.59 | 509 |
| N-(2-{[6-{[2-(acetylamino)ethyl]amino}-2-(4-chlorophenyl)-5-methylpyrimidin-4-yl]amino}ethyl)-3-(trifluoromethyl)benzamide | 2.87 | 535 |
| N-(2-{[6-{[2-(acetylamino)ethyl]amino}-2-(4-chlorophenyl)-5-methylpyrimidin-4-yl]amino}ethyl)-1H-benzimidazole-5-carboxamide | 2.15 | 507 |
| N-(2-{[6-{[2-(acetylamino)ethyl]amino}-2-(4-chlorophenyl)-5-methylpyrimidin-4-yl]amino}ethyl)-3-bromobenzamide | 2.81 | 547 |
| N-(2-{[6-{[2-(acetylamino)ethyl]amino}-2-(4-chlorophenyl)-5-methylpyrimidin-4-yl]amino}ethyl)-4-oxopentanamide | 2.37 | 461 |
| N-(2-{[6-{[2-(acetylamino)ethyl]amino}-2-(4-chlorophenyl)-5-methylpyrimidin-4-yl]amino}ethyl)-2-methyl-1H-benzimidazole-5-carboxamide | 2.19 | 521 |
| N-(2-{[6-{[2-(acetylamino)ethyl]amino}-2-(4-chlorophenyl)-5-methylpyrimidi-4-yl]amino}ethyl)-2-methylpropanamide | 2.49 | 433 |
| (2E)-N-(2-{[6-{[2-(acetylamino)ethyl]amino}-2-(4-chlorophenyl)-5-methylpyrimidin-4-yl]amino}ethyl)-3-(3-cyanophenyl)prop-2-enamide | 2.72 | 518 |
| N-(2-{[6-{[2-(acetylamino)ethyl]amino}-2-(4-chlorophenyl)-5-methylpyrimidin-4-yl]amino}ethyl)-4-(trifluoromethyl)cyclohexanecarboxamide | 2.83 | 541 |
| N-(2-{[6-{[2-(acetylamino)ethyl]amino}-2-(4-chlorophenyl)-5-methylpyrimidin-4-yl]amino}ethyl)-3-ethoxythiophene-2-carboxamide | 2.67 | 517 |
| N-(2-{[6-{[2-(acetylamino)ethyl]amino}-2-(4-chlorophenyl)-5-methylpyrimidin-4-yl]amino}ethyl)-6-hydroxy-2-naphthamide | 2.61 | 533 |
| (2E)-N-(2-{[6-{[2-(acetylamino)ethyl]amino}-2-(4-chlorophenyl)-5-methylpyrimidin-4-yl]amino}ethyl)-3-(4-isopropylphenyl)prop-2-enamide | 3.10 | 535 |
| N-(2-{[6-{[2-(acetylamino)ethyl]amino}-2-(4-chlorophenyl)-5-methylpyrimidin-4-yl]amino}ethyl)-5-(1,2-dithiolan-3-yl)pentanamide | 2.84 | 551 |
| N-(2-{[6-{[2-(acetylamino)ethyl]amino}-2-(4-chlorophenyl)-5-methylpyrimidin-4-yl]amino}ethyl)-2-methyl-5,6-dihydro-1,4-oxathiine-3-carboxamide | 2.58 | 505 |
| (2E)-N-(2-{[6-{[2-(acetylamino)ethyl]amino}-2-(4-chlorophenyl)-5-methylpyrimidin-4-yl]amino}ethyl)-3-pyridin-2-ylprop-2-enamide | 2.39 | 494 |
| N-(2-{[6-{[2-(acetylamino)ethyl]amino}-2-(4-chlorophenyl)-5-methylpyrimidin-4-yl]amino}ethyl)-3-methyl-2-nitrobenzamide | 2.79 | 526 |
| N-(2-{[6-{[2-(acetylamino)ethyl]amino}-2-(4-chlorophenyl)-5-methylpyrimidin-4-yl]amino}ethyl)-3-thien-2-ylpropanamide | 2.70 | 501 |
| N-(2-{[6-{[2-(acetylamino)ethyl]amino}-2-(4-chlorophenyl)-5-methylpyrimidin-4-yl]amino}ethyl)cyclohex-3-ene-1-carboxamide | 2.65 | 471 |

Example 12

Synthesis of Compounds 48.1-48.141

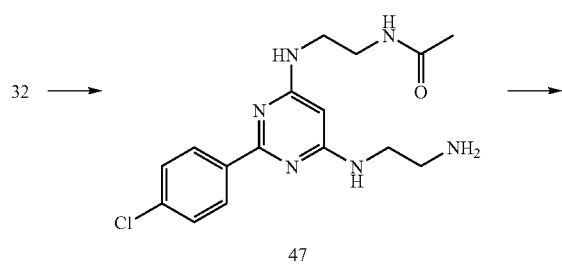

32 ⟶

47

⟶

-continued

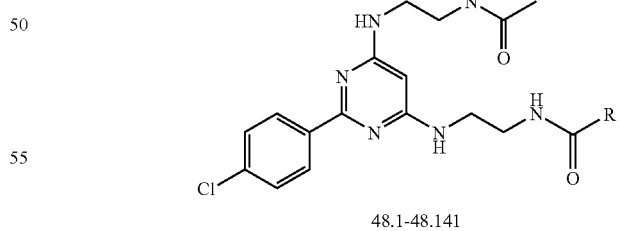

48.1-48.141

N-(2-([6-[(2-Aminoethyl)amino]-2-(4-chlorophenyl)pyrimidin-4-yl]aminoethyl)-acetamide (47)

N-(2-{[6-Chloro-2-(4-chlorophenyl)pyrimidin-4-yl]amino}ethyl)acetamide (0.90 g) was dissolved in ethylenediamine (20 ml) and heated with stirring to reflux for 18 hrs. After cooling to ambient temperature the solution was evaporated onto silica gel. Purification via flash chromatography on silica gel eluting with increasingly polar solvent systems from ethyl acetate to methanol furnished the title compound (0.67 g).

$\delta_H$ (d$^6$-DMSO, trace of water): 1.78 (3H, d), 2.50-2.53 (1H, t, under d$^6$-DMSO peak), 2.66-2.71 (2H, m), 2.96-3.02 (1H, q), 3.23-3.29 (2H, m, under water peak), 3.40-3.50 (2H, m, under water peak), 5.33 (1H, s), 6.55-6.65 (2H, m), 7.42-7.48 (2H, d), 7.90-7.95 (1H, m), 8.23-8.29 (2H, d); m/z (ES$^+$) 349 (MH)$^+$ Library Example:
N-(2-{[6-{[2-(acetylamino)ethyl]amino}-2-(4-chlorophenyl)pyrimidin-4-yl]amino}ethyl)quinoline-2-carboxamide (48.1)

A solution of quinaldic acid (60 μl of a 0.3M solution in NMP), HATU (60 μl of a 0.3M solution in NMP) and diisopropylethylamine (60 μl of a 0.3M solution in NMP) was shaken at ambient temperature in a well of a 96 position microtitre plate for 5 min. N-(2-{[6-[(2-aminoethyl)amino]-2-(4-chlorophenyl)pyrimidin-4-yl]amino}ethyl) acetamide (30 μl of a 0.3M solution in NMP) was then added and the mixture shaken for a further 48 hrs. Purification via ion exchange silica (SCX) yields the title compound.

LCMS (Method A) RT=2.58 min; m/z (ES$^+$) 504 (MH)$^+$

The following compounds 48.2-48.141 were synthesised in an analogous manner:

| Name | Retention Time (min) | Mass Ion (ES$^+$) (MH)$^+$ |
|---|---|---|
| N-(2-{[6-{[2-(acetylamino)ethyl]amino}-2-(4-chlorophenyl)pyrimidin-4-yl]amino}ethyl)isoquinoline-3-carboxamide | 2.53 | 504 |
| N-(2-{[6-{[2-(acetylamino)ethyl]amino}-2-(4-chlorophenyl)pyrimidin-4-yl]amino}ethyl)quinoxaline-2-carboxamide | 2.46 | 505 |
| N-(2-{[6-{[2-(acetylamino)ethyl]amino}-2-(4-chlorophenyl)pyrimidin-4-yl]amino}ethyl)isoquinoline-1-carboxamide | 2.49 | 504 |
| N-(2-{[6-{[2-(acetylamino)ethyl]amino}-2-(4-chlorophenyl)pyrimidin-4-yl]amino}ethyl)-2-hydroxy-5-nitrobenzamide | 2.63 | 514 |
| N-(2-{[6-{[2-(acetylamino)ethyl]amino}-2-(4-chlorophenyl)pyrimidin-4-yl]amino}ethyl)pyrazine-2-carboxamide | 2.37 | 455 |
| N-(2-{[6-{[2-(acetylamino)ethyl]amino}-2-(4-chlorophenyl)pyrimidin-4-yl]amino}ethyl)nicotinamide | 2.29 | 454 |
| N-(2-{[6-{[2-(acetylamino)ethyl]amino}-2-(4-chlorophenyl)pyrimidin-4-yl]amino}ethyl)isonicotinamide | 2.26 | 454 |
| N-(2-{[6-{[2-(acetylamino)ethyl]amino}-2-(4-chlorophenyl)pyrimidin-4-yl]amino}ethyl)-2-hydroxynicotinamide | 2.31 | 470 |
| N-(2-{[6-{[2-(acetylamino)ethyl]amino}-2-(4-chlorophenyl)pyrimidin-4-yl]amino}ethyl)-1H-indole-2-carboxamide | 2.65 | 492 |
| N-(2-{[6-{[2-(acetylamino)ethyl]amino}-2-(4-chlorophenyl)pyrimidin-4-yl]amino}ethyl)-1H-indole-3-carboxamide | 2.52 | 492 |
| N-(2-{[6-{[2-(acetylamino)ethyl]amino}-2-(4-chlorophenyl)pyrimidin-4-yl]amino}ethyl)-3-nitrobenzamide | 2.52 | 498 |
| N-[2-({2-(4-chlorophenyl)-6-[(2-{[1-(2,7-dimethylpyrazolo[1,5-a]pyrimidin-6-yl)vinyl]amino}ethyl)amino]pyrimidin-4-yl}amino)ethyl]acetamide | 2.40 | 522 |
| N-(2-{[6-{[2-(acetylamino)ethyl]amino}-2-(4-chlorophenyl)pyrimidin-4-yl]amino}ethyl)-2-(3-hydroxy-4-methoxyphenyl)acetamide | 2.40 | 513 |
| (2E)-N-(2-{[6-{[2-(acetylamino)ethyl]amino}-2-(4-chlorophenyl)pyrimidin-4-yl]amino}ethyl)-3-(1H-indol-3-yl)prop-2-enamide | 2.66 | 518 |
| (2E)-N-(2-{[6-{[2-(acetylamino)ethyl]amino}-2-(4-chlorophenyl)pyrimidin-4-yl]amino}ethyl)-3-(3-nitrophenyl)prop-2-enamide | 2.67 | 524 |
| N-(2-{[6-{[2-(acetylamino)ethyl]amino}-2-(4-chlorophenyl)pyrimidin-4-yl]amino}ethyl)-3-(1H-benzimidazol-2-yl)propanamide | 2.24 | 521 |
| N-(2-{[6-{[2-(acetylamino)ethyl]amino}-2-(4-chlorophenyl)pyrimidin-4-yl]amino}ethyl)-2-hydroxy-4-methylbenzamide | 2.70 | 483 |
| N-(2-{[6-{[2-(acetylamino)ethyl]amino}-2-(4-chlorophenyl)pyrimidin-4-yl]amino}ethyl)-2-hydroxy-3-methoxybenzamide | 2.53 | 499 |
| N-(2-{[6-{[2-(acetylamino)ethyl]amino}-2-(4-chlorophenyl)pyrimidin-4-yl]amino}ethyl)-2-hydroxy-3-methylbenzamide | 2.78 | 483 |
| N-(2-{[6-{[2-(acetylamino)ethyl]amino}-2-(4-chlorophenyl)pyrimidin-4-yl]amino}ethyl)-2-(1H-indol-3-yl)acetamide | 2.49 | 506 |
| N-(2-{[6-{[2-(acetylamino)ethyl]amino}-2-(4-chlorophenyl)pyrimidin-4-yl]amino}ethyl)-3-(1H-indol-3-yl)propanamide | 2.59 | 520 |
| N-(2-{[6-{[2-(acetylamino)ethyl]amino}-2-(4-chlorophenyl)pyrimidin-4-yl]amino}ethyl)pyridine-2-carboxamide | 2.42 | 454 |
| N-(2-{[6-{[2-(acetylamino)ethyl]amino}-2-(4-chlorophenyl)pyrimidin-4-yl]amino}ethyl)-4-(1H-indol-3-yl)butanamide | 2.58 | 534 |
| N-(2-{[6-{[2-(acetylamino)ethyl]amino}-2-(4-chlorophenyl)pyrimidin-4-yl]amino}ethyl)-5-methylpyrazine-2-carboxamide | 2.37 | 469 |
| N-(2-{[6-{[2-(acetylamino)ethyl]amino}-2-(4-chlorophenyl)pyrimidin-4-yl]amino}ethyl)-5-methyl-2-phenyl-2H-1,2,3-triazole-4-carboxamide | 2.78 | 534 |
| N-(2-{[6-{[2-(acetylamino)ethyl]amino}-2-(4-chlorophenyl)pyrimidin-4-yl]amino}ethyl)-4-oxo-4,5,6,7-tetrahydro-1-benzofuran-3-carboxamide | 2.50 | 511 |
| N-(2-{[6-{[2-(acetylamino)ethyl]amino}-2-(4-chlorophenyl)pyrimidin-4-yl]amino}ethyl)-2-(methylsulfanyl)nicotinamide | 2.47 | 500 |
| N-(2-{[6-{[2-(acetylamino)ethyl]amino}-2-(4-chlorophenyl)pyrimidin-4-yl]amino}ethyl)-1-tert-butyl-3-methyl-1H-pyrazole-5-carboxamide | 2.58 | 513 |

-continued

| Name | Retention Time (min) | Mass Ion (ES+) (MH)+ |
|---|---|---|
| N-(2-{[6-{[2-(acetylamino)ethyl]amino}-2-(4-chlorophenyl)pyrimidin-4-yl]amino}ethyl)-1-benzothiophene-2-carboxamide | 2.71 | 509 |
| N-(2-{[6-{[2-(acetylamino)ethyl]amino}-2-(4-chlorophenyl)pyrimidin-4-yl]amino}ethyl)-4-(trifluoromethoxy)benzamide | 2.76 | 537 |
| N-(2-{[6-{[2-(acetylamino)ethyl]amino}-2-(4-chlorophenyl)pyrimidin-4-yl]amino}ethyl)-5-chloro-2-hydroxynicotinamide | 2.45 | 504 |
| (2E)-N-(2-{[6-{[2-(acetylamino)ethyl]amino}-2-(4-chlorophenyl)pyrimidin-4-yl]amino}ethyl)-4-oxo-4-(2,3,4,5,6-pentamethylphenyl)but-2-enamide | 2.91 | 577 |
| N-(2-{[6-{[2-(acetylamino)ethyl]amino}-2-(4-chlorophenyl)pyrimidin-4-yl]amino}ethyl)-4-(trifluoroacetyl)benzamide | 2.52 | 549 |
| N-{2-[(2-{[6-{[2-(acetylamino)ethyl]amino}-2-(4-chlorophenyl)pyrimidin-4-yl]amino}ethyl)amino]-2-oxoethyl}-4-chlorobenzamide | 2.58 | 544 |
| N-(2-{[6-{[2-(acetylamino)ethyl]amino}-2-(4-chlorophenyl)pyrimidin-4-yl]amino}ethyl)-2,4-dihydroxypyrimidine-5-carboxamide | 2.26 | 487 |
| N-(2-{[6-{[2-(acetylamino)ethyl]amino}-2-(4-chlorophenyl)pyrimidin-4-yl]amino}ethyl)-1,2,3-thiadiazole-4-carboxamide | 2.39 | 461 |
| N-(2-{[6-{[2-(acetylamino)ethyl]amino}-2-(4-chlorophenyl)pyrimidin-4-yl]amino}ethyl)-5-chloro-2-(methylsulfanyl)pyrimidine-4-carboxamide | 2.60 | 535 |
| N-(2-{[6-{[2-(acetylamino)ethyl]amino}-2-(4-chlorophenyl)pyrimidin-4-yl]amino}ethyl)-1-(2-furylmethyl)-5-oxopyrrolidine-3-carboxamide | 2.50 | 540 |
| N-(2-{[6-{[2-(acetylamino)ethyl]amino}-2-(4-chlorophenyl)pyrimidin-4-yl]amino}ethyl)-3-tert-butyl-1-methyl-1H-pyrazole-5-carboxamide | 2.63 | 513 |
| N-(2-{[6-{[2-(acetylamino)ethyl]amino}-2-(4-chlorophenyl)pyrimidin-4-yl]amino}ethyl)-2-(4-nitrophenyl)acetamide | 2.55 | 512 |
| N-(2-{[6-{[2-(acetylamino)ethyl]amino}-2-(4-chlorophenyl)pyrimidin-4-yl]amino}ethyl)-2-(3-methoxyphenyl)acetamide | 2.50 | 497 |
| N-(2-{[6-{[2-(acetylamino)ethyl]amino}-2-(4-chlorophenyl)pyrimidin-4-yl]amino}ethyl)-2-(4-methoxyphenyl)acetamide | 2.49 | 497 |
| N-(2-{[6-{[2-(acetylamino)ethyl]amino}-2-(4-chlorophenyl)pyrimidin-4-yl]amino}ethyl)-2-(2-methoxyphenyl)acetamide | 2.52 | 497 |
| N-(2-{[6-{[2-(acetylamino)ethyl]amino}-2-(4-chlorophenyl)pyrimidin-4-yl]amino}ethyl)-1,2,3,4-tetrahydronaphthalene-2-carboxamide | 2.70 | 507 |
| (2S)-N-(2-{[6-{[2-(acetylamino)ethyl]amino}-2-(4-chlorophenyl)pyrimidin-4-yl]amino}ethyl)-2-hydroxy-3-phenylpropanamide | 2.50 | 497 |
| N-(2-{[6-{[2-(acetylamino)ethyl]amino}-2-(4-chlorophenyl)pyrimidin-4-yl]amino}ethyl)-3,5-dimethylisoxazole-4-carboxamide | 2.76 | 507 |
| N-(2-{[6-{[2-(acetylamino)ethyl]amino}-2-(4-chlorophenyl)pyrimidin-4-yl]amino}ethyl)-1H-pyrrole-2-carboxamide | 2.45 | 442 |
| N-(2-{[6-{[2-(acetylamino)ethyl]amino}-2-(4-chlorophenyl)pyrimidin-4-yl]amino}ethyl)-4-vinylbenzamide | 2.67 | 479 |
| N-(2-{[6-{[2-(acetylamino)ethyl]amino}-2-(4-chlorophenyl)pyrimidin-4-yl]amino}ethyl)-2-cyclohexylacetamide | 2.68 | 473 |
| N-(2-{[6-{[2-(acetylamino)ethyl]amino}-2-(4-chlorophenyl)pyrimidin-4-yl]amino}ethyl)-4-(1H-pyrrol-1-yl)benzamide | 2.74 | 518 |
| N-(2-{[6-{[2-(acetylamino)ethyl]amino}-2-(4-chlorophenyl)pyrimidin-4-yl]amino}ethyl)-2-[1,1'-biphenyl]-4-ylacetamide | 2.78 | 543 |
| N-(2-{[6-{[2-(acetylamino)ethyl]amino}-2-(4-chlorophenyl)pyrimidin-4-yl]amino}ethyl)-2-(6-methoxy-3-oxo-2,3-dihydro-1H-inden-1-yl)acetamide | 2.53 | 551 |
| N-(2-{[6-{[2-(acetylamino)ethyl]amino}-2-(4-chlorophenyl)pyrimidin-4-yl]amino}ethyl)-2-(3-nitrophenyl)acetamide | 2.52 | 512 |
| N-(2-{[6-{[2-(acetylamino)ethyl]amino}-2-(4-chlorophenyl)pyrimidin-4-yl]amino}ethyl)-2-(2-methylphenyl)acetamide | 2.58 | 479 |
| N-(2-{[6-{[2-(acetylamino)ethyl]amino}-2-(4-chlorophenyl)pyrimidin-4-yl]amino}ethyl)-2-(4-methylphenyl)acetamide | 2.58 | 481 |
| N-(2-{[6-{[2-(acetylamino)ethyl]amino}-2-(4-chlorophenyl)pyrimidin-4-yl]amino}ethyl)-3-methylbenzamide | 2.59 | 467 |
| N-(2-{[6-{[2-(acetylamino)ethyl]amino}-2-(4-chlorophenyl)pyrimidin-4-yl]amino}ethyl)-4-methylbenzamide | 2.58 | 467 |
| N-(2-{[6-{[2-(acetylamino)ethyl]amino}-2-(4-chlorophenyl)pyrimidin-4-yl]amino}ethyl)-2-methylbenzamide | 2.53 | 467 |
| N-(2-{[6-{[2-(acetylamino)ethyl]amino}-2-(4-chlorophenyl)pyrimidin-4-yl]amino}ethyl)-2-(3-methylphenyl)acetamide | 2.57 | 481 |
| N-(2-{[6-{[2-(acetylamino)ethyl]amino}-2-(4-chlorophenyl)pyrimidin-4-yl]amino}ethyl)-4-butylbenzamide | 2.92 | 509 |
| N-(2-{[6-{[2-(acetylamino)ethyl]amino}-2-(4-chlorophenyl)pyrimidin-4-yl]amino}ethyl)-4-nitrobenzamide | 2.61 | 498 |
| N-(2-{[6-{[2-(acetylamino)ethyl]amino}-2-(4-chlorophenyl)pyrimidin-4-yl]amino}ethyl)-2-phenoxypropanamide | 2.60 | 497 |
| N-(2-{[6-{[2-(acetylamino)ethyl]amino}-2-(4-chlorophenyl)pyrimidin-4-yl]amino}ethyl)-1,3-benzodioxole-5-carboxamide | 2.52 | 497 |
| N-(2-{[6-{[2-(acetylamino)ethyl]amino}-2-(4-chlorophenyl)pyrimidin-4-yl]amino}ethyl)-2-phenylacetamide | 2.51 | 467 |
| N-(2-{[6-{[2-(acetylamino)ethyl]amino}-2-(4-chlorophenyl)pyrimidin-4-yl]amino}ethyl)bicyclo[2.2.1]hept-5-ene-2-carboxamide | 2.57 | 469 |

-continued

| Name | Retention Time (min) | Mass Ion (ES⁺) (MH)⁺ |
|---|---|---|
| N-(2-{[6-{[2-(acetylamino)ethyl]amino}-2-(4-chlorophenyl)pyrimidin-4-yl]amino}ethyl)-2-hydroxy-2-phenylacetamide | 2.43 | 483 |
| N-(2-{[6-{[2-(acetylamino)ethyl]amino}-2-(4-chlorophenyl)pyrimidin-4-yl]amino}ethyl)-2-(2-naphthyloxy)acetamide | 2.74 | 533 |
| N-(2-{[6-{[2-(acetylamino)ethyl]amino}-2-(4-chlorophenyl)pyrimidin-4-yl]amino}ethyl)-1-phenylcyclopentanecarboxamide | 2.76 | 521 |
| N-(2-{[6-{[2-(acetylamino)ethyl]amino}-2-(4-chlorophenyl)pyrimidin-4-yl]amino}ethyl)-2-sulfanylbenzamide | 2.55 | 483 |
| N-(2-{[6-{[2-(acetylamino)ethyl]amino}-2-(4-chlorophenyl)pyrimidin-4-yl]amino}ethyl)tetrahydrofuran-2-carboxamide | 2.36 | 447 |
| N-(2-{[6-{[2-(acetylamino)ethyl]amino}-2-(4-chlorophenyl)pyrimidin-4-yl]amino}ethyl)-2-cyclopentyl-2-phenylacetamide | 2.83 | 535 |
| N-(2-{[6-{[2-(acetylamino)ethyl]amino}-2-(4-chlorophenyl)pyrimidin-4-yl]amino}ethyl)-4-tert-butylbenzamide | 2.83 | 509 |
| N-(2-{[6-{[2-(acetylamino)ethyl]amino}-2-(4-chlorophenyl)pyrimidin-4-yl]amino}ethyl)adamantane-1-carboxamide | 2.76 | 511 |
| N-(2-{[6-{[2-(acetylamino)ethyl]amino}-2-(4-chlorophenyl)pyrimidin-4-yl]amino}ethyl)-4-methoxybenzamide | 2.55 | 483 |
| N-(2-{[6-{[2-(acetylamino)ethyl]amino}-2-(4-chlorophenyl)pyrimidin-4-yl]amino}ethyl)-4-cyclohexylbenzamide | 3.04 | 535 |
| N-(2-{[6-{[2-(acetylamino)ethyl]amino}-2-(4-chlorophenyl)pyrimidin-4-yl]amino}ethyl)-1-naphthamide | 2.64 | 503 |
| N-(2-{[6-{[2-(acetylamino)ethyl]amino}-2-(4-chlorophenyl)pyrimidin-4-yl]amino}ethyl)benzamide | 2.52 | 453 |
| N-(2-{[6-{[2-(acetylamino)ethyl]amino}-2-(4-chlorophenyl)pyrimidin-4-yl]amino}ethyl)-3-(2,4-dihydroxyphenyl)propanamide | 2.40 | 513 |
| N-(2-{[6-{[2-(acetylamino)ethyl]amino}-2-(4-chlorophenyl)pyrimidin-4-yl]amino}ethyl)-4-bromo-3-methylbenzamide | 2.74 | 547 |
| N-(2-{[6-{[2-(acetylamino)ethyl]amino}-2-(4-chlorophenyl)pyrimidin-4-yl]amino}ethyl)-5-chloro-2-hydroxybenzamide | 2.73 | 503 |
| N-(2-{[6-{[2-(acetylamino)ethyl]amino}-2-(4-chlorophenyl)pyrimidin-4-yl]amino}ethyl)-4-(dimethylamino)benzamide | 2.56 | 496 |
| 2-(acetylamino)-N-(2-{[6-{[2-(acetylamino)ethyl]amino}-2-(4-chlorophenyl)pyrimidin-4-yl]amino}ethyl)acetamide | 2.20 | 448 |
| N-(2-{[6-{[2-(acetylamino)ethyl]amino}-2-(4-chlorophenyl)pyrimidin-4-yl]amino}ethyl)-2-(4-hydroxy-3-methoxyphenyl)acetamide | 2.37 | 513 |
| N-(2-{[6-{[2-(acetylamino)ethyl]amino}-2-(4-chlorophenyl)pyrimidin-4-yl]amino}ethyl)-3-hydroxy-4-methylbenzamide | 2.61 | 483 |
| N-(2-{[6-{[2-(acetylamino)ethyl]amino}-2-(4-chlorophenyl)pyrimidin-4-yl]amino}ethyl)-4-fluoro-1-naphthamide | 2.79 | 521 |
| N-(2-{[6-{[2-(acetylamino)ethyl]amino}-2-(4-chlorophenyl)pyrimidin-4-yl]amino}ethyl)-5-formyl-2-hydroxybenzamide | 2.73 | 497 |
| N-(2-{[6-{[2-(acetylamino)ethyl]amino}-2-(4-chlorophenyl)pyrimidin-4-yl]amino}ethyl)cyclohex-1-ene-1-carboxamide | 2.68 | 457 |
| N-(2-{[6-{[2-(acetylamino)ethyl]amino}-2-(4-chlorophenyl)pyrimidin-4-yl]amino}ethyl)[1,1'-biphenyl]-4-carboxamide | 2.93 | 529 |
| N-(2-{[6-{[2-(acetylamino)ethyl]amino}-2-(4-chlorophenyl)pyrimidin-4-yl]amino}ethyl)-2-(4-bromophenyl)acetamide | 2.74 | 547 |
| N-(2-{[6-{[2-(acetylamino)ethyl]amino}-2-(4-chlorophenyl)pyrimidin-4-yl]amino}ethyl)-2-(methylsulfanyl)benzamide | 2.65 | 499 |
| N-(2-{[6-{[2-(acetylamino)ethyl]amino}-2-(4-chlorophenyl)pyrimidin-4-yl]amino}ethyl)-4-cyanobenzamide | 2.69 | 478 |
| N-(2-{[6-{[2-(acetylamino)ethyl]amino}-2-(4-chlorophenyl)pyrimidin-4-yl]amino}ethyl)-1H-benzimidazole-5-carboxamide | 2.24 | 493 |
| N-(2-{[6-{[2-(acetylamino)ethyl]amino}-2-(4-chlorophenyl)pyrimidin-4-yl]amino}ethyl)-2,2-diphenylacetamide | 2.86 | 543 |
| N-(2-{[6-{[2-(acetylamino)ethyl]amino}-2-(4-chlorophenyl)pyrimidin-4-yl]amino}ethyl)-4-ethylbenzamide | 2.73 | 481 |
| N-(2-{[6-{[2-(acetylamino)ethyl]amino}-2-(4-chlorophenyl)pyrimidin-4-yl]amino}ethyl)-3-bromobenzamide | 2.77 | 533 |
| N-(2-{[6-{[2-(acetylamino)ethyl]amino}-2-(4-chlorophenyl)pyrimidin-4-yl]amino}ethyl)-2-[(4-chlorophenyl)sulfanyl]acetamide | 2.74 | 533 |
| 4-acetyl-N-(2-{[6-{[2-(acetylamino)ethyl]amino}-2-(4-chlorophenyl)pyrimidin-4-yl]amino}ethyl)-3,5-dimethyl-1H-pyrrole-2-carboxamide | 2.55 | 512 |
| (2E)-N-(2-{[6-{[2-(acetylamino)ethyl]amino}-2-(4-chlorophenyl)pyrimidin-4-yl]amino}ethyl)-3-thien-3-ylprop-2-enamide | 2.65 | 485 |
| N-(2-{[6-{[2-(acetylamino)ethyl]amino}-2-(4-chlorophenyl)pyrimidin-4-yl]amino}ethyl)-2-(2-furyl)-2-morpholin-4-ylacetamide | 2.34 | 542 |
| N-(2-{[6-{[2-(acetylamino)ethyl]amino}-2-(4-chlorophenyl)pyrimidin-4-yl]amino}ethyl)-2-methyl-1H-benzimidazole-5-carboxamide | 2.22 | 507 |
| N-(2-{[6-{[2-(acetylamino)ethyl]amino}-2-(4-chlorophenyl)pyrimidin-4-yl]amino}ethyl)-2-methylpropanamide | 2.47 | 419 |
| N-(2-{[6-{[2-(acetylamino)ethyl]amino}-2-(4-chlorophenyl)pyrimidin-4-yl]amino}ethyl)-2-(1H-benzimidazol-2-ylsulfanyl)acetamide | 2.50 | 539 |

-continued

| Name | Retention Time (min) | Mass Ion (ES+) (MH)+ |
|---|---|---|
| N-(2-{[6-{[2-(acetylamino)ethyl]amino}-2-(4-chlorophenyl)pyrimidin-4-yl]amino}ethyl)-2-hydroxyquinoline-4-carboxamide | 2.42 | 520 |
| N-(2-{[6-{[2-(acetylamino)ethyl]amino}-2-(4-chlorophenyl)pyrimidin-4-yl]amino}ethyl)-5-chlorothiophene-2-carboxamide | 2.75 | 493 |
| (2E)-N-(2-{[6-{[2-(acetylamino)ethyl]amino}-2-(4-chlorophenyl)pyrimidin-4-yl]amino}ethyl)-3-(3-cyanophenyl)prop-2-enamide | 2.70 | 504 |
| N-(2-{[6-{[2-(acetylamino)ethyl]amino}-2-(4-chlorophenyl)pyrimidin-4-yl]amino}ethyl)-5-nitrothiophene-3-carboxamide | 2.65 | 504 |
| N-(2-{[6-{[2-(acetylamino)ethyl]amino}-2-(4-chlorophenyl)pyrimidin-4-yl]amino}ethyl)-5-(methylsulfonyl)thiophene-2-carboxamide | 2.57 | 537 |
| N-(2-{[6-{[2-(acetylamino)ethyl]amino}-2-(4-chlorophenyl)pyrimidin-4-yl]amino}ethyl)-4-(trifluoromethyl)cyclohexanecarboxamide | 2.77 | 527 |
| N-(2-{[6-{[2-(acetylamino)ethyl]amino}-2-(4-chlorophenyl)pyrimidin-4-yl]amino}ethyl)-3-ethoxythiophene-2-carboxamide | 2.64 | 503 |
| (2E)-N-(2-{[6-{[2-(acetylamino)ethyl]amino}-2-(4-chlorophenyl)pyrimidin-4-yl]amino}ethyl)-3-(2-furyl)prop-2-enamide | 2.63 | 469 |
| N-(2-{[6-{[2-(acetylamino)ethyl]amino}-2-(4-chlorophenyl)pyrimidin-4-yl]amino}ethyl)-2,3,5,6-tetrafluoro-4-methylbenzamide | 2.82 | 539 |
| N-(2-{[6-{[2-(acetylamino)ethyl]amino}-2-(4-chlorophenyl)pyrimidin-4-yl]amino}ethyl)-5-bromo-2-furamide | 2.57 | 523 |
| N-(2-{[6-{[2-(acetylamino)ethyl]amino}-2-(4-chlorophenyl)pyrimidin-4-yl]amino}ethyl)-4,4,4-trifluoro-3-hydroxy-3-methylbutanamide | 2.56 | 503 |
| (2E)-N-(2-{[6-{[2-(acetylamino)ethyl]amino}-2-(4-chlorophenyl)pyrimidin-4-yl]amino}ethyl)-3-(2,3,4-trifluorophenyl)prop-2-enamide | 2.79 | 533 |
| N-(2-{[6-{[2-(acetylamino)ethyl]amino}-2-(4-chlorophenyl)pyrimidin-4-yl]amino}ethyl)-8-hydroxyquinoline-2-carboxamide | 2.68 | 520 |
| N-(2-{[6-{[2-(acetylamino)ethyl]amino}-2-(4-chlorophenyl)pyrimidin-4-yl]amino}ethyl)-6-hydroxy-2-naphthamide | 2.64 | 519 |
| (2E)-N-(2-{[6-{[2-(acetylamino)ethyl]amino}-2-(4-chlorophenyl)pyrimidin-4-yl]amino}ethyl)-3-(4-isopropylphenyl)prop-2-enamide | 2.97 | 521 |
| (2E)-N-(2-{[6-{[2-(acetylamino)ethyl]amino}-2-(4-chlorophenyl)pyrimidin-4-yl]amino}ethyl)-3-thien-2-ylprop-2-enamide | 2.67 | 485 |
| (3E)-N-(2-{[6-{[2-(acetylamino)ethyl]amino}-2-(4-chlorophenyl)pyrimidin-4-yl]amino}ethyl)-4-phenylbut-3-enamide | 2.72 | 493 |
| N-(2-{[6-{[2-(acetylamino)ethyl]amino}-2-(4-chlorophenyl)pyrimidin-4-yl]amino}ethyl)-1-benzoylpiperidine-4-carboxamide | 2.59 | 564 |
| N-(2-{[6-{[2-(acetylamino)ethyl]amino}-2-(4-chlorophenyl)pyrimidin-4-yl]amino}ethyl)-4-[(aminocarbothioyl)amino]benzamide | 2.46 | 527 |
| N-(2-{[6-{[2-(acetylamino)ethyl]amino}-2-(4-chlorophenyl)pyrimidin-4-yl]amino}ethyl)-5-(1,2-dithiolan-3-yl)pentanamide | 2.81 | 537 |
| N-(2-{[6-{[2-(acetylamino)ethyl]amino}-2-(4-chlorophenyl)pyrimidin-4-yl]amino}ethyl)-2-methyl-5,6-dihydro-1,4-oxathiine-3-carboxamide | 2.59 | 491 |
| N-(2-{[6-{[2-(acetylamino)ethyl]amino}-2-(4-chlorophenyl)pyrimidin-4-yl]amino}ethyl)-2-(1H-tetraazol-1-yl)acetamide | 2.39 | 459 |
| N-(2-{[6-{[2-(acetylamino)ethyl]amino}-2-(4-chlorophenyl)pyrimidin-4-yl]amino}ethyl)-3-(2-furyl)propanamide | 2.62 | 471 |
| (2E,4E)-N-(2-{[6-{[2-(acetylamino)ethyl]amino}-2-(4-chlorophenyl)pyrimidin-4-yl]amino}ethyl)-5-phenylpenta-2,4-dienamide | 2.88 | 505 |
| N-(2-{[6-{[2-(acetylamino)ethyl]amino}-2-(4-chlorophenyl)pyrimidin-4-yl]amino}ethyl)-3-nitropropanamide | 2.46 | 450 |
| N-(2-{[6-{[2-(acetylamino)ethyl]amino}-2-(4-chlorophenyl)pyrimidin-4-yl]amino}ethyl)-2-(4-methylphenoxy)nicotinamide | 2.74 | 560 |
| (2E)-N-(2-{[6-{[2-(acetylamino)ethyl]amino}-2-(4-chlorophenyl)pyrimidin-4-yl]amino}ethyl)-3-pyridin-2-ylprop-2-enamide | 2.41 | 480 |
| N-(2-{[6-{[2-(acetylamino)ethyl]amino}-2-(4-chlorophenyl)pyrimidin-4-yl]amino}ethyl)-3-methyl-2-nitrobenzamide | 2.64 | 512 |
| N-(2-{[6-{[2-(acetylamino)ethyl]amino}-2-(4-chlorophenyl)pyrimidin-4-yl]amino}ethyl)-3-thien-2-ylpropanamide | 2.64 | 487 |
| N-(2-{[6-{[2-(acetylamino)ethyl]amino}-2-(4-chlorophenyl)pyrimidin-4-yl]amino}ethyl)-2-(5-methyl-2,4-dioxo-3,4-dihydropyrimidin-1(2H)-yl)acetamide | 2.40 | 515 |
| N-(2-{[6-{[2-(acetylamino)ethyl]amino}-2-(4-chlorophenyl)pyrimidin-4-yl]amino}ethyl)-4'-hydroxy[1,1'-biphenyl]-4-carboxamide | 2.70 | 545 |
| N-(2-{[6-{[2-(acetylamino)ethyl]amino}-2-(4-chlorophenyl)pyrimidin-4-yl]amino}ethyl)cyclohex-3-ene-1-carboxamide | 2.65 | 457 |
| N-(2-{[6-{[2-(acetylamino)ethyl]amino}-2-(4-chlorophenyl)pyrimidin-4-yl]amino}ethyl)-3-(4-hydroxyphenyl)propanamide | 2.53 | 497 |
| (2E)-N-(2-{[6-{[2-(acetylamino)ethyl]amino}-2-(4-chlorophenyl)pyrimidin-4-yl]amino}ethyl)-3-phenylprop-2-enamide | 2.74 | 479 |
| N-(2-{[6-{[2-(acetylamino)ethyl]amino}-2-(4-chlorophenyl)pyrimidin-4-yl]amino}ethyl)-3-(3,4,5-trimethoxyphenyl)propanamide | 2.62 | 571 |
| N-(2-{[6-{[2-(acetylamino)ethyl]amino}-2-(4-chlorophenyl)pyrimidin-4-yl]amino}ethyl)acetamide | 2.35 | 391 |
| N-(2-{[6-{[2-(acetylamino)ethyl]amino}-2-(4-chlorophenyl)pyrimidin-4-yl]amino}ethyl)propanamide | 2.43 | 405 |

| Name | Retention Time (min) | Mass Ion (ES+) (MH)+ |
|---|---|---|
| N-(2-{[6-{[2-(acetylamino)ethyl]amino}-2-(4-chlorophenyl)pyrimidin-4-yl]amino}ethyl)-2-hydroxy-5-(1H-pyrrol-1-yl)benzamide | 2.88 | 534 |

Example 13

Synthesis of Compounds 49.54-49.55

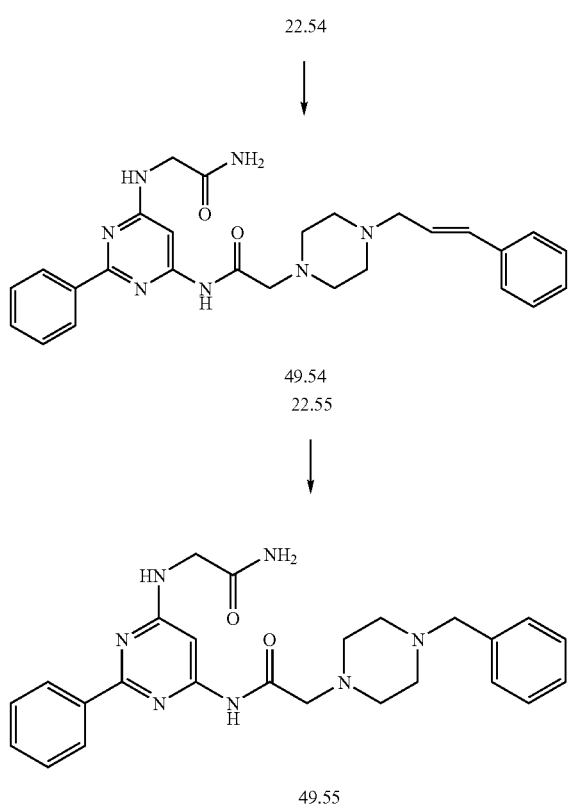

2-({2-Phenyl-6-[({4-[(2E)-3-phenylprop-2-enyl]piperazin-1-yl}acetyl)amino]pyrimidin-4-yl}amino)acetamide (49.54)

To a crude sample of N-(6-chloro-2-phenylpyrimidin-4-yl)-2-{4-[(2E)-3-phenylprop-2-enyl]piperazin-1-yl}acetamide (22.54) (0.75 g in 60 ml DMSO) were added glycinamide hydrochloride (1.85 g in 10 ml DMSO) and N,N-diisopropylethylamine (2.96 ml) and the mixture heated to 100° C. for 16 hrs. The solvent was then removed in vacuo and the residue purified twice by flash chromatography on silica gel using mixtures of dichloromethane and methanol (97:3, 95:5 then 93:7 v/v/v). Further purification by recrystallization from methanol furnished the title compound (32 mg over 2 steps).

$\delta_H$ (CDCl$_3$): 2.50-2.70 (8H, br s), 3.09 (2H, s), 3.17-(2H, d), 4.13-4.18 (2H, d), 5.29-5.43 (2H, m), 6.04-6.12 (1H, m), 6.15-6.25 (1H, m), 6.45-6.55 (1H, m), 7.16-7.19 (3H, m), 7.22-7.26 (1H, m+CDCl$_3$), 7.30-7.42 (2H, m), 7.37-7.42 (3H, m), 8.28-8.32 (2H, m), 9.39-9.43 (1H, br s); m/z (ES+) 486 (MH)+

N-{6-[(2-Amino-2-oxoethyl)amino]-2-phenylpyrimidin-4-yl}-2-(4-benzylpiperidin-1-yl)acetamide (49.55)

To a crude sample of N-(6-chloro-2-phenylpyrimidin-4-yl)-2-(4-benzylpiperidin-1-yl)acetamide (22.55) (0.75 g in 60 ml DMSO) were added glycinamide hydrochloride (1.85 g in 10 ml DMSO) and N,N-diisopropylethylamine (2.96 ml) and the mixture heated to 100° C. for 16 hrs. The solvent was then removed in vacuo and the residue purified by flash chromatography on silica gel using mixtures of dichloromethane and methanol (97:3, 95:5 then 93:7 v/v/v). Further purification by recrystallization from methanol furnished the title compound (326 mg over 2 steps).

$\delta_H$ (CDCl$_3$): 1.40-1.48 (2H, m), 1.58 (1H, s), 1.65-1.75 (2H, d), 2.17-2.23 (2H, t), 2.58-2.61 (2H, d), 2.83-2.90 (2H, d), 3.10 (2H, s), 4.20-4.22 (2H, d), 5.42-5.52 (1H, br s), 5.60-5.63 (1H, m), 6.17-6.25 (1H, br s), 7.15-7.22 (3H, m), 7.27-7.37 (3H, m), 7.43-7.50 (3H, m), 8.35-8.40 (2H, m), 9.57 (1H, s) m/z (ES+) 459 (MH)+

Example 14

The biological activity of the compounds of the present invention was tested by performing a radioligand binding assay. The disclosed compounds 8, 26, 29, 34, 36, 41, 46, 48 and 49 are A$_{2b}$ receptor antagonists. Specifically, the compounds disclosed on pages 11-13 show a greater than tenfold selectivity for the A$_{2b}$ adenosine receptor over the A$_1$, A$_{2A}$, and A$_3$ receptors and K$_i$'s <100 nM. The preparation of the binding assay is described below.

Materials and Methods

Materials. [$^3$H]-DPCPX [cyclopentyl-1,3-dipropylxanthine](120 Ci/mmol) was purchased from New England Nuclear (Boston, Mass.). The adenosine deaminase and complete protease inhibitor cocktail tablets were purchased from Boehringer Mannheim Corp. (Indianapolis, Ind.). Cell culture reagents were from Life Technologies (Grass Island, N.Y.) except for serum that was from Hyclone (Logan, Utah).

Cell line. HEK293 stably expressing the human A$_{2B}$ receptor were used for radioligand binding assays. Cells were grown in DMEM Glutamax containing 10% FBS, 0.2 mg/ml G418 at 37° C. in 5% CO2/95% atmosphere.

Membrane Preparation. Cells were washed with cold PBS buffer twice, scraped off the plates, and centrifuged at 1000×g for 5 minutes. Cells were homogenized with ice-cold buffer of 5 mM Tris, pH 7.4, 5 mM EDTA, 5 mM EGTA, protease inhibitor cocktail tablets and incubated for 10 min on ice. The homogenate was centrifuged at 32,000×g for 30 min.

The membranes were resuspended in buffer of 50 mM Tris, pH 7.4, 0.6 mM EDTA, 5 mM MgCl$_2$, stored at −80° C. until use. Protein concentration was determined by the methods of Bradford.

Radioligand binding assay. Membranes were homogenized in buffer containing 10 mM HEPES-KOH, pH 7.4 containing 1.0 mM EDTA; 2 U/ml adenosine deaminase; and 0.1 mM Benzamidine and incubated for 30 min at room temperature. Dissociation constants of radioligand ($K_d$ values) and maximum binding sites ($B_{max}$) were determined in saturation binding experiments. Saturation binding assays were carried out in a reaction mixture containing 50 µl of membrane suspension, 25 µl of 4% DMSO, 25 µl of increasing amounts of radioligand, [$^3$H]-DPCPX (final concentration 1-200 nM). Competition binding assays were performed in a reaction mixture containing 50 µl of membrane suspension (~5 µg/well), 25 µl of [$^3$H]-DPCPX (final concentration is ~22 nM), and 25 µl compounds. Nonspecific binding was measured in the presence of 100 µM NECA. Compounds were dissolved in DMSO and then diluted with 4% DMSO; the final maximum DMSO concentrations were 1%. Incubations were carried out in triplicate for 1 hr at 23.5° C. Reactions were terminated by rapid filtration over GF/C filters using a cell harvester. The filters were washed ten times with 0.4 ml of ice-cold buffer containing 10 mM HEPES-KOH, pH 7.4. The filters were dried, covered with scintillation fluid and counted with a TopCount.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:
1. A compound having the structure:

wherein,
$R_{13}$ is a substituted or unsubstituted ($C_1$-$C_4$)alkyl, branched alkyl or ($C_3$-$C_7$)cycloalkyl, wherein the substituent is —OH, —OR, —NH$_2$, —NR$_{18}$R$_{19}$, —R$_{20}$NHOCR$_{21}$, R$_{22}$R$_{23}$NCO—, carboxyl, carbamoyl (—R$_{20}$NHOCNR$_{22}$R$_{23}$), carbamate (—R$_{20}$NHOCOR), or a heterocyclic ring; or a substituted or unsubstituted aryl or heterocyclic ring wherein any substituent, if present, is —OH, —OR, halogen, —NH$_2$, or —NHR; wherein R is alkyl, cycloalkyl, aryl, heteroaryl, susbtituted alkyl, aryl, arylalkyl, or heterocyclic;
$R_{14}$ is substituted or unsubstituted phenyl, wherein the substituent, if present, is halogen, —OH, —NH$_2$, —OR, —NHR or a 5-6 membered heterocyclic ring;
$R_{15}$ is H, or alkyl;
$R_{16}$ is H, substituted or unsubstituted alkyl or aryl, or $R_{15}$ and $R_{16}$ are joined to form a heterocyclic ring;
X is —CHR$_{17}$, —CR$_{24}$R$_{25}$, O or —NR;
$R_{17}$ is H, substituted or unsubstituted alkyl, aryl, arylalkyl, heterocyclic, heterocyclic alkyl, —OH, —OR, —NH$_2$, —NR$_{18}$R$_{19}$, R$_{22}$R$_{23}$NCO —, carboxyl, carbamoyl (—R$_{20}$NHOCNR$_{22}$R$_{23}$), carbamate (—R$_{20}$NHOCOR), or ($C_3$-$C_7$) cycloalkyl;
$R_{18}$ and $R_{19}$ are each independently hydrogen, substituted or unsubstituted alkyl or aryl or $R_{18}$NR$_{19}$ together form a heterocyclic ring of between 4 and 8 members;
$R_{20}$ and $R_{21}$ are each independently a substituted or unsubstituted alkyl, aryl, or alkylaryl moiety;
$R_{22}$ and $R_{23}$ are each independently hydrogen, substituted or unsubstituted alkyl, aryl or alkylaryl, or $R_{22}$NR$_{23}$ together form a heterocyclic ring of between 4 and 8 members;
$R_{24}$ and $R_{25}$ are each independently hydrogen, substituted or unsubstituted alkyl, cycloalkyl, aryl, heterocyclic or $R_{24}$ and $R_{25}$ together form a 3-7 membered ring system or a dioxalane or dioxane ring system; and
p is 0, 1 or 2.

2. A pharmaceutical composition comprising the compound of claim 1 and a pharmaceutically acceptable carrier.

3. The pharmaceutical composition of claim 2, formulated for oral, topical, parenteral or nasal administration.

4. A method for treating a subject afflicted with asthma, comprising administering to the subject an effective amount of the compound according to claim 1 so as to thereby treat the subject.

5. The compound of claim 1, wherein the compound is selected from the group consisting of:
N-[6-(2-Acetylaminoethylamino)-2-phenylpyrimidin-4-yl]-2-[4-(3-chlorophenoxy)-piperidin-1-yl]-acetamide;
N-[6-(2-Acetylaminoethylamino)-2-phenylpyrimidin-4-yl]-2-[4-(2-chlorophenoxy)-piperidin-1-yl]-acetamide;
N-[6-(2-Acetylaminoethylamino)-2-phenylpyrimidin-4-yl]-2-[4-(4-methoxybenzyl)-piperidin-1-yl]-acetamide;
N-[6-(2-Acetylaminoethylamino)-2-phenylpyrimidin-4-yl]-2-[4-(4-fluorobenzyl)-piperidin-1-yl]-acetamide;
N-[6-(2-Acetylaminoethylamino)-2-phenylpyrimidin-4-yl]-2-[4-(2-chlorobenzyl)-piperidin-1-yl]-acetamide;
N-[6-(2-Acetylaminoethylamino)-2-phenylpyrimidin-4-yl]-2-[4-(3-chlorobenzyl)-piperidin-1-yl]-acetamide;
N-[6-(2-Acetylaminoethylamino)-2-phenylpyrimidin-4-yl]-2-[4-(4-chlorobenzyl)-piperidin-1-yl]-acetamide;
N-[6-(2-Acetylaminoethylamino)-2-phenylpyrimidin-4-yl]-2-(4-benzylpiperazin-1-yl)-acetamide;
N-[6-(2-Acetylaminoethylamino)-2-phenylpyrimidin-4-yl]-2-[4-(4-methoxybenzyl)-piperazin-1-yl]-acetamide;
N-[6-(2-Acetylaminoethylamino)-2-phenyilpyrimidin-4-yl]-2-[4-(2-methoxybenzyl)-piperazin-1-yl]-acetamide;
N-[6-(2-Acetylaminoethylamino)-2-phenylpyrimidin-4-yl]-2-[4-(3-methoxybenzyl)-piperazin-1-yl]-acetamide;
N-[6-(2-Acetylaminoethylamino)-2-phenylpyrimidin-4-yl]-2-[4-(4-chlorobenzyl)-piperazin-1-yl]-acetamide;
N-[6-(2-Acetylaminoethylamino)-2-phenylpyrimidin-4-yl]-2-[4-(3-chlorobenzyl)-piperazin-1-yl]-acetamide;
N-[6-(2-Acetylaminoethylamino)-2-phenylpyrimidin-4-yl]-2-[4-(2-chlorobenzyl)-piperazin-1-yl]-acetamide;
N-[6-(2-Acetylaminoethylamino)-2-phenylpyrimidin-4-yl]-2-[4-(3-fluorobenzyl)-piperazine-1-yl]-acetamide;
N-[6-(2-Acetylaminoethylamino)-2-phenylpyrimidin-4-yl]-2-[4-(2-fluorobenzyl)-piperazine-1-yl]-acetamide;
N-[6-(2-Acetylaminoethylamino)-2-phenylpyrimidin-4-yl]-2-[4-(3-trifluoromethylbenzyl)-piperazine-1-yl]-acetamide;
N-[6-(2-Acetylaminoethylamino)-2-phenylpyrimidin-4-yl]-2-(4-cyclohexylmethylpiperazin-1-yl)-acetamide;

N-[6-(2-Acetylaminoethylamino)-2-phenylpyrimidin-4-yl]-2-(4-phenethylpiperazin-1-yl)-acetamide;

N-[6-(2-Acetylaminoethylamino)-2-phenylpyrimidin-4-yl]-2-(4-phenethyl-[1,4]diazepan-1-yl)-acetamide;

N-[6-(2-Acetylaminoethylamino)-2-phenylpyrimidin-4-yl]-2-(4-benzyl-[1,4]diazepan-1-yl)-acetamide;

N-[6-(2-Acetylaminoethylamino)-2-phenylpyrimidin-4yl]-2-[4-(2-fluorobenzyl)-[1,4]diazapan-1-yl]-acetamide;

N-[6-(2-Acetylaminoethylamino)-2-phenylpyrimidin-4yl]-2-[4-(3-fluorobenzyl)-[1,4]diazapan-1-yl]-acetamide;

N-[6-(2-Acetylaminoethylamino)-2-phenylpyrimidin-4yl]-2-[4-(4-fluorobenzyl)-[1,4]diazapan-1-yl]-acetamide;

N-[6-(2-Acetylaminoethylamino)-2-phenylpyrilnidin-4yl]-2-[4-(2-trifluoromethylbenzyl)-[1,4]diazapan-1-yl]-acetamide;

N-[6-(2-Acetylaminoethylamino)-2-phenylpyrimidin-4-yl]-2-[4-(3-trifluoromethylbenzyl)-[1,4]diazepan-1-yl]-acetamide;

N-[6-(2-Acetylaminoethylamino)-2-phenylpyrimidin-4yl]-2-[4-(4-trifluoromethylbenzyl)-[1,4]diazapan-1-yl]-acetamide;

N-[6-(2-Acetylaminoethylamino)-2-phenylpyrimidin-4yl]-2-(4-pyridin-3-ylmethyl-[1,4]diazapan-1-yl)-acetamide;

N-[5-(2-Acetylaminoethylamino)-biphenyl-3-yl]-2-[4-(3-chlorobenzyl)-[1,4]diazepan-1-yl]-acetamide;

N-[5-(2-Acetylaminoethylamino)-biphenyl-3-yl]-2-(4-pyridin-2-ylmethyl-[1,4]diazepan-1-yl)-acetamide;

N-[5-(2-Acetylaminoethylamino)-biphenyl-3-yl]-2-[4-(6-methylpyridin-2-ylmethyl)-[1,4]diazepan-1-yl]-acetamide;

N-(6-{[2-(acetylamino)ethyl]amino}-2-phenylpyrimidin-4-yl)-2-{4-[2-nitro-4-(trifluoro-methyl)phenyl]piperazin-1-yl}acetamide;

N-(6-{[2-(acetylamino)ethyl]amino}-2-phenylpyrimidin-4-yl)-2-[4-(4-tert-butylbenzyl)-piperazin-1-yl]acetamide;

N-(6-{[2-(acetylamino)ethyl]amino}-2-phenylpyrimidin-4-yl)-2-{4-[(2E)-3-phenylprop-2-enyl]piperazin-1-yl}acetamide, and N-(6-{[2-(acetylamino)ethyl]amino}-2-phenylpyrimidin-4-yl)-2-(4-benzylpiperidin-1-yl) acetamide.

6. The compound of claim 1, wherein the compound is N-[6-(2-Acetylaminoethylamino)-2-phenylpyrimidin-4-yl]-2-[4-(4-chlorophenyl)-4-hydroxypiperdin-1-yl]-acetamide.

7. A compound having the structure:

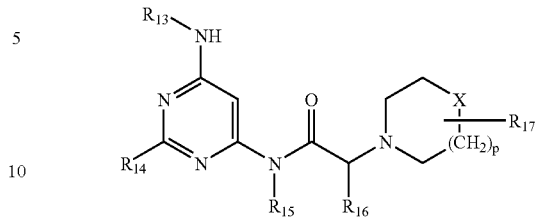

wherein, $R_{13}$ is a substituted or unsubstituted $(C_1-C_4)$alkyl, branched alkyl or $(C_3-C_7)$cycloalkyl, wherein the substituent is —OH, —OR, —NH$_2$, —NR$_{18}$R$_{19}$, R$_{22}$R$_{23}$NCO—, carboxyl, or a heterocyclic ring; or a substituted or unsubstituted aryl or heterocyclic ring wherein any substituent, if present, is —OH, —OR, halogen, —NH$_2$, or —NHR; wherein R is alkyl, cycloalkyl, aryl, heteroaryl, susbtituted alkyl, aryl, arylalkyl, or heterocyclic;

$R_{14}$ is substituted or unsubstituted phenyl, wherein the substituent, if present, is halogen, —OH, —NH$_2$, —OR, NHR or a 5-6 membered heterocyclic ring;

$R_{15}$ is H, or alkyl;

$R_{16}$ is H, substituted or unsubstituted alkyl or aryl, or $R_{15}$ and $R_{16}$ are joined to form a heterocyclic ring;

X is —CHR$_{17}$, —CR$_{24}$R$_{25}$, O or —NR;

$R_{17}$ is H, substituted or unsubstituted alkyl, aryl, arylalkyl, heterocyclic, heterocyclic alkyl, —OH, —OR, —NH$_2$, —NR$_{18}$R$_{19}$, R$_{22}$R$_{23}$NCO—, carboxyl, or $(C_3-C_7)$ cycloalkyl;

$R_{18}$ and $R_{19}$ are each independently hydrogen, substituted or unsubstituted alkyl or aryl or $R_{18}$NR$_{19}$ together form a heterocyclic ring of between 4 and 8 members;

$R_{20}$ and $R_{21}$ are each independently a substituted or unsubstituted alkyl, aryl, or alkylaryl moiety;

$R_{22}$ and $R_{23}$ are each independently hydrogen, substituted or unsubstituted alkyl, aryl or alkylaryl, or $R_{22}$NR$_{23}$ together form a heterocyclic ring of between 4 and 8 members;

$R_{24}$ and $R_{25}$ are each independently hydrogen, substituted or unsubstituted alkyl, cycloalkyl, aryl, heterocyclic or $R_{24}$ and $R_{25}$ together form a 3-7 membered ring system or a dioxalane or dioxane ring system; and p is 0, 1 or 2.

* * * * *